US007482171B2

(12) United States Patent
Acton et al.

(10) Patent No.: US 7,482,171 B2
(45) Date of Patent: *Jan. 27, 2009

(54) ANGIOTENSIN CONVERTING ENZYME HOMOLOG AND USES THEREFOR

(75) Inventors: Susan Acton, Lexington, MA (US); Keith E. Robison, Wilmington, MA (US); Frank Y. Hsieh, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 251 days.

This patent is subject to a terminal disclaimer.

(21) Appl. No.: 11/059,218

(22) Filed: Feb. 16, 2005

(65) Prior Publication Data

US 2005/0147600 A1    Jul. 7, 2005

Related U.S. Application Data

(63) Continuation of application No. 09/635,501, filed on Aug. 9, 2000, now Pat. No. 6,884,771, which is a continuation-in-part of application No. 09/407,427, filed on Sep. 29, 1999, now Pat. No. 6,610,497, which is a continuation-in-part of application No. 09/163,648, filed on Sep. 30, 1998, now Pat. No. 6,989,363, which is a continuation-in-part of application No. 08/989,299, filed on Dec. 11, 1997, now Pat. No. 6,194,556.

(51) Int. Cl.
*G01N 33/566* (2006.01)
(52) U.S. Cl. .................. 436/501; 530/316; 435/7.1
(58) Field of Classification Search ............. None
See application file for complete search history.

(56) References Cited

U.S. PATENT DOCUMENTS

| | | | |
|---|---|---|---|
| 5,359,045 A | 10/1994 | Soubrier et al. | |
| 5,480,793 A | 1/1996 | Soubrier et al. | |
| 5,589,584 A | 12/1996 | Lalouel et al. | 536/24.31 |
| 5,736,323 A | 4/1998 | Soubrier et al. | 435/6 |
| 5,763,168 A | 6/1998 | Lalouel et al. | 435/6 |
| 5,801,040 A | 9/1998 | Soubrier et al. | 435/226 |
| 6,610,497 B1 * | 8/2003 | Acton et al. | 435/7.1 |

FOREIGN PATENT DOCUMENTS

| | | |
|---|---|---|
| EP | 97/4664 | 1/2000 |
| EP | 974664 | 1/2000 |
| WO | WO 90/03435 | 4/1990 |
| WO | WO 91/00354 | 1/1991 |
| WO | WO 91/00354 | 10/1991 |
| WO | WO 97/48801 | 12/1997 |
| WO | WO 98/31835 | 7/1998 |
| WO | WO 00/18899 | 4/2000 |
| WO | WO 00/18899 A2 | 4/2000 |
| WO | WO 00/18899 A3 | 4/2000 |

OTHER PUBLICATIONS

Bernstein et al., "The Isolation of Angiotensin-Converting Enzyme cDNA," J. Biol. Chem. 15:11021-11024 (Aug. 1988).
Bernstein et al., "Mouse Angiotensin-Converting Enzyme is a Protein Composed of Two Homologous Domains," J. Biol. Chem. 264(2): 11945-11951 (Jul. 1989).
Erdos et al., "The Angiotensin I-Converting Enzyme," Lab Invest. 56(4):345-348 (Apr. 1987).
Ehlers et al., "Molecular Cloning of Human Testicular Angiotensin-Converting Enzyme: the Testis Isozyme is Identical to the C-Terminal Half of the endothelial Angiotensin-Converting Enzyme," Proc. Natl. Acad. Sci. U.S.A. 86(2):7741-7745 (Oct. 1989).
Howard et al., Transcription of Testicular Angiotensin-Converting Enzyme (ACE) is Initiated Within the 12$^{th}$ Intron of the Somatic ACE Gene,: Mol. Cell Biol. 10(8):4294-4302 (Aug. 1990).
Lattion et al., "The Testicular Transcript of the Angiotensin I-Converting Enzyme Encodes for the Ancestral, Non-Duplicated Form of the Enzyme," FEBS Lett. 252(1-2):99-104 (Jul. 1989).
Soubrier et al., "Two Putative Active Centers in Human Angiotensin-Converting Enzyme Revealed by Molecular Cloning," Proc. Natl. Acad. Sci. U.S.A. 85(24):9386-9390 (Dec. 1988).
Takeuchi, K. et al., "Purification of Human Lung Antiotensin-Converting Enzyme by High-performance Liquid Chromatography: Properties and N-terminal Amino Acid Sequence," J. Biochem. (Tokyo) 106(3):442-445 (Sep. 1989).
GenBank Accession No. P22966 Angiotensin-Converting Enzyme, Testis-Specific Isoform Precursor (ace-t) (dipeptidyl carboxypeptidase i) kininase ii).
GenBank Accession No. P22967 Angiotensin-Converting Enzyme, Testis-Specific Isoform Precursor (ace-t) (dipeptidyl carboxypeptidase i) (kininase ii).
GenBank Accession No. P22968 Angiotensin-Converting Enzyme, Testis-Specific Isoform Precursor (ace-t) (dipeptidyl carboxypeptidase i) (kininase ii).
GenBank Accession No. P12821 Angiotensin-Converting Enzyme, Somatic Isoform Precursor (ace) (dipeptidyl carboxypeptidase i) (kininase ii) (cd143 antigen).
GenBank Accession No. P12822 Angiotensin-Converting Enzyme, Somatic Isoform Precursor (ace) (dipeptidyl carboxypeptidase i) (kininase ii).
GenBank Accession No. P09470 Angiotensin-Converting Enzyme Precursor, Somatic (ace) (dipeptidyl carboxypeptidase i) (kininase ii).

(Continued)

*Primary Examiner*—Andrew D Kosar
*Assistant Examiner*—Satyanarayana R Gudibande
(74) *Attorney, Agent, or Firm*—Harness, Dickey & Pierce, P.L.C.

(57) ABSTRACT

The present invention relates to the discovery of novel genes encoding an angiotensin converting enzyme, Angiotensin Converting Enzyme-2 (ACE-2). The invention provides therapeutics, prognostic and diagnostics methods for treating blood pressure related disorders as well as various types of allergic conditions, among others. Also disclosed are screening assays for identifying compounds for treating and preventing these conditions.

6 Claims, 23 Drawing Sheets

OTHER PUBLICATIONS

GenBank Accession No. P47820 Angiotensin-Converting Enzyme, Somatic Isoform Precursor (ace) (dipeptidyl carboxypeptidase i) (kininase ii).
GenBank Accession No. Q10714 Angiotensin Converting Enzyme Precursor (dipeptidyl carboxypeptidase i) (kininase ii).
GenBank Accession No. U56966 Caenorhabditis Elegans Cosmid C42D8.
GenBank Accession No. X16295 Human mRNA for Angiotensin I Converting Enzyme (ACE).
GenBank Accession No. J04144 Human Angiotensin I-Converting Enzyme mRNA, complete cds.
GenBank Accession No. A00914 *H. sapiens* Gene for Antiotensin Conversion Enzyme (ACE).
GenBank Accession No. A31567 *H-sapiens* testicular ECA gene.
GenBank Accession No. M26657 Human Testicular Angiotensin Converting Enzyme mRNA, complete cds.
GenBank Accession No. M26658 Human Testicular Angiotensin Converting Enzyme mRNA (5'variant), complete cds.
GenBank Accession No. J04946 Mouse Angiotensin-Converting Enzyme mRNA, 3' end, clone ACE.5.
GenBank Accession No. J04947 Angiotensin-Converting Enzyme mRNA, 3' end, clone ACE.11.
GenBank Accession No. M55333 Mouse Testis-Specific Angiotensin-Converting Enzyme mRNA, complete cds.
GenBank Accession No. J03940 Mouse Angiotensin-Converting Enzyme mRNA, 5' end.
GenBank Accession No. U03734 Rattus Norvegicus Wistar-Kyoto (Heidelberg) Angiotensin-Converting Enzyme (ACE) mRNA, complete cds.
GenBank Accession No. U03708 Rattus Norvegicus Heidelberg Angiotensin Converting Enzyme (ACE) mRNA, complete cds.
GenBank Accession No. AA397955 zt79h12.r1 soares_testis_nht *Homo sapiens* cDNA Clone Image: 728615 5', mRNA sequence.
GenBank Accession No. AA420969 zt79h12.s1 soares_testis_nht *Homo sapiens* cDNA Clone Image: 728615 3', mRNA sequence.
GenBank Accession No. AA162058 ms31h11.r1 stratagene mouse skin (#937313) mus musculus cDNA Clone Image: 608613 5' similar to sw:ace_mouse p09470 Angiotensin-Converting Enzyme Precursor, Somatic; mRNA sequence.
GenBank Accession No. AA416585 zu05f02.s1 soares_testis_nht *Homo sapiens* cDNA Clone Image: 730971 3', mRNA sequence.
GenBank Accession No. AA421125 zu05f02.s1 soares_testis_nht *Homo sapiens* cDNA Clone Image: 730971 5', mRNA sequence.
GenBank Accession No. AL110224 for *Homo sapiens* mRNA; cDNA DKFZp434A014 (from clone DKFZp434a014); partial cds.
DGENE Accession No. AAY84562 for "A Human Angiotensin Converting Enzyme-2 (ACE-2) Protein," Jul. 25, 2000.
DGENE Accession No. AAA12764 for "cDNA Encoding a Human Angiotensin converting Enzyme-2 (ACE-2)," Jul. 25, 2000.
DGENE Accession No. AAY67310 for "Human MPROT 15 amino acid sequence #1," Apr. 11, 2000.
DGENE Accession No. AAZ59465 for "Human MPROT 15 coding sequence #1," Apr. 11, 2000.
DGENE Accession No. AAZ59465 for "Human MPROT 15 coding sequence #1," Apr. 11, 2000.
EMBL Accession No. AF241254 for "*Homo sapiens* angiotensin converting enzyme-like protein mRNA, complete cds," Jul. 1, 2000.
SWALL Accession No. Q9NRA7 for "Angiotensin Converting Enzyme-like Protein (ACE-related carboxypeptidase ACE2)", Oct. 1, 2000.

Bernstein, K. E., "Two ACEs and a heart," Nature 417:801-802 (Jun. 2002).
Donoghue, M. et al., "A Novel Angiotensin-Converting Enzyme-Related Carboxypeptidase (ACE2) converts angiotensin I to angiotensin 1-9," Circulation Research 87(5):e1-e9 (Sep. 1, 2000).
Tipnis, S. R., et al., "A Human Homolog of antiotensin-converting enzyme. Cloning and functional expression as a captopril-insensitive carboxypeptidase," journal of Biological chemistry 275(43):33238033243 (Oct. 2000).
Bernstein et al. (1988) J. Biological Biochemistry 263(23), 11021-11024.
Bernstein et al. (1989) J. Biological Chemistry 264(20), 11945-11951.
Bernstein (2002) Nature 417, 799,801-802.
DGENE Accession No. AAA 12764 (2000).
DGENE Accession No. AAY 67310 (2000).
DGENE Accession No. AAY 84562 (2000).
DGENE Accession No. AAZ 59465 (2000).
Donoghue et al. (2000) Circulation Research 87(5), e1-e9.
Ehlers et al. (1989) Proc. Natl. Acad. Sci. 86(20), 7741-7745.
EMBL Accession No. AF241254 (2000).
Erdös et al. (1987) Laboratory Investigation 56(4), 345-348.
GenBank Accession No. AL110224.
GenBank Accession No. P22966 (1996).
GenBank Accession No. P22967 (1996).
GenBank Accession No. P22968 (1998).
GenBank Accession No. P12821 (1998).
GenBank Accession No. P12822 (1997).
GenBank Accession No. P09470 (1996).
GenBank Accession No. P47820 (1996).
GenBank Accession No. Q10714 (1997).
GenBank Accession No. U56966 (1996).
GenBank Accession No. X16295 (1991).
GenBank Accession No. J04144 (1994).
GenBank Accession No. A00914 (1993).
GenBank Accession No. A31567 (1996).
GenBank Accession No. M26657 (1995).
GenBank Accession No. M26658 (1995).
GenBank Accession No. J04946 (1990).
GenBank Accession No. J04947 (1990).
GenBank Accession No. M55333 (1991).
GenBank Accession No. J03940 (1988).
GenBank Accession No. U03734 (1995).
GenBank Accession No. U03708 (1995).
Hillier et al., GenBank Accession No. AA162058 (1997).
Hillier et al., GenBank Accession No. AA397955 (1997).
Hillier et al., GenBank Accession No. AA416585 (1997).
Hillier et al., GenBank Accession No. AA420969 (1997).
Hillier et al., GenBank Accession No. AA421125 (1997).
Howard et al. (1990) Molecular and Cellular Biology 10(8), 4294-4302.
Lattion et al. (1989) FEBS Letters 252(1-2), 99-104.
Maria et al. (1998) J. of Hypertension 16(12), pp. 2063-2074.
Ngo et al. (1994) The Protein Folding Problem and Tertiary Structure Prediction, pp. 491-495.
Rudinger (1976) Peptide Hormones, pp. 1-7.
Science (1992) 256, pp. 441.
Soubrier et al. (1988) Natl. Acad. Sci. 85(24), 9386-9390.
SWALL Accession No. Q9NRA7 (2000).
Takeuchi et al. (1989) J. Biochem. 106(3), 442-445.
Tipnis et al. (2000) J. Biological Chemistry 275(43) 33238-33243.

* cited by examiner

```
GAATTCGGCTTCCATCCTAATACGACTCACTATAGGGCTCGAGCGGCCGCCCGGGGCAGGTATCTTGGCTCACAGGGGA  79
      M   S   S   S   S   W   L   L   L   S   L   V   A   V   T   A   A   Q   S    19
   CG ATG TCA AGC TCT TCC TGG CTC CTT CTC AGC CTT GTT GCT GTA ACT GCT GCT CAG TCC  138
    T   I   E   E   Q   A   K   T   F   L   D   K   F   N   H   E   A   E   D   L   39
   ACC ATT GAG GAA CAG GCC AAG ACA TTT TTG GAC AAG TTT AAC CAC GAA GCC GAA GAC CTG 198
    F   Y   Q   S   S   L   A   S   W   N   Y   N   T   N   I   T   E   E   N   V   59
   TTC TAT CAA AGT TCA CTT GCT TCT TGG AAT TAT AAC ACC AAT ATT ACT GAA GAG AAT GTC 258
              intron 1
    Q   N   M   N   N   A   G   D   K   W   S   A   F   L   K   E   Q   S   T   L   79
   CAA AAC ATG AAT AAT GCT GGG GAC AAA TGG TCT GCC TTT TTA AAG GAA CAG TCC ACA CTT 318
    A   Q   M   Y   P   L   Q   E   I   Q   N   L   T   V   K   L   Q   L   Q   A   99
   GCC CAA ATG TAT CCA CTA CAA GAA ATT CAG AAT CTC ACA GTC AAG CTT CAG CTG CAG GCT 378
                                                                      intron 2
    L   Q   Q   N   G   S   S   V   L   S   E   D   K   S   K   R   L   N   T   I  119
   CTT CAG CAA AAT GGG TCT TCA GTG CTC TCA GAA GAC AAG AGC AAA CGG TTG AAC ACA ATT 438
    L   N   T   M   S   T   I   Y   S   T   G   K   V   C   N   P   D   N   P   Q  139
   CTA AAT ACA ATG AGC ACC ATC TAC AGT ACT GGA AAA GTT TGT AAC CCA GAT AAT CCA CAA 498
                                       intron 3
    E   C   L   L   L   E   P   G   L   N   E   I   M   A   N   S   L   D   Y   N  159
   GAA TGC TTA TTA CTT GAA CCA GGT TTG AAT GAA ATA ATG GCA AAC AGT TTA GAC TAC AAT 558
    E   R   L   W   A   W   E   S   W   R   S   E   V   G   K   Q   L   R   P   L  179
   GAG AGG CTG TGG GCT TGG GAA AGC TGG AGA TCT GAG GTC GGC AAG CAG CTG AGG CCA TTA 618
                                                                  intron 4
    Y   E   E   Y   V   V   L   K   N   E   M   A   R   A   N   H   Y   E   D   Y  199
   TAT GAA GAG TAT GTG GTC TTG AAA AAT GAG ATG GCA AGA GCA AAT CAT TAT GAG GAC TAT 678
    G   D   Y   W   R   G   D   Y   E   V   N   G   V   D   G   Y   D   Y   S   R  219
   GGG GAT TAT TGG AGA GGA GAC TAT GAA GTA AAT GGG GTA GAT GGC TAT GAC TAC AGC CGC 738
    G   Q   L   I   E   D   V   E   H   T   F   E   E   I   K   P   L   Y   E   H  239
   GGC CAG TTG ATT GAA GAT GTG GAA CAT ACC TTT GAA GAG ATT AAA CCA TTA TAT GAA CAT 798
    L   H   A   Y   V   R   A   K   L   M   N   A   Y   P   S   Y   I   S   P   I  259
   CTT CAT GCC TAT GTG AGG GCA AAG TTG ATG AAT GCC TAT CCT TCC TAT ATC AGT CCA ATT 858
                                           intron 5
    G   C   L   P   A   H   L   L   G   D   M   W   G   R   F   W   T   N   L   Y  279
   GGA TGC CTC CCT GCT CAT TTG CTT GGT GAT ATG TGG GGT AGA TTT TGG ACA AAT CTG TAC 918
    S   L   T   V   P   F   G   Q   K   P   N   I   D   V   T   D   A   M   V   D  299
   TCT TTG ACA GTT CCC TTT GGA CAG AAA CCA AAC ATA GAT GTT ACT GAT GCA ATG GTG GAC 978
       intron 6
    Q   A   W   D   A   Q   R   I   F   K   E   A   E   K   F   F   V   S   V   G  319
   CAG GCC TGG GAT GCA CAG AGA ATA TTC AAG GAG GCC GAG AAG TTC TTT GTA TCT GTT GGT 1038
    L   P   N   M   T   Q   G   F   W   E   N   S   M   L   T   D   P   G   N   V  339
   CTT CCT AAT ATG ACT CAA GGA TTC TGG GAA AAT TCC ATG CTA ACG GAC CCA GGA AAT GTT 1098
                                                      intron 7
    Q   K   A   V   C   H   P   T   A   W   D   L   G   K   G   D   F   R   I   L  359
   CAG AAA GCA GTC TGC CAT CCC ACA GCT TGG GAC CTG GGG AAG GGC GAC TTC AGG ATC CTT 1158
    M   C   T   K   V   T   M   D   D   F   L   T   A   H   H   E   M   G   H   I  379
   ATG TGC ACA AAG GTG ACA ATG GAC GAC TTC CTG ACA GCT CAT CAT GAG ATG GGG CAT ATC 1218  ZBD
    Q   Y   D   M   A   Y   A   A   Q   P   F   L   L   R   N   G   A   N   E   G  399
   CAG TAT GAT ATG GCA TAT GCT GCA CAA CCT TTT CTG CTA AGA AAT GGA GCT AAT GAA GGA 1278
    F   H   E   A   V   G   E   I   M   S   L   S   A   A   T   P   K   H   L   K  419
   TTC CAT GAA GCT GTT GGG GAA ATC ATG TCA CTT TCT GCA GCC ACA CCT AAG CAT TTA AAA 1338
                                                              intron 8
    S   I   G   L   L   S   P   D   F   Q   E   D   N   E   T   E   I   N   F   L  439
   TCC ATT GGT CTT CTG TCA CCC GAT TTT CAA GAA GAC AAT GAA ACA GAA ATA AAC TTC CTG 1398
    L   K   Q   A   L   T   I   V   G   T   L   P   F   T   Y   M   L   E   K   W  459
   CTC AAA CAA GCA CTC ACG ATT GTT GGG ACT CTG CCA TTT ACT TAC ATG TTA GAG AAG TGG 1458
    R   W   M   V   F   K   G   E   I   P   K   D   Q   W   M   K   K   W   W   E  479
   AGG TGG ATG GTC TTT AAA GGG GAA ATT CCC AAA GAC CAG TGG ATG AAA AAG TGG TGG GAG 1518
```

Fig. 1A

```
       M   K  |intron 9
                R   E   I   V   G   V   V   E   P   V   P   H   D   E   T   Y   C   D   499
      ATG AAG  CGA GAG ATA GTT GGG GTG GTG GAA CCT GTG CCC CAT GAT GAA ACA TAC TGT GAC 1578
       P   A   S   L   F   H   V   S   N   D   Y   S   F   I   R |intron 10
                                                                    Y   Y   T   R   T   519
      CCC GCA TCT CTG TTC CAT GTT TCT AAT GAT TAC TCA TTC ATT CGA TAT TAC ACA AGG ACC 1638
       L   Y   Q   F   Q   F   Q   E   A   L   C   Q   A   A   K   H   E   G   F   L   539
      CTT TAC CAA TTC CAG TTT CAA GAA GCA CTT TGT CAA GCA GCT AAA CAT GAA GGC CCT CTG 1698
       H   K   C   D   I   S   N   S   T   E   A   G   Q   K   L  |intron 11
                                                                    F   N   M   L   R   559
      CAC AAA TGT GAC ATC TCA AAC TCT ACA GAA GCT GGA CAG AAA CTG  TTC AAT ATG CTG AGG 1758
       L   G   K   S   E   P   W   T   L   A   L   E   N   V   V   G   A   K   N   M   579
      CTT GGA AAA TCA GAA CCC TGG ACC CTA GCA TTG GAA AAT GTT GTA GGA GCA AAG AAC ATG 1818
       N   V   R   P   L   L   N   Y   F   E   P   L   F   T   W   L   K   D   Q   N   599
      AAT GTA AGG CCA CTG CTC AAC TAC TTT GAG CCC TTA TTT ACC TGG CTG AAA GAC CAG AAC 1878
       K   N   S   F   V   G   W   S   T   D   W   S   E |intron 12
                                                           Y   A   D   Q   S   I   K   619
      AAG AAT TCT TTT GTG GGA TGG AGT ACC GAC TGG AGT CCA  TAT GCA GAC CAA AGC ATC AAA 1938
       V   R   I   S   L   K   S   A   L   G   D   K   A |intron 13
                                                           Y   E   W   N   D   N   E   639
      GTG AGG ATA AGC CTA AAA TCA GCT CTT GGA GAT AAA GCA  TAT GAA TGG AAC GAC AAT GAA 1998
       M   Y   L   F   R   S   S   V   A   Y   A   M   R   Q   Y   F   L   K   V   K   659
      ATG TAC CTG TTC CGA TCA TCT GTT GCA TAT GCT ATG AGG CAG TAC TTT TTA AAA GTA AAA 2058
                              intron 14
       N   Q   M   I   L   F   G  |E   E   D   V   R   V   A   N   L   K   P   R   I   679
      AAT CAG ATG ATT CTT TTT GGG  GAG GAG GAT GTG CGA GTG GCT AAT TTG AAA CCA AGA ATC 2118
       S   F   N   F   F   V   T   A   P   K   N   V   S   D   I   I   F   R   T   E   699
      TCC TTT AAT TTC TTT GTC ACT GCA CCT AAA AAT GTG TCT GAT ATC ATT CCT AGA ACT GAA 2178
                                  intron 15
       V   E   K   A   I   R |    M   S   R   S   R   I   N   D   A   F   R   L   N   D   719
      GTT GAA AAG GCC ATC AGG     ATG TCC CGG AGC CGT ATC AAT GAT CCT TTC CGT CTG AAT GAC 2238
     ┌─N   S   L   E   F   L   G   I   Q   P   T   L   G   P   P   N   Q   P   F   V   739
     │AAC AGC CTA GAG TTT CTG GGG ATA CAG CCA ACA CTT GGA CCT CCT AAC CAG CCC CCT GTT 2298
     │ S  │I   W   L   I   V   F   G   V   V   M   G   V   I   V   V   G   I   V   I   759
     │TCC │ATA TGG CTG ATT GTT TTT GGA GTT GTG ATG GGA GTG ATA GTG GTT GGC ATT GTC ATC 2358  TMD
     │    │                             intron 16
     │ L   I   F   T   G   I│  R   D   R   K   K |K   N   K   A   R   S   G   E   N   779
     │CTG ATC TTC ACT GGG ATC│ AGA GAT CGG AAG AAG AAA AAT AAA GCA AGA AGT GGA GAA AAT 2418
       P   Y   A   S   I   D   I   S   K   G   E   N   N   P   G   F   Q   N   T   D   799
      CCT TAT GCC TCC ATC GAT ATT AGC AAA GGA GAA AAT AAT CCA GGA TTC CAA AAC ACT GAT 2478
       D   V   Q   T   S   F   *                                                       806
      GAT GTT CAG ACC TCC TTT TAG                                                      2499
      AAAAATCTATGTTTTTCCTCTTGAGGTGATTTTGTTGTATGTAAATGTTAATTTCATGGTATAGAAAATATAAGATGAT 2578
      AAAGATATCATTAAATGTCAAAACTATGACTCTGTTCAGAAAAAAATTGTCGAAAGACAACATGGCCAAGGAGAGAGC  2657
      ATCTTCATTGACATTGCTTTCAGTATTTATTTCTGTCTCTGGATTTGACTTCTGTTCTGTTTCTTAATAAGGATTTTGT 2736
      ATTAGAGTATATTAGGGAAAGTGTGTATTTGGTCTCACAGGCTGTTCAGGGATAATCTAAATGTAAATGTCTGTTGAAT 2815
      TTCTGAAGTTGAAAACAA GATATATCATTGGAGCAAGTGTTGGATCTTGTATGGAATATGGATGGATCACTTGTAAGG 2894
      ACAGTGCCTGGGAACTGGTGTAGCTGCAAGGATTGAGAATGGCATGCATTAGCTCACTTTCATTTAATCCATTGTCAAG 2973
      GATGACATGCTTTCTTCACAGTAACTCAGTTCAAGTACTATGGTGATTTGCCTACAGTGATGTTTGGAATCGATCATGC 3052
      TTTCTTCAAGGTGACAGGTCTAAAGAGAGAAGAATCCAGGGAACAGGTAGAGGACATTGCTTTTTCACTTCCAAGGTGC 3131
      TTGATCAACATCTCCCTGACAACACAAAACTAGAGCCAGGGGCCTCCGTGAACTCCCAGAGCATGCCTGATAGAAACTC 3210
      ATTTCTACTGTTCTCTAACTGTGGAGTGAATGGAAATTCCAACTGTATGTTCACCCTCTGAAGTGGGTACCCAGTCTCT 3289
      TAAATCTTTTGTATTTGCTCACAGTGTTTGAGCAGTGCTGAGCACAAAGCAGACACTCAATAAATGCTAGATTTACACA 3368
      ┌intron 17
      CTC AAAAAAAAAAAAAAAAGGGCGGCCGC                                                   3396
```

Fig. 1B

```
ace-2
hu-ACET
mu-ACET
rb-ACET
hu-ACE     MGAASGRRGPGLLLPLP-----LLLLL-PPQFALALDPGLQPGNFSADEAGAQLFAQSYN
mu-ACE     MGAASGQRGRWPLSPPLLMLSLLVLLQP-SPAPA;DPGLQPGNFSPDEAGAQLFAESYN
rat-ACE    MGAASGQRGRWPLSPPLLMLSLLLLLLLPPSPAPALDPGLQPGNFSADEAGAQLFADSYN
rb-ACE     MGAAPGRRGPRLLRPPPPLL-LLLLLLRPPPAALTLDPGLLPGDFAADEAGARLFASSYN ace-2
hu-ACET
mu-ACET
rb-ACET
hu-ACE     SSAEQVLFQSVAASWAHDTNITAENARRQEEAALLSQEFAEAWGQKAKELYEPIWQNFTD
mu-ACE     SSAEVVMFQSTVASWAHDTNITEENARRQEEAALVSQEFAEVWGKKAKELYESIWQNFTD
rat-ACE    SSAEVVMFQSTAASWAHDTNITEENARLQEEAALINQEFAEVWGKKAKELYESIWQNFTD
rb-ACE     SSAEQVLFRSTAASWAHDTNITAENARRQEEEALLSQEFAEAWGRRLRSSMTRCGRTSFT ace-2
hu-ACET
mu-ACET
rb-ACET
hu-ACE     PQLRRIIGAVRTLGSANLPLAKRQQYNALLSNMSRIYSTAKVCLPNKTATCWSLDPDLTN
mu-ACE     SKLRRIIGSIRTLGPANLPLAQRQQYNSLLSNMSRIYSTGKVCFPNKTATCWSLDPELTN
rat-ACE    QKLRRIIGSVQTLGFANLPLTQRQYNSLLSNMSRIYSTGKVCFPNKTATCWSLDPELTN
rb-ACE     QSCAGSSGLCAFWPCQPAP-GQAAADNSLLSNMSQIYSTGRSASPTPLPAAWSLDPDLNN ace-2
hu-ACET
mu-ACET
rb-ACET
hu-ACE     ILASSRSYAMLLFAWEGWHNAAGIPLKPLYEDFTALSNEAYKQDGFTDTGAYWRSWYNSP
mu-ACE     ILASSRSYAKLLFAWEGWHDAVGIPLKPLYQDFTAISNEAYRQDDFSDTGAFWRSWYESP
rat-ACE    ILASSRNYAKVLFAWEGWHDAVGIPLRPLYQDFTALSNEAYRQDGFSDTGAYWRSWYESP
rb-ACE     ILASSRSYAMLLFAWEGWHNAVGIPLKPLYQEFTALSNEAYRQDGFSDTGAYWRSWYDSP ace-2
hu-ACET
mu-ACET
rb-ACET
hu-ACE     TFEDDLEHLYQQLEPLYLNLHAFVRRALHRRYGDRYINLRGPIPAHLLGDMWAQSWENIY
mu-ACE     SFEESLEHIYHQLEPLYLNLHAYVRRALHRRYGDKYVNLRGPIPAHLLGDMWAQSWENIY
rat-ACE    SFEESLEHLYHQVEPLYLNLHAFVRRALHRRYGDKYINLRGPIPAHLLGDMWAQSWENIY
rb-ACE     TFEEDLERIYHQLEPLYLNLHAYVRRVLHRRYGDRYINLRGPIPAHLLGNMWAQSWESIY ace-2
hu-ACET
mu-ACET
rb-ACET
hu-ACE     DMVVPFPDKPNLDVTSTMLQQGWNATHMFRVAEEFFTSLELSPMPPEFWEGSMLEKPADG
mu-ACE     DMVVPFPDKPNLDVTSTMVQKGWNATHMFRVSEEFFTSLGLSPMPPEFWAESMLEKPTDG
rat-ACE    DMVVPFPDKPNLDVTSTMVQKGWNATHMFRVAEEFFTSLGLSPMPPEFWAESMLEKPADG
rb-ACE     DMVVPFPDKPNLDVTSTMVQKGWNATHMFRVAEEFFTSLGLLPMPPEFWAESMLEKPEDG ace-2
hu-ACET
mu-ACET
rb-ACET
hu-ACE     REVVCHASAWDFYNRKDFRIKQCTRVTMDQLSTVHHEMGHIQYYLQYKDLPVSLRRGANP
mu-ACE     REVVCHASAWDFYNRKDFRIKQCTRVTMEQLATVHHEMGHVQYYLQYKDLHVSLRRGANP
rat-ACE    REVVCHASAWDFYNRKDFRIKQCTRVTMDQLSTVHHEMGHVQYYLQYKDLHVSLRRGANP
rb-ACE     REVVCHASAWDFYNRKDFRIKQCTQVTMDQLSTVHHEMGHVQYYLQYKDQPVSLRR-ANP
```

Fig. 2A

```
ace-2    ------------------------------------------------------------
hu-ACET  ------------------------------------------------------------
mu-ACET  ------------------------------------------------------------
rb-ACET  ------------------------------------------------------------
hu-ACE   GFHEAIGDVLALSVSTPEHLHKIGLLDRVTNDTESDINYLLKMALEKIAFLPFGYLVDQW
mu-ACE   GFHEAIGDVLALSVSTPAHLHKIGLLDHVTNDIESDINYLLKMALEKIAFLPFGYLVDQW
rat-ACE  GFHEAIGDVLALSVSTPAHLHKIGLLDRVANDIESDINYLLKMALEKIAFLPFGYLVDQW
rb-ACE   GFHEAIGDVLALSVSTPAHLHKIGLLDHVTNDTESDINYLLKMALEKIAFLPFGYLVDQW ace-2    ------------------------------------------------------------
hu-ACET  ------------------------------------------------------------
mu-ACET  ------------------------------------------------------------
rb-ACET  ------------------------------------------------------------
hu-ACE   RWGVFSGRTPPSRYNFDWWYLRTKYQGICPPVTRNETHFDAGAKFHVPNVTPYIRYFVSF
mu-ACE   RWGVFSGRTPPSRYNFDWWYLRTKYQGICPPVARNETHFDAGAKFHIPNVTPYIRYFVSF
rat-ACE  RWGVFSGRTPPSRYNYDWWYLRTKYQGICPPVARNETHFDAGAKEHIPSVTPYIRYFVSF
rb-ACE   RWGVFSGRTPSSRYNFDWWYLRTKYQGICPPVVRNETHEDAGAKFHIPSVTPYIRYFVSF ace-2    ------------------------------------------------------------
hu-ACET  -----------------------------------------MGQGWATAGLPSLLFLLLC
mu-ACET  -----------------------------------MGQGWATPGLPSFLFLL---LC
rb-ACET  ----------------------------------MGQGWAAPGLPSLLLLLLCCGHSLL
hu-ACE   VLQFQFHEALCKEAGYEGPLHQCDIYRSTKAGAKLRKVLQAGSSRPWQEVLKDMVGLDAL
mu-ACE   VLQFQFHQALCKEAGHQGPLHQCDIYQSTQAGAKLKQVLQAGCSRPWQEVLKDLVGSDAL
rat-ACE  VLQFQFHQALCKEAGHQGPLHQCDIYQSTKAGAKLQQVLQAGCSRPWQEVLKDLVGSDAL
rb-ACE   VLQFQFHQALCMEAGHQHPLHQCDIYQSTRAGAKLRAVLQAGCSRPWQEVLKDMVASDAL ace-2    ---------------------MSSSSWLLLSLVAVTAA---QSTIEEQAKTEL
hu-ACET  YGHPLLVPSQEASQQVTVTHGTSSQATTSSQTTTHQATAHQTSAQSFNLVTDEAEASKFV
mu-ACET  CGHHLLVLSQVATDHVTANQGITNQATTRSQTTTHQATIDQTTQI-PNLETDEAKADRFV
rb-ACET  VPSRVAARRVTVNQGTTSQATTTSKATTSIRATTHQTTAHQTTQS-PNLVTDEAEASRFV
hu-ACE   DAQPLLKYFQPVTQWLQEQNQQNGEVLGWPEYQWHPPLPDNYPEG-IDLVTDEAEASKFV
mu-ACE   DAKALLEYFQPVSQWLEEQNQRNGEVLGWPENQWRPPLPDNYPEG-IDLETDEAKADRFV
rat-ACE  DASALMEYFQPVSQWLQEQNQRNGEVLGWPEYQWRPPLPDNYPEG-IDLETDEAKANRFV
rb-ACE   DAQPLLDYFQPVTQWLQEQNERNGEVLGWPEYQWRPPLPNNYPEG-IDLVTDEAEASRFV
                              *  *:. *:

ace-2    DKFNHEAEDLFYQSSLASWNYNTNITEENVQNMNNAGDKWSAFLKEQSTLAQMYFLQEIQ
hu-ACET  EEYDRTSQVVWNEYAEANWNYNTNITTETSKILLQKNMQIANHTLKYGTQARKFDVNQLQ
mu-ACET  EEYDRTAQVLLNEYAEANWQYNTNITIEGSKILLEKSTEVSNHTLKYGTRAKTFDVSNFQ
rb-ACET  EEYDRSFQAVWNEYAEANWNYNTNITTEASKILLQKNMQIANHTLKYGNWARRFDVSNFQ
hu-ACE   EEYDRTSQVVWNEYAEANWNYNTNITTETSKILLQKNMQIANHTLKYGTQARKFDVNQLQ
mu-ACE   EEYDRTAQVLLNEYAEANWQYNTNITIEGSKILLEKSTEVSNHTLKYGTRAKTFDVSNFQ
rat-ACE  EEYDRTAKVLWNEYAEANWHYNTNITIEGSKILLNKEVSNHTLKYGTWAKTFDVSNFQ
rb-ACE   EEYDRSFQAVWNEYAEANWNYNTNITTEASKILLQKNMQIANHTLKYGNWARRFDVSNFQ
         :::::  : :  : :*.*;****** *   : : ::.   .. *: : :..:;* ace-2    NLTVKLQLQALQQNGSSVLSEDKSKRLNTILNTMSTIYSTGKVCNPDNPQECLLLEPGLN
hu-ACET  NTTIKRIIKKVQDLERAALPAQELEEYNKILLDMETTYSVATVCHPNG--SCLQLEPDLT
mu-ACET  NSSIKRIIKKLQNLDRAVLPPKELEEYNQILLDMETTYSLSNICYTNG--TCMPLEPDLT
rb-ACET  NATSKRIIKKVQDLQRAVLPVKELEEYNQILLDMETIYSVANVCRVDG--SCLQLEPDLT
hu-ACE   NTTIKRIIKKVQDLERAALPAQELEEYNKILLDMETTYSVATVCHPNG--SCLQLEPDLT
mu-ACE   NSSIKRIIKKLQNLDRAVLPPKELEEYNQILLDMETTYSLSNICYTNG--TCMPLEPDLT
rat-ACE  NSTIKRIIKKVQNVDRAVLPPNELEEYNQILLDMETIYSVANVCYTNG--TCLSLEPDLT
rb-ACE   NATSKRIIKKVQDLQRAVLPVKELEEYNQILLDMETIYSVANVCRVDG--SCLQLEPDLT
         * : *  :: :*:  :.*. .: :. * ** *.* **  ..:*  :.  *: ***.*.

ace-2    EIMANSLDYNERLWAWESWRSEVGKQLRPLYEEYVVLKNEMARANHYEDYGDYWRGDYEV
hu-ACET  NVMATSRKYEDLLWAWEGWRDKAGRAILQFYPKYVELINQAARLNGYVDAGDSWRSMYET
mu-ACET  NMMATSRKYEELLWAWKSWRDKVGRAILPFFPKYVEFSNKIAKLNGYTDAGDSWRSLYES
rb-ACET  NLMATSRKYDELLWVWTSWRDKVGRAILPYFPTNKAARLNGYVDAGDSWRSMYET
hu-ACE   NVMATSRKYEDLLWAWEGWRDKAGRAILQFYPKYVELINQAARLNGYVDAGDSWRSMYET
mu-ACE   NMMATSRKYEELLWAWKSWRDKVGRAILPFFPKYVEFSNKIAKLNGYTDAGDSWRSLYES
rat-ACE  NIMATSRKYEELLWVWKSWRDKVGRAILPFFPKYVDFSNKLAKLNGYSDAGDSWRSSYES
rb-ACE   NLMATSRKYDELLWVWTSWRDKVGRAILPYFPKYVEFTNKAARLNGYVDAGDSWRSMYET
         :.**.*  .*:: **.* . **.:.*: :  : :** : *: * * ** **. **
```

Fig. 2B

```
ace-2    NGVDGYDYSRGQLIEDVEHTFEEIKPLYEHLHAYVRAKLMNAY-PSYISPIGCLPAHLLG
hu-ACET  P------------SLEQDLERLFQELQPLYLNLHAYVRRALHRHYGAQHINLEGPIPAHLLG
mu-ACET  D------------NLEQDLEKLYQELQPLYLNLHAYVRRSLHRHYGSEYINLDGPIPAHLLG
rb-ACET  P------------TLEQDLERLFQELQPLYLNLHAYVGRALHRHYGAQHINLEGPIPAHLLG
hu-ACE   P------------SLEQDLERLFQELQPLYLNLHAYVRRALHRHYGAQHINLEGPIPAHLLG
mu-ACE   D------------NLEQDLEKLYQELQPLYLNLHAYVRRSLHRHYGSEYINLDGPIPAHLLG
rat-ACE  D------------DLEQDLEKLYQELQPLYLNLHAYVRRSLHRHYGSEYINLDGPIPAHLLG
rb-ACE   P------------TLEQDLERLFQELQPLYLNLHAYVGRALHRHYGAQHINLEGPIPAHLLG
                     *:*:*;  ::*;;:* ;***     *  .*   ..:*.  * :****** ace-2    DMWGRFWTNLYSLTVPFGQKPNIDVTDAMVDQAWDAQRIFKEAEKFFVSVGLPNMTQGFW
hu-ACET  NMWAQTWSNIYDLVVPFPSAPSMDTTEAMLKQGWTPRRMFKEADDFFTSLGLLPVPPEFW
mu-ACET  NMWAQTWSNIYDLVAPFPSAPNIDATEAMIKQGWTPRRIFKEADNFFTSLGLLPVPPEFW
rb-ACET  NMWAQTWSNIYDLVAPFPSASTMDATEAMIKQGWTPRRMFEEADKFFISLGLLPVPPEFW
hu-ACE   NMWAQTWSNIYDLVVPFPSAPSMDTTEAMLKQGWTPRRMFKEADDFFTSLGLLPVPPEFW
mu-ACE   NMWAQTWSNIYDLVAPFPSAPNIDATEAMIKQGWTPRRIFKEADNFFTSLGLLPVPPEFW
rat-ACE  NMWAQTWSNIYDLVAPFPSAPSIDATEAMIKQGWTPRRIFKEADNFFTSLGLLPVPPEFW
rb-ACE   NMWAQTWSNIYDLVAPFPSASTMDATEAMIKQGWTPRRMFEEADKFFISLGLLPVPPEFW
         :**.: *:*:*.*...**  .  ...*.*:**:.*.*  .:*:*:**:.** *;**   ;.   **

ace-2    ENSMLTDPGNVQKAVCHPTAWDLGKG-DFRILMCTKVTMDDFLTAHHEMGHIQYDMAYAA
hu-ACET  NKSMLEKPTDGREVVCHASAWDFYNGKDFRIKQCTTVNLEDLVVAHHEMGHIQYFMQYKD
mu-ACET  NKSMLEKPTDGREVVCHPSAWDFYNGKDFRIKQCTSVNMEDLVIAHHEMGHIQYFMQYKD
rb-ACET  NKSMLEKPTDGREVVCHASAWDFYNGKDFRIKQCTTVNMEDLVVVHHEMGHIQYFMQYKD
hu-ACE   NKSMLEKPTDGREVVCHASAWDFYNGKDFRIKQCTTVNLEDLVVAHHEMGHIQYFMQYKD
mu-ACE   NKSMLEKPTDGREVVCHPSAWDFYNGKDFRIKQCTSVNMEDLVIAHHEMGHIQYFMQYKD
rat-ACE  NKSMLEKPTDGREVVCHASAWDFYNGKDFRIKQCTSVNMEELVIAHHEMGHIQYFMQYKD
rb-ACE   NKSMLEKPTDGREVVCHASAWDFYNGKDFRIKQCTTVNMEDLVVVHHEMGHIQYFMQYKD
         ::***  .*  :  ::.*.:*;  :* **  .*.:;:;   .********* * * ace-2    QPFLLRNGANEGFHEAVGEIMSLSAATPKHLKSIGLLSPDFQEDNETEINFLLKQALTIV
hu-ACET  LPVALREGANPGFHEAIGDVLALSVSTPKHLHSLNLLSSEGGSD-EHDINFLMKMALDKI
mu-ACET  LPVTFREGANPGFHEAIGDIMALSVSTPKHLYSLNLLSTEGSGY-EYDINFLMKMALDKI
rb-ACET  LPVALREGANPGFHEAIGDVLALSVSTPKHLHSINLLSSEGGGY-EHDINFLMKMALDKI
hu-ACE   LPVALREGANPGFHEAIGDVLALSVSTPKHLHSLNLLSSEGGSD-EHDINFLMKMALDKI
mu-ACE   LPVTFREGANPGFHEAIGDIMALSVSTPKHLYSLNLLSTEGSGY-EYDINFLMKMALDKI
rat-ACE  LPVTFREGANPGFHEAIGDVLALSVSTPKHLHSLNLLSSEGSGY-EHDINFLMKMALDKI
rb-ACE   LPVALREGANPGFHEAIGDVLALSVSTPKHLHSINLLSSEGGGY-EHDINFLMKMALDKI
         *.. :*:*** *****;*:;::**.;***** *:.***.:     * :*****:* **  ;

ace-2    GTLPFTYMLEKWRWMVFKGEIPKDQWMKKWWEMKREIVGVVEPVPHDETYCDPASLFHVS
hu-ACET  AFIPFSYLVDQWRWRVFDGSITKENYNQEWWSLRLKYQGLCPPVPRTQGDFDPGAKFHIP
mu-ACET  AFIPFSYLIDQWRWRVFDGSITKENYNQEWWSLRLKYQGLCPPVPRSQGDFDPGSKFHVP
rb-ACET  AFIPFSYLVDEWRWRVFDGSITKENYNQEWWSLRLKYQGLCPPAPRSQGDFDPGAKFHIP
hu-ACE   AFIPFSYLVDQWRWRVFDGSITKENYNQEWWSLRLKYQGLCPPVPRTQGDFDPGAKFHIP
mu-ACE   AFIPFSYLIDQWRWRVFDGSITKENYNQEWWSLRLKYQGLCPPVPRSQGDFDPGSKFHVP
rat-ACE  AFIPFSYLIDQWRWRVFDGSITKENYNQEWWSLRLKYQGLCPPVPRSQGDFDPGSKFHVP
rb-ACE   AFIPFSYLVDEWRWRVFDGSITKENYNQEWWSLRLKYQGLCPPAPRSQGDFDPGAKFHIP
         . :**:*:;::*** **.*.*.*:::  ::**.::  :  *;  *.*  : :  **.: **;.

ace-2    NDYSFIRYYTRTLYQFQFQEALCQAAKHEGPLHKCDISNSTEAGQKLFNMLRLGKSEPWT
hu-ACET  SSVPYIRYFVSFIIQFQFHEALCQAAGHTGPLHKCDIYQSKEAGQRLATAMKLGFSRPWP
mu-ACET  ANVPYVRYFVSFIIQFQFHEALCRAAGHTGPLHKCDIYQSKEAGKLLADAMKLGYSKPWP
rb-ACET  SSVPYIRYFVSFIIQFQFHEALCKAAGHTGPLHTCDIYQSKEAGKRLADAMKLGYSKPWP
hu-ACE   SSVPYIRYFVSFIIQFQFHEALCQAAGHTGPLHKCDIYQSKEAGQRLATAMKLGFSRPWP
mu-ACE   ANVPYVRYFVSFIIQFQFHEALCRAAGHTGPLHKCDIYQSKEAGKLLADAMKLGYSKPWP
rat-ACE  ANVPYIRYFISFIIQFQFHEALCRAAGHTGPLYKCDIYQSKEAGKLLADAMKLGYSKQWP
rb-ACE   SSVPYIRYFVSFIIQFQFHEALCKAAGHTGPLHTCDIYQSKEAGKRLADAMKLGYSKPWP
         . .:;**;   : ****;****;** * ***;.*** ;*.***; *  ::** *. *.

ace-2    LALENVVGAKNMNVRPLLNYFEPLFTWLKDQNKNSFVGWSTDWSPYADQSIKVRISLKSA
hu-ACET  EAMQLITGQPNMSASAMLSYFKPLLDWLRTENEL--------------------HGEK
mu-ACET  EAMKLITGQPNMSASAMMNYFKPLTEWLVTENRR--------------------HGET
rb-ACET  EAMKVITGQPNMSASAMMNYFKPLMDWLLTENGR--------------------HGEK
hu-ACE   EAMQLITGQPNMSASAMLSYFKPLLDWLRTENEL--------------------HGEK
mu-ACE   EAMKLITGQPNMSASAMMNYFKPLTEWLVTENRR--------------------HGET
rat-ACE  EAMKIITGQPNMSASAIMNYFKPLTEWLVTENRR--------------------HGET
rb-ACE   EAMKVITGQPNMSASAMMNYFKPLMDWLLTENGR--------------------HGEK
         *::  :.*  **..  .:;:.** **:** **     **   :*
```

Fig. 2C

```
ace-2     LGDKAYEWNDNEMYLFRSSVAYAMRQYFLKVKNQMILFGEEDVRVANLKPRISFNFFVTA
hu-ACET   LGWPQYNWTPN-------------------------------------------------
mu-ACET   LGWPEYNWAPN-------------------------------------------------
rb-ACET   LGWPQYTWTPN-------------------------------------------------
hu-ACE    LGWPQYNWTPN-------------------------------------------------
mu-ACE    LGWPEYNWAPN-------------------------------------------------
rat-ACE   LGWPEYTWTPN-------------------------------------------------
rb-ACE    LGWPQYTWTPN-------------------------------------------------
          **   *  * * ace-2     PKNVSDIIPRTEVEKAIRMSRSRINDAFRLNDNSLEFLGIQPTLGPPNQPPVSIWLIVFG TMD
hu-ACET   -------SARSE---------GPLPDSGRVS-----FLGLDLD---AQQARVGQWLLLFL
mu-ACET   -------TARAE---------GSTAESNRVN-----FLGLYLE---PQQARVGQWVLLFL
rb-ACET   -------SARSE---------GSLPDSGRVN-----FLGMNLD---AQQARVGQWVLLFL
hu-ACE    -------SARSE---------GPLPDSGRVS-----FLGLDLD---AQQARVGQWLLLFL
mu-ACE    -------TARAE---------GSTAESNRVN-----FLGLYLE---PQQARVGQWVLLFL
rat-ACE   -------TARAE---------GSLPESSRVN-----FLGMYLE---PQQARVGQWVLLFL
rb-ACE    -------SARSE---------GSLPDSGRVN-----FLGMNLD---AQQARVGQWVLLFL
          .*:*        .   ::  *:.    ***:       .:*. *. *:;:* ace-2     VVMGVIVVGIVILIFTGIRDRKKKNKARSGENPYASIDISKGENNPGFQNTDDVQTSFN
hu-ACET   GIALLVATLGLSQRLFSIR-HRSLHRHSHG---------------PQFGSEVELRHS--
mu-ACET   GVALLVATVGLAHRLYNIRNHHSLRRPHRG---------------PQFGSEVELRHS--
rb-ACET   GVALLLASLGLTQRLFSIR-YQSLRQPHHG---------------PQFGSEVELRHS--
hu-ACE    GIALLVATLGLSQRLFSIR-HRSLHRHSHG---------------PQFGSEVELRHS--
mu-ACE    GVALLVATVGLAHRLYNIRNHHSLRRPHRG---------------PQFGSEVELRHS--
rat-ACE   GVALLVATVGLAHRLYNIHNHHSLRRPHRG---------------PQFGSEVELRHS--
rb-ACE    GVALLLASLGLTQRLFSIR-YQSLRQPHHG---------------PQFGSEVELRHS--
          :  ::.   :   : .*:  :. .: *                  * * .  ::: *
```

Fig. 2D

```
HUM_tACE   --------------------------------------------------
HUM_ACE    MGAASGRRGPGLLLPLPLLLLLPPQPALALDPGLQPGNFSADEAGAQLFAQSYNSSAEQV
DROME_ACE  --------------------------------------------------
ace-2      --------------------------------------------------
CE_ACE     --------------------------------------------------

HUM_tACE   --------------------------------------------------
HUM_ACE    LFQSVAASWAHDTNITAENARRQEEAALLSQEFAEAWGQKAKELYEPIWQNFTDPQLRRI
DROME_ACE  --------------------------------------------------
ace-2      --------------------------------------------------
CE_ACE     --------------------------------------------------

HUM_tACE   --------------------------------------------------
HUM_ACE    IGAVRTLGSANLPLAKRQQYNALLSNMSRIYSTAKVCLPNKTATCWSLDPDLTNILASSR
DROME_ACE  --------------------------------------------------
ace-2      --------------------------------------------------
CE_ACE     --------------------------------------------------

HUM_tACE   --------------------------------------------------
HUM_ACE    SYAMLLFAWEGWHNAAGIPLKPLYEDFTALSNEAYKQDGFTDTGAYWRSWYNSPTFEDDL
DROME_ACE  --------------------------------------------------
ace-2      --------------------------------------------------
CE_ACE     --------------------------------------------------

HUM_tACE   --------------------------------------------------
HUM_ACE    EHLYQQLEPLYLNLHAFVRRALHRRYGDRYINLRGPIPAHLLGDMWAQSWENIYDMVVPF
DROME_ACE  --------------------------------------------------
ace-2      --------------------------------------------------
CE_ACE     --------------------------------------------------

HUM_tACE   --------------------------------------------------
HUM_ACE    PDKPNLDVTSTMLQQGWNATHMFRVAEEFETSLELSPMPPEFWEGSMLEKPADGREVVCH
DROME_ACE  --------------------------------------------------
ace-2      --------------------------------------------------
CE_ACE     --------------------------------------------------

HUM_tACE   --------------------------------------------------
HUM_ACE    ASAWDFYNRKDFRIKQCTRVTMDQLSTVHHEMGHIQYYLQYKDLPVSLRRGANPGFHEAI
DROME_ACE  --------------------------------------------------
ace-2      --------------------------------------------------
CE_ACE     --------------------------------------------------

HUM_tACE   --------------------------------------------------
HUM_ACE    GDVLALSVATPEHLHKIGLLDRVTNDTESDINYLLKMALEKIAFLPFGYLVDQWRWGVFS
DROME_ACE  --------------------------------------------------
ace-2      --------------------------------------------------
CE_ACE     ----------------------------------------MKFHILLLLLV HUM_tACE   --------------------------------------------------
HUM_ACE    GRTPPSRYNFDWWYLRTKYQGICPPVTRNETHFDAGAKFHVPNVTPYIRYFVSFVLQFQF
DROME_ACE  --------------------------------------------------
ace-2      --------------------------------------------------
CE_ACE     GACLPVFTQEIKPKPELLPADEAPKDPEAVFSEGEPFELTDALDTPKNGSVPVPEPEPKP
```

Fig. 3A

```
HUM_tACE    ------------------------------------MGQGWATAGLPSLLFLLLCYGHPLL
HUM_ACE     HEALCKEAGYEGPLHQCDIYRSTKAGAKLRKVLQAGSSRPWQEVLKDMVGLDALDAQPLL
DROME_ACE   ------------------------------------------------------------
ace-2       ------------------------------------------------------------
CE_ACE      EPEPEPEPKPEPEPSPTPEPEPAIKFDNIESEDYGDVAETAASTQPDELNTEVIEQLVDT HUM_tACE    VPSQEASQQVTVTHGTSSQATTSSQTTTHQATAHQTSAQSPNLVTDEAEASKFVEEYDRT
HUM_ACE     KYGQPVTQWLQEQNQQNGEVLGWPEYQWHPPLPDNYPEG-IDLVTDEAEASKFVEEYDRT
DROME_ACE   ------------------------MRLFLLLALLATLAVTQALVKEEIQAKEYLENLNKE
ace-2       -------------------------MSSSSWLLLSLVAVTAAQSTIEEQAKTFLDKFNHE
CE_ACE      FLNTGSIASNKTNKGPVFANPVAQALVNSSNYWKTDNLQAPGSIKDEEKLRSWLAGYEAE
                                     . *  :     ::         :

HUM_tACE    SQVVWNEYAEANWNYNTNITTETSKILLQKNMQLANHTLKYGTQARKFDVNQLQNTTIKR
HUM_ACE     SQVVWNEYAEANWNYNTNITTETSKILLQKNMQLANHTLKYGTQARKFDVNQLQNTTIKR
DROME_ACE   LAKRTNVETEAAWAYGSNITDENEKKKNEISAELAKFMKEVASDTTKFQWFSYQSEDLKR
ace-2       AEDLFYQSSLASWNYNTNITEENVQNMNNAGDKWSAFLKEQSTLAQMYPLQEIQNLTVKL
CE_ACE      AIKVLREVALSGWRYFNDASPSLKLALDEAENVLTMFVRSTSMQAKQFDMASVTDEKVMR
              :   :  * .:  :              :        :.

HUM_tACE    IIKKVQDLERAALPAQELEEYNKILLDMETTYSVATVCHPNGS---CLQLEPDLTNVMAT
HUM_ACE     IIKKVQDLERAALPAQELEEYNKILLDMETTYSVATVCHPNGS---CLQLEPDLTNVMAT
DROME_ACE   QFKALTKLGYAALPEDDYAELLDTLSAMESNFAKVKVCDYKDSTKCDLALDPEIEEVISK
ace-2       QLQALQQNGSSVLSEDKSKRLNTILNTMSTIYSTGKVCNPDNPQE-CLLLEPGLNEIMAN
CE_ACE      QLGYVSFEGMSALAPSRFADYSQAQAALNRDSKDSTICDKDVPPP-CALQKIDMDSIFRN
             :   :       :.*.          .:*.            .:.:  .

HUM_tACE    SRKYEDLLWAWEGWRDKAGRAILQFYPKYVELINQAARLNGYVDAGDSWRSMYETP----
HUM_ACE     SRKYEDLLWAWEGWRDKAGRAILQFYPKYVELINQAARLNGYVDAGDSWRSMYETP----
DROME_ACE   SRDHEELAYYWREFYDKAGTAVRSQFERYVELNTKAAKLNNFTSGAEAWLDEYEDD----
ace-2       SLDYNERLWAWESWRSEVGKQLRPLYEEYVVLKNEMARANHYEDYGDYWRGDYEVNGVDG
CE_ACE      EKDASRLQHLWVSYVTAIAKSK-PSYNNIITISNEGAKLNGFANGGAMWRSAFDMSS--K
             ...   *         :  .  :.: :.: *:  * :  .   * . ::

HUM_tACE    ------SLEQDLERLFQELQPLYLNLHAYVRRALHRHYG-AQHINLEGPIPAHLLGNMWA
HUM_ACE     ------SLEQDLERLFQELQPLYLNLHAYVRRALHRHYG-AQHINLEGPIPAHLLGNMWA
DROME_ACE   ------TFEQQLEDIFADIRPLYQQIHGYVRFRLRKHYG-DAVVSETGPIPMHLLGNMWA
ace-2       YDYSRGQLIEDVEHTFEEIKPLYEHLHAYVRAKLMNAY--PSYISPIGCLPAHLLGDMWG
CE_ACE      VHKAEFDLNKQIDKIYSTIQPFYQLLHAYMRRQLAGIYSNPVGLSKDGPIPAHLFGSLDG
                  : ::::  :  ::*:*  :*.*:*  *   *     *. * :* **:*.:.

HUM_tACE    QTWSNIYDLVVPFPSA--PSMDTTEAMLKQGWTPRRMFKEADDFFTSLGLLPVPPEFWNK
HUM_ACE     QTWSNIYDLVVPFPSA--PSMDTTEAMLKQGWTPRRMFKEADDFFTSLGLLPVPPEFWNK
DROME_ACE   QQWSEIADIVSPFPEK--PLVDVSAEMEKQAYTPLKMFQMGDDFFTSMNLTKLPQDFWDK
ace-2       RFWTNLYSLTVPFGQK--PNIDVTDAMVDQAWDAQRIFKEAEKFFVSVGLPNMTQGFWEN
CE_ACE      GDWSAHYEQTKPFEEESETPEAMLSAFNTQNYTTKKMFVTAYRYFKSAGFPHLPKSYWTS
             *:   .  . **.  .       :    * *  *: .   :* *  .: :.   :* .

HUM_tACE    SMLEKPTDGREVVCHAS-AWDFYNGKDFRIKQCTTVNLEDLVVAHHEMGHIQYFMQYKDL
HUM_ACE     SMLEKPTDGREVVCHAS-AWDFYNGKDFRIKQCTTVNLEDLVVAHHEMGHIQYFMQYKDL
DROME_ACE   SIIEKPTDGRDLVCHAS-AWDFYLIDDVRIKQCTRVTQDQLFTVHHELGHIQYFLQYQHQ
ace-2       SMLTDPGNVQKAVCHPT-AWDLGKG-DFRIIMCTKVTMDDFLTAHHEMGHIQYDMAYAAQ
CE_ACE      SIFAR-VWSKDMICHPAAALDMRAPNDFRVKACAQLGEPDFEQAHSLLVQTYYQYLYKDQ
             *::         .  :. *:  ..:* *: *;     *.*:    *:   :: * *

HUM_tACE    PVALREGANPGFHEAIGDVLALSVSTPKHLHSLNLLSSEGGSD--EHDINFLMKMALDKI
HUM_ACE     PVALREGANPGFHEAIGDVLALSVSTPKHLHSLNLLSSEGGSD--EHDINFLMKMALDKI
DROME_ACE   PFVYRTGANPGFHEAVGDVLSLSVSTPKHLEKIGLLKDYVRDD--EARINQLFLTALDKI
ace-2       PFLLRNGANEGFHEAVGEIMSLSAATPKHLKSIGLLSPDFQEDN-ETEINFLLKQALTIV
CE_ACE      SLLFREQASPVITDAIANAFAHLSTNPHYLYSQKLVPSEHLDIKDSVIINKLYKESLESF
             .. *  *.   :  :*:.: ::   :: .*::*  . *:      . ** *   :*  .
```

Fig. 3B

```
HUM_tACE    AFIPFSYLVDQWRWRVFDGSITKENYNQEWWSLRLKYQGLCPPVPRTQGDFDPGAKFHIP
HUM_ACE     AFIPFSYLVDQWRWRVFDGSITKENYNQEWWSLRLKYQGLCPPVPRTQGDFDPGAKFHIP
DROME_ACE   VFLPFAFTMDKYRWSLFRGEVDKANWNCAFWKLRDEYSGIEPPVVRSEKDFDAPAKYHIS
ace-2       GTLPFTYMLEKWRWMVFKGEIPKDQWMKKWWEMKREIVGVVEPVPHDETYCDPASLFHVS
CE_ACE      TKLPFTIAADNWRYELFDGTVPKNKLNDRWWEIRNKYEGVRSPQPYNTSNLDALIHNSVS
              :**:    :::*:  :* *  : *  :      :*.:: :   *: *    *.    :.

HUM_tACE    -SSVPYIRYFVSFIIQFQFHEALCQAAGHTG------PLHKCDIYQSKEAGQRLATAMKL
HUM_ACE     -SSVPYIRYFVSFIIQFQFHEALCQAAGHTG------PLHKCDIYQSKEAGQRLATAMKL
DROME_ACE   -ADVEYLRYLVSFIIQFQFYKSACIKAGQYDPDNVELPLDNCDIYGSARAGAAFHNMLSM
ace-2       -NDYSFIRYYTRTLYQFQFQEALCQAAKHEG------PLHKCDISNSTEAGQKLFNMLRL
CE_ACE      QVHSPATRTLISYVLKFQILKALCQRELFWL------SEGCTLSEDTT---EKLRETMKL
                  *   :  :**: ::  *         .        :      :   :  :

HUM_tACE    GFSRPWPEAMQLITGQPNMSASAMLSYFKPLLDWLRTEN---------------------
HUM_ACE     GFSRPWPEAMQLITGQPNMSASAMLSYFKPLLDWLRTEN---------------------
DROME_ACE   GASKPWPDALEAFNGERIMSGKAIAEYFEPLRVWLEAEN---------------------
ace-2       GKSEPWTLALENVVGAKNMNVRPLLNYFEPLFTWLKDQNKNSFVGWSTDWSPYADQSIKV
CE_ACE      GSSITWLKALEMISGKGELDAQPLLEYYEPLINWLRNTN---------------------
             *  .*   *::  .  *      :.  .:  .*::** **.  *

HUM_tACE    -ELHGEKLGWPQYNWTPNSAR---------------------------------------
HUM_ACE     -ELHGEKLGWPQYNWTPNSAR---------------------------------------
DROME_ACE   -IKNNVHIGWTTSNKCVSS-----------------------------------------
ace-2       RISLKSALGDKAYEWNDNEMYLFRSSVAYAMRQYFLKVKNQMILFGEEDVRVANLKPRIS
CE_ACE      -EIDQVVVGWDGEGTPFTVEEIPKTRQPGDGGNGLPSEDRVAFPGGE-------------
              :*        .

HUM_tACE    -------------------------SEGPLPDSGRVSFLGLDLDAQQARVG-------Q
HUM_ACE     -------------------------SEGPLPDSGRVSFLGLDLDAQQARVG-------Q
DROME_ACE   ------------------------------------------------------------
ace-2       FNFFVTAPKNVSDIIPRTEVEKAIRMSRSRINDAFRLNDNSLEFLGIQPTLGPPNQPPVS
CE_ACE      -----------------CVNGQECLLDSHCNGTICVCNDGLYTLEIGNTFN---CVPGN HUM_tACE    WLLLFLGIALLVATLGLSQRLFS-IRHR----------------SLHRHSGPQFGSEVE
HUM_ACE     WLLLFLGIALLVATLGLSQRLFS-IRHR----------------SLHRHSGPQFGSEVE
DROME_ACE   ------------------------------------------------------------
ace-2       IWLIVFGVVMGVIVVGIVILIFTGIRDRKKKNKARSGENPYASIDISKGENNPGFQNTDD  TMD
CE_ACE      PADSGFGDKGGLVIGLFNNEVTTPEPSAEPEP--TAKTTTKMPPRVRAATSPFSLYLTV HUM_tACE    LRHS----
HUM_ACE     LRHS----
DROME_ACE   --------
ace-2       VQTSFN--
CE_ACE      LLIIYFAL
```

Fig. 3C

```
GAATTCGGCTTCCATCCTAATACGACTCACTATAGGGCTCGAGCGGCCGCCCGGGGCAGGTATCTTGGCTCACAGGGGACGATGTCAAG
CTCTTCCTGGCTCCTTCTCAGCCTTGTTGCTGTAACTGCTGCTCAGTCCACCATTGAGGAACAGGCCAAGACATTTTTGGACAAGTTTAAC
CACGAAGCCGAAGACCTGTTCTATCAAAGTTCACTTGCTTCTTGGAATTATAACACCAATATTACTGAAGAGAATGTCCAAAACAT    /
GAATAATGCTGGGGACAAATGGTCTGCCTTTTTAAAGGAACAGTCCACACTTGCC
CAAATGTATCCACTACAAGAAATTCAGAATCTCACAGTCAAGCTTCAGCTGCAGGCTCTTCAGCAAAATGGGTCTTCAGTGCTCTCAGAA
GACAAGAGCAAACGG    /    TTGAACACAATTCTAAAT                                                    G-A INTRONIC
                                                                                              3a/3b

ACAATGAGCACCATCTACAGTACTGGAAAAGTTTGTAACCCAGATAATCCACAAGAATGCTTATTACTTGAACCAGG    /
TTTGAATGAAATAATGGCAAACAGTTTAGACTACAATGAGAGGCTCTGGGC
TTGGGAAAGCTGGAGATCTGAGGTCGGCAAGCAGCTGAGGCCATTATATGAAGAGTATGTGGTCTTGAAAAATGAGATGGCAAGAGCAA
ATC    /    ATTATGAGGACTATGGGGATTATTGGAGAGGAG
ACTATGAAGTAAATGGGGTAGATGGCTATGACTACAGCCGCGGCCAGTTGATTGAAGATGTGGAACATACCTTTGAAGAG    /
ATTAAACCATTATATGAACATCTTCATGCCTATGTGAGGGC
AAAGTTGATGAATGCCTATCCTTCCTATATCAGTCCAATTGGATGCCTCCCTGCTCATTTGCTTGG    /
TGATATGTGGGGTAGATTTTGGACAAAATCTGTACTCTTTGACAGTTCCCTTTGGACAGAAA
CCAAACATCGATGTTACTGATGCAATGGTGGACCAG    /    GCCTGGGATGCACAGAGAATATT
CAAGGAGGCCGAGAAGTTCTTTGTATCTGTTGGTCTTCCTAATATGACTCAAGGATTCTGGGAAAATTCCATGCTAACGGACCCAGGAAA
TGTTCAGAAAGCAGTCTGCCATCCCACAGCTTGGGACCTGGG    /
GAAGGGCGACTTCAGGATCCTTATGTGCACAAAGGTGACAATGGACGACTTCCTG
ACAGCTCATCATGAGATGGGCATATCCAGTATGATATGGCATATGCTGCACAACCTTTTCTGCTAAGAAATGGAGCTAATGAAGGATTC    5 bp INSERTION
CATGAAGCTGTTGGGGAAATCATGTCACTTTCTGCAGCCACACCTAAGCATTTAAAATCCATTGGTCTTCTGTCACCCGATTTTCAAGAAG    (CTTAT)
                                                                                              INTRONIC
ACAATG    /    AAACAGAAATAAACTTCCTGCTCAAACAAGCACTCACGATTGTTGGGACTCTGCCATTTACTTA              9a/9b
CATGTTAGAGAAGTGGAGGTGGATGGTCTTTAAAGGGGAAATTCCCAAAGACCAGTGGATGAAAAAGTGGTGGGAGATGAAG    /
CGAGAGATAGTTGGGGTGGTGGAACCTGTGCCCCATGATGAAA
CATACTGTGACCCCGCATCTCTGTTCCATGTTTCTAATGATTACTCATTCATTCG    /    ATATTACA
CAAGGACCCTTTACCAATTCCAGTTTCAAGAAGCACTTTGTCAAGCAGCTAAACATGAAGGCCCT
CTGCACAAATGTGACATCTCAAACTCTACAGAAGCTGGACAGAAACTG    /
TTCAATATGCTGAGGCTTGGAAAATCAGAACCCTGGACCCTAGCATTGGAAAATGTTGTAGGAGCAAAGAACATGAATGTAAGGCCACT
GCTCAACTACTTTGAGCCCTTATTTACCTGGCTGAAAGACCAGAACAAGAATTCTTTTGTGGGATGGAGTACCGACTGGAGTCC    /
ATATGCAGACCAAAGCATCAAAGTGAGGATAAG                                                            T-G INTRONIC
                                                                                              14a/14b
CCTAAAATCAGCTCTTGGAGATAAAGC    /    ATATGAATGGAACGACAATGAAATGTACC
TGTTCCGATCATCTGTTGCATATGCTATGAGGCAGTACTTTTTAAAAGTAAAAAATCAGATGATTCTTTTTGGG    /
GAGGAGGATGTGCGAGTGGCTAATTTGAAACCAAGAATCTCCTTTAATTTCTTT                                       A-G ASN-ASP
GTCACTGCACCTAAAAATGTGTCTGATATCATTCCTAGAACTGAAGTTGAAAAGGCCATCAGG    /                         17c/17d
ATGTCCGGAGCCGTATCAATGATGCTTTCCGTCTGAATGACAACAGCCTAGAGTTTCTGGG
GATACAGCCAACACTTGACCTCCTAACCAGCCCCCTGTTTCCATATGGCTGATTGTTTTTGGAGTTGTGATGGGAGTGATAGTGGTTGG
CATTGTCATCCTGATCTTCACTGGGATCAGAGATCGGAAGAAG    /
AAAAATAAAGCAAGAAGTGGAGAAAATCCTTATGCCTCCATCGATATTAGCAAAGGA
GAAAATAATCCAGGATTCCAAAACACTGATGATGTTCAGACCTCCTTTTAGAAAAATCTATGTTTTTCCTCTTGAGGTGATTTTGTTGTATG
TAAATGTTAATTTCATGGTATAGAAAATATAAGATGATAAAGATATCATTAAATGTCAAAACTATGACTCTGTTCAGAAAAAAAATTGTCCA
AAGACAACATGGCCAAGGAGAGAGCATCTTCATTGACATTGCTTTCAGTATTTATTTCTGTCTCTGGATTTGACTTCTGTTCTGTTTCTTAA
TAAGGATTTTGTATTAGAGTATATTAGGGAAAGTGTGTATTTGGTCTCACAGGCTGTTCAGGGATAATCTAAATGTAAATGTCTGTTGAATT
                                                                                              G-T 3'UTR
TCTGAAGTTGAAAACAAGGATATATCATTGGAGCAAGTGTTGGATCTTGTATGGAATATGGATGGATCACTTGTAAGGACAGTGCCTGG    18e/18f
GAACTGGTGTAGCTGCAAGGATTGAGAATGGCATGCATTAGCTCACTTTCATTTAATCATTGTCAAGGATGACATGCTTTCTTCACAGTA
ACTCAGTTCAAGTACTATGGTGATTTGCCTACAGTGATGTTTGGAATCGATCATGCTTTCTTCAAGGTGACAGGTCTAAAGAGAAGAAT
CCAGGGAACAGGTAGAGGACATTGCTTTTTCACTTCCAAGGTGCTTGATCAACATCTCCCTGACAACACAAAACTAGAGCCAGGGGCCT
CCGTGAACTCCCAGAGCATGCCTGATAGAAACTCATTTCTACTGTTCTCTAACTGTGGAGTGAATGGAAATTCCAACTGTATGTTCACCCT
CTGAAGTGGGTACCCAGTCTCTTAAATCTTTTGTATTTGCTCACAGTGTTTGAGCAGTGCTGAGCACAAAGCAGACACTCAATAAATGCTA
GATTTACACACTC    /    AAAAAAAAAAAAAAAAGGGCGGCCGC
```

Fig. 9B

```
GAATTCGGCTTCCATCCTAATACGACTCACTATAGGGCTCGAGCGGCCGCCCGGGGCAGGTATCTTGGCTCACAGGGGACGATGTCAAG    A-G INTRONIC
CTCTTCCTGGCTCCTTCTCAGCCTTGTTGCTGTAACTGCTGCTCAGTCCACCATTGAGGAACAGGCCAAGACATTTTTGGACAAGTTTAAC   1c/1d
CACGAAGCCGAAGACCTGTTCTATCAAAGTTCACTTGCTTCTTGGAATTATAACACCAATATTACTGAAGAGAATGTCCAAAACAT   /
GAATAATGCTGGGGACAAATGGTCTGCCTTTTTAAAGGAACAGTCCACACTTGCC
CAAATGTATCCACTACAAGAAATTCAGAATCTCACAGTCAAGCTTCAGCTGCAGGCTCTTCAGCAAAATGGGTCTTCAGTGCTCTCAGAA
GACAAGAGCAAACGG   /   TTGAACACAATTCTAAAT                                                     G-A INTRONIC
                                                                                              A-G INTRONIC
ACAATGAGCACCATCTACAGTACTGGAAAAGTTTGTAACCCAGATAATCCACAAGAATGCTTATTACTTGAACCAGG   /            3a/3b
TTTGAATGAAATAATGGCAAACAGTTTAGACTACAATGAGAGGCTCTGGGC
TTGGGAAAGCTGGAGATCTGAGGTCGGCAAGCAGCTGAGGCCATTATATGAAGAGTATGTGGTCTTGAAAAATGAGATGGCAAGAGCAA
ATC   /   ATTATGAGGACTATGGGGATTATTGGAGAGGAG
ACTATGAAGTAAATGGGGTAGATGGCTATGACTACAGCCGCGGCCAGTTGATTGAAGATGTGGAACATACCTTTGAAGAG   /
ATTAAACCATTATATGAACATCTTCATGCCTATGTGAGGGC
AAAGTTGATGAATGCCTATCCTTCCTATATCAGTCCAATTGGATGCCTCCCTGCTCATTTGCTTGG   /
TGATATGTGGGGTAGATTTTGGACAAATCTGTACTCTTTGACAGTTCCCTTTGGACAGAAA
CCAAACATAGATGTTACTGATGCAATGGTGGACCAG   /   GCCTGGGATGCACAGAGAATATT
CAAGGAGGCCGAGAAGTTCTTTGTATCTGTTGGTCTTCCTAATATGACTCAAGGATTCTGGGAAAATTCCATGCTAACGGACCCAGGAAA
TGTTCAGAAAGCAGTCTGCCATCCCACAGCTTGGGACCTGGG   /
GAAGGGCGACTTCAGGATCCTTATGTGCACAAAGGTGACAATGGACGACTTCCTG
ACAGCTCATCATGAGATGGGGCATATCCAGTATGATATGGCATATGCTGCACAACCTTTTCTGCTAAGAAATGGAGCTAATGAAGGATTC   5 bp INSERTION
CATGAAGCTGTTGGGGAAATCATGTCACTTTCTGCAGCCACACCTAAGCATTTAAAATCCATTGGTCTTCTGTCACCCGATTTTCAAGAAG   (CTTAT)
                                                                                              INTRONIC
ACAATG   /   AAACAGAAATAAACTTCCTGCTCAAACAAGCACTCACGATTGTTGGGACTCTGCCATTTACTTA                 9a/9b
CATGTTAGAGAAGTGGAGGTGGATGGTCTTTAAAGGGGAAATTCCCAAAGACCAGTGGATGAAAAAGTGGTGGGAGATGAAG   /
CGAGAGATAGTTGGGGTGGTGGAACCTGTGCCCCATGATGAAA
CATACTGTGACCCCGCATCTCTGTTCCATGTTTCTAATGATTACTCATTCATTCG   /   ATATTACA
CAAGGACCCTTTACCAATTCCAGTTTCAAGAAGCACTTTGTCAAGCAGCTAAACATGAAGGCCCT
CTGCACAAATGTGACATCTCAAACTCTACAGAAGCTGGACAGAAACTG   /
TTCAATATGCTGAGGCTTGGAAAATCAGAACCCTGGACCCTAGCATTGGAAAATGTTGTAGGAGCAAAGAACATGAATGTAAGGCCACT
GCTCAACTACTTTGAGCCCTTATTTACCTGGCTGAAAGACCAGAACAAGAATTCTTTTGTGGGATGGAGTACCGACTGGAGTCC   /
ATATGCAGACCAAAGCATCAAAGTGAGGATAAG                                                            T-G INTRONIC
                                                                                              14a/14b
CCTAAAAATCAGCTCTTGGAGATAAAGC   /   ATATGAATGGAACGACAATGAAATGTACC
TGTTCCGATCATCTGTTGCATATGCTATGAGGCAGTACTTTTTAAAAGTAAAAAAATCAGATGATTCTTTTTGGG   /
GAGGAGGATGTGCGAGTGGCTAAATTTGAAACCAAGAATCTCCTTTAATTTCTTT                                      A-G ASN-ASP
GTCACTGCACCTAAAAATGTGTCTGATATCATTCCTAGAACTGAAGTTGAAAAGGCCATCAGG   /                          17c/17d
ATGTCCCGGAGCCGTATCAATGATGCTTTCCGTCTGAATGACAACAGCCTAGAGTTTCTGGG
GATACAGCCAACACTTGGACCTCCTAACCAGCCCCCTGTTTCCATATGGCTGATTGTTTTTGGAGTTGTGATGGGAGTGATAGTGGTTGG
CATTGTCATCCTGATCTTCACTGGGATCAGAGATCGGAAGAAG   /
AAAAATAAAGCAAGAAGTGGAGAAAATCCTTATGCCTCCATCGATATTAGCAAAGGA
GAAAATAATCCAGGATTCCAAAACACTGATGATGTTCAGACCTCCTTTTAGAAAAATCTATGTTTTTCCTCTTGAGGTGATTTTGTTGTATG
TAAATGTTAATTTCATGGTATAGAAAATATAAGATGATAAAGATATCATTAAATGTCAAAACTATGACTCTGTTCAGAAAAAAAATTGTCCA
AAGACAACATGGCCAAGGAGAGAGCATCTTCATTGACATTGCTTTCAGTATTTATTTCTGTCTCTGGATTTGACTTCTGTTCTGTTTCTTAA    A-G 3'UTR
TAAGGATTTTGTATTAGAGTATATTAGGGAAAGTGTGTATTTGGTCTCACAGGCTGTTCAGGGATAATCTAAATGTAAATGTCTGTTGAATT    18c/18d
TCTGAAGTTGAAAACAAGGATATATCATTGGAGCAAGTGTTGGATCTTGTATGGAATATGGATGGATCACTTGTAAGGACAGTGCCTGG     G-T 3'UTR
GAACTGGTGTAGCTGCAAGGATTGAGAATGGCATGCATTAGCTCACTTTCATTTAATCCATTGTCAAGGATGACATGCTTTCTTCACAGTA    18e/18f
ACTCAGTTCAAGTACTATGGTGATTTGCCTACAGTGATGTTTGGAATCGATCATGCTTTCTTCAAGGTGACAGGTCTAAAGAGAGAAGAAT
CCAGGGAACAGGTAGAGGACATTGCTTTTTCACTTCCAAGGTGCTTGATCAACATCTCCCTGACAACACAAAACTAGAGCCAGGGCCT
CCGTGAACTCCCAGAGCATGCCTGATAGAAACTCATTTCTACTGTTCTCTAACTGTGGAGTGAATGGAAATTCCAACTGTATGTTCACCCT
CTGAAGTGGGTACCCAGTCTCTTAAATCTTTTGTATTTGCTCACAGTGTTTGAGCAGTGCTGAGCACAAAGCAGACACTCAATAAATGCTA
GATTTACACACTC   /   AAAAAAAAAAAAAAAGGGCGGCCGC
```

Fig. 13B

ANGIOTENSIN CONVERTING ENZYME HOMOLOG AND USES THEREFOR

RELATED APPLICATIONS

This application is a continuation of U.S. application No. 09/635,501, filed Aug. 9, 2000, now U.S. Pat. No. 6,884,771, which is a continuation in part of U.S. application No. 09/407,427, filed on Sep. 29, 1999, now U.S. Pat. No. 6,610,497 which is a continuation in part of U.S. application No. 09/163,648, filed on Sep. 30, 1998, now U.S. Pat. No. 6,989,363 which is a continuation in part of U.S. application No. 08/989,299, filed on Dec. 11, 1997, now U.S. Pat. No. 6,194,556, each of which are incorporated herein in their entirety by this reference.

BACKGROUND OF THE INVENTION

Hypertension, or high blood pressure, is the most common disease affecting the heart and blood vessels. Statistics indicate that hypertension occurs in more than 50 million Americans. The prevalence of hypertension increases with age. Between 85 and 90% of cases are primary (i.e., essential) hypertension, i.e., a persistently elevated blood pressure that cannot be attributed to any particular organic cause. The remaining percentage of cases are secondary hypertension, i.e., elevated blood pressure having an identifiable underlying cause such as kidney disease and adrenal hypersecretion.

Hypertension is of considerable concern because of the harm it can do to the heart, brain, and kidneys if it remains uncontrolled. The heart is most commonly affected by high blood pressure. When blood pressure is high, the heart uses more energy in pumping against the increased resistance caused by the elevated arterial blood pressure. Because of the increased effort, the heart muscle thickens and the heart becomes enlarged and needs more oxygen. If it cannot meet the demands put on it, angina pectoris or even myocardial infarction may develop. Hypertension can result in numerous complications include left ventricular failure; atherosclerotic heart disease; retinal hermorrhages, exudates, papilledema, and vascular accidents; cerebrovascular insufficiency with or without stroke; and renal failure. An untreated hypertensive patient is at great risk of developing disabling or fatal left ventricular failure, myocardial infarction, cerebral hemorrhage or infarction, or renal failure at early age. Hypertension is the most important risk factor predisposing to stroke and is an important risk factor predisposing to coronary atherosclerosis.

An abnormal blood pressure can also result from specific conditions or diseases, such as heart failure. Heart failure is a chronic or acute state that results when the heart is not capable of providing sufficient cardiac output to satisfy the metabolic needs of the body. Heart failure is commonly referred to as congestive heart failure (CHF), since symptoms of increased venous pressure (pulmonary congestion with left heart failure and peripheral edema with right heart failure) are often predominant. Symptoms and signs of CHF include fatigue, peripheral and pulmonary edema, and visceral congestion (e.g., dyspnea). These symptoms are produced by diminished blood flow to the various tissues of the body and by accumulation of excess blood in the various organs, that results from the heart being incapable of pumping out the blood. Heart failure can result from several underlying diseases, most commonly in industrialized nations from atherosclerotic coronary artery disease with myocardial infarction. Myocardidis, various cardiomyopathies, and valvular and congenital defects may also result in heart failure (Anderoli et al., Cecil: Essentials of Medicine, Third Edition, WB Saunders Company, 1993). A major problem in CHF is the inability of the failing left ventricle to maintain a normal blood pressure, thus resulting in increased pre- and afterload, and leading to progressive ventricular dilation with wall remodeling. Vasodilators which induce a reduction in pre- and afterload, i.e., reduction of the systemic vascular resistance and reduction of the peripheral vascular resistance, respectively, are currently used to treat CHF (Lionel H. Opie, Drugs for the Heart, Third Edition, WB Saunders Company, 1991).

One important system involved in regulating blood pressure is the renin-angiotensin-aldosterone system. In this system, renin, a proteolytic enzyme formed in the granules of the juxtaglomerular apparatus cells catalyzes the conversion of angiotensinogen (a plasma protein) into angiotensin I, a decapeptide. This inactive product is then cleaved by a converting enzyme, termed angiotensin converting enzyme (ACE) mainly in the lung, but also in the kidney and brain, to an octapeptide, angiotensin II, which is a potent vasoconstrictor and also stimulates the release of aldosterone. Aldosterone is an adrenal cortex hormone that promotes the retention of salt and water by the kidneys and thus increases plasma volume, resulting in an increase in blood pressure. Angiotensin II also stimulates the release of norepinephrine from neural cells which interacts with specific receptors on blood vessels, thereby resulting in an increase in calcium and vasocontriction. Another mechanism by which angiotensin II induces vasoconstriction is by interacting with specific receptors on blood vessels, thereby resulting in an opening of calcium channels and an increase in calcium, resulting in vasoconstriction.

ACE, also referred to as peptidyl dipeptidase A (EC 3.4.15.1) and kininase II is a metallopeptidase, more particularly a zinc peptidase which hydrolyses angiotensin I and other biologically active polypeptides, such as kinins, e.g., bradykinin. Bradykinin is a vasodilator, which acts at least in part by inducing release of vasodilator prostaglandins, and which is inactivated upon hydrolysis by ACE. Thus, ACE increases blood pressure at least in part by producing angiotensin II, a vasoconstrictor, and by inactivating bradykinin, a vasodilator. Bradykinin is also involved in other biological activities including mediation of pain and inflammatory reactions.

The role of ACE in regulating blood pressure is further demonstrated at least by the efficacy of ACE inhibitors in reducing hypertension and treating CHF in individuals. ACE inhibitors have major roles as vasodilators in hypertension and CHF and are among the most efficient drugs for treating these disorders (see, e.g., Opie et al., Angiotensin Converting Enzyme Inhibitors and Conventional Vasodilators, in Lionel H. Opie, Drugs for the Heart, Third Edition, WB Saunders Company, 1991, p106). Several clinical trials indicate that ACE inhibitors prolong survival in a broad spectrum of patients with myocardial infarction and heart failure, ranging from those who are asymptomatic with ventricular dysfunction to those who have symptomatic heart failure but are normotensive and hemodynamically stable. For example, one study demonstrated a 40% reduction in mortality at 6 months in patients with severe heart failure (The CONSENSUS Trial Study Group, N. Engl. J. Med. 316:1429 (1987); The CONSENSUS Trial Study Group, N. Engl. J. Med. 325:293 (1991)).

ACE cleaves substrates other than angiotensin I and bradykinin. For example, ACE cleaves enkephalins, as well as heptapeptide and octapeptide enkephalin precursors. ACE also hydrolyzes the tridecapeptide neurotensin to a dipeptide and undecapeptide (Skidgel et al. In Neuropeptides and Their Peptidases, Ed. Turner A J, Chichester, U K, Ellis-Horwood, (1987)). ACE can also cleave and thereby inactivate substance P (Skidgel et al., supra).

Several ACE inhibitors are currently available on the market (e.g., Captopril, Enalapril, Fosinopril, Lisinopril, and Ramipril). However, ACE inhibitors in large doses can cause a variety of undesirable secondary effects including nephrotic syndrome, membraneous glomerulonephritis, nephritis, and leukopenia, as well as angioedema.

The isolation of novel nucleic acids coding novel ACE proteins would be useful, e.g., in developing drugs which are capable of regulating the activity of ACE without having the negative secondary effects.

SUMMARY OF THE INVENTION

The present invention is based, at least in part, on the discovery of a novel gene encoding a novel human protein, having sequence homologies with known angiotensin converting enzymes (ACEs). Thus, the newly identified proteins and nucleic acids described herein are referred to as "angiotensin converting enzyme-2" or "ACE-2". The human ACE-2 gene transcript is shown in FIG. 1 (SEQ ID NO:1) and includes 5' and 3' untranslated regions and a 2415 base pair open reading frame (SEQ ID NO:3) encoding an 805 amino acid polypeptide having SEQ ID NO:2. The mature protein, i.e., the full length protein without the signal sequence is comprised of about 787 amino acids. ACE-2 is expressed predominantly in kidney and testis. A nucleic acid comprising the cDNA encoding the full length human ACE-2 polypeptide has been deposited at the American Type Culture Collection (12301 Parklawn Drive, Rockville, Md.) on Dec. 3, 1997 has been assigned ATCC Designation No. 209510.

An amino acid and nucleotide sequence analysis using the BLAST program (Altschul et al. (1990) J. Mol. Biol. 215: 403) revealed that certain portions of the amino acid and nucleic acid sequences of the newly identified human ACE-2 protein and nucleic acid have a sequence similarity with certain regions of angiotensin converting enzymes. In particular, the amino acid sequence of the zinc binding domain, which is conserved in all ACE proteins identified to date and which is located in the catalytic site of the enzyme and necessary for catalytic activity, is also found in ACE-2. Amino acids which have been identified as either contacting the zinc atom and/or involved in the catalysis and are conserved among all ACE proteins, are present in ACE-2. Thus, ACE-2 is believed to share at least some of the biological activities of ACE proteins, in particular the peptidase activity. In fact, as shown herein (see Example 5.4), ACE-2 cleaves the C-terminal amino acid from angiotensin I to produce Ang (1-9). ACE-2 also comprises a transmembrane domain which is present in most ACE proteins and which is likely to mediate protein attachment to the cell membrane. Except for the presence of other small regions of homology between ACE-2 and known ACE proteins, the other portions of ACE-2 are significantly different from those of known ACE proteins.

In one aspect, the invention features isolated ACE-2 nucleic acid molecules. In one embodiment, the ACE-2 nucleic acid is from a vertebrate. In a preferred embodiment, the ACE-2 nucleic acid is from a mammal, e.g. a human. In an even more preferred embodiment, the nucleic acid has the nucleic acid sequence set forth in SEQ ID NO:1 and/or 3 or a portion thereof. The disclosed molecules can be non-coding, (e.g. a probe, antisense, or ribozyme molecules) or can encode a functional ACE-2 polypeptide (e.g. a polypeptide which specifically modulates biological activity, by acting as either an agonist or antagonist of at least one bioactivity of the human ACE-2 polypeptide). In one embodiment, the nucleic acid molecules can hybridize to the ACE-2 gene contained in ATCC designation No. 209510. In another embodiment, the nucleic acids of the present invention can hybridize to a vertebrate ACE-2 gene or to the complement of a vertebrate ACE-2 gene. In a further embodiment, the claimed nucleic acid can hybridize with a nucleic acid sequence shown in FIG. 1 (SEQ ID NOs: 1 and 3) or complement thereof. In a preferred embodiment, the hybridization is conducted under mildly stringent or stringent conditions.

In further embodiments, the nucleic acid molecule is an ACE-2 nucleic acid that is at least about 70%, preferably about 80%, more preferably about 85%, and even more preferably at least about 90% or 95% homologous to the nucleic acid shown as SEQ ID NOs: 1 or 3 or to the complement of the nucleic acid shown as SEQ ID NOs: 1 or 3. In a further embodiment, the nucleic acid molecule is an ACE-2 nucleic acid that is at least about 70%, preferably at least about 80%, more preferably at least about 85% and even more preferably at least about 90% or 95% similar in sequence to the ACE-2 nucleic acid contained in ATCC designation No. 209510 or shown set forth in SEQ ID NOs: 1 and/or 3 or complement thereof.

The invention also provides probes and primers comprising substantially purified oligonucleotides, which correspond to a region of nucleotide sequence which hybridizes to at least about 6 at least about 10, and at least about 15, at least about 20, or preferably at least about 25 consecutive nucleotides of the sequence set forth as SEQ ID NO:1 or complements of the sequence set forth as SEQ ID NO:1 or naturally occurring mutants or allelic variants thereof, such as those described in the Examples. In preferred embodiments, the probe/primer further includes a label group attached thereto, which is capable of being detected.

For expression, the subject nucleic acids can be operably linked to a transcriptional regulatory sequence, e.g., at least one of a transcriptional promoter (e.g., for constitutive expression or inducible expression) or transcriptional enhancer sequence. Such regulatory sequences in conjunction with an ACE-2 nucleic acid molecule can provide a useful vector for gene expression. This invention also describes host cells transfected with said expression vector whether prokaryotic or eukaryotic and in vitro (e.g. cell culture) and in vivo (e.g. transgenic) methods for producing ACE-2 proteins by employing said expression vectors.

In another aspect, the invention features isolated ACE-2 polypeptides, preferably substantially pure preparations, e.g. of plasma purified or recombinantly produced polypeptides. The ACE-2 polypeptide can comprise a full length protein or can comprise smaller fragments corresponding to one or more particular motifs/domains, or fragments comprising at least about 5, 10, 25, 50, 75, 100, 125, 130, 135, 140 or 145 amino acids in length. In particularly preferred embodiments, the subject polypeptide has an ACE-2 bioactivity, for example, it is capable of interacting with and/or hydrolyzing a target peptide, such as angiotensin I, kinetensin, bradykinin or neurotensin.

In a preferred embodiment, the polypeptide is encoded by a nucleic acid which hybridizes with the nucleic acid sequence represented in SEQ ID NOs: 1 and 3. In a further preferred embodiment, the ACE-2 polypeptide is comprised of the amino acid sequence set forth in SEQ ID NO:2. The subject ACE-2 protein also includes within its scope modified proteins, e.g. proteins which are resistant to post-translational modification, for example, due to mutations which alter modification sites (such as tyrosine, threonine, serine or aspargine residues), or which prevent glycosylation of the protein, or which prevent interaction of the protein with intracellular proteins involved in signal transduction.

The ACE-2 polypeptides of the present invention can be glycosylated, or conversely, by choice of the expression system or by modification of the protein sequence to preclude glycosylation, reduced carbohydrate analogs can also be provided. Glycosylated forms can be obtained based on derivatization with glycosaminoglycan chains. Also, ACE-2 polypeptides can be generated which lack an endogenous signal sequence (though this is typically cleaved off even if present in the pro-form of the protein).

In yet another preferred embodiment, the invention features a purified or recombinant polypeptide, which has the ability to modulate, e.g., mimic or antagonize, an activity of a wild-type ACE-2 protein, e.g., its ability to bind and/or hydrolyze angiotensin I, kinetensin, bradykinin, or neurotensin, or a peptide having a significant amino acid homology thereto. Preferably, the polypeptide comprises an amino acid sequence identical or homologous to a sequence designated in SEQ ID No: 2.

Another aspect of the invention features chimeric molecules (e.g., fusion proteins) comprising an ACE-2 protein. For instance, the ACE-2 protein can be provided as a recombinant fusion protein which includes a second polypeptide portion, e.g., a second polypeptide having an amino acid sequence unrelated (heterologous) to the ACE-2 polypeptide. A preferred ACE-2 fusion protein is an immunoglobulin-ACE-2 fusion protein, in which an immunoglobulin constant region is fused to an ACE-2 polypeptide.

Yet another aspect of the present invention concerns an immunogen comprising an ACE-2 polypeptide in an immunogenic preparation, the immunogen being capable of eliciting an immune response specific for an ACE-2 polypeptide; e.g. a humoral response, an antibody response and/or cellular response. In a preferred embodiment, the immunogen comprises an antigenic determinant, e.g. a unique determinant of a protein encoded by the nucleic acid set forth in SEQ ID NO:1 or 3; or as set forth in SEQ ID NO:2.

A still further aspect of the present invention features antibodies and antibody preparations specifically reactive with an epitope of an ACE-2 protein.

The invention also features transgenic non-human animals which include (and preferably express) a heterologous form of an ACE-2 gene described herein, or which misexpress an endogenous ACE-2 gene (e.g., an animal in which expression of one or more of the subject ACE-2 proteins is disrupted). Such transgenic animals can serve as animal models for studying cellular and/or tissue disorders comprising mutated or mis-expressed ACE-2 alleles or for use in drug screening. Alternatively, such transgenic animals can be useful for expressing recombinant ACE-2 polypeptides.

The invention further features assays and kits for determining whether an individual's ACE-2 genes and/or proteins are defective or deficient (e.g in activity and/or level), and/or for determining the identity of ACE-2 alleles. In one embodiment, the method comprises the step of determining the level of ACE-2 protein, the level ACE-2 mRNA and/or the transcription rate of an ACE-2 gene. In another preferred embodiment, the method comprises detecting, in a tissue of the subject, the presence or absence of a genetic alteration, which is characterized by at least one of the following: a deletion of one or more nucleotides from a gene; an addition of one or more nucleotides to the gene; a substitution of one or more nucleotides of the gene; a gross chromosomal rearrangement of the gene; an alteration in the level of a messenger RNA transcript of the gene; the presence of a non-wild type splicing pattern of a messenger RNA transcript of the gene; and/or a non-wild type level of the ACE-2 protein.

For example, detecting a genetic alteration or the presence of a specific polymorphic region can include (i) providing a probe/primer comprised of an oligonucleotide which hybridizes to a sense or antisense sequence of an ACE-2 gene or naturally occurring mutants thereof, or 5' or 3' flanking sequences naturally associated with the ACE-2 gene; (ii) contacting the probe/primer with an appropriate nucleic acid containing sample; and (iii) detecting, by hybridization of the probe/primer to the nucleic acid, the presence or absence of the genetic alteration. Particularly preferred embodiments comprise: 1) sequencing at least a portion of an ACE-2 gene, 2) performing a single strand conformation polymorphism (SSCP) analysis to detect differences in electrophoretic mobility between mutant and wild-type nucleic acids; and 3) detecting or quantitating the level of an ACE-2 protein in an immunoassay using an antibody which is specifically immunoreactive with a wild-type or mutated ACE-2 protein.

Information obtained using the diagnostic assays described herein (alone or in conjunction with information on another genetic defect, which contributes to the same disease) is useful for diagnosing or confirming that a symptomatic subject (e.g. a subject symptomatic for hypertension, hypotension, CHF, or a kinetensin-associated condition), has a genetic defect (e.g. in an ACE-2 gene or in a gene that regulates the expression of an ACE-2 gene), which causes or contributes to the particular disease or disorder. Alternatively, the information (alone or in conjunction with information on another genetic defect, which contributes to the same disease) can be used prognostically for predicting whether a non-symptomatic subject is likely to develop a disease or condition, which is caused by or contributed to by an abnormal ACE-2 activity or protein level (e.g. hypertension, hypotension, CHF, or a kinetensin-associated condition) in a subject. In particular, the assays permit to ascertain an individual's predilection to develop a condition associated with a mutation in ACE-2, where the mutation is a single nucleotide polymorphism (SNP). Based on the prognostic information, a doctor can recommend a regimen (e.g. diet or exercise) or therapeutic protocol useful for preventing or prolonging onset of the particular disease or condition in the individual.

In addition, knowledge of the particular alteration or alterations, resulting in defective or deficient ACE-2 genes or proteins in an individual, alone or in conjunction with information on other genetic defects contributing to the same disease (the genetic profile of the particular disease) allows customization of therapy for a particular disease to the individual's genetic profile, the goal of "pharmacogenomics". For example, an individual's ACE-2 genetic profile or the genetic profile of a disease or condition, to which ACE-2 genetic alterations cause or contribute, can enable a doctor: 1) to more effectively prescribe a drug that will address the molecular basis of the disease or condition; and 2) to better determine the appropriate dosage of a particular drug. For example, the expression level of ACE-2 proteins, alone or in conjunction with the expression level of other genes, known to contribute to the same disease, can be measured in many patients at various stages of the disease to generate a transcriptional or expression profile of the disease. Expression patterns of individual patients can then be compared to the expression profile of the disease to determine the appropriate drug and dose to administer to the patient.

The ability to target populations expected to show the highest clinical benefit, based on the ACE-2 or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of ACE-2 as a marker is useful for optimizing effective dose).

In another aspect, the invention provides methods for identifying a compound which modulates an ACE-2 activity, e.g. the interaction between an ACE-2 polypeptide and a target peptide, e.g., angiotensin I, a kinin, kinetensin or neurotensin. In a preferred embodiment, the method includes the steps of (a) forming a reaction mixture including: (i) an ACE-2 polypeptide, (ii) an ACE-2 binding partner (e.g., a target peptide, such as angiotensin I or kinetensin), and (iii) a test compound; and (b) detecting interaction of the ACE-2 polypeptide and the ACE-2 binding protein. A statistically significant change (potentiation or inhibition) in the interaction of the ACE-2 polypeptide and ACE-2 binding protein in the presence of the test compound, relative to the interaction in the absence of the test compound, indicates a potential agonist (mimetic or potentiator) or antagonist (inhibitor) of ACE-2 bioactivity for the test compound. The reaction mixture can be a cell-free protein preparation, e.g., a reconstituted protein mixture or a cell lysate, or it can be a recombinant cell including a heterologous nucleic acid recombinantly expressing the ACE-2 binding partner.

In preferred embodiments, the step of detecting interaction of the ACE-2 and ACE-2 binding partner (e.g., angiotensin I or kinetensin) is a competitive binding assay.

In preferred embodiments, at least one of the ACE-2 polypeptide and the ACE-2 binding partner comprises a detectable label, and interaction of the ACE-2 and ACE-2 binding partner is quantified by detecting the label in the complex. The detectable label can be, e.g., a radioisotope, a fluorescent compound, an enzyme, or an enzyme co-factor. In other embodiments, the complex is detected by an immunoassay.

The invention also provides a methods for identifying an ACE-2 therapeutic, comprising contacting in a reaction mixture an ACE-2 polypeptide, a target peptide or analog thereof or portion thereof, and a test compound, in conditions wherein, but for the presence of the test compound, the ACE-2 polypeptide cleaves one or more amino acids from the target peptide or analog thereof or portion thereof to produce an ACE-2 target peptide conversion product, and detecting the presence of at least one of the target peptide or analog thereof or portion thereof, the ACE-2 target peptide conversion product, and one or more amino acids. A preferred method for determining the presence and/or the amount of at least one of the target peptide or analog thereof or portion thereof, the ACE-2 target peptide conversion product, and one or more amino acids comprises obtaining a mass spectrum of the reaction mixture or of a part thereof.

Yet another exemplary embodiment provides an assay for screening test compounds to identify agents which modulate the amount of ACE-2 produced by a cell. In one embodiment, the screening assay comprises contacting a cell transfected with a reporter gene operably linked to an ACE-2 promoter with a test compound and determining the level of expression of the reporter gene. The reporter gene can encode, e.g., a gene product that gives rise to a detectable signal such as: color, fluorescence, luminescence, cell viability, relief of a cell nutritional requirement, cell growth, and drug resistance. For example, the reporter gene can encode a gene product selected from the group consisting of chloramphenicol acetyl transferase, luciferase, beta-galactosidase and alkaline phosphatase.

Also within the scope of the invention are methods for treating diseases or disorders which are associated with an aberrant ACE-2 level or activity or which can benefit from modulation of the activity or level of ACE-2, in particular diseases or conditions which are improved by modulation of the level of one or more angiotensin I conversion products, e.g., by an increase or decrease in the production of Ang.(1-9), Ang.(1-5), and/or Ang.(1-8) (angiotensin II); conditions that are improved by modulation of kinetensin or kinetensin (1-8) level; conditions that are improved by modulation of bradykinin (1-8) or bradykinin (1-7); or conditions that are improved by modulation of neurotensin (1-13) or neurotensin (1-12). Thus, the invention provides methods for treating hypertension, CHF, inflammatory reactions, allergic reactions, and methods to reduce pain. The methods comprise administering, e.g., either locally or systemically to a subject, a pharmaceutically effective amount of a composition comprising an ACE-2 therapeutic. Depending on the condition, the therapeutic can be an ACE-2 agonist or an ACE-2 antagonist. For example, an ACE-2 antagonist therapeutic can be administered to a subject having hypertension or CHF. In another embodiment, an ACE agonist is administered locally to a subject to reduce the inflammation and pain resulting from an insect sting or bite, which was accompanied by an injection of bradykinin.

In a particular embodiment of the invention, an ACE-2 antagonist is administered to a subject alone or together with an ACE antagonist. Thus, a dual therapy comprising administering to a subject an antagonist of ACE-2 and an antagonist of ACE can be used to prevent the accumulation of angiotensin II, e.g., to thereby reduce the blood pressure of the subject and prevent the development or appearance of conditions related thereto.

The invention also provides methods for identifying other potential substrates of an ACE-2 polypeptide as well as the product of the enzymatic reaction. In a preferred embodiment, the method comprises contacting a preparation containing an ACE-2 polypeptide with a test compound, e.g., a peptide, for a time sufficient for the enzymatic reaction to occur, and subjecting the reaction mixture, or a portion thereof, to mass spectrometry. The comparison of the mass spectra of the test compound with that of the reaction mixture after incubation to allow the enzymatic reaction to occur, will indicate whether the test compound was converted into a new compound, in which case the test compound is a substrate of the ACE-2 polypeptide.

Other features and advantages of the invention will be apparent from the following detailed description and claims.

BRIEF DESCRIPTION OF THE FIGURES

FIG. 1(A-B) shows the nucleotide sequence of a full length cDNA encoding human ACE-2 including 5' and 3' untranslated regions and coding sequences (SEQ ID NO:1) and the deduced amino acid sequence of the ACE-2 protein (SEQ ID NO 2). The signal sequence is underlined, and the zinc binding domain (ZBD) and transmembrane (TMD) domain are boxed. The position of the introns is indicated. The two single chain polymorphisms are indicated by boxes around the nucleotides.

FIG. 2(A-D) shows an alignment of the amino acid sequence of human ACE-2 having SEQ ID NO:2 with human testicular ACE (hu-ACET; SEQ ID NO:4; GenBank Accession No. P22966), murine testicular ACE (mu-ACET; SEQ ID NO:5; GenBank Accession No. P22967), rabbit testicular ACE (rb-ACET; SEQ ID NO:6; GenBank Accession No. P22968), human endothelial ACE hu-ACE; SEQ ID NO:7;

GenBank Accession No. P12821; U.S. Pat. No. 5,539,045 by Soubrier et al.; and described in Soubrier et al. (1988) Proc. Natl. Acad. Sci. USA 85:9386), murine endothelial ACE (mu-ACE; SEQ ID NO:8; GenBank Accession No. P09470), rat endothelial ACE (rat-ACE; SEQ ID NO:9; GenBank Accession No. P47820) and rabbit endothelial ACE (rb-ACE; SEQ ID NO:10; GenBank Accession No. P12822). Stars indicate amino acids which are common to all sequences. Two dots indicate that all amino acids at that position are conserved and one dot indicates that two or more sequences share the amino acid at that position, but that at least one sequence has an amino acid that is not a conservative substitution at that position. The zinc binding domain (ZBD) and the transmembrane domain (TMD) are boxed.

FIG. 3(A-C) shows an amino acid alignment of the human ACE-2 protein having SEQ ID NO:2 with human testicular ACE (HUM_tACE; SEQ ID NO:4; GenBank Accession No. P22966), human endothelial ACE (HUM_ACE; SEQ ID NO:7; GenBank Accession No. P12821, *Drosophila melanogaster* ACE (DROME_ACE; SEQ ID NO:11; GenBank Accession No. Q10714), and *C. elegans* ACE (CE_ACE) SEQ ID NO:12; GenBank Accession No. U56966). Stars indicate amino acids which are common to all sequences. Two dots indicate that all amino acids at that position are conserved and one dot indicates that two or more sequences share the amino acid at that position, but that at least one sequence has an amino acid that is not a conservative substitution at that position. The zinc binding domain (ZBD) and the transmembrane domain (TMD) are boxed.

Figure 4:
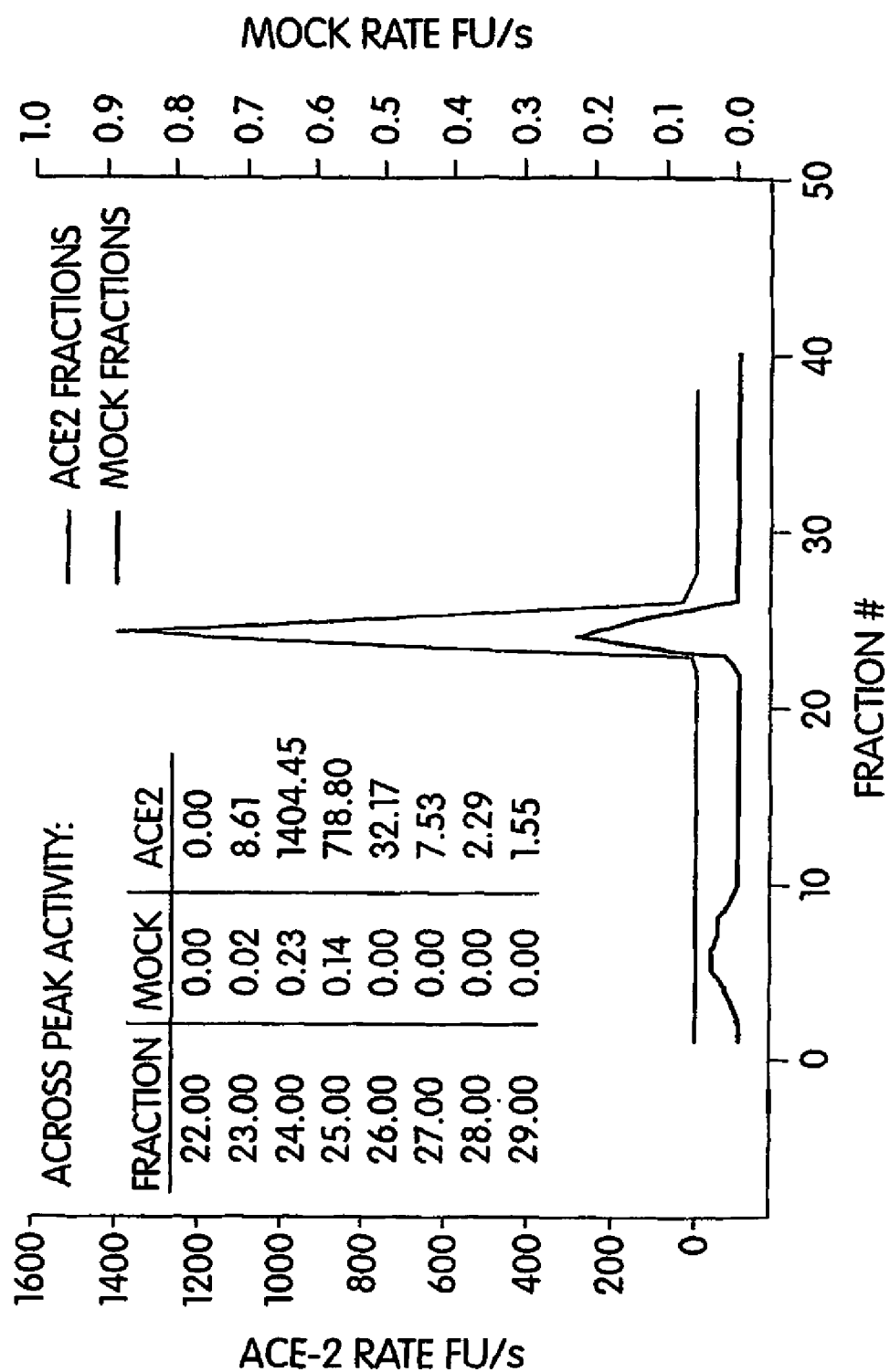

FIG. 4 shows the activity of baculovirus expressed ACE-2 in different fractions from the column.

FIG. 5 (panels A and B) show mass spectra of angiotensin I (panel A) and its conversion product after reaction with ACE-2 (panel B).

FIG. 6 (panels A and B) show mass spectrum of neurotensin (1-13) (panel A) and its conversion product after reaction with ACE-2 (panel B).

FIG. 7 (panels A and B) show mass spectrum of bradykinin (panel A) and its conversion product after reaction with ACE-2 (panel B).

Figure 8:
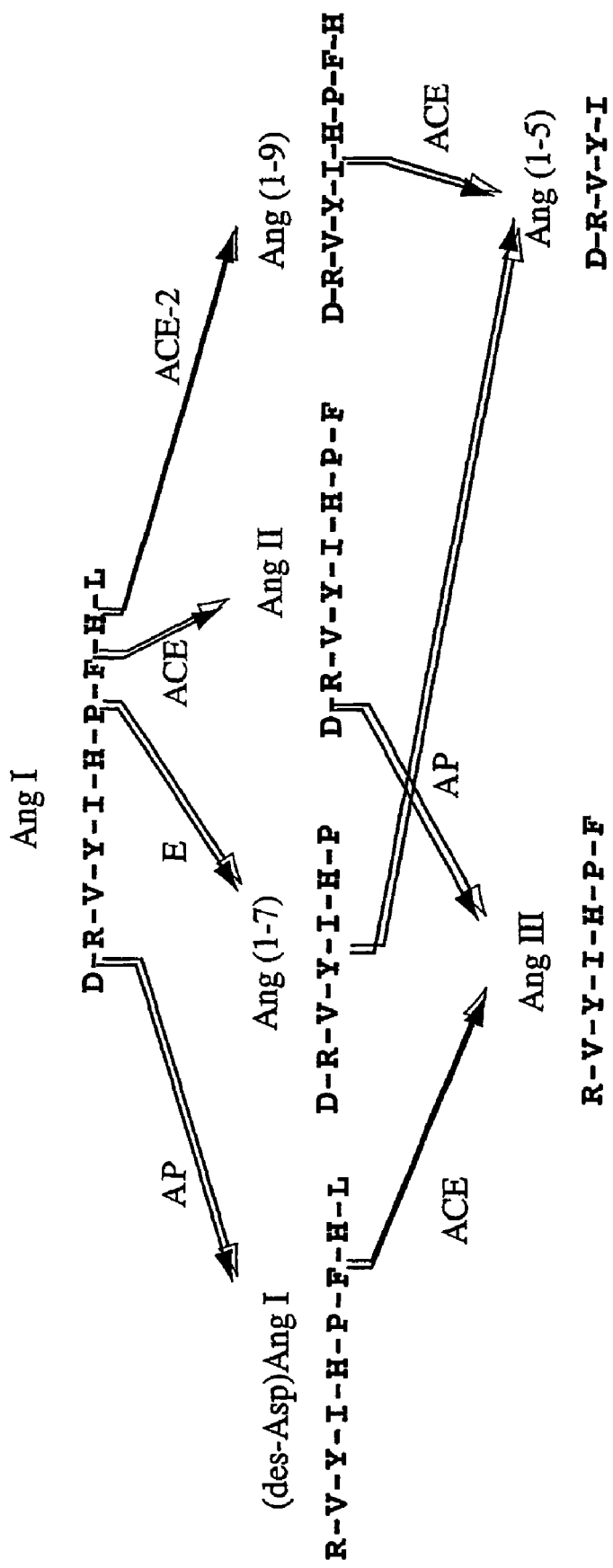

FIG. 8 shows at least some angiotensin I conversion products and enzymes catalyzing these reactions (E=endopeptidase, e.g., neprilysin; AP=aminopeptidase).

Figure 9A:
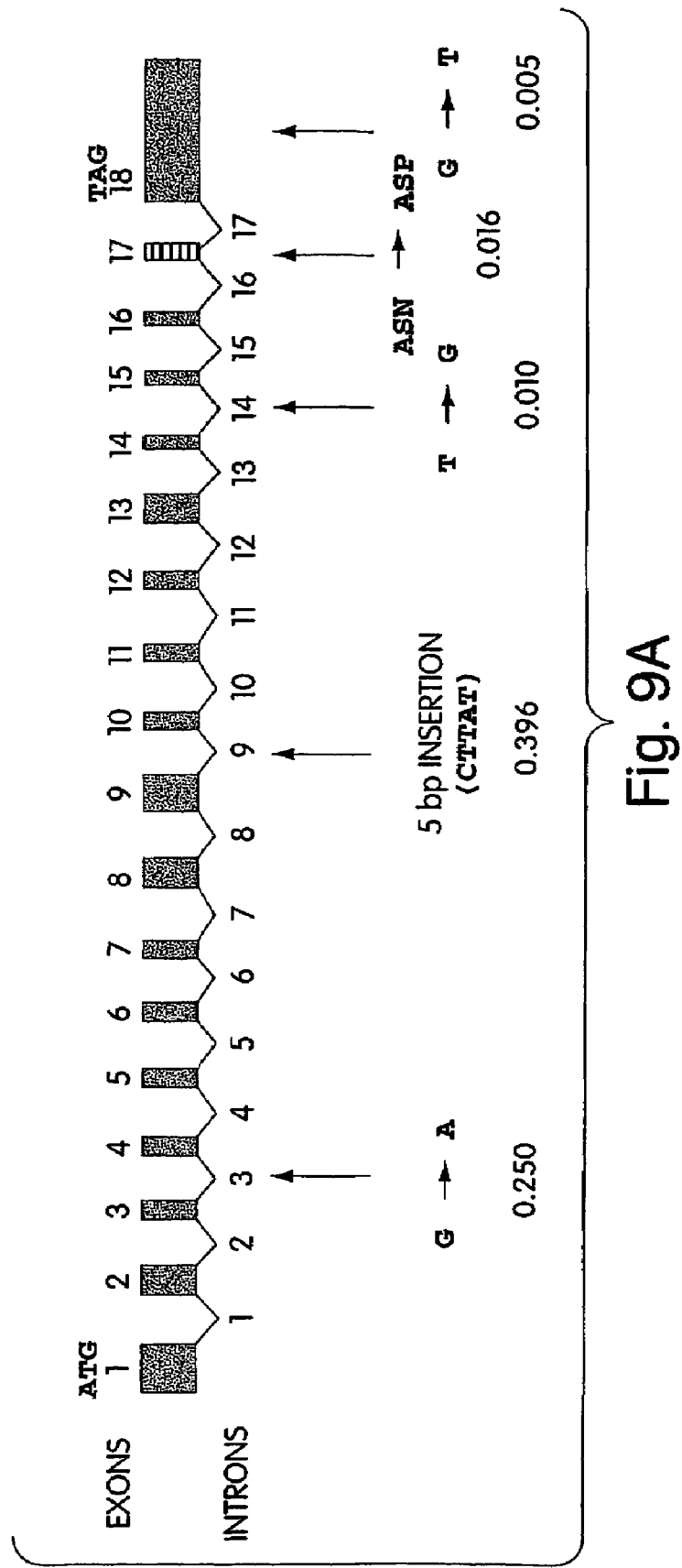

FIG. 9A is a diagram of the structure of the human ACE-2 gene and the location of the polymorphisms.

FIG. 9B is a diagram of the cDNA sequence of human ACE-2 (SEQ ID NO:1) indicating the position of the introns and indicating the polymorphisms.

Figure 10A:
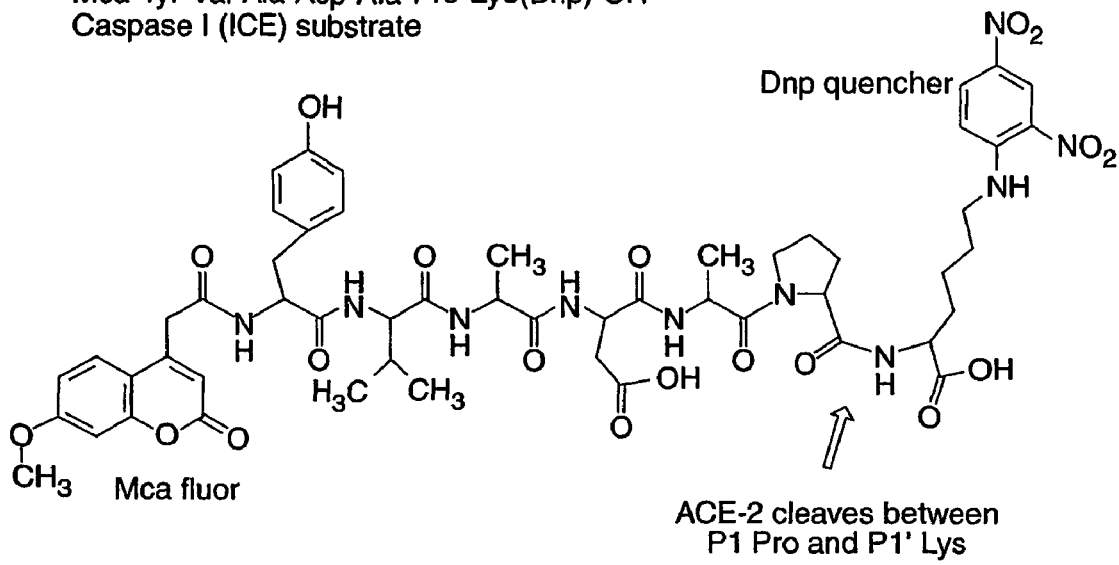

FIG. 10 panels A and B show ACE-2 target peptides.

Figure 11A:
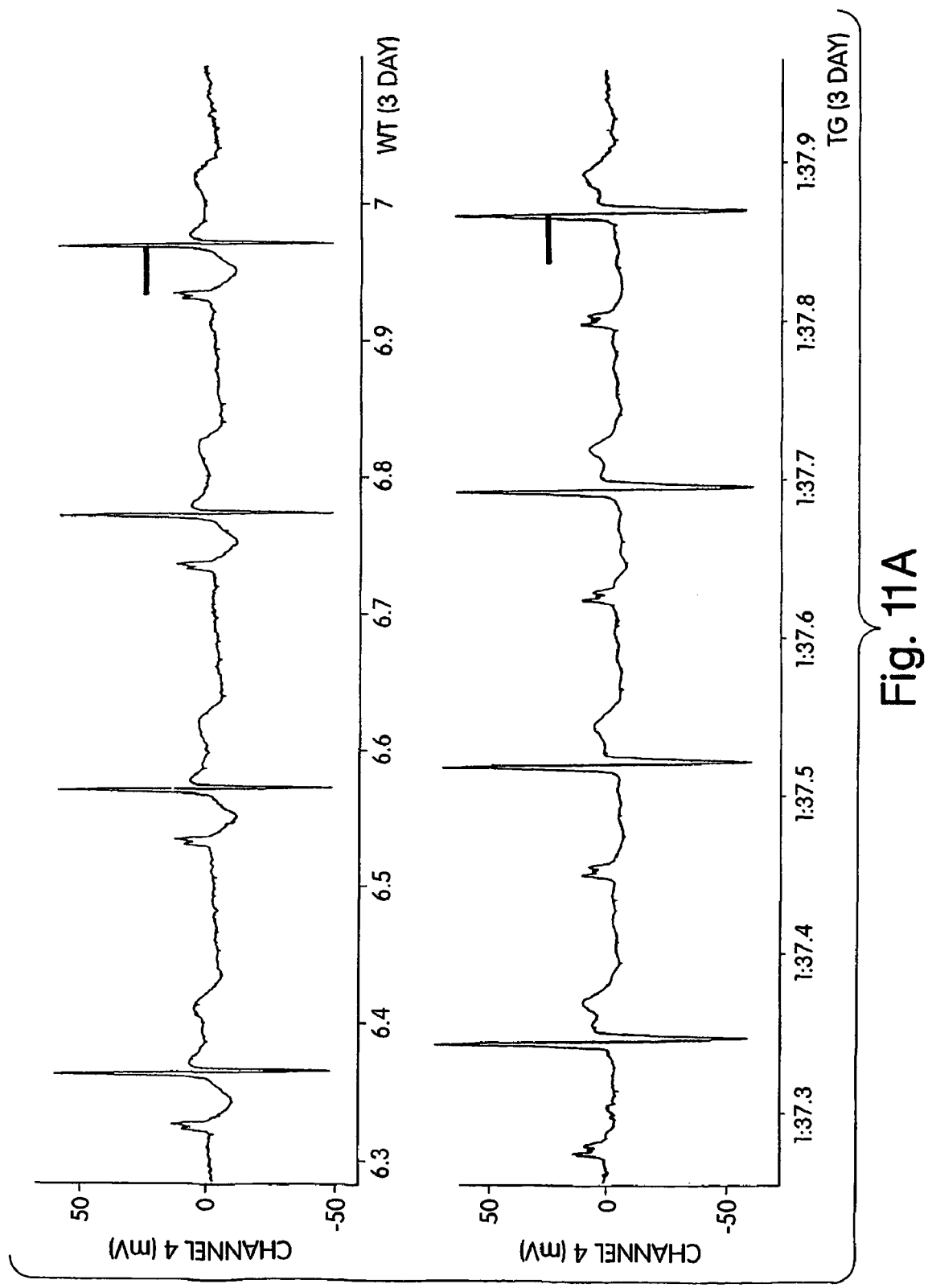
Figure 11B:
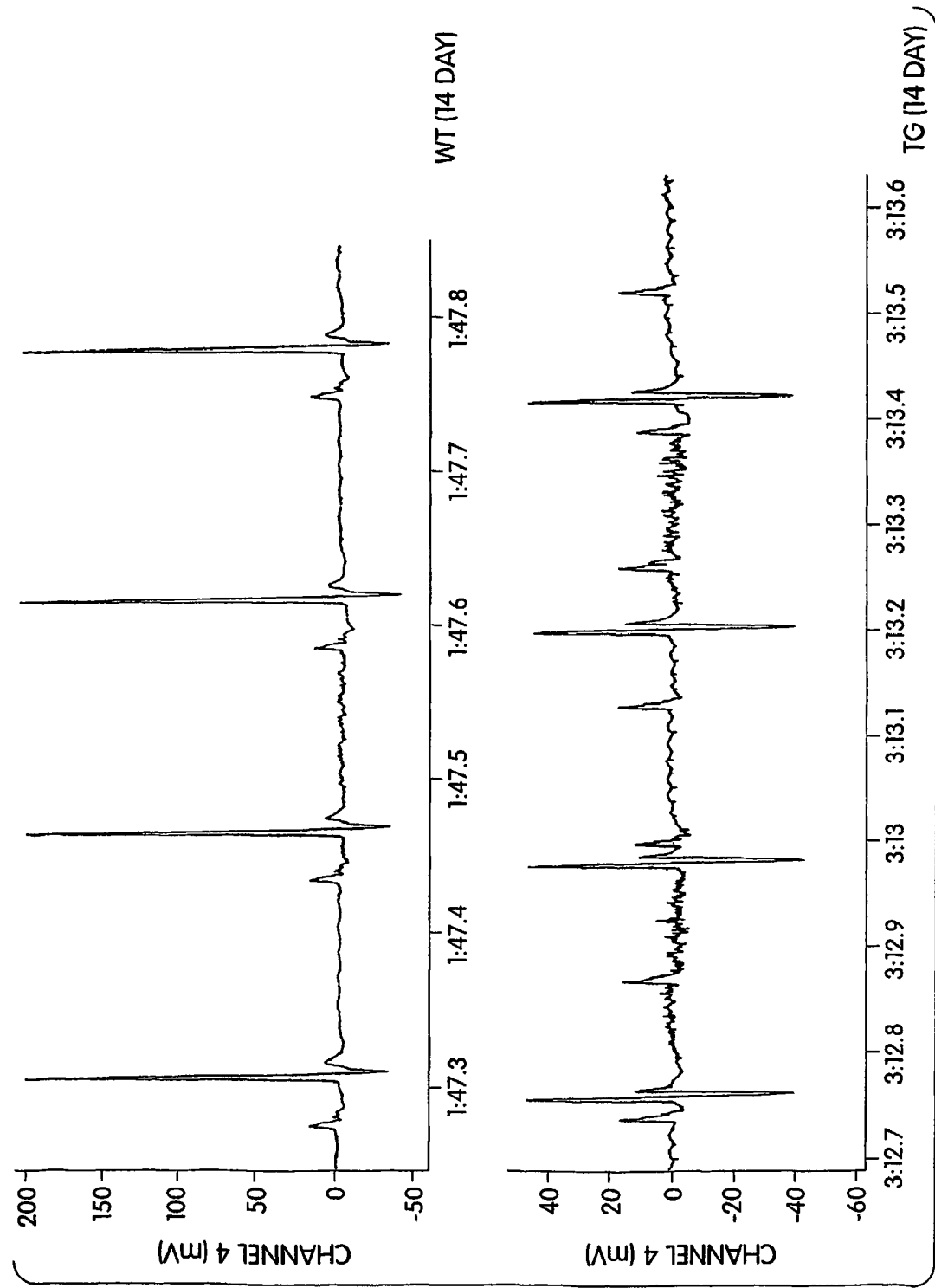
Figure 11C:
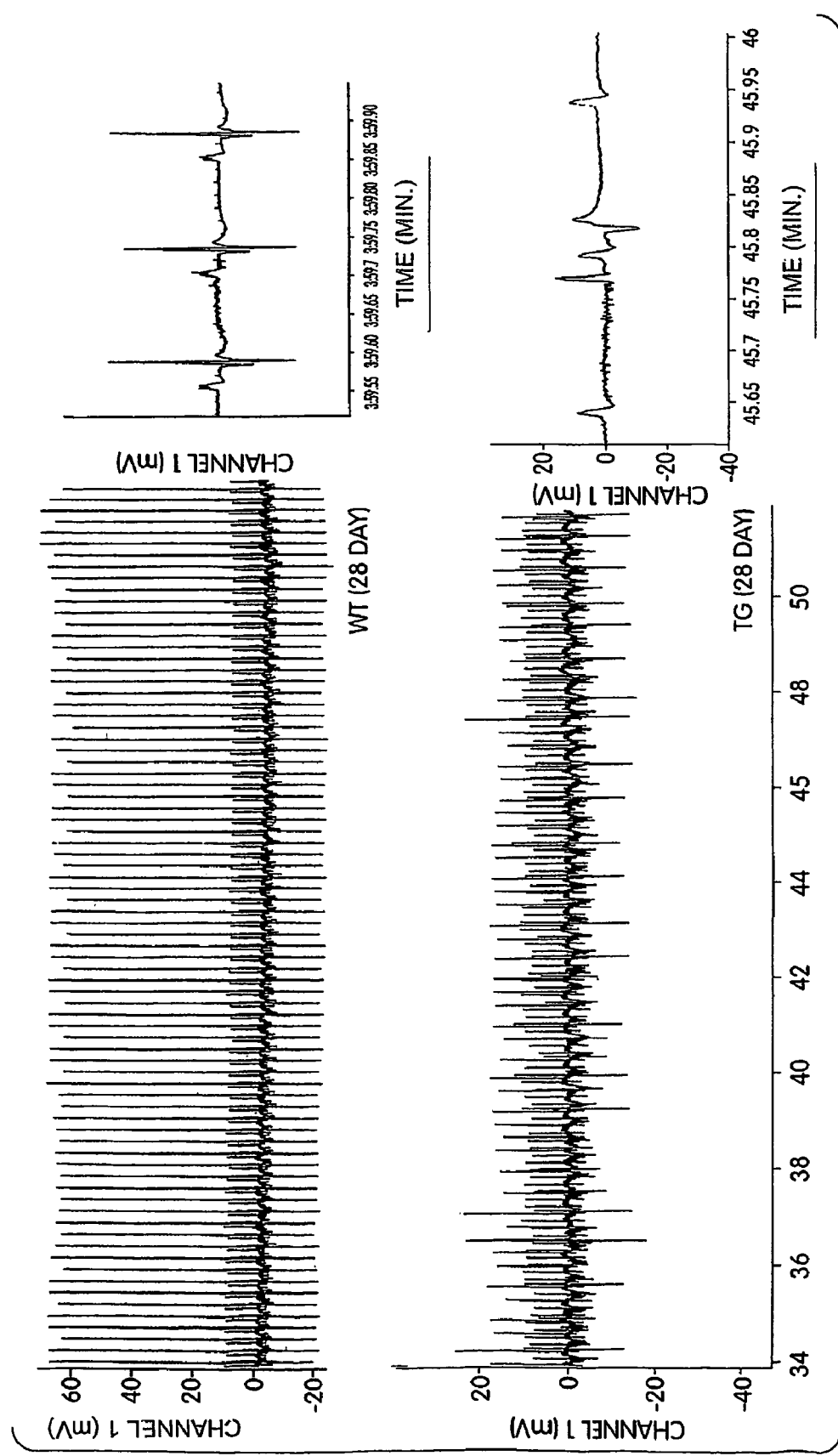

FIGS. 11A-C depict mouse surface EKGs in wild type (WT) and ACE-2 transgenic mice at 3 days (FIG. 11A), 14 days (FIG. 11B) and 28 days (FIG. 11C).

Figure 12:
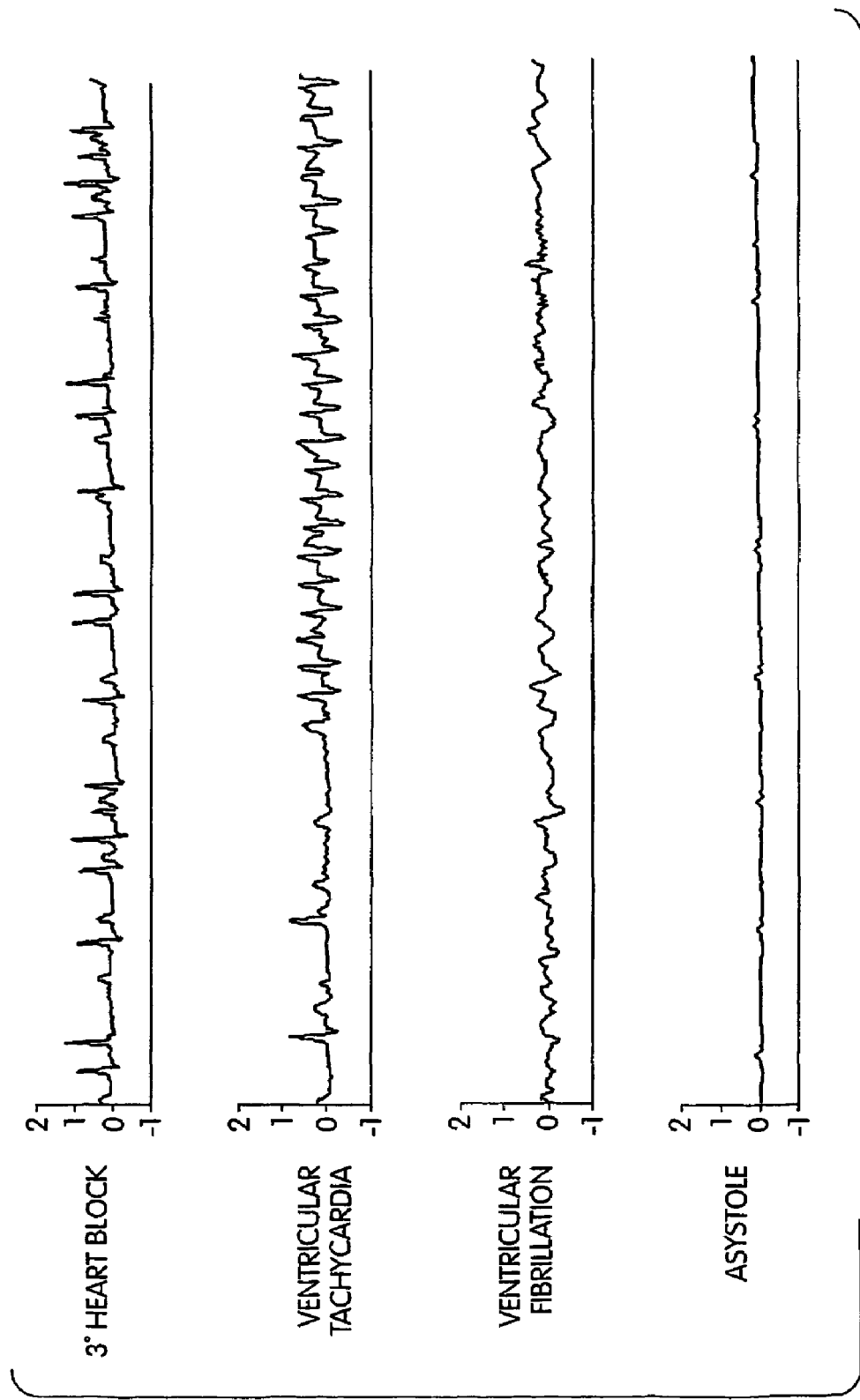

FIG. 12 depicts the results from the Holter monitoring experiments showing evidence of non sustained ventricular tachycardia which progressed into ventricular fibrillation and ultimately resulted in asystole and death in one of the transgenic mice that were tested.

Figure 13A:
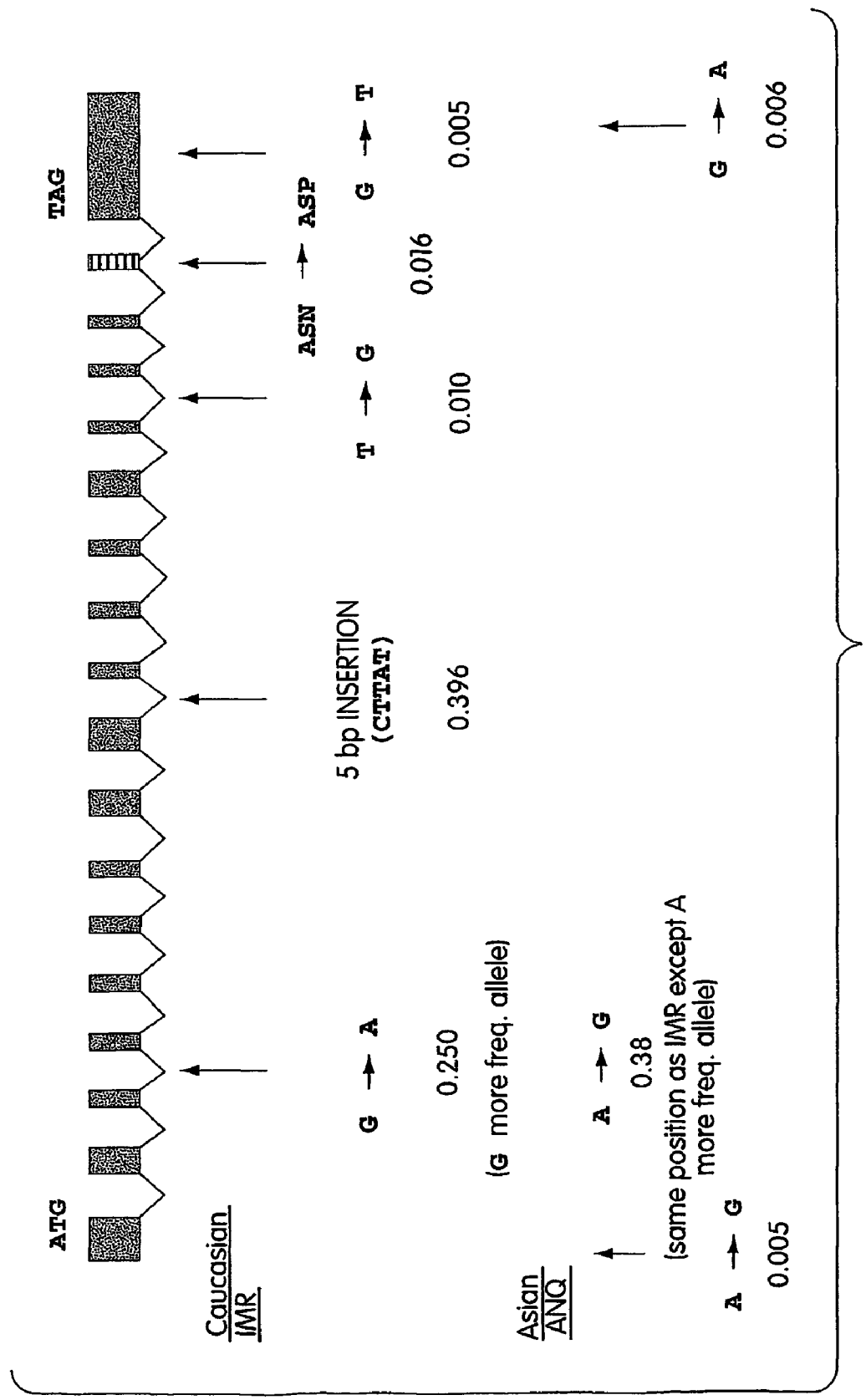

FIG. 13A is a diagram of the structure of the human ACE-2 gene and the location of the polymorphisms in the Caucasian as well as the Asian population.

FIG. 13B is a diagram of the cDNA sequence of human ACE-2 (SEQ ID NO:1) indicating the position of the introns and indicating the polymorphisms in the Caucasian as well as the Asian population.

DETAILED DESCRIPTION OF THE INVENTION

1. General

The invention is based at least in part on the discovery of a gene encoding a protein having regions which are significantly homologous to regions of known angiotensin converting enzymes (ACEs). Thus, the genes and proteins disclosed herein are referred to as Angiotensin Converting Enzyme 2 (ACE-2) genes and proteins. The sequence of the full length cDNA encoding ACE-2 was determined from a clone obtained from a cDNA library prepared from mRNA of a human heart of a subject who had congestive heart failure. The cDNA encoding the full length human ACE-2 protein and comprising 5' and 3' untranslated regions is 3396 nucleotides long and has the nucleotide sequence shown in FIG. 1 and is set forth as SEQ ID NO:1. The full length human ACE-2 protein is 805 amino acids long and has the amino acid sequence shown in FIG. 1 and set forth in SEQ ID NO:2. The coding portion (open reading frame) of SEQ ID NO:1 is set forth as SEQ ID NO:3 and corresponds to nucleotides 82 to 2496 of SEQ ID NO:1. The cDNA encoding the full length ACE-2 protein has been deposited at the American Type Culture Collection (12301 Parklawn Drive, Rockville, Md.) on Dec. 3, 1997 has been assigned ATCC Designation No. 209510.

The protein comprises a signal peptide from amino acid 1 to amino acid 18, which is encoded by nucleotides 82 to 135 of SEQ ID NO:1. Thus, the mature ACE-2 protein has 787 amino acids and has the amino acid sequence from amino acid 19 to amino acid 805 of SEQ ID NO:2.

ACE-2 protein further comprises several functional domains. ACE-2 comprises a zinc binding domain (ZBD) from amino acid 374 to amino acid 378 of SEQ ID NO:2, which is encoded by the nucleotide sequence from nucleotide 1201 to 1215 of SEQ ID NO:1 and referred to herein as minimum zinc binding domain. It is in fact likely that at least some of the adjacent amino acids participate in binding zinc. This minimum zinc binding domain has the amino acid sequence HHEMGH (SEQ ID NO:14), and is identical to the zinc binding domain that is present in all ACE proteins (see below) which have been identified as being located in the catalytic site of the enzyme (Lattion et al. (1989) FEBS Letters 252:99). Since amino acids 372-381 of SEQ ID NO:2 are conserved in all ACE proteins (see below), it is likely that amino acids 372, 373, 379, 380, and 381 of SEQ ID NO:2 are involved in binding zinc. In addition, all the amino acids which have been reported as interacting with the zinc atom or involved in catalysis in ACE proteins are present in ACE-2. Thus, by comparison, His 374, 378 and Glu 402 are probably the amino acids coordinating the zinc atom and Glu 375 and His 417 are probably involved in catalysis. It is also believed that Glu 406 is involved in the catalytic activity of the enzyme.

ACE-2 also has a hydrophobic region in its C-terminal region, having the amino acid sequence from about amino acid 741 to about amino acid 765 of SEQ ID NO:2 and is encoded by the nucleotide sequence from about nucleotide 2302 to about nucleotide 2376 of SEQ ID NO:1. This hydrophobic region is a transmembrane domain, similar to that present in ACE proteins (see below).

A BLAST search (Altschul et al. (1990) J. Mol. Biol. 215:403) of the nucleic acid and the amino acid sequences of ACE-2 revealed that certain portions of the ACE-2 protein and cDNA have a significant homology to certain regions of previously identified angiotensin converting enzymes. Two forms of ACE proteins have been described previously: a larger form, referred to as endothelial or somatic ACE, since it is present in numerous somatic tissues, including vascular endothelium, renal tubular epithelium, ciliated gut epithelium, stimulated macrophages, areas of the brain and testis. The smaller form of ACE is referred to as the testicular form, since it is found essentially only in developing sperm cells in the testis.

The previously cloned mature endothelial human ACE protein consists of 1277 amino acid residues and is organized into two large homologous domains, each bearing a putative active site (Soubrier et al. (1988) Proc. Natl. Acad. Sci. U.S.A. 85:9386). Each of these two domains contain short amino acid sequences identical to those located around critical residues of the active site of other metalloproteinases (thermmolysin, neutral endopeptidase, and collagenase) and therefore bears a putative active site. Zinc has been reported as essential for the activity of ACE (Bunning and Riordan (1985) J. Inorg. Biochem. 24:183). Only one of these sites is probably involved in catalyzing angiotensin II, since only one Zn atom has been reported to be associated per ACE molecule. However, another study showed that both domains have activity, as shown by measuring the activity of each domain as a separate protein. The human ACE protein exist in a soluble and in a membrane bound form. Membrane attachment is likely to be mediated by the C-terminal hydrophobic sequence located near the carboxyterminus of the protein (Soubrier et al, supra), which is also present in ACE-2. The human testicular ACE contains 732 residues (including the signal peptide) contains only one of these two large repetitive domains of endothelial ACE, i.e., the carboxyterminal domain (WO 91/00354 and Ehlers et al. (1989) Proc. Natl. Acad. Sci. U.S.A. 86:7741). This domain is located N-terminal of a 67 amino acids stretch and a serine-threonine rich region that is specific to the testicular form of ACE. Testicular ACE is encoded by the same gene as that encoding the larger ACE protein, but is encoded by a mRNA transcribed from a site located in the 12$^{th}$ intron of the ACE gene encoding the endothelial protein (Howard et al. (1990) Mol. Cell. Biol. 10:4294).

As shown in FIGS. 2 and 3, which show amino acid sequence alignments of ACE-2 with human, mouse, rabbit, rat, testicular and endothelial ACE proteins and *Drosophila* and *C. elegans* ACE proteins, certain portions of ACE-2 are homologous to certain regions of ACE proteins. In particular, the zinc binding domain is conserved in all ACE proteins. Thus, since the zinc binding domain is located in the catalytic site of the protein that is responsible for its peptidase activity, the function of ACE-2 is likely to be similar to that of other ACE proteins. In fact, as predicted by the homology between the amino acid sequences of ACE-2 and ACE, ACE-2 is capable of hydrolyzing angiotensin I and thereby cleaving off the last C-terminal amino acid (i.e., leucine) from angiotensin I. This 9 amino acid peptide ("Ang.(1-9)") can be further hydrolyzed by ACE into a 5 amino acid peptide containing the first five amino acids from angiotensin I (see FIG. 8). As shown in the Examples, ACE-2 is also capable of catalyzing the hydrolysis of other peptides, including kinins, neurotensin and kinetensin, and is involved in regulating blood pressure in a similar manner as endothelial ACE protein.

Another homology between ACE-2 and other ACE proteins is the presence of a transmembrane domain in the carboxy terminal portion of the proteins. Thus, ACE-2 can be in a membrane bound form. ACE proteins have also been found in a soluble form, which may result either from leakage of the protein from the surface or, from specific hydrolysis by a protease, or the soluble form may be encoded by a differentially spliced mRNA. Accordingly, ACE-2 exists in a soluble form.

The amino acid sequence alignment indicates the existence of other regions of strong homology between ACE-2 and ACE proteins (see FIGS. 2 and 3). However, the overall similarity of ACE-2 with ACE proteins is relatively weak. In fact, the overall percent identity and similarity between human ACE-2 and the human testicular ACE protein (which is the ACE protein with which ACE-2 has the highest overall similarity) is about 42.9% and 62% respectively. At the nucleotide level, human ACE-2 and human testicular ACE have about 50.8% identity.

Northern blot hybridizations indicated that the mRNA encoding human ACE-2 is about 4 kb, which correlates with the size of the full length cDNA. ACE-2 mRNA is expressed predominantly in kidney, heart, and testis. Thus, the pattern of expression of ACE-2 is more specific than that of endothelial ACE.

Accordingly, the invention provides nucleic acids encoding ACE-2 proteins, fragments thereof and homologs or variants thereof. The invention also provides ACE-2 polypeptides, fragments thereof and homologs or variants thereof.

Based at least on the observation of sequence homologies between ACE-2 and angiotensin converting enzymes, as well as the fact that ACE-2 is capable of hydrolyzing angiotensin I into Ang.(1-9), the invention further provides methods and compositions for regulating arterial blood pressure, which can be used, e.g., for treating or preventing arterial hypertension, hypotension, or congestive heart failure. In addition, since ACEs have been shown to hydrolyze other peptides, e.g., kinins, such as bradykinin, the compositions of the invention can also be used as analgesics, or for treating inflammatory diseases or conditions. Based at least on the fact that ACE-2 is also homologous to the testicular ACE, methods and compositions of the invention could also be used to treat and prevent diseases or conditions relating to fertility. Furthermore, based on the observation, described herein, that ACE-2 catalyzes the hydrolysis of kinetensin, ACE-2 therapeutics can be used for treating and preventing diseases associated with excessive histamine release or abnormal blood vessel permeability. Moreover, based on the observation described herein that ACE-2 transgenic mice exhibit non sustained ventricular tachycardia which progresses into ventricular fibrillation and ultimately results in asystole and death, methods and compositions of the invention may be used to treat disorders associated with abnormalities in the conduction system of the heart, such as arrhythmias. An arrhythmia is an abnormality or irregularity in the heart rhythm. An arrhythmia results when there is a disturbance in the conduction system of the heart, for example, due to faulty production of electrical impulses or faulty conduction of impulses as they pass through the system. Examples of arrhythmias include heart block (e.g, atrioventricular heart block), atrial flutter, atrial fibrillation, ventricular fibrillation, and extrasystole (premature contraction).

The invention further provides diagnostic and prognostic methods, e.g., methods for determining whether a subject is at risk of developing or has developed a disease associated with an aberrant ACE-2 activity, e.g., arterial hypertension, hypotension, arrhythmia, or CHF. Such assays can, for example, consist of determining whether the subject has a genetic alteration in an ACE-2 gene or an abnormal level of ACE-2 protein. Also within the scope of the invention are methods for identifying ACE-2 therapeutics, i.e., compounds, which are either ACE-2 agonists or ACE-2 antagonists.

Other disorders which may be treated or diagnosed by the methods described herein include, but are not limited to, azotemia, renal disease, renal failure, glomerular disease, glomerulonephritis (vasculitis), nephritis, acute tubular necrosis, proteinuria, hematuria, pyuria, pyelonephritis, polyuria, fluid and electrolyte (e.g., sodium and patassium) disturbances, hypovolemia, hyponatremia, hypernatremia, hypokalemia (Liddle's Syndrome, Bartter's Syndrome), hyperkalemia (Gordon's Syndrome), acidosis, alkalosis and hyperchloremic metabolic disorders.

Other aspects of the invention are described below or will be apparent to those skilled in the art in light of the present disclosure.

2. Definitions

For convenience, the meaning of certain terms and phrases employed in the specification, examples, and appended claims are provided below.

The term "ACE-2 nucleic acid" refers to a nucleic acid encoding an ACE-2 protein, such as nucleic acids having SEQ ID NO:1 or 3, fragments thereof, complement thereof, and derivatives thereof.

The terms "ACE-2 polypeptide" and "ACE-2 protein" are intended to encompass polypeptides comprising the amino acid sequence SEQ ID NO:2, fragments thereof, and homologs thereof and include agonist and antagonist polypeptides.

The term "ACE-2 therapeutic" refers to various forms of ACE-2 polypeptides, as well as peptidomimetics, nucleic acids, or small molecules, which can modulate at least one activity of an ACE-2 polypeptide, e.g., interaction with and/or hydrolysis of a target peptide, by mimicking or potentiating (agonizing) or inhibiting (antagonizing) the effects of a naturally-occurring ACE-2 polypeptide. An ACE-2 therapeutic which mimics or potentiates the activity of a wild-type ACE-2 polypeptide is a "ACE-2 agonist". Conversely, an ACE-2 therapeutic which inhibits the activity of a wild-type ACE-2 polypeptide is a "ACE-2 antagonist".

The term "agonist", as used herein, is meant to refer to an agent that mimics or upregulates (e.g. potentiates or supplements) an ACE-2 bioactivity. An ACE-2 agonist can be a wild-type ACE-2 protein or derivative thereof having at least one bioactivity of the wild-type ACE-2. An ACE-2 therapeutic can also be a compound that upregulates expression of an ACE-2 gene or which increases at least one bioactivity of an ACE-2 protein. An agonist can also be a compound which increases the interaction of an ACE-2 polypeptide with another molecule, e.g, a target peptide.

"Antagonist" as used herein is meant to refer to an agent that downregulates (e.g. suppresses or inhibits) at least one ACE-2 bioactivity. An ACE-2 antagonist can be a compound which inhibits or decreases the interaction between an ACE-2 protein and another molecule, e.g., a target peptide, such as angiotensin I or a kinin. Accordingly, a preferred antagonist is a compound which inhibits or decreases hydrolysis of a target peptide. An antagonist can also be a compound that downregulates expression of an ACE-2 gene or which reduces the amount of ACE-2 protein present. An ACE-2 antagonist can be a dominant negative form of an ACE-2 polypeptide, e.g., a form of an ACE-2 polypeptide which is capable of interacting with a target peptide, e.g., angiotensin I, but which is not capable of hydrolysing the target peptide. The ACE-2 antagonist can also be a nucleic acid encoding a dominant negative form of an ACE-2 polypeptide, an ACE-2 antisense nucleic acid, or a ribozyme capable of interacting specifically with an ACE-2 RNA. Yet other ACE-2 antagonists are molecules which bind to an ACE-2 polypeptide and inhibit its action. Such molecules include peptides, e.g., forms of ACE-2 target peptides which do not have biological activity, and which inhibit hydrolysis of target peptides by ACE-2 by competition with the target peptides. Thus, such peptides will bind the active site of ACE-2 and prevent it from interacting with target peptides, e.g., angiotensin I. Yet other ACE-2 antagonists include antibodies interacting specifically with an epitope of an ACE-2 molecule, such that binding interferes with hydrolysis. In yet another preferred embodiment, the ACE-2 antagonist is a small molecule, such as a molecule capable of inhibiting the interaction between an ACE-2 polypeptide and a target peptide and/or binding to the catalytic site of the enzyme. Alternatively, the small molecule can be antagonist by interacting with sites other than the catalytic site, and inhibit the catalytic activity of ACE-2 by, e.g., altering the tertiary or quaternary structure of the enzyme.

The term "ACE-2 substrate conversion product" or "ACE-2 target peptide conversion product" refers to a product, in particular a peptide, which result from the enzymatic cleavage of the ACE-2 substrate by ACE-2.

The term "kinetensin conversion product" refers to a product resulting from enzymatic cleavage of kinetensin by ACE-2, e.g., kinetensin (1-8) having SEQ ID NO:24.

The term "angiotensin conversion product" refers to a peptide resulting from hydrolysis of angiotensin I. Examples of such peptides and the enzymes catalyzing their production are shown in FIG. 7. Angiotensin conversion products include Ang.(1-9), Ang.(1-8), Ang.(1-7), Ang.(1-6), Ang.(1-5), Ang. III, and (des-Asp)AngI.

The term "angiotensin (1-9) or "Ang.(1-9)" refers to an angiotensin I peptide (DRVYIHPFHL; SEQ ID NO:15) in which the C-terminal leucine is absent, i.e., a peptide having the amino acid sequence DRVYIHPFH (SEQ ID NO:16). The term "angiotensin (1-8) or "Ang.(1-8)" refers to angiotensin II, i.e., a peptide having the amino acid sequence DRVYIHPF (SEQ ID NO:17). The term "angiotensin (1-7)" or "Ang.(1-7)" refers to an angiotensin I peptide in which the last 3 C-terminal amino acids are absent, i.e., a peptide having the amino acid sequence DRVYIHP (SEQ ID NO:18). The term "angiotensin (1-6) or "Ang.(1-6)" refers to an angiotensin I peptide in which the last 4 C-terminal amino acids are absent, i.e., a peptide having the amino acid sequence DRVYIH (SEQ ID NO:19). The term "angiotensin (1-5)" or "Ang.(1-5)" refers to an angiotensin I peptide in which the last 5 C-terminal amino acids are absent, i.e., a peptide having the amino acid sequence DRVYI (SEQ ID NO:20). The term "(des-Asp)Ang. I" refers to an angiotensin I peptide lacking the N-terminal amino acid, i.e., a peptide having the amino acid sequence RVYIHPFHL (SEQ ID NO:21). The term "angiotensin III" or "Ang. III" refers to an angiotensin I peptide lacking the C-terminal amino acid and the last two N-terminal amino acids, i.e., a peptide having the amino acid sequence RVYIHPF (SEQ ID NO:22).

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

The term "allelic variant of a polymorphic region of an ACE-2 gene" refers to a region of an ACE-2 gene having one of several nucleotide sequences found in that region of the gene in other individuals.

The term "analog of a target peptide of an ACE-2 polypeptide" refers to a compound which has sufficient structural similarities with the target peptide, that it shares a biological activity of the target peptide, e.g., binding of the target peptide to an ACE-2 polypeptide or the ability to be hydrolyzed by an ACE-2 polypeptide. An analog can be, e.g, a peptidomimetic or any modified peptide.

"Biological activity" or "bioactivity" or "activity" or "biological function", which are used interchangeably, for the purposes herein means an effector or antigenic function that is directly or indirectly performed by an ACE-2 polypeptide (whether in its native or denatured conformation), or by any subsequence thereof. Biological activities include binding to a target peptide, e.g., angiotensin I, a kinin, or kinetensin; binding to other proteins or molecules; the capability to catalyze hydrolysis of a target peptide (function as a carboxypeptidase or endopeptidase), e.g., angiotensin I, a kinin, or kinetensin; and interaction with a metal ion, e.g., $Zn^{2+}$ $Co^{2+}$, and $Mn^{2+}$. An ACE-2 bioactivity can be modulated by affecting directly an ACE-2 polypeptide. Alternatively, an ACE-2 bioactivity can be modulated by modulating the level of an ACE-2 polypeptide, such as by modulating expression of an ACE-2 gene.

As used herein the term "bioactive fragment of an ACE-2 polypeptide" refers to a fragment of a full-length ACE-2 polypeptide, wherein the fragment specifically mimics or antagonizes the activity of a wild-type ACE-2 polypeptide. The bioactive fragment preferably is a fragment capable of interacting with a target peptide, such as angiotensin I or kinetensin.

The term "an aberrant activity", as applied to an activity of a polypeptide such as ACE-2, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant ACE-2 activity due to overexpression or underexpression of the gene encoding ACE-2.

The term "abnormal blood pressure" refers to hypertension and hypotension.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding one of the subject ACE-2 polypeptides with a second amino acid sequence defining a domain (e.g. polypeptide portion) foreign to and not substantially homologous with any domain of an ACE-2 polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms. In general, a fusion polypeptide can be represented by the general formula X-ACE-2-Y, wherein ACE-2 represents a portion of the polypeptide which is derived from an ACE-2 polypeptide, and X and Y are independently absent or represent amino acid sequences which are not related to an ACE-2 sequence in an organism, including naturally occurring mutants.

The term "nucleotide sequence complementary to the nucleotide sequence set forth in SEQ ID NO: x" refers to the nucleotide sequence of the complementary strand of a nucleic acid strand having SEQ ID NO: x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO: x refers to the complementary strand of the strand having SEQ ID NO: x or to any nucleic acid having the nucleotide sequence of the complementary strand of SEQ ID NO: x. When referring to a single stranded nucleic acid having the nucleotide sequence SEQ ID NO: x, the complement of this nucleic acid is a nucleic acid having a nucleotide sequence which is complementary to that of SEQ ID NO: x. The nucleotide sequences and complementary sequences thereof are always given in the 5' to 3' direction.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an ACE-2 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

A disease, disorder or condition "associated with" or "characterized by" an aberrant ACE-2 activity refers to a disease, disorder or condition in a subject which is caused by or contributed to by an aberrant ACE-2 activity.

"Histamine-associated condition" refers to a condition, disease or disorder caused by or contributed to by excessive release of histamine, e.g., conditions resulting from excessive endothelial cell contraction, leakage of plasma into the tissues, and/or vasodilation. Examples of such conditions include topical and systemic allergies, excema, asthma, and anaphylactic shock "Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the ACE-2 sequences of the present invention.

The term "interact" as used herein is meant to include detectable relationships or association (e.g. biochemical interactions) between molecules, such as interaction between protein-protein, protein-nucleic acid, nucleic acid-nucleic acid, and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject ACE-2 polypeptides preferably includes no more than 10 kilobases (kb) of nucleic acid sequence which naturally immediately flanks the ACE-2 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

"Kinetensin (1-8)" refers to kinetensin (SEQ ID NO:23) lacking the C-terminal leucine, i.e., IARRHPYF (SEQ ID NO:24).

The term "kinetensin associated condition" refers to a condition resulting from an abnormal level of kinetensin or kinetensin conversion product in plasma or in tissues of a subject and includes histamine associated conditions.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant ACE-2 genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding an ACE-2 polypeptide is inserted into a suitable expression vector which is in turn used to transform a host cell to produce the heterologous protein. Moreover, the phrase "derived from", with respect to a recombinant ACE-2 gene, is meant to include within the meaning of "recombinant protein" those proteins having an amino acid sequence of a native ACE-2 polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate an ACE-2 bioactivity.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably an ACE-2 gene.

The term "target peptide" refers to a peptide which can be hydrolyzed by an ACE or ACE-2 protein. Target peptides include angiotensin I, kinins such as bradykinin, kinetensin, enkephalins, and neuropeptides such as substance P.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the ACE-2 genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of ACE-2 polypeptide.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of an ACE-2 polypeptide or, in the case of anti-sense expression from the transferred gene, the expression of a naturally-occurring form of the ACE-2 polypeptide is disrupted.

As used herein, the term "transgene" means a nucleic acid sequence (encoding, e.g., one of the ACE-2 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the ACE-2 polypeptide, e.g. either agonistic or antagonistic forms. However, transgenic animals in which the recombinant ACE-2 gene is silent are also contemplated, as for example, the FLP or CRE recombinase dependent constructs described below. Moreover, "transgenic animal" also includes those recombinant animals in which gene disruption of one or more ACE-2 genes is caused by human intervention, including both recombination and antisense techniques.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

3. Nucleic Acids of the Present Invention

The invention provides ACE-2 nucleic acids, homologs thereof, and portions thereof. Preferred nucleic acids have a sequence at least 70%, and more preferably 75% homologous and more preferably 80% and even more preferably at least 85% homologous with a nucleotide sequence of an ACE-2 gene, e.g., such as a sequence shown in one of SEQ ID NOs: 1 or 3 or complement thereof or the ACE-2 nucleic acid having ATCC Designation No. 209510. Nucleic acids at least 90%, more preferably 95%, and most preferably at least about 98-99% homologous with a nucleic sequence represented in one of SEQ ID NOs: 1 or 3 or complement thereof are of course also within the scope of the invention. In preferred embodiments, the nucleic acid is mammalian and in particularly preferred embodiments, includes all or a portion of the nucleotide sequence corresponding to the coding region of one of SEQ ID NOs: 1 or 3.

The invention also pertains to isolated nucleic acids comprising a nucleotide sequence encoding ACE-2 polypeptides, variants and/or equivalents of such nucleic acids. The term equivalent is understood to include nucleotide sequences encoding functionally equivalent ACE-2 polypeptides or functionally equivalent peptides having an activity of an ACE-2 protein such as described herein. Equivalent nucleotide sequences will include sequences that differ by one or more nucleotide substitution, addition or deletion, such as allelic variants; and will, therefore, include sequences that differ from the nucleotide sequence of the ACE-2 gene shown in SEQ ID NOs: 1 or 3 due to the degeneracy of the genetic code.

Preferred variant ACE-2 nucleic acids are those described in the Examples, such as nucleic acids comprising one or more of SEQ ID NO:87, 89, 91, 93, and 95.

Preferred nucleic acids are vertebrate ACE-2 nucleic acids. Particularly preferred vertebrate ACE-2 nucleic acids are mammalian. Regardless of species, particularly preferred ACE-2 nucleic acids encode polypeptides that are at least 70%, 80%, 90%, or 95% similar or identical to an amino acid sequence of a vertebrate ACE-2 protein. In one embodiment, the nucleic acid is a cDNA encoding a polypeptide having at least one bio-activity of the subject ACE-2 polypeptide. Preferably, the nucleic acid includes all or a portion of the nucleotide sequence corresponding to the nucleic acid of SEQ ID No 1 or 3.

Still other preferred nucleic acids of the present invention encode an ACE-2 polypeptide which is comprised of at least 2, 5, 10, 25, 50, 100, 150 or 200 amino acid residues. For example, such nucleic acids can comprise about 50, 60, 70, 80, 90, or 100 base pairs. Also within the scope of the invention are nucleic acid molecules for use as probes/primer or antisense molecules (i.e. noncoding nucleic acid molecules), which can comprise at least about 6, 12, 20, 30, 50, 60, 70, 80, 90 or 100 base pairs in length.

Another aspect of the invention provides a nucleic acid which hybridizes under stringent conditions to a nucleic acid represented by SEQ ID NOs: 1 or 3 or complement thereof or the nucleic acid having ATCC Designation No. 209510. In a particularly preferred embodiment, an ACE-2 nucleic acid of the present invention will bind to one of SEQ ID NOs: 1 or 3 or complement thereof under high stringency conditions. As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3× SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\#\ of\ A+T\ bases)+4(\#\ of\ G+C\ bases)$. For hybrids between 18 and 49 base pairs in length, $T_m(° C.)=81.5+16.6(\log_{10}[Na^+])+0.41\ (\%\ G+C)-(600/N)$, where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991-1995, (or alternatively 0.2×SSC, 1% SDS).

Nucleic acids having a sequence that differs from the nucleotide sequences shown in one of SEQ ID NOs: 1 or 3 or complement thereof due to degeneracy in the genetic code are also within the scope of the invention. Such nucleic acids encode functionally equivalent peptides (i.e., a peptide having a biological activity of an ACE-2 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of an ACE-2 polypeptide. However, it is expected that DNA sequence polymorphisms that do lead to changes in the amino acid sequences of the subject ACE-2 polypeptides will exist among mammals. One skilled in the art will appreciate that these variations in one or more nucleotides (e.g., up to about 3-5% of the nucleotides) of the nucleic acids encoding polypeptides having an activity of an ACE-2 polypeptide may exist among individuals of a given species due to natural allelic variation.

Nucleic acids of the invention can encode one or more of the following domains of an ACE-2 protein: the signal peptide, the extracellular domain comprising the zinc binding domain, the transmembrane domain, and the cytoplasmic domain. The amino acid sequences of these domains in human ACE-2 (SEQ ID NO:2) and the position of the nucleotide sequence in SEQ ID NO:1 encoding these domains are indicated in Table I:

TABLE I

Position of Domains in Human ACE-2

| Domain | Nucleotides | Amino acids |
| --- | --- | --- |
| signal sequence | 82-135 | 1-18 |
| extracellular domain | 136-2301 | 19-740 |
| min. zinc binding domain | 1201-1215 | 374-378 |
| transmembrane domain | 2302-2376 | 741-765 |
| cytoplasmic domain | 2377-2496 | 766-805 |

The polynucleotide sequence of the present invention may encode a mature form of the ACE-2, i.e., a form of ACE-2 which does not comprise the leader peptide, e.g., an ACE-2 protein which does not comprise about amino acids 1-18 of SEQ ID NO:2. For example, a preferred nucleic acid of the invention comprises at least a portion of a nucleotide sequence encoding ACE-2, but does not include about nucleotides 82-135 of SEQ ID NO:1. The mature form of an ACE-2 polypeptide can be a secreted ACE-2 polypeptide or a membrane bound ACE-2 polypeptide. In fact, ACE has been found in the form of a membrane enzyme at the surface of the vascular endothelial cells and renal epithelial cells. Alternatively, ACE has also been observed to be a secreted protein, and has been found, e.g., in plasma (see, e.g., Erdos et al. (1987) Lab. Invest. 56:345, Cardwell et al. (1976) Science 191:1050; and Ryan et al. (1976) Tissue Cell 8:125). Thus, nucleic acids encoding secreted as well as membrane bound forms of ACE-2 proteins are within the scope of the invention.

In the case of ACE proteins, it has been reported that a soluble form of the enzyme results from proteolytic cleavage by a specific enzyme termed "secretase" (Parvathy et al. (1997) Biochem. J. 327:37). Thus, it is possible that a similar mechanism of solubilization of ACE-2 proteins occur. Accordingly, in cases in which the ACE-2 protein is desired as a purely membrane form as opposed to a soluble form, it may be preferable to change the nucleotide sequence of ACE-2 such that it does not encode a site recognizable and cleavable by a secretase.

A recombinant soluble form of ACE-2 can be produced, e.g, by deleting at least a portion of the transmembrane domain which spans amino acids 741-765 of SEQ ID NO:2, such that the protein is not capable to localize itself to a cell membrane. Thus, nucleic acids of the invention include those which encode at least a portion of an ACE-2 protein, but which lacks a portion from about nucleotide 2302 to about nucleotide 2376 of SEQ ID NO:1. For example, a preferred nucleic acid encoding a soluble human ACE-2 protein comprises a nucleotide sequence from about nucleotide 136 to about nucleotide 2301 of SEQ ID NO:1. Preferred soluble ACE-2 proteins comprise at least a portion of the extracellular domain of ACE-2 which corresponds to about amino acid 19 to about amino acid 740 of SEQ ID NO:2 and is encoded by the nucleotide sequence from about nucleotide 136 to about nucleotide 2301 of SEQ ID NO:1.

The polynucleotide sequence may also encode a leader sequence, e.g., the natural leader sequence or a heterologous leader sequence. Human ACE-2 has a leader sequence from amino acid 1 to amino acid 18 of SEQ ID NO:2. Accordingly, the polynucleotide may encode the natural ACE-2 leader sequence. Alternatively, the nucleic acid can be engineered such that the natural leader sequence is deleted and a heterologous leader sequence inserted in its place. The term "leader sequence" is used interchangeably herein with the term "signal peptide". For example, the desired DNA sequence may be fused in the same reading frame to a DNA sequence which aids in expression and secretion of the polypeptide from the host cell, for example, a leader sequence which functions as a secretory sequence for controlling transport of the polypeptide from the cell. The protein having a leader sequence is a preprotein and may have the leader sequence cleaved by the host cell to form the mature form of the protein.

The polynucleotide of the present invention may also be fused in frame to a marker sequence, also referred to herein as "Tag sequence" encoding a "Tag peptide", which allows for marking and/or purification of the polypeptide of the present invention. In a preferred embodiment, the marker sequence is a hexahistidine tag, e.g., supplied by a PQE-9 vector. Numerous other Tag peptides are available commercially. Other frequently used Tags include myc-epitopes (e.g., see Ellison et al. (1991) *J Biol Chem* 266:21150-21157) which includes a 10-residue sequence from c-myc, the pFLAG system (International Biotechnologies, Inc.), the pEZZ-protein A system (Pharmacia, N.J.), and a 16 amino acid portion of the *Haemophilus influenza* hemagglutinin protein. Furthermore, any polypeptide can be used as a Tag so long as a reagent, e.g., an antibody interacting specifically with the Tag polypeptide is available or can be prepared or identified.

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

Other preferred ACE-2 fusion proteins include ACE-2-immunoglobulin (ACE-2-Ig) polypeptides. The ACE-2-Ig polypeptide can comprise the entire extracellular domain of ACE-2, e.g, human ACE-2, or a variant thereof. For example, an ACE-2-Ig polypeptide can comprise an amino acid sequences from about amino acid 1 to about amino acid 740 of SEQ ID NO:2. A nucleic acid encoding an ACE-2Ig fusion protein can comprise, e.g., about nucleotides 82 to 2301 of SEQ ID NO:1 fused in frame to a nucleic acid encoding a constant Ig chain. ACE-2-Ig fusion proteins can be prepared as described e.g., in U.S. Pat. No. 5,434,131.

As indicated by the examples set out below, ACE-2 protein-encoding nucleic acids can be obtained from mRNA present in any of a number of eukaryotic cells, e.g., from cardiac tissue or kidney. It should also be possible to obtain nucleic acids encoding ACE-2 polypeptides of the present invention from genomic DNA from both adults and embryos. For example, a gene encoding an ACE-2 protein can be cloned from either a cDNA or a genomic library in accordance with protocols described herein, as well as those generally known to persons skilled in the art. cDNA encoding an ACE-2 protein can be obtained by isolating total mRNA from a cell, e.g., a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding an ACE-2 protein can also be cloned using established polymerase chain reaction techniques in accordance with the nucleotide sequence information provided by the invention. The nucleic acid of the invention can be DNA or RNA or analogs thereof. A preferred nucleic acid is a cDNA represented by a sequence selected from the group consisting of SEQ ID NOs: 1 or 3.

Preferred nucleic acids encode a vertebrate ACE-2 polypeptide comprising an amino acid sequence that is at least about 60% homologous, more preferably at least about 70% homologous and most preferably at least about 80% homologous with amino acid sequence contained in SEQ ID No: 2. Nucleic acids which encode polypeptides at least about 90%, more preferably at least about 95%, and most preferably at least about 98-99% homology with an amino acid sequence represented in SEQ ID No: 2 are also within the scope of the invention. In one embodiment, the nucleic acid is a cDNA encoding a peptide having at least one activity of the subject vertebrate ACE-2 polypeptide. Preferably, the nucleic acid includes all or a portion of the nucleotide sequence corresponding to the coding region of SEQ ID NOs:1 and 3.

Preferred nucleic acids encode a bioactive fragment of a vertebrate ACE-2 polypeptide comprising an amino acid sequence at least about 60% homologous or identical, more preferably at least about 70% homologous or identical and most preferably at least about 80% homologous or identical with an amino acid sequence of SEQ ID No: 2. Nucleic acids which encode polypeptides which are at least about 90%, more preferably at least about 95%, and most preferably at least about 98-99% homologous or identical, with an amino acid sequence represented in SEQ ID No: 2 are also within the scope of the invention.

Bioactive fragments of ACE-2 polypeptides can be polypeptides having one or more of the following biological activities: the capability to catalyze an enzymatic reaction, e.g., the hydrolysis of a target peptide, such as the hydrolysis of an angiotensin I peptide into Ang.(1-9) peptide, the hydrolysis of a kinin or derivative thereof, e.g., bradykinin or hydrolysis of kinetensin; binding to a metal ion, e.g., zinc, interacting with a substrate, e.g., angiotensin I, a kinin, or kinetensin. A bioactive fragment of an ACE-2 polypeptide can also be a polypeptide having an analgesic activity, an anti-inflammatory activity and/or an anti-allergenic activity, the capability to modulate cell growth, to interact with another molecule, e.g., a target peptide or a receptor. Assays for determining whether an ACE-2 polypeptide has any of these or other biological activities are known in the art and are further described herein.

Nucleic acids encoding proteins having an ACE-2 activity include nucleic acids comprising a nucleotide sequence encoding a zinc binding domain, such as the zinc binding domain of ACE-2 consisting of about amino acids 374-378 of SEQ ID NO:2. Such a nucleic acid can be represented by the generic formula: X-(ZBD)-Y, wherein ZBD represents nucleotides 1201-1215 of SEQ ID NO:1, and X and Y represent a certain number of nucleotides located 5' and 3' of the ZBD, respectively. For example, a nucleic acid of the invention can comprise nucleotides 1201-1215 of SEQ ID NO:1 and X and Y selected from any of 0, 10, 20, 30, 50, 100, 150, 200, 300, 400, 500, 600, 700, 800, 900, or about 1000 nucleotides. Alternatively, ZBD can represent the nucleotide sequence from nucleotide 1192 to 1221 or 1195 to 1224 of SEQ ID NO:1 or any sequence substantially similar thereto, or comprising one or more nucleotides at the 5' and/or 3' end. Another preferred ZBD is an extended ZBD, i.e., comprising nucleotides encoding amino acids which are located outside of amino acids 371-380, but which are functionally active. For example, a preferred nucleic acid comprises a nucleotide sequence from about nucleotide 1201 to about nucleotide 1331 of SEQ ID NO:1 and encoding all the amino acids which either contact the zinc atom or which are involved in catalysis.

These nucleic acids preferably encode a protein having a biological activity, e.g., the capability to catalyze the hydrolysis of a peptide. Alternatively such polypeptides are devoid of biological activity. Accordingly, the invention provides nucleic acids comprising nucleotide sequence from about nucleotide 1201 to about nucleotide 1331 of SEQ ID NO:1, in which codons encoding residues 374, 375, 378, 402, 406, and/or 417 are mutated.

Nucleic acids encoding modified forms or mutant forms of ACE-2 also include those encoding ACE-2 proteins having mutated glycosylation sites, such that either the encoded ACE-2 protein is not glycosylated, partially glycosylated and/or has a modified glycosylation pattern. Seven potential N-linked glycosylation sites have been identified in human ACE-2 and these are located at amino acids 53, 90, 103, 322, 432, 546, and 690 in SEQ ID NO:2. Glycosylation sites, N-glycosylation or O-glycosylation sites can also be added to the protein. Amino acid sequence motifs required for the attachment of a sugar unit are well known in the art.

Other preferred nucleic acids of the invention include nucleic acids encoding derivatives of ACE-2 polypeptides which lack one or more biological activities of ACE-2 polypeptides. For example, the invention provides derivatives of ACE-2 polypeptides having an anti-inflammatory activity but which are essentially incapable of hydrolyzing angiotensin I. Such nucleic acids can be obtained, e.g., by a first round of screening of libraries for the presence or absence of a first activity and a second round of screening for the presence or absence of another activity.

Also within the scope of the invention are nucleic acids encoding splice variants or nucleic acids representing transcripts synthesized from an alternative transcriptional initiation site, such as those whose transcription was initiated from a site in an intron., as is the case with the testicular ACE mRNAs. Such homologs can be cloned by hybridization or PCR, as further described herein.

In preferred embodiments, the ACE-2 nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup B. et al. (1996) *Bioorganic & Medicinal Chemistry* 4 (1): 5-23). As used herein, the terms "peptide nucleic acids" or "PNAS" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *PNAS* 93: 14670-675.

PNAs of ACE-2 can be used in therapeutic and diagnostic applications and are further described herein in section 4.3.2. Such modified nucleic acids can be used as antisense or antigene agents for sequence-specific modulation of gene expression or in the analysis of single base pair mutations in a gene by, e.g., PNA directed PCR clamping or as probes or primers for DNA sequence and hybridization (Hyrup B. et al (1996) supra; Perry-O'Keefe supra).

PNAs of ACE-2 can further be modified, e.g., to enhance their stability or cellular uptake, e.g., by attaching lipophilic or other helper groups to the ACE-2 PNA, by the formation of PNA-DNA chimeras, or by the use of liposomes or other techniques of drug delivery known in the art. ACE-2 PNAs can also be linked to DNA as described, e.g., in Hyrup B.

(1996) supra and Finn P. J. et al. (1996) *Nucleic Acids Research* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric moleclues can be synthesized with a 5' DNA segment and a 3' PNA segment (Peterser, K. H. et al. (1975) Bioorganic Med Chem. Lett. 5: 1119-11124).

In other embodiments, ACE-2 nucleic acids may include other appended groups such as peptides (e.g., for targeting host cell receptors in vivo), or agents that facilitate transport across the cell membrane as described in section 4.3.2. herein.

3.1. Probes and Primers

The nucleotide sequences determined from the cloning of ACE-2 genes from mammalian organisms will further allow for the generation of probes and primers designed for use in identifying and/or cloning ACE-2 homologs in other cell types, e.g., from other tissues, as well as ACE-2 homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from the group consisting of SEQ ID No: 1 or 3 or naturally occurring mutants thereof. For instance, primers based on the nucleic acid represented in SEQ ID NOs:1 or 3 can be used in PCR reactions to clone ACE-2 homologs.

Likewise, probes based on the subject ACE-2 sequences can be used to detect transcripts or genomic sequences encoding the same or homologous proteins, for use, e.g, in prognostic or diagnostic assays (further described below). In preferred embodiments, the probe further comprises a label group attached thereto and able to be detected, e.g., the label group is selected from amongst radioisotopes, fluorescent compounds, enzymes, and enzyme co-factors. Preferred probes for detecting polymorphisms are described in the Examples.

Probes and primers can be prepared and modified as described in the other sections herein relating to nucleic acids.

3.2 Antisense, Ribozyme and Triplex Techniques

Another aspect of the invention relates to the use of the isolated nucleic acid in "antisense" therapy. As used herein, "antisense" therapy refers to administration or in situ generation of oligonucleotide molecules or their derivatives which specifically hybridize (e.g., bind) under cellular conditions, with the cellular mRNA and/or genomic DNA encoding one or more of the subject ACE-2 proteins so as to inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an ACE-2 protein. Alternatively, the antisense construct is an oligonucleotide probe which is generated ex vivo and which, when introduced into the cell causes inhibition of expression by hybridizing with the mRNA and/or genomic sequences of an ACE-2 gene. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668. With respect to antisense DNA, oligodeoxyribonucleotides derived from the translation initiation site, e.g., between the −10 and +10 regions of the ACE-2 nucleotide sequence of interest, are preferred.

Antisense approaches involve the design of oligonucleotides (either DNA or RNA) that are complementary to ACE-2 mRNA. The antisense oligonucleotides will bind to the ACE-2 mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of an ACE-2 gene could be used in an antisense approach to inhibit translation of endogenous ACE-2 mRNA. Oligonucleotides complementary to the 5' untraslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of ACE-2 mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. W088/09810, published Dec. 15, 1988) or the blood-brain barrier (see, e.g., PCT Publication No. W089/10134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1 996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641). The oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448-7451), etc.

While antisense nucleotides complementary to the ACE-2 coding region sequence can be used, those complementary to the transcribed untranslated region and to the region comprising the initiating methionine are most preferred.

The antisense molecules can be delivered to cells which express ACE-2 in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous ACE-2 transcripts and thereby prevent translation of the ACE-2 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct which can be introduced directly into the tissue site. Alternatively, viral vectors can be used which selectively infect the desired tissue, in which case administration may be accomplished by another route (e.g., systematically).

Ribozyme molecules designed to catalytically cleave ACE-2 mRNA trnscripts can also be used to prevent translation of ACE-2 mRNA and expression of ACE-2 (See, e.g., PCT International Publication WO90/11364, published Oct. 4, 1990; Sarver et al., 1990, Science 247:1222-1225 and U.S. Pat. No. 5,093,246). While ribozymes that cleave mRNA at site specific recognition sequences can be used to destroy ACE-2 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591. There are a number of potential hammerhead ribozyme cleavage sites within the nucleotide sequence of human ACE-2 cDNA (FIG. 1). Preferably the ribozyrne is engineered so that the cleavage recognition site is located near the 5' end of the ACE-2 mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in an ACE-2 gene.

As in the antisense approach, the ribozymes can be composed of modified oligonucleotides (e.g., for improved stability, targeting, etc.) and should be delivered to cells which express the ACE-2 gene in vivo. A preferred method of delivery involves using a DNA construct "encoding" the robozyme under the control of a strong constitutive pol III or pol II promoter, so that transfected cells will produce sufficient quantities of the ribozyme to destroy endogenous ACE-2 messages and inhibit translation. Because ribozymes unlike antisense molecules, are catalytic, a lower intracellular concentration is required for efficiency.

Endogenous ACE-2 gene expression can also be reduced by inactivating or "knocking out" the ACE-2 gene or its promoter using targeted homologous recombination. (E.g., see Smithies et al., 1985, Nature 317:230-234; Thomas & Capecchi, 1987, Cell 51:503-512; Thompson et al., 1989 Cell 5:313-321; each of which is incorporated by reference herein in its entirety). For example, a mutant, non-functional ACE-2 (or a completely unrelated DNA sequence) flanked by DNA homologous to the endogenous ACE-2 gene (either the coding regions or regulatory regions of the ACE-2 gene) can be used, with or without a selectable marker and/or a negative selectable marker, to transfect cells that express ACE-2 in vivo. Insertion of the DNA construct, via targeted homologous recombination, results in inactivation of the ACE-2 gene. Such approaches are particularly suited in the agricultural field where modifications to ES (embryonic stem) cells can be used to generate animal offspring with an inactive ACE-2 (e.g., see Thomas & Capecchi 1987 and Thompson 1989, supra). However this approach can be adapted for use in humans provided the recombinant DNA constructs are directly administered or targeted to the required site in vivo using appropriate viral vectors.

Alternatively, endogenous ACE-2 gene expression can be reduced by targeting deoxyribonucleotide sequences complementary to the regulatory region of the ACE-2 gene (i.e., the ACE-2 promoter and/or enhancers) to form triple helical structures that prevent transcription of the ACE-2 gene in target cells in the body. (See generally, Helene, C. 1991, Anticancer Drug Des., 6(6):569-84; Helene, C., et al., 1992, Ann. N.Y. Acad. Sci., 660:27-36; and Maher, L. J., 1992, Bioassays 14(12):807-15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

3.3. Vectors Encoding ACE-2 Proteins and ACE-2 Expressing Cells

The invention further provides plasmids and vectors encoding an ACE-2 protein, which can be used to express an ACE-2 protein in a host cell. The host cell may be any prokaryotic or eukaryotic cell. Thus, a nucleotide sequence derived from the cloning of mammalian ACE-2 proteins, encoding all or a selected portion of the full-length protein, can be used to produce a recombinant form of an ACE-2 polypeptide via microbial or eukaryotic cellular processes.

Ligating the polynucleotide sequence into a gene construct, such as an expression vector, and transforming or transfecting into hosts, either eukaryotic (yeast, avian, insect or mammalian) or prokaryotic (bacterial) cells, are standard procedures well known in the art.

Vectors that allow expression of a nucleic acid in a cell are referred to as expression vectors. Typically, expression vectors used for expressing an ACE-2 protein contain a nucleic acid encoding an ACE-2 polypeptide, operably linked to at least one transcriptional regulatory sequence. Regulatory sequences are art-recognized and are selected to direct expression of the subject ACE-2 proteins. Transcriptional regulatory sequences are described in Goeddel; Gene Expression Technology: Methods in Enzymology 185, Academic Press, San Diego, Calif. (1990). In one embodiment, the expression vector includes a recombinant gene encoding a peptide having an agonistic activity of a subject ACE-2 polypeptide, or alternatively, encoding a peptide which is an antagonistic form of an ACE-2 protein.

Suitable vectors for the expression of an ACE-2 polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, an ACE-2 polypeptide is produced recombinantly utilizing an expression vector generated by sub-cloning the coding sequence of one of the ACE-2 genes represented in SEQ ID NOs:1 or 3.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2$^{nd}$ Ed., ed. by Sambrook, Fritsch and Maniatis (Cold Spring Harbor Laboratory Press: 1989) Chapters 16 and 17.

In some instances, it may be desirable to express the recombinant ACE-2 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III). Production of ACE-2 in this system is further described in the Examples.

When it is desirable to express only a portion of an ACE-2 protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751-757) and Salmonella typhimurium and its in vitro activity has been demonstrated on recombinant proteins (Miller et al. (1987) PNAS 84:2718-1722). Therefore, removal of an N-terminal methionine, if desired, can be achieved either in vivo by expressing ACE-2 derived polypeptides in a host which produces MAP (e.g., E. coli or CM89 or S. cerevisiae), or in vitro by use of purified MAP (e.g., procedure of Miller et al., supra).

Moreover, the gene constructs of the present invention can also be used as part of a gene therapy protocol to deliver nucleic acids encoding either an agonistic or antagonistic form of one of the subject ACE-2 proteins. Thus, another aspect of the invention features expression vectors for in vivo or in vitro transfection and expression of an ACE-2 polypeptide in particular cell types so as to reconstitute the function of, or alternatively, abrogate the function of ACE-2 in a tissue. This could be desirable, for example, when the naturally-occurring form of the protein is misexpressed or the natural protein is mutated and less active.

In addition to viral transfer methods, non-viral methods can also be employed to cause expression of a subject ACE-2 polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject ACE-2 polypeptide gene by the targeted cell. Exemplary targeting means of this type include liposomal derived systems, poly-lysine conjugates, and artificial viral envelopes.

In other embodiments transgenic animals, described in more detail below could be used to produce recombinant proteins.

4. Polypeptides of the Present Invention

The present invention makes available isolated ACE-2 polypeptides which are isolated from, or otherwise substantially free of other cellular proteins. The term "substantially free of other cellular proteins" (also referred to herein as "contaminating proteins") or "substantially pure or purified preparations" are defined as encompassing preparations of ACE-2 polypeptides having less than about 20% (by dry weight) contaminating protein, and preferably having less than about 5% contaminating protein. Functional forms of the subject polypeptides can be prepared, for the first time, as purified preparations by using a cloned gene as described herein.

Preferred ACE-2 proteins of the invention have an amino acid sequence which is at least about 60%, 70%, 80%, 85%, 90%, or 95% identical or homologous to an amino acid sequence of SEQ ID NO:2. Even more preferred ACE-2 proteins comprise an amino acid sequence which is at least about 97, 98, or 99% homologous or identical to an amino acid sequence of SEQ ID NO:2. Such proteins can be recombinant proteins, and can be, e.g., produced in vitro from nucleic acids comprising a nucleotide sequence set forth in SEQ ID NO:1 or 3, or homologs thereof. For example, recombinant polypeptides preferred by the present invention can be encoded by a nucleic acid, which is at least 85% homologous and more preferably 90% homologous and most preferably 95% homologous with a nucleotide sequence set forth in SEQ ID NOs: 1 or 3. Polypeptides which are encoded by a nucleic acid that is at least about 98-99% homologous with the sequence of SEQ ID NOs: 1 or 3 are also within the scope of the invention.

In a preferred embodiment, an ACE-2 protein of the present invention is a mammalian ACE-2 protein. In a particularly preferred embodiment an ACE-2 protein is set forth as SEQ ID No: 2. In another preferred embodiment, the human ACE-2 protein consists of the amino acid sequence set forth in SEQ ID NO:106, which is identical to SEQ ID NO:2, except for the presence of an aspartic acid at residue 720. In particularly preferred embodiment, an ACE-2 protein has an ACE-2 bioactivity. It will be understood that certain post-translational modifications, e.g., phosphorylation and the like, can increase the apparent molecular weight of the ACE-2 protein relative to the unmodified polypeptide chain.

ACE-2 polypeptides preferably are capable of functioning in one of either role of an agonist or antagonist of at least one biological activity of a wild-type ("authentic") ACE-2 protein of the appended sequence listing. The term "evolutionarily related to", with respect to amino acid sequences of ACE-2 proteins, refers to both polypeptides having amino acid sequences which have arisen naturally, and also to mutational variants of human ACE-2 polypeptides which are derived, for example, by combinatorial mutagenesis.

Full length proteins or fragments corresponding to one or more particular motifs and/or domains or to arbitrary sizes, for example, at least 5, 10, 25, 50, 75 and 100, amino acids in length are within the scope of the present invention.

For example, isolated ACE-2 polypeptides can be encoded by all or a portion of a nucleic acid sequence shown in any of SEQ ID NOs: 1 or 3. Isolated peptidyl portions of ACE-2 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an ACE-2 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") ACE-2 protein.

An ACE-2 polypeptide can be a membrane bound form or a soluble form. A preferred soluble ACE-2 polypeptide is a polypeptide which does not contain the transmembrane domain located from about amino acid 741 to about amino acid 765 of SEQ ID NO:2. It is likely that there are natural forms of ACE-2 which fail to contain this domain. Alternatively, such proteins can be created by genetic engineering by methods known in the art. Soluble ACE-2 proteins can comprise an amino acid sequence from about amino acid 19 to about amino acid 740 of SEQ ID NO:2 or homologs thereof. Such proteins can further comprise the amino acid sequence from about amino acid 765 to about amino acid 805 of SEQ ID NO:2. Alternatively, soluble ACE-2 proteins can comprise the signal sequence, i.e., amino acids 1-18 of SEQ ID NO:2 or a heterologous signal sequence, which is necessary for obtaining secretion of the protein.

It has been reported membraneous ACE proteins can become detached from the membrane to become soluble forms of ACE as the result of a post-translational proteolytic processing event. A metalloprotease responsible for this effect has been isolated and referred to as "secretase" (see, e.g., Parvathy et al. (1997) Biochem. J. 327:37). Accordingly, it is likely that ACE-2 proteins are similarly rendered soluble. Thus, the invention also provides ACE-2 proteins in which the site of cleavage is modified, such that a secretase would not be able to hydrolyze ACE-2.

In general, polypeptides referred to herein as having an activity (e.g., are "bioactive") of an ACE-2 protein are defined as polypeptides which include an amino acid sequence encoded by all or a portion of the nucleic acid sequences shown in one of SEQ ID NOs: 1 or 3 and which mimic or antagonize all or a portion of the biological/biochemical activities of a naturally occurring ACE-2 protein. Examples of such biological activity include the ability to catalyze hydrolysis of angiotensin I into Ang.(1-9), the ability to catalyze hydrolysis of a kinin or derivative thereof; the ability to catalyze the hydrolysis of kinetensin; the ability to bind to a metal ion, e.g., zinc, the ability to interact with a substrate, e.g., angiotensin I or a kinin, the ability to compete with ACE for a target peptide, e.g., angiotensin I; the ability to function as an analgesic, the ability to function as an anti-inflammatory agent the ability to modulate release of histamine from mast cells, and the ability to modulate blood cell wall permeability, blood pressure or vasocontriction. Other biological activities of the subject ACE-2 proteins are described herein or will be reasonably apparent to those skilled in the art. According to the present invention, a polypeptide has biological activity if it is a specific agonist or antagonist of a naturally-occurring form of an ACE-2 protein.

A preferred ACE-2 polypeptide having a biological activity is an ACE-2 polypeptide comprising a zinc binding domain, e.g, an amino acid sequence from amino acid 374 to amino acid 378 of SEQ ID NO:2. Such a zinc binding domain is present in all ACE proteins identified to this date and has been identified as being located in the catalytic site of the enzyme (Lattion et al. (1989) FEBS Letters 252:99). All the amino acids which have been reported as interacting with the zinc atom or involved in catalysis in ACE proteins are present in ACE-2. Thus, by comparison, His374, 378 and Glu402 are probably the amino acids coordinating the zinc atom and Glu375 and His417 are probably involved in catalysis, as well as Glu 406. Thus, preferred ACE-2 polypeptides can be generally represented by the formula: X-(ZBD)-Y, wherein ZBD corresponds to amino acids 374 to 378, 371 to 380, or 372 to 381 and X and Y represent a certain number of amino acids located upstream and downstream of ZBD, respectively. X and Y can be any number of amino acids, including 0, 1, 2, 5, 10, 20, 50, 100, 200, or 300. The ZBD can also be an extended ZBD, e.g., including the amino acid sequence from about amino acid 374 to about amino acid 420 of SEQ ID NO:2 and containing all the amino acids likely to be involved in the active site of the enzyme. ZBD can also be a mutant ZBD, which is, e.g, incapable of binding a zinc atom, and thus incapable of catalyzing the hydrolysis of a peptide. For example, a mutant ZBD can be a ZBD in which His 374, Glu 375, His 378, Glu 402, Glu 406, and/or His 417 are replaced by another amino acid. Mutated ACE-2 proteins can be used, e.g., as dominant negative ACE-2 proteins which is capable of interacting with the target peptide, but fails to hydrolyze the target peptide and thus competes with the wild-type ACE-2 or with an ACE protein.

Assays for determining whether a compound, e.g., a protein, such as an ACE-2 protein or variant thereof, has one or more of the above biological activities are well known in the art. For example, assays for determining whether an ACE-2 protein, homolog, or fragment thereof is capable of catalyzing hydrolysis of a peptide can be performed as described in the Examples. Peptides for use as test substrates can be prepared according to methods known in the art or can be obtained commercially.

Other preferred proteins of the invention are those encoded by the nucleic acids set forth in the section pertaining to nucleic acids of the invention. In particular, the invention provides fusion proteins, e.g., ACE-2-immunoglobulin fusion proteins. Such fusion proteins can provide, e.g., enhanced stability and solubility of ACE-2 proteins and may thus be useful in therapy. Fusion proteins can also be used to produce an immunogenic fragment of an ACE-2 protein. For example, the VP6 capsid protein of rotavirus can be used as an immunologic carrier protein for portions of the ACE-2 polypeptide, either in the monomeric form or in the form of a viral particle. The nucleic acid sequences corresponding to the portion of a subject ACE-2 protein to which antibodies are to be raised can be incorporated into a fusion gene construct which includes coding sequences for a late vaccinia virus structural protein to produce a set of recombinant viruses expressing fusion proteins comprising ACE-2 epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an ACE-2 protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple antigen peptide system for peptide-based immunization can also be utilized to generate an immunogen, wherein a desired portion of an ACE-2 polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of ACE-2 proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the ACE-2 polypeptides of the present invention. For example, ACE-2 polypeptides can be generated as glutathione-S-transferase (GST-fusion) proteins. Such GST-fusion proteins can enable easy purification of the ACE-2 polypeptide, as for example by the use of glutathione-derivatized matrices (see, for example, Current Protocols in Molecular Biology, eds. Ausubel et al. (N.Y.: John Wiley & Sons, 1991)).

The present invention further pertains to methods of producing the subject ACE-2 polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant ACE-2 polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant ACE-2 polypeptide is a fusion protein containing a domain which facilitates its purification, such as GST fusion protein.

Moreover, it will be generally appreciated that, under certain circumstances, it may be advantageous to provide homologs of one of the subject ACE-2 polypeptides which function in a limited capacity as one of either an ACE-2 agonist (mimetic) or an ACE-2 antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of ACE-2 proteins.

Homologs of each of the subject ACE-2 proteins can be generated by mutagenesis, such as by discrete point mutation(s), or by truncation. For instance, mutation can give rise to homologs which retain substantially the same, or merely a subset, of the biological activity of the ACE-2 polypeptide from which it was derived. Alternatively, antagonistic forms of the protein can be generated which are able to inhibit the function of the naturally occurring form of the protein, such as by competitively binding to an ACE-2 receptor.

The recombinant ACE-2 polypeptides of the present invention also include homologs of the wildtype ACE-2 proteins, such as versions of those proteins which are resistant to proteolytic cleavage, as for example, due to mutations which alter ubiquitination or other enzymatic targeting associated with the protein.

ACE-2 polypeptides may also be chemically modified to create ACE-2 derivatives by forming covalent or aggregate conjugates with other chemical moieties, such as glycosyl groups, lipids, phosphate, acetyl groups and the like. Covalent derivatives of ACE-2 proteins can be prepared by linking the chemical moieties to functional groups on amino acid sidechains of the protein or at the N-terminus or at the C-terminus of the polypeptide.

Modification of the structure of the subject ACE-2 polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the ACE-2 polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed. by L. Stryer, WH Freeman and Co.: 1981). Whether a change in the amino acid sequence of a peptide results in a functional ACE-2 homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject ACE-2 proteins as well as truncation mutants, and is especially useful for identifying potential variant sequences (e.g., homologs). The purpose of screening such combinatorial libraries is to generate, for example, novel ACE-2 homologs which can act as either agonists or antagonist, or alternatively, possess novel activities all together. Thus, combinatorially-derived homologs can be generated to have an increased potency relative to a naturally occurring form of the protein.

In one embodiment, the variegated library of ACE-2 variants is generated by combinatorial mutagenesis at the nucleic acid level, and is encoded by a variegated gene library. For instance, a mixture of synthetic oligonucleotides can be enzymatically ligated into gene sequences such that the degenerate set of potential ACE-2 sequences are expressible as individual polypeptides, or alternatively, as a set of larger fusion proteins (e.g., for phage display) containing the set of ACE-2 sequences therein.

There are many ways by which such libraries of potential ACE-2 homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential ACE-2 sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

Likewise, a library of coding sequence fragments can be provided for an ACE-2 clone in order to generate a variegated population of ACE-2 fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of an ACE-2 coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of ACE-2 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate ACE-2 sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811-7815; Yourvan et al., 1992, Parallel Problem Solving from Nature, 2., In Maenner and Manderick, eds., Elsevir Publishing Co., Amsterdam, pp. 401-410; Delgrave et al., 1993, Protein Engineering 6(3): 327-331).

The invention also provides for reduction of the ACE-2 proteins to generate mimetics, e.g., peptide or non-pepide agents, such as small molecules, which are able to disrupt binding of an ACE-2 polypeptide of the present invention with a molecule, e.g. target peptide. Thus, such mutagenic techniques as described above are also useful to map the determinants of the ACE-2 proteins which participate in protein-protein interactions involved in, for example, binding of the subject ACE-2 polypeptide to a target peptide. To illustrate, the critical residues of a subject ACE-2 polypeptide which are involved in molecular recognition of its receptor can be determined and used to generate ACE-2 derived peptidomimetics or small molecules which competitively inhibit binding of the authentic ACE-2 protein with that moiety. By employing, for example, scanning mutagenesis to map the amino acid residues of the subject ACE-2 proteins which are involved in binding other proteins, peptidomimetic compounds can be generated which mimic those residues of the ACE-2 protein which facilitate the interaction. Such mimetics may then be used to interfere with the normal function of an ACE-2 protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the $9^{th}$ American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun126:419; and Dann et al. (1986) Biochem Biophys Res Commun 134:71).

Also within the scope of the invention are kinetensin conversion products, such as ACE-2 kinetensin conversion products. A preferred conversion product is kinetensin (1-8) (SEQ ID NO:24). Analogs of such conversion products are also within the scope of the invention and can be, e.g., peptidomimetics.

5. Anti-ACE-2 Antibodies and Uses Therefor

Another aspect of the invention pertains to an antibody specifically reactive with a mammalian ACE-2 protein, e.g., a wild-type or mutated ACE-2 protein. For example, by using immunogens derived from an ACE-2 protein, e.g., based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian ACE-2 polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of an ACE-2 protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of an ACE-2 protein of a mammal, e.g., antigenic determinants of a protein set forth in SEQ ID No: 2 or closely related homologs (e.g., at least 90% homologous, and more preferably at least 94% homologous). Exemplary antibodies were obtained and are set forth in the Examples.

Following immunization of an animal with an antigenic preparation of an ACE-2 polypeptide, anti-ACE-2 antisera can be obtained and, if desired, polyclonal anti-ACE-2 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a mammalian ACE-2 polypeptide of the present invention and monoclonal antibodies isolated from a culture comprising such hybridoma cells. In one embodiment anti-human ACE-2 antibodies specifically react with the protein encoded by a nucleic acid having SEQ ID NO:1.

The term antibody as used herein is intended to include fragments thereof which are also specifically reactive with one of the subject mammalian ACE-2 polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for an ACE-2 protein conferred by at least one CDR region of the antibody. In preferred embodiments, the antibodies, the antibody further comprises a label attached thereto and able to be detected, (e.g., the label can be a radioisotope, fluorescent compound, enzyme or enzyme co-factor).

Anti-ACE-2 antibodies can be used, e.g., to monitor ACE-2 protein levels in an individual for determining, e.g., whether a subject has a disease or condition associated with an aberrant ACE-2 protein level, or allowing determination of the efficacy of a given treatment regimen for an individual afflicted with such a disorder. The level of ACE-2 polypeptides may be measured from cells and/or in bodily fluid, such as in blood samples saliva, urine, and sweat.

Another application of anti-ACE-2 antibodies of the present invention is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an ACE-2 protein, e.g., other orthologs of a particular ACE-2 protein or other paralogs from the same species, can then be detected with antibodies, as, for example, reacting nitrocellulose filters lifted from infected plates with anti-ACE-2 antibodies. Positive phage detected by this assay can then be isolated from the infected plate. Thus, the presence of ACE-2 homologs can be detected and cloned from other animals, as can alternate isoforms (including splice variants) from humans.

Antibodies specifically binding to an ACE-2 conversion product are also within the scope of the invention. In an illustrative embodiment, the invention provides antibodies which specifically bind to kinetensin (1-8) and not to kinetensin (1-9).

6. Transgenic Animals

The invention further provides for transgenic animals, which can be used for a variety of purposes, e.g., to identify ACE-2 therapeutics. Transgenic animals of the invention include non-human animals containing a heterologous ACE-2 gene or fragment thereof under the control of an ACE-2 promoter or under the control of a heterologous promoter. Accordingly, the transgenic animals of the invention can be animals expressing a transgene encoding a wild-type ACE-2 protein or fragment thereof or variants thereof, including mutants and polymorphic variants thereof. Such animals can be used, e.g., to determine the effect of a difference in amino acid sequence of an ACE-2 protein from the sequence set forth in SEQ ID NO:2, such as a polymorphic difference.

These animals can also be used to determine the effect of expression of an ACE-2 protein in a specific site or for identifying ACE-2 therapeutics or confirming their activity in vivo. Exemplary transgenic mice are described in the Examples.

The transgenic animals can also be animals containing a transgene, such as reporter gene, under the control of an ACE-2 promoter or fragment thereof. These animals are useful, e.g., for identifying ACE-2 drugs that modulate production of ACE-2, such as by modulating ACE-2 gene expression. An ACE-2 gene promoter can be isolated, e.g., by screening of a genomic library with an ACE-2 cDNA fragment and characterized according to methods known in the art.

Yet other non-human animals within the scope of the invention include those in which the expression of the endogenous ACE-2 gene has been mutated or "knocked out". These animals could be useful to determine whether the absence of ACE-2 will result in a specific phenotype, in particular whether these mice have or are likely to develop a specific disease, such as high susceptibility to inflammatory reactions. These animals are also useful for determining the effect of a specific amino acid difference in an ACE-2 gene. In fact these knock out animals can be crossed with transgenic animals expressing, e.g., a mutated form of ACE-2, thus resulting in an animal which expresses only the mutated protein and not the wild-type ACE-2 protein. Exemplary knock out mice are described in the Examples.

Methods for obtaining transgenic and knockout non-human animals are well known in the art.

7. Screening Assays for ACE-2 Therapeutics

The invention further provides screening methods for identifying ACE-2 therapeutics, e.g., for treating diseases or conditions caused by, or contributed to by an abnormal ACE-2 activity or which can benefit from a modulation of an ACE-2 activity or protein level, e.g., hypertension, hypotension, arrhythmia, or CHF. An ACE-2 therapeutic can be any type of compound, including a protein, a peptide, peptidomimetic, small molecule, and nucleic acid. A nucleic acid can be, e.g., a gene, an antisense nucleic acid, a ribozyme, or a triplex molecule. An ACE-2 therapeutic of the invention can be an agonist or an antagonist. Preferred ACE-2 agonists include ACE-2 proteins or derivatives thereof which mimic at least one ACE-2 activity, e.g., the capability to catalyze hydrolysis of a target peptide or nucleic acids encoding such. Other preferred agonists include compounds which are capable of increasing the production of an ACE-2 protein in a cell, e.g., compounds capable of upregulating the expression of an ACE-2 gene, and compounds which are capable of enhancing an ACE-2 activity and/or the interaction of an ACE-2 protein with another molecule, such as a target peptide. Preferred ACE-2 antagonists include ACE-2 proteins which are dominant negative proteins, which, e.g., are capable of binding to, but not to hydrolyze target peptides. Other preferred antagonists include compounds which decrease or inhibit the production of an ACE-2 protein in a cell and compounds which are capable of downregulating expression of an ACE-2 gene, and compounds which are capable of donwregulating an ACE-2 activity and/or interaction of an ACE-2 protein with another molecule, such as a target peptide, e.g, angiotensin I, a kinin, kinetensin, or neurotensin. In another preferred embodiment, an ACE-2 antagonist is a modified form of a target peptide, which is capable of interacting with the catalytic site of an ACE-2 protein, but which does not have biological activity, e.g., which is not vasopressive.

The invention also provides screening methods for identifying ACE-2 therapeutics which are capable of binding to an ACE-2 protein, e.g., a wild-type ACE-2 protein or a mutated form of an ACE-2 protein, and thereby modulate the catalytic activity of the ACE-protein or degrades or causes the ACE-2 protein to be degraded. For example, such an ACE-2 therapeutic can be an antibody or derivative thereof which interacts specifically with an ACE-2 protein (either wild-type or mutated).

Thus, the invention provides screening methods for identifying ACE-2 agonist and antagonist compounds, comprising selecting compounds which are capable of interacting with an ACE-2 protein or with a molecule interacting with an ACE-2 protein such as a target peptide and/or compounds which are capable of modulating the interaction of an ACE-2 protein with another molecule, such as a target peptide. In general, a molecule which is capable of interacting with an ACE-2 protein is referred to herein as "ACE-2 binding partner" and can be a target peptide, e.g., angiotensin I, a kinin, kinetensin, or neurotensin or an analog thereof or a portion thereof, so long as the analog or portion of the target peptide is capable of binding to an ACE-2 polyptide and optionally of being cleaved by an ACE-2 polypeptide. An ACE-2 binding partner can also be a polypeptide which is not a target peptide and which may, e.g., interact with an ACE-2 protein at sites other than the catalytic site.

The compounds of the invention can be identified using various assays depending on the type of compound and activity of the compound that is desired. Set forth below are at least some assays that can be used for identifying ACE-2 therapeutics. It is within the skill of the art to design additional assays for identifying ACE-2 therapeutics.

7.1 Cell-Free Assays

Cell-free assays can be used to identify compounds which are capable of interacting with an ACE-2 protein or binding partner, to thereby modify the activity of the ACE-2 protein or binding partner. Such a compound can, e.g., modify the structure of an ACE-2 protein or binding partner and thereby effect its activity. Cell-free assays can also be used to identify compounds which modulate the interaction between an ACE-2 protein and an ACE-2 binding partner, such as a target peptide. In a preferred embodiment, cell-free assays for identifying such compounds consist essentially in a reaction mixture containing an ACE-2 protein and a test compound or a library of test compounds in the presence or absence of a binding partner. A preferred binding partner is angiotensin I or kinetensin or portions thereof sufficient for interacting with ACE-2. A test compound can be, e.g., a derivative of an ACE-2 binding partner, e.g., an biologically inactive target peptide, or a small molecule.

Accordingly, one exemplary screening assay of the present invention includes the steps of contacting an ACE-2 protein or functional fragment thereof or an ACE-2 binding partner with a test compound or library of test compounds and detecting the formation of complexes. For detection purposes, the molecule can be labeled with a specific marker and the test compound or library of test compounds labeled with a different marker. Interaction of a test compound with an ACE-2 protein or fragment thereof or ACE-2 binding partner can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the ACE-2 protein, functional fragment thereof, ACE-2 analog or ACE-2 binding partner is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an ACE-2 polypeptide, (ii) an ACE-2 binding partner (e.g., angiotensin I, a kinin, or kinetensin), and (iii) a test compound; and (b) detecting interaction of the ACE-2 and the ACE-2 binding protein. The ACE-2 polypeptide and ACE-2 binding partner can be produced recombinantly, purified from a source, e.g., plasma, or chemically synthesized, as described herein. A statistically significant change (potentiation or inhibition) in the interaction of the ACE-2 and ACE-2 binding protein in the presence of the test compound, relative to the interaction in the absence of the test compound, indicates a potential agonist (mimetic or potentiator) or antagonist (inhibitor) of ACE-2 bioactivity for the test compound. The compounds of this assay can be contacted simultaneously. Alternatively, an ACE-2 protein can first be contacted with a test compound for an appropriate amount of time, following which the ACE-2 binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified ACE-2 polypeptide or binding partner is added to a composition containing the ACE-2 binding partner or ACE-2 polypeptide, and the formation of a complex is quantitated in the absence of the test compound.

Complex formation between an ACE-2 protein and an ACE-2 binding partner may be detected by a variety of techniques. Modulation of the formation of complexes can be quantitated using, for example, detectably labeled proteins such as radiolabeled, fluorescently labeled, or enzymatically labeled ACE-2 proteins or ACE-2 binding partners, by immunoassay, or by chromatographic detection.

Typically, it will be desirable to immobilize either ACE-2 or its binding partner to facilitate separation of complexes from uncomplexed forms of one or both of the proteins, as well as to accommodate automation of the assay. Binding of ACE-2 to an ACE-2 binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/ACE-2 (GST/ACE-2) fusion proteins can be adsorbed onto glutathione sepharose beads (Sigma Chemical, St. Louis, Mo.) or glutathione derivatized microtitre plates, which are then combined with the ACE-2 binding partner, e.g. an $^{35}$S-labeled ACE-2 binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of ACE-2 protein or ACE-2 binding partner found in the bead fraction quantitated from the gel using standard electrophoretic techniques such as described in the appended examples.

Other techniques for immobilizing proteins on matrices are also available for use in the subject assay. For instance, either ACE-2 or its cognate binding partner can be immobilized utilizing conjugation of biotin and streptavidin. For instance, biotinylated ACE-2 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with ACE-2 can be derivatized to the wells of the plate, and ACE-2 trapped in the wells by antibody conjugation. As above, preparations of an ACE-2 binding protein and a test compound are incubated in the ACE-2 presenting wells of the plate, and the amount of complex trapped in the well can be quantitated. Exemplary methods for detecting such complexes, in addition to those described above for the GST-immobilized complexes, include immunodetection of complexes using antibodies reactive with the ACE-2 binding partner, or which are reactive with ACE-2 protein and compete with the binding partner; as well as enzyme-linked assays which on rely detecting an enzymatic activity associated with the binding partner, either intrinsic or extrinsic activity. In the instance of the latter, the enzyme can be chemically conjugated or provided as a fusion protein with the ACE-2 binding partner. To illustrate, the ACE-2 binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-ACE-2 antibodies, can be used. Alternatively, the protein to be detected in the complex can be "epitope tagged" in the form of a fusion protein which includes, in addition to the ACE-2 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

Cell-free assays can also be used to identify compounds which interact with an ACE-2 protein and modulate an activity of an ACE-2 protein. Accordingly, in one embodiment, an ACE-2 protein is contacted with a test compound and the catalytic activity of ACE-2 is monitored. In one embodiment, the abililty of ACE-2 to bind to and/or to hydrolyze a target peptide, e.g, angiotensin I, a kinin, such as bradykinin, or kinetensin, is determined. The binding affinity of ACE-2 to a target peptide can be determined according to methods known in the art. Determination of the enzymatic activity of ACE-2 can be performed as further described herein. In particular, enzymatic activity can be demonstrated by subjecting a reaction mixture containing an ACE-2 enzyme and a target peptide after incubation, to mass spectometry, as described in the Examples.

In a preferred embodiment, the invention provides a screening method which comprises combining an ACE-2 polypeptide and a target peptide together with a test compound in a reaction mixture in conditions sufficient for the ACE-2 polypeptide to cleave the target peptide in the absence of the test compound. The method further comprises monitoring the presence of the target peptide, the target peptide conversion product, and/or of the one or more amino acids cleaved from the target peptide, such that a difference in the amount of at least one of the target peptide, the target peptide conversion product or one or more amino acids in the reaction mixture incubated with the test compound relative to a reaction mixture that does not contain the test compound indicates that the test compound is an ACE-2 therapeutic. In an even more preferred embodiment of the invention, the presence and/or the amount of the target peptide, the target peptide conversion product, and/or of the one or more amino acids in the reaction mixture is determined by spectrometric analysis of the reaction mixture or of a part thereof., e.g., as described in the Examples.

Assays can also be developed for identifying compounds which interact and optionally inhibit (i) ACE-2, but not ACE; (ii) ACE, but not ACE-2; and (iii) ACE-2 and ACE. This can be done by a two step screening assay, wherein each step can be conducted as described herein.

7.2. Cell Based Assays

In addition to cell-free assays, such as described above, ACE-2 proteins as provided by the present invention, facilitate the generation of cell-based assays, e.g., for identifying small molecule agonists or antagonists. In one embodiment, a cell expressing an ACE-2 protein on the outer surface of its cellular membrane is incubated in the presence of a test compound alone or a test compound and a molecule which is known to interact with ACE-2 and the interaction between ACE-2 and a test compound is detected, e.g., by using a microphysiometer (McConnell et al. (1992) Science 257: 1906). An interaction between the ACE-2 protein the test compound is detected by the microphysiometer as a change in the acidification of the medium.

Cell based assays can also be used to identify compounds which modulate expression of an ACE-2 gene, modulate translation of an ACE-2 mRNA, or which modulate the stability of an ACE-2 mRNA or protein. Accordingly, in one embodiment, a cell which is capable of producing ACE-2, e.g., a kidney cell, is incubated with a test compound and the amount of ACE-2 produced in the cell medium is measured and compared to that produced from a cell which has not been contacted with the test compound. The specificity of the compound vis a vis ACE-2 can be confirmed by various control analysis, e.g., measuring the expression of one or more control genes.

Compounds which can be tested include small molecules, proteins, and nucleic acids. In particular, this assay can be used to determine the efficacity of ACE-2 antisense molecules or ribozymes.

In another embodiment, the effect of a test compound on transcription of an ACE-2 gene is determined by transfection experiments using a reporter gene operatively linked to at least a portion of the promoter of an ACE-2 gene. A promoter region of a gene can be isolated, e.g., from a genomic library according to methods known in the art. The reporter gene can be any gene encoding a protein which is readily quantifiable, e.g, the luciferase or CAT gene, well known in the art.

This invention further pertains to novel agents identified by the above-described screening assays and uses thereof for treatments as described herein.

8. Predictive Medicine

The invention further features predictive medicines, which are based, at least in part, on the identity of the novel ACE-2 genes and alterations in the genes and related pathway genes, which affect the expression level and/or function of the encoded ACE-2 protein in a subject.

For example, information obtained using the diagnostic assays (Diagnomics™ molecular diagnostics) described herein (alone or in conjunction with information on another genetic defect, which contributes to the same disease) is useful for diagnosing or confirming that a symptomatic subject (e.g. a subject symptomatic for hypertension, hypotension, CHF, or a kinetensin associated condition), has a genetic defect (e.g. in an ACE-2 gene or in a gene that regulates the expression of an ACE-2 gene), which causes or contributes to the particular disease or disorder. Alternatively, the information (alone or in conjunction with information on another genetic defect, which contributes to the same disease) can be used prognostically for predicting whether a non-symptomatic subject is likely to develop a disease or condition, which is caused by or contributed to by an abnormal ACE-2 activity or protein level (e.g. hypertension, hypotension, CHF, or a kinetensin associated condition) in a subject. For example, the amount of ACE-2 protein in a bodily fluid, e.g., blood, serum, saliva or urine, can be determined and compared to levels found in individuals that are not known to suffer from any ACE-2 associated diseases. Based on the prognostic information, a doctor can recommend a regimen (e.g. diet or exercise) or therapeutic protocol, useful for preventing or prolonging onset of the particular disease or condition in the individual.

In addition, knowledge of the particular alteration or alterations, resulting in defective or deficient ACE-2 genes or proteins in an individual (the ACE-2 genetic profile), alone or in conjunction with information on other genetic defects contributing to the same disease (the genetic profile of the particular disease) allows customization of therapy for a particular disease to the individual's genetic profile, the goal of "pharmacogenomics". For example, an individual's ACE-2 genetic profile or the genetic profile of a disease or condition, to which ACE-2 genetic alterations cause or contribute, can enable a doctor: 1) to more effectively prescribe a drug that will address the molecular basis of the disease or condition; and 2) to better determine the appropriate dosage of a particular drug. For example, the expression level of ACE-2 proteins, alone or in conjunction with the expression level of other genes, known to contribute to the same disease, can be measured in many patients at various stages of the disease to generate a transcriptional or expression profile of the disease. Expression patterns of individual patients can then be compared to the expression profile of the disease to determine the appropriate drug and dose to administer to the patient.

The ability to target populations expected to show the highest clinical benefit, based on the ACE-2 or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of ACE-2 as a marker is useful for optimizing effective dose).

These and other methods are described in further detail in the following sections.

8.1. Prognostic and Diagnostic Assays

The present methods provide means for determining if a subject has (diagnostic) or is at risk of developing (prognostic) a disease, condition or disorder that is associated with an aberrant ACE-2 activity, e.g., an aberrant level of ACE-2 protein or an aberrant bioactivity. As set forth below, diseases or conditions that can be caused by or contributed to an abnormal ACE-2 level or bioactivity include diseases or conditions, which are caused by or contributed to by an abnormal amount of a target peptide of ACE-2 or level of angiotensin or kinetensin conversion product, resulting, e.g., from inappropriate hydrolysis. For example, the target peptide can be angiotensin I and the disease or condition associated with an aberrant level of an angiotensin conversion product, e.g., angiotensin II level (in this case abnormally high level) can be hypertension or congestive heart failure. In fact, in at least some tissues, an abnormally high angiotensin II level could result from an abnormally low activity of an ACE-2 enzyme, thereby allowing most or all of the angiotensin I to be converted into angiotensin II, instead of Ang.(1-9). Diseases associated with an abnormal kinetensin or kinetensin conversion product include histamine associated conditions such as allergies. The target peptide can also be a kinin, and the diseases or conditions associated with an aberrant kinin level (in this case an abnormally high kinin level) include inflammatory diseases, and pain. Furthermore, an abnormally high ACE-2 mRNA level has been found in cardiac tissue from individuals which had CHF (see Examples). Similarly, ACE has been found to be present at increased levels in the free wall, septum and apex of the hypertrophied left ventricle (Schunkert et al. (1990) J. Clin. Invest. 86:1913). Thus, it is believed that an abnormally high level of ACE-2 correlates with heart failure. Accordingly, the invention provides methods for determining whether a subject has or is likely to develop hypertension, hypotension, congestive heart failure, or a kinetensin associated condition, for example, comprising determining the level of an ACE-2 gene or protein, an ACE-2 bioactivity and/or the presence of a mutation or particular polymorphic variant in the ACE-2 gene. The invention also provides methods for determining whether the pain of a subject is caused by an abnormally low level of ACE-2.

Since ACE-2 catalyzes hydrolysis of yet other peptides, e.g, neuropeptides such as neurotensin, the invention also provides methods for diagnosing, for example, neurological diseases or other diseases caused by inappropriate levels of ACE-2 target peptides, or conversion products thereof. Thus, ACE-2 therapeutics may be used for the treatment of neuropsychiatric disorders, especially those associated with a dysfunction of the dopaminergic systems, for example psychoses, more especially schizophrenia, and diseases of movement such as Parkinson's disease (D. R. Handrich et al., Brain Research, 1982, 231, 216-221 and C. B. Nemeroff, Biological Psychiatry, 1980, 15 (2), 283-302). They may be used to diagnose and/or treat malignant neoplastic diseases, for example human meningiomas which are not surgically accessible (P. Mailleux, Peptides, 1990, 11, 1245-1253), cancers of the prostate (I. Sehgal et al., Proc. Nat. Acad. Sci., 1994, 91, 4673-4677) and small cell cancers of the lung (T. Sethi et al., Cancer Res., 1991, 51, 3621-3623). They may be used in the treatment of motor, secretory, ulcerous and/or tumoral gastrointestinal disorders (review by A. Shulkes in "Gut Peptides: Biochemistry and Physiology, Ed. J. Waish and G. J. Dockray, 1994"). ACE-2 therapeutics can be used in the treatment of complaints such as: irritable bowel syndrome, diarrhoea, colitis, ulcers, tumours of the gastrointestinal tract, dyspepsia, pancreatitis and oesophagitis. They may also be of value as modulators of food intake (Beck, B. Metabolism, 1995, 44, 972-975). The compounds according to the invention may be indicated as diuretics, and for treating certain disorders caused by stress, such as migraines, neurogenic pruritus and interstitial cystitis (Theoharides T. C. et al., Endocrinol., 1995, 136, 5745-5750). The compounds of the present invention may also be of value in analgesia, by acting on the effects of morphine (M. O. Urban, J. Pharm. Exp. Ther., 1993, 265, 2, 580-586).

Since ACE-2 also appears to be involved in disorders associated with abnormalities in the conduction system of the heart, such as arrhythmias, the present invention also provides methods for determining if a subject has or is at risk of developing a disorder associated with abnormalities in the conduction system of the heart, such as an arrhythmia.

In one embodiment, the method comprises determining whether a subject has an abnormal mRNA and/or protein level of ACE-2, such as by Northern blot analysis, reverse transcription-polymerase chain reaction (RT-PCR), in situ hybridization, immunoprecipitation, Western blot hybridization, or immunohistochemistry. According to the method, cells are obtained from a subject and the ACE-2 protein or mRNA level is determined and compared to the level of ACE-2 protein or mRNA level in a healthy subject. An abnormal level of ACE-2 polypeptide or mRNA level is likely to be indicative of an aberrant ACE-2 activity.

In another embodiment, the method comprises measuring at least one activity of ACE-2. For example, the catalytic activity of ACE-2, e.g., capability to catalyze hydrolysis of certain peptides, e.g., angiotensin and/or kinins, can be determined, e.g., as described herein. Similarly, the constant of affinity of an ACE-2 protein of a subject with a target peptide, e.g. angiotensin or a kinin, can be determined. Comparison of the results obtained with results from similar analysis performed on ACE-2 proteins from healthy subjects will be indicative of whether a subject has an abnormal ACE-2 activity. Measurement of Ang.(1-9), Ang.(1-5), and/or kinetensin (1-8), level can also be used as an indicator of the activity of an ACE-2 enzyme in a subject. Such measurements can be done by spectrometry, as described herein.

In preferred embodiments, the methods for determining whether a subject has or is at risk for developing a disease associated with an aberrant ACE-2 activity is characterized as comprising detecting, in a sample of cells from the subject, the presence or absence of a genetic alteration characterized by at least one of (i) an alteration affecting the integrity of a gene encoding an ACE-2 polypeptide, or (ii) the mis-expression of the ACE-2 gene. To illustrate, such genetic alterations can be detected by ascertaining the existence of at least one of (i) a deletion of one or more nucleotides from an ACE-2 gene, (ii) an addition of one or more nucleotides to an ACE-2 gene, (iii) a substitution of one or more nucleotides of an ACE-2 gene, (iv) a gross chromosomal rearrangement of an ACE-2 gene, (v) a gross alteration in the level of a messenger RNA transcript of an ACE-2 gene, (vii) aberrant modification of an ACE-2 gene, such as of the methylation pattern of the genomic DNA, (vii) the presence of a non-wild type splicing pattern of a messenger RNA transcript of an ACE-2 gene, (viii) a non-wild type level of an ACE-2 polypeptide, (ix) allelic loss of an ACE-2 gene, and/or (x) inappropriate post-translational modification of an ACE-2 polypeptide. As set out below, the present invention provides a large number of assay techniques for detecting alterations in an ACE-2 gene. These methods include, but are not limited to, methods involving sequence analysis, Southern blot hybridization, restriction enzyme site mapping, and methods involving detection of absence of nucleotide pairing between the nucleic acid to be analyzed and a probe. These and other methods are further described infra.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene, such as a single nucleotide polymorphism ("SNP"), in a subject can render the subject susceptible to developing a specific disease or disorder. Polymorphic regions have been identified in the human ACE-2 gene (see Examples). The link with a specific disease can now readily be determined by studying specific populations of individuals, e.g, individuals which developed a specific disease, such as hypertension or CHF. A polymorphic region can be located in any region of a gene, e.g., exons, in coding or non coding regions of exons, introns, and promoter region.

Allelic variants of the human ACE gene have also been described and in some cases allelic variants have been found to be strongly associated with a higher risk for acute coronary events, sudden cardiac death, vascular restenosis after angioplasty, and idiopathic and hypertrophic cardiomyopathy (Malik et al. (1997) Am Heart J. 134:514). Thus, the invention provides methods for determining the identity of the allele or allelic variant of a polymorphic region of an ACE-2 gene, and optionally ACE gene, in a subject, to thereby determine whether the subject has or is at risk of developing a disease or disorder associated with a specific allelic variant of a polymorphic region.

In an exemplary embodiment, there is provided a nucleic acid composition comprising a nucleic acid probe including a region of nucleotide sequence which is capable of hybridizing to a sense or antisense sequence of an ACE-2 gene or naturally occurring mutants thereof, or 5' or 3' flanking sequences or intronic sequences naturally associated with the subject ACE-2 genes or naturally occurring mutants thereof. The nucleic acid of a cell is rendered accessible for hybridization, the probe is contacted with the nucleic acid of the sample, and the hybridization of the probe to the sample nucleic acid is detected. Such techniques can be used to detect alterations or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region, e.g., probes comprising or hybridizing specifically to SEQ ID NOs:87, 89, 91, 93, 95, 97, 99, and 101. Preferably these probes do not hybridize to SEQ ID NOs:86, 88, 90, 92, 94, 96, 98, or 100 or the complements thereof. Other preferred probes hybridize specifically to SEQ ID NOs: 86, 88, 90, 92, 94, 96, 98, or 100 or complement thereof, but not to SEQ ID NOs: 87, 89, 91, 93, 95, 97, 99, and 101 or complement thereof. In a preferred embodiment of the invention, several probes capable of hybridizing specifically to allelic variants, such as single nucleotide polymorphisms, are attached to a solid phase support, e.g., a "chip". Oligonucleotides can be bound to a solid support by a variety of processes, including lithography. For example a chip can hold up to 250,000 oligonucleotides. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the alteration comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) Science 241:1077-1080; and Nakazawa et al. (1994) PNAS 91:360-364), the latter of which can be particularly useful for detecting point mutations in the ACE-2 gene (see Abravaya et al. (1995) Nuc Acid Res 23:675-682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to an ACE-2 gene under conditions such that hybridization and amplification of the ACE-2 gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Preferred hybridization primers are set forth in the Examples.

Alternative amplification methods include: self sustained sequence replication (Guatelli, J. C. et al., 1990, Proc. Natl. Acad. Sci. USA 87:1874-1878), transcriptional amplification system (Kwoh, D. Y. et al., 1989, Proc. Natl. Acad. Sci. USA 86:1173-1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in, or allelic variants, of an ACE-2 gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the ACE-2 gene and detect mutations by comparing the sequence of the sample ACE-2 with the corresponding wild-type (control) sequence. Exemplary sequencing reactions include those based on techniques developed by Maxim and Gilbert (Proc. Natl Acad Sci USA (1977) 74:560) or Sanger (Sanger et al (1977) Proc. Nat. Acad. Sci 74:5463). It is also contemplated that any of a variety of automated sequencing procedures may be utilized when performing the subject assays (Biotechniques (1995) 19:448), including sequencing by mass spectrometry (see, for example PCT publication WO 94/16101; Cohen et al. (1996) Adv Chromatogr 36:127-162; and Griffin et al. (1993) Appl Biochem Biotechnol 38:147-159). It will be evident to one skilled in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type ACE-2 sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymod. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in ACE-2 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on an ACE-2 sequence, e.g., a wild-type ACE-2 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations or the identity of the allelic variant of a polymorphic region in ACE-2 genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125-144; and Hayashi (1992) *Genet Anal Tech Appl* 9:73-79). Single-stranded DNA fragments of sample and control ACE-2 nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations or the identity of the allelic variant of a polymorphic region include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al., Science 241:1077-1080 (1988). The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923-8927 (1990). In this method, PCR is used to achieve the exponential amplification of target DNA, which is then detected using OLA.

Several techniques based on this OLA method have been developed and can be used to detect specific allelic variants of a polymorphic region of an ACE-2 gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996)Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in an ACE-2 gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650, 840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA □ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids. Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA TM in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al., Amer.J. Hum. Genet. 52:46-59 (1993)).

For mutations that produce premature termination of protein translation, the protein truncation test (PTT) offers an efficient diagnostic approach (Roest, et. al., (1993) *Hum. Mol. Genet.* 2:1719-21; van der Luijt, et. al., (1994) *Genomics* 20:1-4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

The methods described herein may be performed, for example, by utilizing pre-packaged diagnostic kits comprising at least one probe nucleic acid, primer set; and/or antibody reagent described herein, which may be conveniently used, e.g., in clinical settings to diagnose patients exhibiting symptoms or family history of a disease or illness involving an ACE-2 polypeptide.

Any cell type or tissue may be utilized in the diagnostics described below. In a preferred embodiment a bodily fluid, e.g., blood or urine, is obtained from the subject to determine the presence of a mutation or the identity of the allelic variant of a polymorphic region of an ACE-2 gene. A bodily fluid, e.g, blood, can be obtained by known techniques (e.g. venipuncture). Alternatively, nucleic acid tests can be performed on dry samples (e.g. hair or skin). For prenatal diagnosis, fetal nucleic acid samples can be obtained from maternal blood as described in International Patent Application No. WO91/07660 to Bianchi. Alternatively, amniocytes or chorionic villi may be obtained for performing prenatal testing.

When using RNA or protein to determine the presence of a mutation or of a specific allelic variant of a polymorphic region of an ACE-2 gene, the cells or tissues that may be utilized must express the ACE-2 gene. Preferred cells for use in these methods include kidney cells and cardiac cells (see Examples). Alternative cells or tissues that can be used, can be identified by determining the expression pattern of the specific ACE-2 gene in a subject, such as by Northern blot analysis.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutatnt ACE-2 polypeptides or allelic variant thereof, which are discussed above, may also be used in disease diagnostics and prognostics. Such diagnostic methods, may be used to detect abnormalities in the level of ACE-2 polypeptide expression, or abnormalities in the structure and/or tissue, cellular, or subcellular location of an ACE-2 polypeptide. Structural differences may include, for example, differences in the size, electronegativity, or antigenicity of the mutant ACE-2 polypeptide relative to the normal ACE-2 polypeptide. Protein from the tissue or cell type to be analyzed may easily be detected or isolated using techniques which are well known to one of skill in the art, including but not limited to western blot analysis. For a detailed explanation of methods for carrying out Western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of ACE-2 polypeptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the ACE-2 polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-ACE-2 polypeptide specific antibody is via linkage to an enzyme and use in an enzyme immunoassay (EIA) (Voller, "The Enzyme Linked Immunosorbent Assay (ELISA)", *Diagnostic Horizons* 2:1-7, 1978, Microbiological Associates Quarterly Publication, Walkersville, Md.; Voller, et al., J. Clin. Pathol. 31:507-520 (1978); Butler, Meth. Enzymol. 73:482-523 (1981); Maggio, (ed.) *Enzyme Immunoassay,* CRC Press, Boca Raton, Fla., 1980; Ishikawa, et al., (eds.) *Enzyme Immunoassay,* Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays,* Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a gene or gene product or polymorphic variants can be used to monitor the course of treatment or therapy.

In yet other diagnostic methods, the amount of one or more ACE-2 target peptide or conversion product thereof is determined. Such amounts can be indicative of the existence of an aberrrant ACE-2 level or activity and can be predictive of diseases or disorders associated therewith.

8.2. Pharmacogenomics

Knowledge of the particular alteration or alterations, resulting in defective or deficient ACE-2 genes or proteins in an individual (the ACE-2 genetic profile), alone or in conjunction with information on other genetic defects contributing to the same disease (the genetic profile of the particular disease) allows a customization of the therapy for a particular disease to the individual's genetic profile, the goal of "pharmacogenomics". For example, subjects having a specific allele of an ACE-2 gene may or may not exhibit symptoms of a particular disease or be predisposed of developing symptoms of a particular disease. Further, if those subjects are symptomatic, they may or may not respond to a certain drug, e.g., a specific ACE-2 therapeutic, but may respond to another. Thus, generation of an ACE-2 genetic profile, (e.g., categorization of alterations in ACE-2 genes which are associated with the development of a particular disease), from a population of subjects, who are symptomatic for a disease or condition that is caused by or contributed to by a defective and/or deficient ACE-2 gene and/or protein (an ACE-2 genetic population profile) and comparison of an individual's ACE-2 profile to the population profile, permits the selection or design of drugs that are expected to be safe and efficacious for a particular patient or patient population (i.e., a group of patients having the same genetic alteration).

For example, an ACE-2 population profile can be performed, by determining the ACE-2 profile, e.g., the identity of ACE-2 genes, in a patient population having a disease, which is caused by or contributed to by a defective or deficient ACE-2 gene. Optionally, the ACE-2 population profile can further include information relating to the response of the population to an ACE-2 therapeutic, using any of a variety of methods, including, monitoring: 1) the severity of symptoms associated with the ACE-2 related disease, 2) ACE-2 gene expression level, 3) ACE-2 mRNA level, and/or 4) ACE-2 protein level. and (iii) dividing or categorizing the population based on the particular genetic alteration or alterations present in its ACE-2 gene or an ACE-2 pathway gene. The ACE-2 genetic population profile can also, optionally, indicate those particular alterations in which the patient was either responsive or non-responsive to a particular therapeutic. This information or population profile, is then useful for predicting which individuals should respond to particular drugs, based on their individual ACE-2 profile.

In a preferred embodiment, the ACE-2 profile is a transcriptional or expression level profile and step (i) is comprised of determining the expression level of ACE-2 proteins, alone or in conjunction with the expression level of other genes, known to contribute to the same disease, can be measured in many patients at various stages of the disease.

Pharmacogenomic studies can also be performed using transgenic animals. For example, one can produce transgenic mice, e.g., as described herein, which contain a specific allelic variant of an ACE-2 gene. These mice can be created, e.g, by replacing their wild-type ACE-2 gene with an allele of the human ACE-2 gene. The response of these mice to specific ACE-2 therapeutics can then be determined.

8.3. Monitoring of Effects of ACE-2 Therapeutics During Clinical Trials

The ability to target populations expected to show the highest clinical benefit, based on the ACE-2 or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of ACE-2 as a marker is useful for optimizing effective dose).

The treatment of an individual with an ACE-2 therapeutic can be monitored by determining ACE-2 characteristics, such as ACE-2 protein level or activity, ACE-2 mRNA level, ACE-2 transcriptional level, and/or level of one or more angiotensin or kinetensin conversion products, e.g., Ang.(1-9). This measurements will indicate whether the treatment is effective or whether it should be adjusted or optimized. Thus, ACE-2 can be used as a marker for the efficacy of a drug during clinical trials.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a preadministration sample from a subject prior to administration of the agent; (ii) detecting the level of expression of an ACE-2 protein, mRNA, or genomic DNA and/or level of one or more angiotensin or kinetensin conversion products, e.g., Ang.(1-9) in the preadministration sample; (iii) obtaining one or more post-administration samples from the subject; (iv) detecting the level of expression or activity of the ACE-2 protein, mRNA, or genomic DNA and/or level of one or more angiotensin or kinetensin conversion products, e.g., Ang.(1-9) in the post-administration samples; (v) comparing the level of expression or activity of the ACE-2 protein, mRNA, or genomic DNA and/or level of one or more angiotensin or kinetensin conversion products, e.g., Ang.(1-9) in the preadministration sample with that in the post administration sample or samples; and (vi) altering the administration of the agent to the subject accordingly. For example, increased administration of the agent may be desirable to increase the expression or activity of ACE-2 to higher levels than detected, i.e., to increase the effectiveness of the agent. Alternatively, decreased administration of the agent may be desirable to decrease expression or activity of ACE-2 to lower levels than detected, i.e., to decrease the effectiveness of the agent.

Cells of a subject may also be obtained before and after administration of an ACE-2 therapeutic to detect the level of expression of genes other than ACE-2, to verify that the ACE-2 therapeutic does not increase or decrease the expression of genes which could be deleterious. This can be done, e.g., by using the method of transcriptional profiling. Thus, mRNA from cells exposed in vivo to an ACE-2 therapeutic and mRNA from the same type of cells that were not exposed to the ACE-2 therapeutic could be reverse transcribed and hybridized to a chip containing DNA from numerous genes, to thereby compare the expression of genes in cells treated and not treated with an ACE-therapeutic. If, for example an ACE-2 therapeutic turns on the expression of a proto-oncogene in an individual, use of this particular ACE-2 therapeutic may be undesirable.

8.4. Use of ACE-2 Molecules as Surrogate Markers

The ACE-2 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the ACE-2 molecules of the invention may be detected, and may be correlated with one or more biological states in vivo. For example, the ACE-2 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1 994) *AIDS Treatment News Archive* 209.

The ACE-2 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., an ACE-2 marker) transcription or expression, the amplified marker may be in a quantity which is more readily detectable than the drug itself. Also, the marker may be more easily detected due to the nature of the marker itself; for example, using the methods described herein, anti-ACE-2 antibodies may be employed in an immune-based detection system for an ACE-2 polypeptide marker, or ACE-2-specific radiolabeled probes may be used to detect an ACE-2 mRNA marker. Furthermore, the use of a pharmacodynanic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The ACE-2 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or polypeptide (e.g., ACE-2 polypeptide or RNA) for specific tumor markers in a subject, a drug or course of treatment may be selected that is optimized for the treatment of the specific tumor likely to be present in the subject. Similarly, the presence or absence of a specific sequence mutation in ACE-2 DNA may correlate ACE-2 drug response. The use of pharmacogenomic markers therefore permits the application of the most appropriate treatment for each subject without having to administer the therapy.

9. Methods of Treatment

The present invention provides for both prophylactic and therapeutic methods of treating a subject having or likely to develop a disorder associated with aberrant ACE-2 expression or activity or aberrant level of angiotensin or other target peptide or conversion product thereof, e.g., disorders or diseases associated with an abnormal blood pressure.

9.1. Prophylactic Methods

In one aspect, the invention provides a method for preventing in a subject, a disease or condition associated with an aberrant ACE-2 expression or activity or an abnormal amount of target peptide or abnormal blood pressure or abnormal conductance, by administering to the subject an agent which modulates ACE-2 expression or at least one ACE-2 activity. Subjects at risk for such a disease can be identified by a diagnostic or prognostic assay, e.g., as described herein. Administration of a prophylactic agent can occur prior to the manifestation of symptoms characteristic of the ACE-2 aberrancy, such that a disease or disorder is prevented or, alternatively, delayed in its progression. Depending on the type of ACE-2 aberrancy, for example, a ACE-2 agonist or ACE-2 antagonist agent can be used for treating the subject prophylactically. In particular, an ACE-2 therapeutic can be administered prophylactically in a subject having elevated levels of angiotensin II, before any other symptoms are present. Such a prophylactic treatment could thus prevent the development of a abnormally high blood pressure. An agonist can also be administered prophylactically to prevent the development of a kinetensin associated condition, e.g., allergies. An antagonist may also be administered prophylactically to prevent the development of a disorder associated with abnormal conductance, such as an arrhythmia. The prophylactic methods are similar to therapeutic methods of the present invention and are further discussed in the following subsections.

9.2. Therapeutic Methods

In general, the invention provides methods for treating a disease caused by or contributed to by an aberrant ACE-2 activity or an abnormal blood pressure or abnormal amount of target peptide or angiotensin conversion product in a subject, comprising administering to the subject an effective amount of a pharmaceutical composition comprising a compound which is capable of modulating an ACE-2 activity, such that the disease is treated or prevented in the subject. Among the approaches which may be used to ameliorate disease symptoms involving an aberrant ACE-2 activity are, for example, antisense, ribozyme, and triple helix molecules described above. Examples of suitable compounds include the antagonists, agonists or homologues described in detail herein, as well as angiotensin conversion products or derivatives thereof.

9.3. Diseases or Conditions that can be Treated or Prevented with ACE-2 Therapeutics As set forth herein, ACE-2 has significant sequence homologies with ACE enzymes and has also been shown to hydrolyze angiotensin I into Ang.(1-9) (see Examples). It has also been described that Ang.(1-9) can further be hydrolyzed by ACE into Ang.(1-5). Thus, ACE-2 competes with ACE for the substrate angiotensin I and hydrolyzes angiotensin I into Ang.(1-9), instead of angiotensin II (Ang.(1-8)), a potent vasoconstrictor. Angiotensin I can also be converted into other peptides, having either vasoconstrictive or anti-hypertensive activity (e.g., Ang.(1-7), see, e.g., Chappel et al. (1998) Hypertension 31: 362). Various angiotensin conversion pathways are shown in FIG. 8. Thus, based at least on the fact that ACE-2 has the same substrate as ACE and that both types of enzymes share significant sequence homologies in functional domains, ACE-2 therapeutics can be used for similar therapeutic and preventive purposes as ACE, as well as additional ones. ACE-2 therapeutics can thus be used not only for treating or preventing diseases or disorders associated with an aberrant ACE-2 activity, but also for treating or preventing diseases or disorders associated with an aberrant ACE activity or activity of any other enzyme that is involved in the conversion of a substrate of ACE-2, such as angiotensin I. For example, ACE-2 therapeutics can be useful for treating diseases associated with an abnormal Ang.(1-5), Ang.(1-7) level, or Ang.(1-8) (i.e., angiotensin II) level. In a preferred embodiment, an ACE-2 antagonist is used for treating or preventing hypertension, hypotension, or arrhythmias and related diseases in a subject.

In certain embodiments, treating or preventing a disease in a subject includes administrating to the subject an ACE-2 therapeutic which is also an ACE therapeutic or administering to the subject both an ACE-2 and an ACE therapeutic. For example, the ACE-2 therapeutic is an antagonist of both ACE-2 and ACE. Thus, administration of such a compound to a subject will result in inhibition of hydrolysis of angiotensin I into angiotensin II as well as into Ang.(1-9). Alternatively, the ACE-2 therapeutic can be an agonist of both ACE-2 or ACE.

The identity of the therapeutic compound for use in treating or preventing individual diseases or disorders can be determined by performing in vitro and/or in vivo assays. Preferred assays are those using animal models, such as animal models for hypertension. In an illustrative embodiment, a hypertensive rat of the transgenic rat strain TGR(mREN2)27 harboring the murine Ren-2 gene or a transgenic rat comprising a transgene encoding human angiotensinogen and/or human renin (U.S. Pat. No. 5,731,489) are used. These transgenic rats develop fulminant hypertension at an early age (Lee et al. (1996) Am J Physiol 270: E919) and are thus useful for testing ACE-2 therapeutics. Such animal models can also be used for determining the effect of a specific angiotensin conversion product on a disorder, e.g., hypertension, and thereby allow to predict whether an agonist or an antagonist should be used for treating a specific disease or condition.

Accordingly, in a preferred embodiment, the compounds of the present invention are useful for regulating blood pressure and in particular arterial hypertension. The method comprises, e.g., administering to the subject an effective amount of a pharmaceutical composition comprising an ACE-2 therapeutic compound. An ACE-2 therapeutic compound can be, e.g., a compound which inhibits the formation of angiotensin II, a potent vasoconstrictor, such as an ACE-2 agonist, which, e.g., hydrolyzes angiotensin I into Ang.(1-9). Thus, in an illustrative example, an ACE-2 antagonist is administered for decreasing blood pressure and an agonist is administered for increasing blood pressure in a subject.

Blood pressure refers to the pressure exerted by the blood upon the walls of the blood vessels, e.g., arteries, and is usually measured on the radial artery by means of a sphygmomanometer, and expressed in millimeters of mercury. The following ranges of blood pressure are usually used a standard for normal versus abnormal blood pressure: a normal blood pressure corresponds to a diastolic blood pressure of less than 85 mm Hg; a high normal blood pressure corresponds to a diastolic blood pressure between 85 and 89 mm Hg; a mild hypertension corresponds to a diastolic blood pressure between 90-104 mm Hg; a moderate hypertension corresponds to a diastolic blood pressure between 105 and 114 mm Hg; and severe hypertension corresponds to a diastolic blood pressure higher than 115 mm Hg. Abnormal blood pressure can also be determined based on the systolic blood pressure (when the diastolic pressure is less than 90 mm Hg). Thus, a normal blood pressure corresponds to a systolic blood pressure of less than 140 mm Hg; a borderline systolic hypertension corresponds to a systolic blood pressure between 140 and 159 mm Hg; and isolated systolic hypertension corresponds to a systolic blood pressure higher than 160 mm Hg. This classification is borrowed from *Cecil: Essentials of Medicine,* Third Edition by Andreoli et al. W. B. Saunders Company (1993).

A diagnosis of hypertension, also referred to herein as "abnormally high blood pressure", is usually made in an adult over 18 years of age if the average of two or more blood pressure measurements on at least two subsequent visits is 90 mm Hg or higher diastolic or 140 mm Hg systolic. Since children and pregnant women have a lower blood pressure, a blood pressure over 120/80 (i.e., 120 mm Hg systolic blood pressure/80 mm Hg diastolic blood pressure), is considered abnormal. Isolated systolic hypertension (ISH) refers to a condition in which the systolic blood pressure is greater than 160 mm Hg and the diastolic blood pressure is less than 85 mm Hg. ISH is associated with enhanced morbidity.

ACE-2 therapeutics can also be used to treat other blood pressure related diseases or conditions, e.g., CHF, chronic heart failure, left ventricular hypertrophy, acute heart failure, myocardial infarction, and cardiomyopathy. In a preferred embodiment, ACE-2 therapeutics are used to treat CHF. CHF is characterized by the inability of the left ventricle to maintain a normal blood pressure. This results in a baroflex-mediated reflex increase in sympathetic discharge, which stimulates the myocardium to beat faster and stronger, yet increases peripheral vasoconstriction so that the afterload rises and the load on the failing myocardium augments (Lionel H. Opie, Drugs for the Heart, Third Edition, W. B. Saunders Co., 1991). Excess adrenergic activity also results in enhanced activity of the renin-angiotensin system, further increasing peripheral vascular resistance and contributing to fluid retention (edema) by stimulation of the secretion of aldosterone. In addition, angiotensin promotes the release of vasopressin to contribute to abnormal volume regulation and hyponatremia in severe CHF. Overloading of the left ventricle also results in hypertrophy of the ventricular muscle, resulting in a decrease in its contractility, further contributing to the condition. As described in the background section, vasodilators such as ACE-inhibitors are efficient in treating CHF and reducing mortality. ACE-inhibitors are particularly preferred therapeutics for treating CHF since they are able to inhibit the deleterious neurohumoral viscious circle involving angiotensin-renin-aldosterone. Thus, it is believed that ACE-2 therapeutics, which also modulate angiotensin hydrolysis, will also be useful for treating and preventing CHF.

Since ACE-2 has been found to hydrolyze neurotensin, ACE-2 therapeutics can be used for treating or preventing conditions associated with neurotensin. Neurotensin, is a 13 amino acid peptide having the following amino acid sequence: pGlu-Leu-Tyr-Glu-Asn-Lys-Pro-Arg-Arg-Pro-Tyr-Ile-Leu (SEQ ID NO:107) is a putative neurotransmitter/neuromodulator in the central and peripheral nervous system. It has been shown to decrease blood pressure in rats after i.v. injection (Di Paola and Richelson (1990) Eur. J. Pharmacol. 175: 279), to increase coronary blood flow in open-chest dogs (Bauer et al. (1995) J. Cardiovasc. Pharmacol. 25:756), and to inhibit endogenous norepinephrine releas in rats during peri-arterial nerve stimulation (Tsuda et al. (1993) Am. J. Hypertens. 6:473). In a rat failure model (moncrotaline treated rats), neurotensin levels are decreased in both ventricles. Thus, based on these results, modulation of neurotensin and conversion products thereof can be used for modulating blood pressure.

In another embodiment, ACE-2 therapeutics may be used to treat a disorder associated with abnormal conductance, such as an arrhythmia.

In another embodiment, ACE-2 therapeutics may be used to treat a disorder such as azotemia, renal disease, renal failure, glomerular disease, glomerulonephritis (vasculitis), nephritis, acute tubular necrosis, proteinuria, hematuria, pyuria, pyelonephritis, polyuria, fluid and electrolyte (e.g., sodiuma nd patassium) disturbances, hypovolemia, hyponatremia, hypernatremia, hypokalemia (Liddle's Syndrome, Bartter's Syndrome), hyperkalemia (Gordon's Syndrome), acidosis, alkalosis and hyperchloremic metabolic disorders.

Since neurotensin is found mainly in gut endocrine cells of the ileum and is released following a meal, ACE-2 therapeutics could be used for digestive purposes, and for treating and/or preventing disorders relating to digestion.

In another embodiment, the invention provides methods for regulating cell proliferation, such as smooth cell proliferation. Smooth muscle cell proliferation in the intima of muscular arteries is a primary cause of vascular stenosis in atherosclerosis, after vascular surgery, and after coronary angioplasty. Several animal studies have indicated that the renin-angiotensin system plays an important role in this vascular response to injury. In particular, it has been shown that chronic treatment with ACE inhibitors reduced myointimal thickening following balloon injury in rat carotid artery or aorta (Powell et al. (1991) J. Am. Coll. Cardiol. 17:137B-42B). The stimulatory effect of angiotensin II on cell growth and replication in the cardiovascular system, which may result in myocardial hypertrophy and hypertrophy or hyperplasia of conduit and resistance vessels in certain subjects is mediated through angiotensin II receptors (subtype AT1) (Rosendorff C. (1996) J. Am. Coll. Cardiol.28: 803). The importance of ACE in atherosclerosis is further described, e.g, in Malik et al. (1997) Am. Heart J. 134:514. It has also been shown, that angiotensin caused myocyte hypertrophy and fibroblast proliferation associated with the induction of mRNA for several early response genes (c-fos, c-jun, jun B, Egr-1 and c-myc), angiotensinogen and transforming growth factor beta (TGFβ) (Rosendorff (1996) J. Am. Coll. Cardiol. 28: 803-12; Paquet et al. (1990) J. Hypertens.: 8: 565-72).

Accordingly, in one embodiment, the invention provides a method for reducing or inhibiting smooth muscle cell proliferation, comprising administering to a subject an efficient amount of a composition comprising an ACE-2 therapeutic. In one embodiment, the therapeutic is administered systemically. However, the ACE-2 therapeutic can also be administered locally, e.g., at a site of vascular injury.

ACE-2 therapeutics can further be used in treating kidney diseases or disorders. Angiotensin and ACEs are important in the development and for the maintenance of the functional and structural integrity of the adult kidney (see, e.g, Hilgers et al. (1997) Semin. Nephrol. 17:492). Chronic renal disease evolves to end-stage renal failure through events, including enhanced intraglomerular pressure and plasma protein ultrafiltration, mediated at least in part by angiotensin II. It has been reported that ACE inhibitors reduce intracapillary pressure and ameliorate glomerular size-selective function (see, e.g., Ruggenenti and Remuzzi (1997) Curr. Opin. Nephrol. Hypertens. 6:489). Thus, based at least in part on the fact that ACE-2 is expressed in kidney and is homologous to ACE, ACE-2 therapeutics an be used for treating and preventing renal diseases.

The role of angiotensin inhibitors in the release of norepinephrine from the terminal adrenergic neurons leads to the proposal that angiotensin inhibitors should be useful for treating various other hyperadrenergic states, such as acute myocardial infarction (AMI) and some ventricular arrthythmias.

The invention further provides methods for treating kinetensin associated conditions. As described herein, ACE-2 cleaves the C-terminal amino acid (leucine) from kinetensin. Kinetensin is a nine amino acid peptide having SEQ ID NO:23 which has been reported to induce a dose-dependent release of histamine from mast cells, as well as induce a dose-dependent increase in vascular permeability when injected intradermally (Sydborn et al. (1989) *Agents Actions* 27: 68) into rats. Accordingly, modulating the plasma and/or tissue level of kinetensin, such as by modulating the hydrolysis of the C-terminal amino acid from kinetensin, should be useful for treating conditions that are caused by, or contributed to by, an abnormal kinetensin level. Such conditions include those caused by, or contributed to by, an abnormal histamine release from mast cells and/or by an abnormal vascular permeability. Since excessive histamine release is associated with local or systemic allergic reactions, including exzema, asthma, anaphylactic shock, ACE-2 therapeutics are believed to be useful for treating these conditions.

In another preferred embodiment, the invention provides a method for decreasing or inhibiting an inflammatory reaction. In fact, based at least in part on the homology between ACE and ACE-2 and the fact that ACE is capable of hydrolysing polypeptides other than angiotensin I, such as kinins, e.g., bradykinin, ACE-2 is likely to hydrolyze kinins. In fact, ACE-2 hydrolyzes bradykinin (see Examples). Kinins (e.g., bradykinin and kallidin) are generally involved in inflammation. In fact, part of the initiation process of an inflammatory reaction is mediated by peptide kinins, such as bradykinin, which are liberated by kallikrein proteases upon tissue destruction. The kinins or other peptide messengers, act on specific cell receptors at the inflammation site to activate the phospholipase enzymes A2 and/or C, to initiate the arachidonate cascade.

Bradykinins are involved in inflammatory reactions on various tissues. For example, it has been found that bradykinin is produced in inflammatory reactions in the intestine, provoking contraction of smooth muscle and secretion of fluid and ions. The existence of specific bradykinin receptors in the mucosal lining of the intestine and in intestinal smooth muscle is demonstrated by Manning et al. (Nature 229: 256 (1982)), showing the influence of bradykinin in very low concentrations upon fluid and ion secretion. Thus, the invention can be used to treat inflammatory reactions in the intestine.

Similarly, the compounds of the present invention are also expected to be effective in treating other diseases or conditions such as SIRS (Systemic Inflammatory Response Syndromes)/sepsis, polytrauma, inlanmmatory bowel disease, acute and chronic pain, bone destruction in rheumatoid and osteo arthritis and periodontal disease, dysmenorrhea, premature labor, brain edema following focal injury, diffuse axonal injury, stroke, reperfusion injury and cerebral vasospasm after subarachnoid hemorrhage, allergic disorders including asthma, adult respiratory distress syndrome, wound healing and scar formation.

Furthermore, the invention also provides analgesic methods. In fact, bradykinin is known to be one of the most potent naturally occurring stimulators of C-fiber afferents mediating pain. The production of bradykinin results in pain at the site of the pathological condition, and the overproduction intensifies the pain directly or via stimulation by bradykinin of the activation of the arachidonic acid pathway which produces prostaglandins and leukotrienes, more distal mediators of inflammation (Handbook of Experimental Pharmacology, Vol.25, Springer-Verlag (1969), and Vol. 25 Supplement (1979); Stewart, in "Mediators of the Inflammatory Process," Henson and Murphy, eds., Elsevier,(1989)). For example, direct application of bradykinin to denuded skin or intra-arterial or visceral injection results in the sensation of pain in animals and in man. Kinin-like materials have been isolated from inflammatory sites produced by a variety of stimuli. In addition, bradykinin receptors have been localized to nociceptive peripheral nerve pathways and bradykinin has been demonstrated to stimulate central fibers mediating pain sensation. Bradykinin has also been shown to be capable of causing hyperalgesia in animal models of pain. (Burch et al., J. Med. Chem., 30:237-269 (1990) and Clark, W. G. Handbook of Experimental Pharmacology, Vol. XXV: Bradykinin, kallidin, and kallikrein. Erdo, E. G. (ed.), 311-322 (1979)). Furthermore, a number of studies have demonstrated that bradykinin antagonists are capable of blocking or ameliorating both pain as well as hyperalgesia in both animals and man (Ammons, W. S. et al. The American Physiological Society, 0363-6119 (1985); Clark, Handbook of Experimental Pharmacology, Vol. XXV: Bradykinin, kallidin, and kallikrein. Erdo, E. G. (ed.), 311-322 (1979); Costello al., European Journal of Pharmacology, 171:259-263 (1989); Laneuville et al. European Journal of Pharmacology, 137:281-285 (1987); Steranka et al, European Journal of Pharmacology, 16:261-262 (1987); and Steranka et al, Neurobiology, 85:3245-3249 (1987)). Similarly, Whalley et al, in Naunyn Schmiederberg's Arch. Pharmacol.,336:652-655 (1987) have demonstrated that bradykinin antagonists are capable of blocking bradykinin-induced pain in a human blister base model. Thus, the compositions of the invention comprising an ACE-2 agonist therapeutics can be applied topically to hydrolyze and thereby inactive bradykinin and/or related kinins to thereby inhibit or reduce pain in burned skin, e.g. in severely burned patients in whom large doses of narcotics are required over long periods of time and for the local treatment of relatively minor burns or other forms of local skin injury.

Similarly, the production of bradykinin seems to be associated with the pain in angina and myocardial ischemia (Kimura et al., Amer. Heart J. 85: 635 (1973); Staszewska-Barczak et al., Cardiovasc. Res. 10: 314 (1976)). Thus, ACE-2 therapeutics could be used to relieve pain in subjects suffering from angina or myocardial ischemia by degradation of bradykinin.

The use of the compounds of the invention for reducing or inhibiting pain have significant advantages over currently accepted therapeutic approaches to analgesia. In fact, while mild to moderate pain can be alleviated with the use of non-steroidal anti-inflammatory drugs and other mild analgesics, severe pain such as that accompanying surgical procedures, burns and severe trauma requires the use of narcotic analgesics. These drugs carry the limitations of abuse, potential, physical and psychological dependence, altered mental status and respiratory depression which significantly limit their usefulness. On the contrary, the compounds of the invention, i.e., ACE-2 agonist therapeutics, are likely to be devoid of such undesirable secondary effects.

Other disease states in which ACE-2 agonist therapeutics can be useful include in the treatment of burns, perioperative pain, migraine and other forms of pain, shock, central nervous system injury, rhinitis, premature labor, etc. Yet other diseases or conditions in which bradykinin is overproduced and in which ACE-2 agonist therapeutics capable of inactivating bradykinin can be useful include pathological conditions such as septic (Robinson et al., Am. J. Med. 59: 61 (1975)) and hemorrhagic (Hirsch et al., J. Surg. Res. 17: 147 (1974)) shock, anaphylaxis (Collier and James, J. Physiol. 160: 15P (1966)), arthritis (Jasani et al., Ann. Rheum. Dis. 28: 497 (1969); Hamberg et al., Agents Actions 8: 50(1978); Sharma et al., Arch. Int. Pharmacodyn. 262: 279 (1983)), rhinitis (Proud et al., J. Clin. Invest. 72: 1678 (1983); Naclerio et al., Clin. Res. 33: 613A (1985)), asthma (Christiansen et al., J. Clin. Invest. 79: 188 (1987)), inflammatory bowel disease (Zeitlin and Smith, Gut 14: 133 (1973)), sarcoidosis (*Cecil: Essentials of Medicine,* Third Edition by Andreoli et al. W.B. Saunders Company (1993)), and certain other conditions including acute pancreatitis, post-gastrectomy dumping syndrome, carcinoid syndrome, migraine, and hereditary angioedema.

Furthermore, bradykinin and bradykinin-related kinins are not only produced endogenously, but may also be injected into an animal, e.g., a human, via stings or bites. It is known that insects such as hornets and wasps inject bradykinin related peptides that cause pain, swelling and inflammation. Accordingly, the method provides methods and compounds for treating insect stings or bites, comprising administering either locally or systemically to a subject having an insect bite or sting an ACE-2 agonist therapeutic, to thereby relieve the pain and reduce the inflammation.

Based at least on the presence of ACE-2 in testis, ACE-therapeutics could also have a utility in treating infertility or other disorders relating to gamete maturation.

In addition, it has been discovered that ACE inhibitors are useful in treating cognitive disorders [German Application No. 3901-291-A, published Aug. 3, 1989]. Accordingly, ACE-2 antagonists of the invention are also likely to be useful in treating cognitive disorders.

9.4. Effective Dose

Toxicity and therapeutic efficacy of such compounds can be determined by standard pharmaceutical procedures in cell cultures or experimental animals, e.g., for determining The $Ld_{50}$ (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

9.5. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for the therapeutic ACE-2 gene can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054-3057). An ACE-2 gene, such as any one of the sequences represented in the group consisting of SEQ ID NOS 1 and 3 or a sequence homologous thereto can be delivered in a gene therapy construct by electroporation using techniques described, for example, by Dev et al. ((1994) Cancer Treat Rev 20:105-115).

The pharmaceutical preparation of the gene therapy construct or compound of the inventioncan consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

10. Kits

The invention further provides kits for use in diagnostics or prognostic methods or for treating a disease or condition associated with an aberrant ACE-2 activity, ACE-2 target peptide level, or angiotensin or kinetensin conversion product level. The invention also provides kits for determining which ACE-2 therapeutic should be administered to a subject. The invention encompasses kits for detecting the presence of ACE-2 mRNA or protein in a biological sample or for determining the presence of mutations or the identity of polymorphic regions in an ACE-2 gene. For example, the kit can comprise a labeled compound or agent capable of detecting ACE-2 protein or mRNA in a biological sample; means for determining the amount of ACE-2 in the sample; and means for comparing the amount of ACE-2 in the sample with a standard. The compound or agent can be packaged in a suitable container. The kit can further comprise instructions for using the kit to detect ACE-2 mRNA or protein.

In one embodiment, the kit comprises a pharmaceutical composition containing an effective amount of an ACE-2 therapeutic and instruction for use in treating or preventing hypertension. In another embodiment, the kit comprises a pharmaceutical composition comprising an effective amount of an ACE-2 agonist therapeutic and instructions for use in treating insect bites. Generally, the kit comprises a pharmaceutical composition comprising an effective amount of an ACE-2 agonist or antagonist therapeutic and instructions for use as an analgesic.

Yet other kits can be used to determine whether a subject has or is likely to develop a disease or condition associated with an aberrant ACE-2 activity. Such a kit can comprise, e.g., one or more nucleic acid probes capable of hybridizing specifically to at least a portion of an ACE-2 gene or allelic variant thereof, or mutated form thereof.

11. Additional Uses for ACE-2 Proteins and Nucleic Acids

The ACE-2 nucleic acids of the invention can further be used in the following assays. In one embodiment, the human ACE-2 nucleic acid having SEQ ID NO:1 or a portion thereof, or a nucleic acid which hybridizes thereto can be used as a chromosomal marker in genomic linkage analysis. Human ACE-2 has been localized to chromosome Xp21-22. Comparison of the chromosomal location of the ACE-2 gene with the location of chromosomal regions which have been shown to be associated with specific diseases or conditions, e.g., by linkage analysis (coinheritance of physically adjacent genes), can be indicative of diseases or conditions in which ACE-2 may play a role. A list of chromosomal regions which have been linked to specific diseases can be found, for example, in V. McKusick, Mendelian Inheritance in Man (available on line through Johns Hopkins University Welch Medical Library) and at http://www3.ncbi.nlm.nih.gov/Omim/(Online Mendelian Inheritance in Man). Furthermore, the ACE-2 gene can also be used as a chromosomal marker in genetic linkage studies involving genes other than ACE-2.

If the ACE-2 gene is shown to be localized in a chromosomal region which cosegregates, i.e., which is associated, with a specific disease, the differences in the cDNA or genomic sequence between affected and unaffected individuals are determined. The presence of a mutation in some or all of the affected individuals but not in any normal individuals, will be indicative that the mutation is likely to be causing or contributing to the disease.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization(B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

1. Cloning and Analysis of Human ACE-2

A full length cDNA encoding human ACE-2 was isolated as follows. A cDNA library was prepared from a human heart of a subject who had congestive heart failure. Random sequencing of clones from the library identified a 1.6 kb clone that has homology to human angiotensin converting enzyme, and which is thus referred to as ACE-2.

5' RACE was used to clone the 5' end of the ACE-2 gene. RACE was performed using Clontech's Marathon cDNA Amplification Kit. First strand cDNA synthesis was performed using the cDNA synthesis primer supplied with the kit and 1 µg poly $A^+$ RNA prepared from the heart of a 43 year old woman with an idiopathic cardiomyopathy using 100 u MMLV reverse transcriptase. Second strand cDNA synthesis was then performed using the second strand enzyme cocktail of the Clontech kit. The Marathon cDNA adaptor was ligated to the double stranded cDNA with T4 DNA ligase. A gene specific primer was designed starting about 400 bp downstream of the 5' end of the 1.6 kb ACE-2 clone. The primer had the nucleotide sequence 5' CAC AGG TTC CAC CAC CCC AAC TAT CTC 3' (SEQ ID NO:13, which corresponds to nucleotides 1528-1554 of SEQ ID NO:1) and the hybridization temperature (Tm) used was 62.7° C. (GC content of 55%). The gene specific primer and an adaptor primer were used for 5' RACE using the Advantage Klentaq polymerase mix under the following conditions: 1 cycle at 94° C. for 2 minutes; 35 cycles of 94° C. for 30 sec., 60° C. for 45 sec., 72° C. for 30 sec.; and 1 cycle at 72° C. for 5 minutes. A comparison of the partial ACE-2 clone with the previously cloned ACE genes indicated that about 1000 bp were necessary to have the full length clone if both genes have a similar length. RACE products of the expected size were obtained. These products were Southern blotted and shown to hybridize with a probe, corresponding to nucleotides 1152 to 1318 of SEQ ID NO:1, from the partial ACE-2 clone. The RACE products were run on a 1.2% agarose gel, the expected size fragments were visualized, excised and purified using the Jetsorb Gel Extraction kit (Genomed). The fragments were then ligated into the TA cloning vector pCR2.1 (InVitrogen). A clone containing a 1.6 kb insert was sequenced and found to have the 5' end of the gene.

A full length ACE encoding DNA was then prepared as follows. An EcoRI-BamHI fragment of the 5' RACE clone and a BamHI-NotI fragment of the partial clone containing the 3' end of the ACE-2 cDNA described above were ligated into the EcoRI-NotI sites of pCDNA3.1+ vector (InVitrogen). The clones were analyzed by restriction mapping and sequencing. This confirmed that full length cDNA clones encoding human ACE were obtained.

The cDNA described herein encoding ACE-2 is 3396 nucleotides long and has the nucleotide sequence shown in FIG. 1 and set forth in SEQ ID NO:1. A nucleic acid comprising this cDNA has been deposited at the American Type Culture Collection (12301 Parklawn Drive, Rockville, Md.) on Dec. 3, 1997 has been assigned ATCC Designation No. 209510. This cDNA has an open reading frame from nucleotide 82 to nucleotide 2496 of SEQ ID NO: 1 which is set forth in SEQ ID NO:3 and encodes a protein of 805 amino acids having the amino acid sequence shown in FIG. 1 and set forth in SEQ ID NO:2. The ACE-2 protein having SEQ ID NO:2 contains a hydrophobic signal sequence from amino acid 1 to amino acid 18. Thus, the mature ACE-2 protein has the amino acid sequence from about amino acid 19 to amino acid 805 of SEQ ID NO:2. The presence of the signal peptide indicates that the ACE-2 protein is secreted and/or membrane bound.

The ACE-2 protein further comprises a Zinc binding domain, from about amino acid 374 to amino acid 378 of SEQ ID NO:2 which is encoded by the nucleotide sequence from nucleotide 1201 to nucleotide 1215 of SEQ ID NO:1. The ACE-2 protein also comprises a hydrophobic transmembrane domain corresponding to amino acids 741 to amino acid 765 of SEQ ID NO:2 which is encoded by the nucleotide sequence from nucleotide 2302 to nucleotide 2376 of SEQ ID NO:1. This transmembrane domain could be mediating membrane attachment of the ACE-2 to a cell membrane.

A BLAST search (Altschul et al. (1990) J. Mol. Biol. 215:403) of the nucleic acid and the amino acid sequences of ACE-2 revealed that ACE-2 has significant homology to portions of angiotensin converting enzymes. An alignment of the amino acid sequence of human ACE-2 having SEQ ID NO:2 with human testicular ACE (SEQ ID NO:4; GenBank Accession No. P22966), murine testicular ACE (SEQ ID NO:5; GenBank Accession No. P22967), rabbit testicular ACE (SEQ ID NO:6; GenBank Accession No. P22968), human endothelial ACE (SEQ ID NO:7; GenBank Accession No. P12821; U.S. Pat. No. 5,539,045 by Soubrier et al.; and described in Soubrier et al. (1988) Proc. Natl. Acad. Sci. USA 85:9386), murine endothelial ACE (SEQ ID NO:8; GenBank Accession No. P09470), rat endothelial ACE (SEQ ID NO:9; GenBank Accession No. P47820) and rabbit endothelial ACE (SEQ ID NO:10; GenBank Accession No. P12822) is shown in FIG. 2. The alignment was performed using CLUSTAL W (1.7). This alignment shows that the zinc binding domain is conserved among all ACE proteins. Other regions of the ACE-2 disclosed herein, such as the N-terminal region, are significantly different from the other ACE proteins. As further described herein, the previously described ACE proteins exist in two forms, a long form, referred to as endothelial ACE, and a short form, referred to as testicular ACE. Endothelial ACE is expressed in various tissues, whereas testicular ACE is expressed predominantly in developing sperm cells in the testis. Both of these forms derive from the same gene by alternative transcription initiation. The testicular ACE is in fact encoded by a mRNA whose transcription initiation site is located in an intron of the ACE gene. Thus, except for the first 67 N-terminal residues (including the 31 amino acid long signal peptide), human testis ACE is identical to the second half of the human endothelial ACE (Ehlers et al. (1989) Proc. Natl. Acad. Sci. USA 86:7741). Furthermore, the previously cloned ACE proteins from different species have a significant homology to each other, which is stronger than the homology of ACE-2 to any of the ACE proteins. Thus, the ACE-2 protein is encoded by a newly identified gene, having sequence similarities with some regions of the genes encoding the previously described ACE proteins, such as in the zinc binding domain.

The amino acid sequence comparison indicates that ACE-2 having SEQ ID NO:2 has the highest overall similarity to the human testicular ACE and that it is 42.9% identical and 62% similar to the amino acid sequence of human testicular ACE. The cDNAs encoding human testicular ACE and ACE-2 (SEQ ID NO:1) have an overall identity of 50.8%.

FIG. 3 shows an amino acid alignment of the ACE-2 protein having SEQ ID NO:2 and ACE proteins from *Drosophila Melanogaster* (SEQ ID NO:11; GenBank Accession No. Q10714) and *C. Elegans* (SEQ ID NO:12; GenBank Accession No. U56966), as well as human testicular and endothelial ACE. This alignment indicates that ACE-2 has a certain degree of homology with the *Drosophila* ACE protein, in particular in the zinc binding domain. However, ACE-2 does not have any significant homology with the *C. elegans* ACE protein.

Thus, based on the results of the BLAST analysis, ACE-2 is likely to be a second member of a novel family of angiotensin converting enzymes.

The BLAST analysis of GenBank with ACE-2 nucleic acid also indicated homologies of portions of human ACE-2 with the following ESTs:

TABLE II

Homologies of hu ACE-2 cDNA Sequence with EST Sequences

| Accession No. | Species | Nucleotides of SEQ ID NO: 1 | % Identity |
|---|---|---|---|
| AA397955 | human | 2759-3202 (3' UTR) | 99% |
| AA420969 | human | 2936-3368 (3' UTR) | 99% |

TABLE II-continued

Homologies of hu ACE-2 cDNA Sequence with EST Sequences

| Accession No. | Species | Nucleotides of SEQ ID NO: 1 | % Identity |
| --- | --- | --- | --- |
| AA162058 | mouse | 457-1012 (coding region) | 87% |
| AA416585 | human | 2985-3368 (3' UTR) | 100% |
| AA421125 | human | 2987-3287 (3' UTR) | 100% |
| AA072298 | mouse | 1485-1742 (coding region) | 83% |

Among these ESTs, only AA162058 was annotated in GenBank as being homologous to ACE. A 208 bp fragment of a gene having Accession No. Q04027, annotated as human angiotensin converting enzyme, is 61% identical to nucleotides 1144-1353 of human ACE-2 cDNA having SEQ ID NO: 1.

2. Tissue Distribution of ACE-2

A 167 bp fragment of human ACE-2 cDNA, corresponding to nucleotides 1152-1318 of SEQ ID NO:1, was labeled with $^{32}$P using the Multiprime Labeling System from Amersham and hybridized at $10^6$ cpm/ml to Human Multiple Tissue Northern blots from Clontech overnight at 65° C. in Nylon Wash. The blots were then washed three times for 30 minutes at 65° C. in 0.5× Nylon Wash. The results indicated that the ACE-2 probe hybridized to a mRNA of about 4 kb in kidney, heart, and testis. The results indicate that ACE-2 has a more specific tissue distribution than does endothelial ACE which is produced by many somatic tissues.

mRNA level of ACE-2 was also determined in a normal heart and compared to that of a heart of a congestive heart failure patient. For this, a 167 bp probe, corresponding to nucleotides 1152-1318 of SEQ ID NO:1, from the ACE homolog was hybridized to heart RNA from a normal and from 3 congestive heart failure patients, by Northern blot hybridization. 10 µg RNA was run per lane on a 1.2% MOPS/formaldehyde gel, which was then transferred to Hybond N (Amersham) in 10×SSC and crosslinked in a Stratalinker (Stratagene). The blot was hybridized overnight at 65° C. with $1×10^6$ cpm/ml of Nylon wash. The ACE-2 probe hybridizes to the normal heart sample and to two of the three congestive heart failure samples 3. In Situ Analysis of ACE-2 mRNA and Protein In situ hybridization of a human ACE-2 probe to human and monkey tissues demonstrated the presence of ACE-2 mRNA in endothelial cells and focally in normal and hypertrophic myocytes in human heart. In monkey kidneys, ACE-2 mRNA was detected in proximal convoluted tubules.

For studying ACE-2 protein, five rabbit polyclonal antipeptide antibodies were generated against human ACE-2: I82283M, which is directed against amino acids 51-69 of SEQ ID NO:2, i.e., NTN ITE ENV QNM NNA GDK W (SEQ ID NO:25); I82284M, which is directed against amino acids 194-214 of SEQ ID NO:2, i.e., NHY EDY GDY WRG DYE VNG VDG (SEQ ID NO:26); K70417K, which is directed against amino acids 489-508 of SEQ ID NO:2, i.e, EPV PHD ETY CDP ASL FHV SN (SEQ ID NO:27); K70418M, which is directed against amino acids 704-723 of SEQ ID NO:2, i.e., IRM SRS RIN DAF RLN DNS LE (SEQ ID NO:28); and K70419M, which is directed against amino acids 785-802 of SEQ ID NO:2, i.e, DIS KGE NNP GFQ NTD DVQ (SEQ ID NO:29). All five antibodies are functional for Western blotting and antibody I82283M is particularly efficient in immunhistochemistry.

ACE-2 protein was evaluated in rat, human and monkey tissues using an antibody generated against a fragment of the human peptide. In rat and human heart, ACE-2 protein was apparent in endothelial cells. In normal human kidneys, ACE-2 was limited to endothelial cells (arterial/venous). In addition to endothelial cell expression, ACE-2 was detected in vascular smooth muscle cells of abnormal renal vessels and damaged (sclerotic) glomeruli of hypertensive human kidneys. In clinically healthy monkey kidneys, ACE-2 protein was found in endothelial cells, epithelial cells of Bowman's capsule and proximal tubules.

4. Expression of Recombinant ACE-2 in COS Cells

This example describes a method for producing recombinant full length human ACE-2 in a mammalian expression system.

An expression construct containing a nucleic acid encoding a full length human ACE-2 protein, or a soluble ACE-2 protein which is devoid of the signal sequence and the transmembrane domain was constructed as follows. A nucleic acid encoding the full length human ACE-2 protein or the soluble ACE-2 protein is obtained by reverse transcription (RT-PCR) of mRNA extracted from human cells expressing ACE-2, e.g., human kidney cells using PCR primers based on the sequence set forth in SEQ ID NO:1. The PCR primers further contain appropriate restriction sites for introduction into the expression plasmid. The amplified nucleic acid is then inserted in a eukaryotic expression plasmid such as pcDNAI/Amp (InVitrogen) containing: 1) SV40 origin of replication, 2) ampicillin resistance gens, 3) E. coli replication origin, 4) CMV promoter followed by a polylinker region, a SV40 intron and polyadenylation site. A DNA fragment encoding the full length human ACE-2 and a HA or myc tag fused in frame to its 3' end is then cloned into the polylinker region of the. The HA tag corresponds to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to ACE-2 allows easy detection of the recombinant protein with an antibody that recognizes the HA epitope.

For expression of the recombinant ACE-2, COS cells are transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the ACE-2—HA protein can be detected by radiolabelling and immunoprecipitation with an anti-HA antibody. (E. Harlow, D. Lane, Antibodies: A Laboratory Manual, Cold Spring Harbor Laboratory Press, (1988)). For this, transfected cells are labelled with $^{35}$S-cysteine two days post transfection. The cells, or alternatively the culture media (e.g., for the soluble ACE-2) is then collected and the ACE-2 protein immunoprecipitated with an HA specific monoclonal antibody. To determine whether full length ACE-2 is a membrane protein, and/or a secreted protein, the cells transfected with a vector encoding the full length ACE-2 protein can be lysed with detergent (RIPA buffer (150 mM NaCl 1% NP-40, 0.1% SDS, 1% NP-40, 0.5% DOC, 50 mM Tris, pH 7.5). (Wilson, I. et al., Id. 37:767 (1984)). Proteins precipitated can then be analyzed on SDS-PAGE gel. Thus, the presence of ACE-2 in the cell will be indicative that the full length ACE-2 can be membrane bound and the presence of ACE-2 in the supernatant will be indicative that the protein can also be in a soluble form, whether produced as a secreted protein or released by leakage from the cell.

5. Expression of Recombinant ACE-2 in the Baculovirus System cDNA encoding human ACE-2 protein was cloned in the vector pBac Pak9 (Clonetech) and expressed in the baculovirus system as follows. A 10 L fermentation run was carried out with SF9 cells grown to $1.3×10^6$ cells/ml in SF900II SFM (Gibco/Life Technologies), 18 mM L-Glutamine, and 1× antibiotic-antimycotic (from 100×stock Gibco/Life Technologies) at 27° C. Cells were infected at multiplicity of infection of 0.1 with ACE2 baculovirus of titer $1.1 \times 10^9$ pfu/ml. At 96 hours post infection, cells were pelleted at 5000 g centrifugation, and the culture supernatant was collected, frozen and stored at −80° C.

After purification of the protein, as described in the next Example, purified baculovirus expressed human ACE-2 protein was tested for its activity and compared to a negative control (from supernatant of mock transfected cells). For this assay, 10 μl of each fraction from the column was combined with 90 μl of 55 μM MIPH-1 ACE-2 substrate (AnaSpec custom synthesis; 7-Methoxycoumarin-4-yl)acetyl-Ala-Pro-Lys(2,4-Dinitrophenyl)-OH, stored in DMSO at 5 mg/ml) in assay buffer (50 mM Mes pH 6.5 (4-Morpholine-ethanesulphonic acid; Boehringer-Mannheim, 223 794); 300 mM NaCl; 0.01% Brij 35 (Pierce 28316)), and the reaction monitored for 30 minutes. For the most active ACE-2 fractions, a re-assay using 1 in 100 diluted fractions was carried out. The results, which are shown in FIG. 4, indicate strong ACE-2 activity in fraction 24.

6. Purification of ACE-2 Protein

This Example describes a method of purification of ACE-2 protein from supernatant.

All the steps are carried out at 4° C. Two 1 L. bottles of ACE-2 containing supernatant were thawed at 4° C. for 50 hours. The two liter supernatant (pH 6.3) was then adjusted at pH7 with about 6 ml of 2N NaOH added dropwise while stirring. The pH adjusted supernatant was filtered in a 0.2 μm Nalgene SFCA filter unit. 800 ml of filtered supernatant was loaded onto a 20.1 ml (16 mmd/100 mml) Pharmacia MonoQ strong anion exchange column at 8 ml/min (239 cm/h). The column had been equilibrated in 50 mM BisTrisPropane/Tris HCl pH7 (Buffer A). After loading the supernatant, the column was washed to baseline with 40 CV Buffer A. ACE-2 was then eluted with a 0-250 mM NaCl gradient in Buffer A over 20 CV while collecting 1 ml fractions. The ACE-2 containing fractions were resolved by SDS-PAGE analysis and collected in two major pools based on minor differences in purity. A second 800 ml load was completed and two major pools were made based on chromatographic simililarity to the first run. The four elution pools were dialyzed into 10 mM HEPES pH 7; 15 mM NaCl overnight. After quantitating protein yield based on Bradford assay and A280, followed by comparison of activity relative to a reference sample (071399) generated during assay development, all four pools were pooled together. The purified ACE-2 was then concentrated in a Filtron Omegacell unit with a 10K MWCO membrane. Concentrated ACE was 0.22 μm filtered in a Millex-GV 25 mm syringe filter in a laminar hood and final concentration was determined by Bradford assay.

The purified ACE-2 protein was then used in a high throughput screening assay described below.

7. Angiotensin I, Neurotensin (1-13) and des-Arg Bradykinin (1-8) are Substrates of ACE-2

This Example demonstrates that angiotensin I, Neurotensin (1-13) and des-Arg Bradykinin (1-8) are substrates of ACE-2 and that ACE-2 cleaves the C-terminal amino acid from each of these peptides. In particular, ACE-2 cleaves Angiotensin I into Ang. (1-9) having the amino acid sequence DRVYIHPFH (SEQ ID NO:16).

The effect of ACE-2 on these peptides was tested by incubating mixtures containing buffer (10 mM Tris, pH 7) and 5 μL of angiotensin I (DRVYIHPFHL; SEQ ID NO:15) (15 pmol/μL obtained from Sigma-Aldrich Corp. (St. Louis, Mo.), 5 μL Neurotensin, or 5 μL des-Arg Bradykinin (1-8) at 15 pmol/μL made by standard procedures with or without 10 μL ACE-2, for 30 minutes at 37° C. The human ACE-2 protein used in these assays was produced from a cDNA in which a stop codon was inserted after the serine immediately preceding the transmembrane domain. The protein was purified as described supra. A stock solution of the ACE-2 protein was kept in 10 mM HEPES (Sigma), 15 nM NaCl (Sigma) stored as aliquots at −70° C.

After the enzymatic reaction, 1 μL samples were removed from each reaction microtube and the enzymatic reaction was quenched by the addition of 1 μL of a low-pH MALDI matrix compound, 10 g/L α-cyano-4 hydroxycinnamic acid (α-CHCA) in a 1:1 mixture of acetonitrile and water (MALDI matrix solution). 1 μL of each of the resulting quenched reaction mixtures was applied to the surface of a MALDI plate. The plate was then air-dried and inserted into the sample introduction port of a Voyager Elite Biospectrometry MALDI time-of-flight (TOF) mass spectrometer (PerSeptive Biosystems, Inc., Framingham, Mass.). The resulting signal was digitized at 1 GHz frequency and accumulated for 64 scans.

Figure 5A:
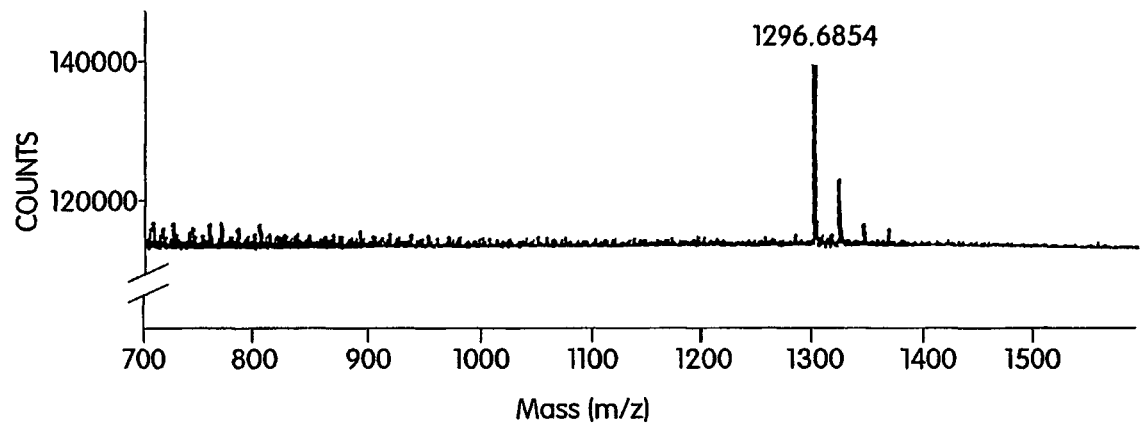
Figure 5B:
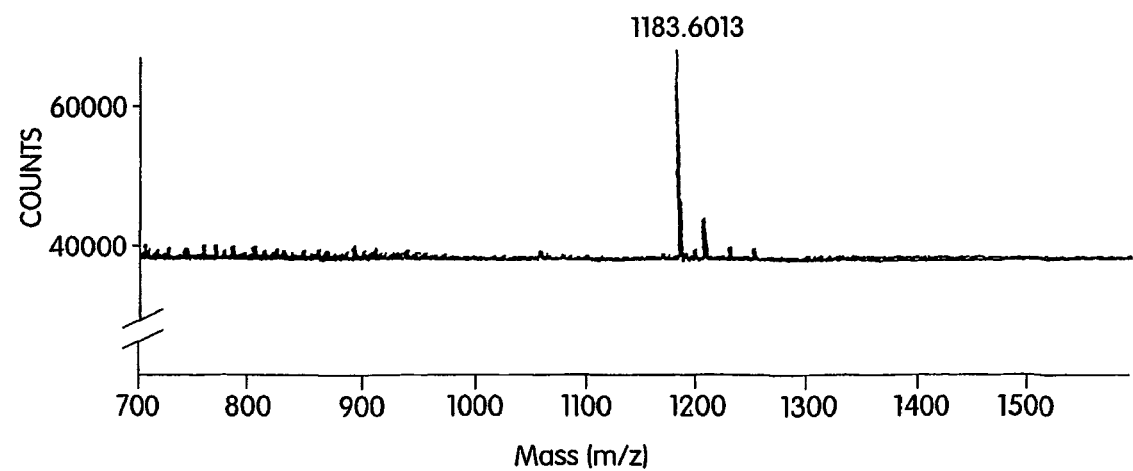
Figure 6A:
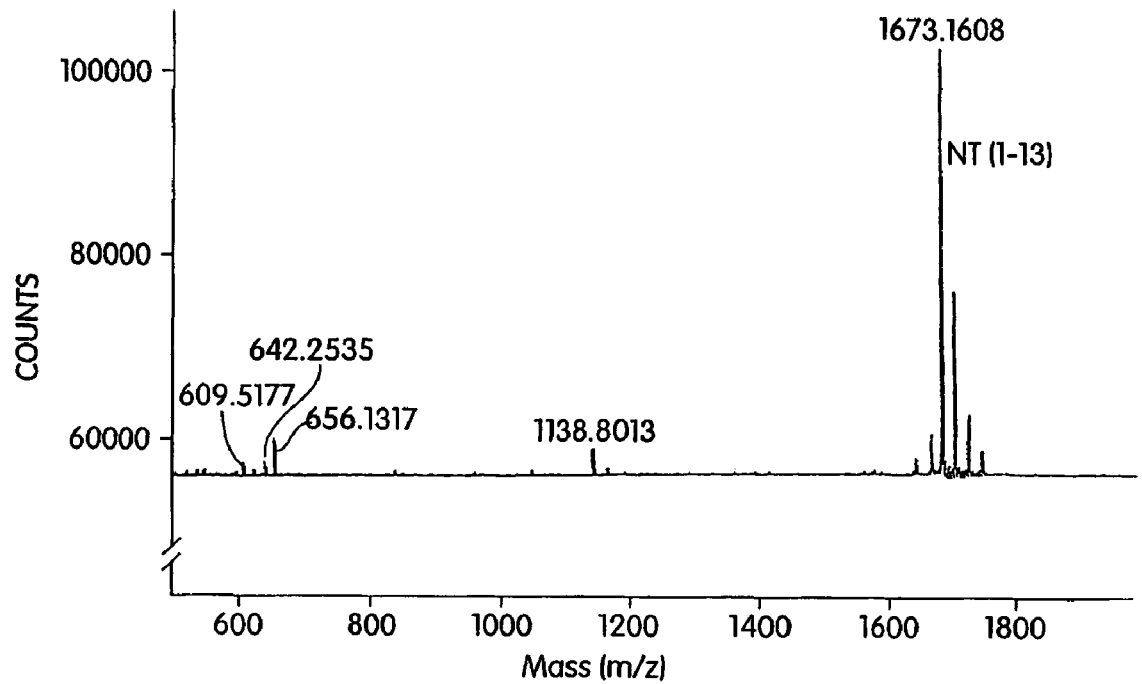
Figure 6B:
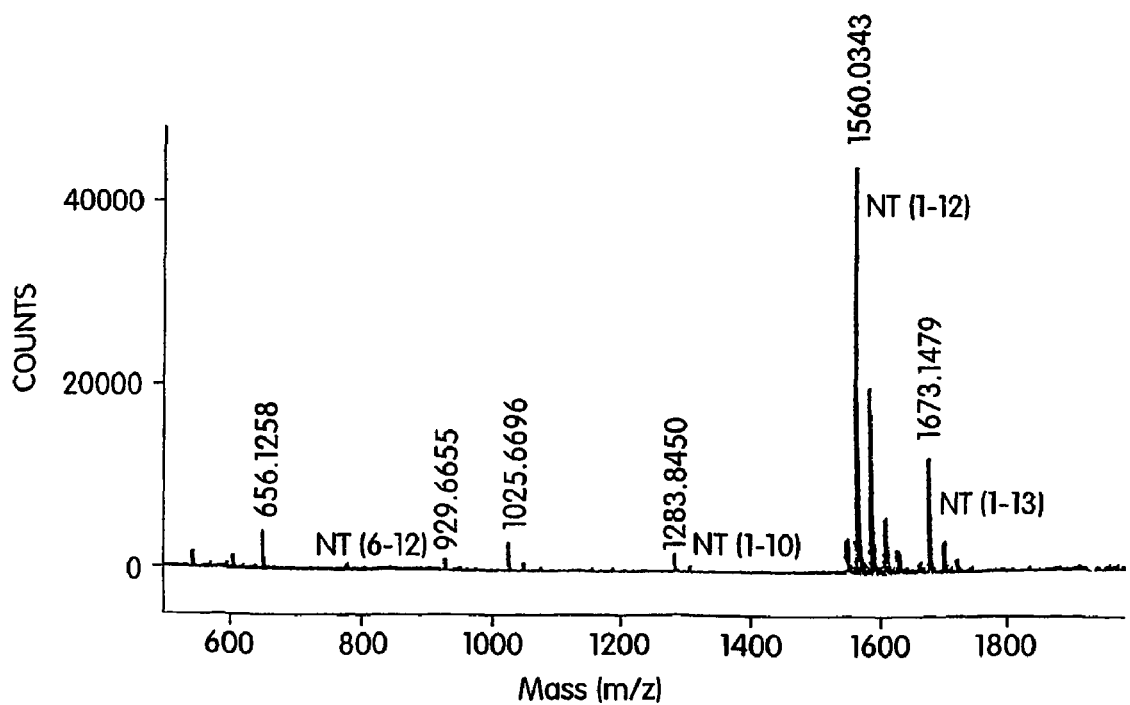
Figure 7A:
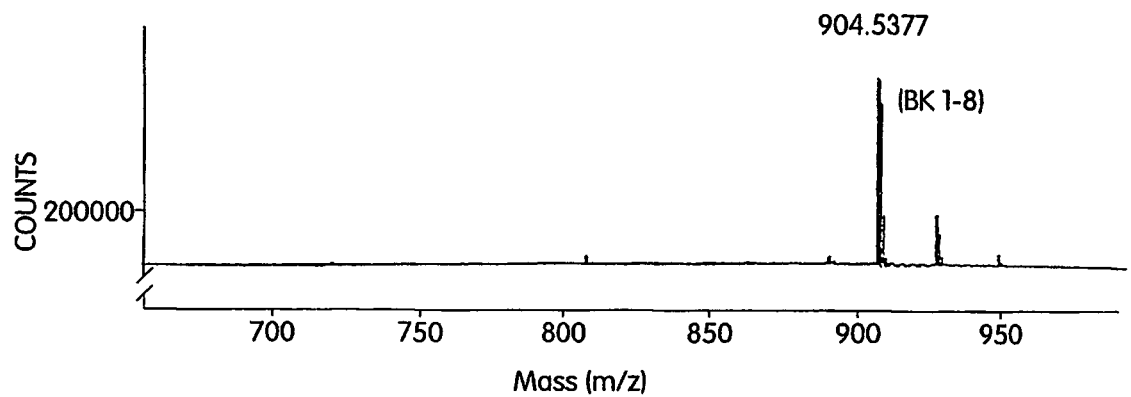
Figure 7B:
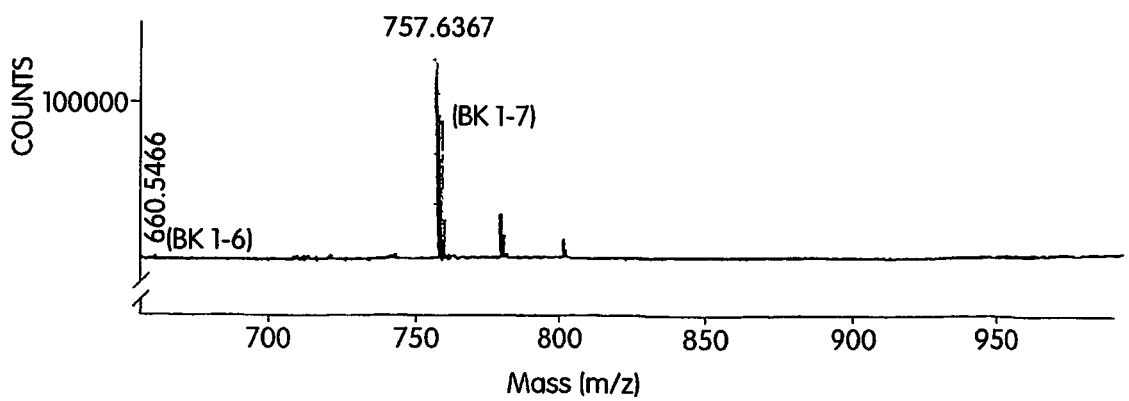

Mass spectrometry data for the ACE-2 hydrolysis of angiotensin I (1-10) to angiotensin (1-9) is shown in FIG. 5B, whereas mass spectrometry date of angiotensin in the absence of ACE-2 is shown in FIG. 5A. FIG. 5A shows that no hydrolysis occurs in the absence of ACE-2 in the reaction. Similarly, FIGS. 6A and 6B show that ACE-2 hydrolyzes Neurotensin (1-13) into Neurotensin (1-12) (FIG. 6B). No conversion occurs in the absence of ACE-2 (FIG. 6A). The mass spectrometry data for des-Arg bradykinin (1-8) to des-Arg bradykinin (1-7) is shown in FIG. 7B. No conversion of bradykinin occurs in the absence of ACE-2 (FIG. 7A).

Thus, this Example demonstrates that ACE-2 is a carboxypeptidase that accepts a variety of P1' amino acids with a free carboxylic acid group.

8. Kinetensin is a Substrate of ACE-2

This Example demonstrates that kinetensin is a substrate of ACE-2 and that ACE-2 cleaves the C-terminal leucine residue from kinetensin.

Kinetensin (IARRHPYFL; SEQ ID NO:23) obtained from Sigma-Aldrich Corp. (St. Louis, Mo.) was incubated at 15 pmol/μL with ACE-2 produced in CHO cells as described above, and the reaction mixture was then subjected to mass spectrometry, also as described above. The results indicate that ACE-2 cleaves the C-terminal leucine residue from kinetensin, thus producing an 8-mer peptide having the amino acid sequence IARRHPYF (SEQ ID NO:24).

9. Effect of ACE-2 on Other Peptides

Mass spectroscopy studies showed that ACE-2 cleaves the terminal amino acid of a peptide only if it contains the free carboxylic acid group. Two commercially available, peptide based substrates Mca-YVADAPK(Dnp), a substrate for caspase I (Bachem M-2195) and Mca-PLGP-[D-Lys](Dnp), a substrate for thimet oligopeptidase (Bachem M-2270) with free carboxylic acid groups were used. These types of substrate are known as intramolecularly quenched fluorescent substrates. The presence of the Dnp substituted onto the terminal lysine causes quenching of the Mca fluor that is relieved only when an intervening bond is cleaved. When Mca-YVADAPK(Dnp) was tested as a substrate for ACE-2, an increase of fluorescence was measured. No such increase in fluorescence was seen with Mca-PLGP-[D-Lys](Dnp). It was inferred from these data that the cleavage of Mca-YVA-DAPK(Dnp) occurred between the proline and lysine residues and required the lysine to be in the L configuration. The site of peptide cleavage was confirmed by mass spectroscopy (see FIG. 10A)

Figure 10B:
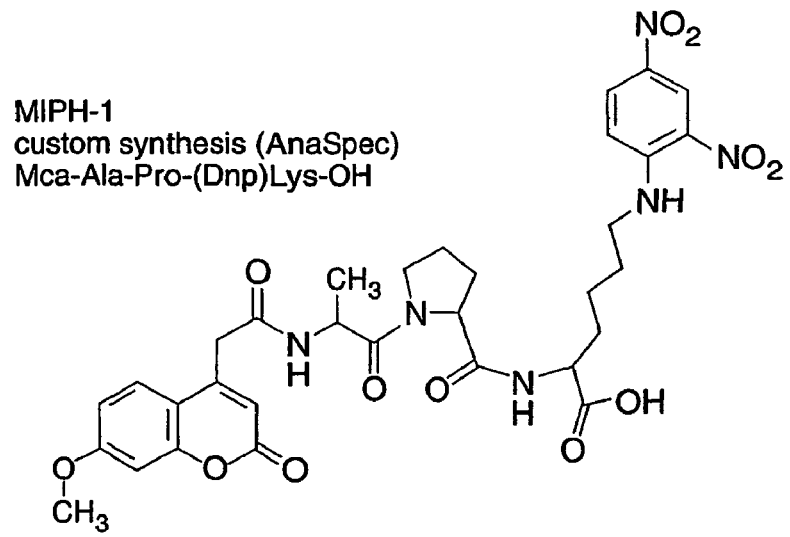

Following the discovery that Mca-YVADAPK(Dnp) is an ACE-2 substrate, a shortened form was custom synthesised by AnaSpec (San Jose, Calif., USA) (see FIG. 10B). This substrate, MIPH-1, was found to have higher turnover and lower background fluorescence.

To determine whether ACE-2 is capable of cleaving other peptides, ACE-2 produced in CHO cells, alone or with testicular ACE produced in CHO cells, was incubated as described above in 5 μL reactions containing 15 pmol/μL of each of the following peptides: angiotensin II (=angiotensin (1-8)), angiotensin (1-7), angiotensin (1-9), angiotensin (2-10), luteinizing hormone releasing hormone (LHRH), des-Gly$^{10}$-LHRH Ethylamide, LHRH fragment 4-10, oxytocin, Arg$^8$-Vasopressin, litorin, eledoisin, ranatensin, bombesin, renin substrate tetradecapeptide, and adrenocorticotropic hormone fragment 18-39. These peptides were obtained from-Aldrich Corp. (St. Louis, Mo.). MS spectrum of the reactions were obtained as described in the previous Example. The results showed that ACE-2 had no effect on any of these peptides, alone or in the presence of testicular ACE.

10. Human ACE-2 Variants

This Example describes variants, e.g., polymorphic variants, of the human ACE-2 gene which were found by performing single strand conformation polymorphism (SSCP) studies of the ACE-2 gene in DNA of 96 individuals from a randomly ascertained U.S. Caucasian population.

Prior to analyzing ACE-2 variants, the genomic structure of human ACE-2 was elucidated. The coding region of the human ACE-2 is comprised in 18 exons, the first exon containing the ATG and the 18th exon containing the TAG codon. The exon/intron borders are shown on FIG. 1. Human genomic ACE-2 DNA sequence is set forth in GenBank Accession No. AC003669.

PCR was performed with the primer pairs listed in Table III, using 20 ng of template genomic DNA in a final volume of 15 μl. The PCR reactions were performed by mixing 5 μl template DNA 10 ng/μl; 1.5 μl 10× Perkin Elmer PCR Buffer; 1.2 μl Pharmacia dNTP mix 2.5 mM; 1.15 μl Forward primer 6.6 μM; 1.15 μl Reverse primer 6.6 μM; 5 μl Gibco/BRL Platinum Taq 0.05 U/μl (Hot Start); by heating the reaction at 95° C. for 10'; conducting 35 cycles of [94° C. for 40"; 57° C. for 40"; 72° C. for 40"] and terminating by incubating the reactions at 72° C. for 5'. Then, 3.5 μl of PCR reaction was added to 4.5 μl SSCP buffer (95% Formamide; 0.1% Bromophenol Blue; 0.1% Xylene Cyanol; 20 mM EDTA). Each amplicon was denatured at 97° C. for 10 seconds, immediately chilled on ice, and 8 μl are loaded onto and separated on a nondenaturing, 10% polyacrylamide (39:1) SSCP gel that was run at 12 volts/gel for 5-6 hours at 4° C. Amplicons with variant SSCP bands along with several non variant samples were sequenced on an ABI 377. ABI traces from both strands of each amplicon were compared to identify nucleotide differences between SSCP variant and non variant samples.

TABLE III

PCR Primers Used in SSCP Analysis of Human ACE-2

| | | | |
|---|---|---|---|
| ace2e1a/b | ace2e1a | TTCCCTTTTCAGTTTCACGGGCAG | (SEQ ID NO:30) |
| | ace2e1b | TCTTCCTGGCTCCTTCTCAGC | (SEQ ID NO:31) |
| ace2e1c/d | ace2e1c | TCTTGGCCTGTTCCTCAATGGTG | (SEQ ID NO:32) |
| | ace2e1d | AGCGCCCAACCCAAGTTCAAAG | (SEQ ID NO:33) |
| ace2e2a1/b | ace2e2a1 | ATGGACACCTTACCTAGGCATAGAG | (SEQ ID NO:34) |
| | ace2e2b | ATCTCACAGTCAAGCTTCAGCTGC | (SEQ ID NO:35) |
| ace2e2c/d | ace2e2c | TGCTCTTGTCTTCTGAGAGCACTG | (SEQ ID NO:36) |
| | ace2e2d | TCTGTTCTATCTCTTCAAGCAATGCC | (SEQ ID NO:37) |
| ace2e3a/b | ace2e3a | CATCTATGTGTTGAAACACACATATCTGC | (SEQ ID NO:38) |
| | ace2e3b | AGGATATCTTTATATTAGCATTCTCTTCAGC | (SEQ ID NO:39) |
| ace2e4a/b | ace2e4a | TAATGCAGAAGAAATAGCCCCGTGG | (SEQ ID NO:40) |
| | ace2e4b | TTGTGTGCTTTGGGATAACAGGTTTG | (SEQ ID NO:41) |
| ace2e5a/b | ace2e5a | ATGTGTTAAGAATGAGCCAGAATGCC | (SEQ ID NO:42) |
| | ace2e5b | CTCTTTCTTTCCCTTATGTTCTTCCC | (SEQ ID NO:43) |
| ace2e6a/b | ace2e6a | GCGATTTCTACAATGTTACTAACCAC | (SEQ ID NO:44) |
| | ace2e6b | GTGGAATGGAAATTAGAATTGGTTAC | (SEQ ID NO:45) |
| ace2e7a/b | ace2e7a | CTGCTTTTCCATGAAACTATAGCTAC | (SEQ ID NO:46) |
| | ace2e7b | GGTGATATGTGGGGTAGATTTTGGA | (SEQ ID NO:47) |
| ace2e7c/d | ace2e7c | GGTCCACCATTGCATCAGTAACAT | (SEQ ID NO:48) |
| | ace2e7d | CCAACACTAGGAATTACTAACAGCTT | (SEQ ID NO:49) |

TABLE III-continued

PCR Primers Used in SSCP Analysis of Human ACE-2

| | | | |
|---|---|---|---|
| ace2e8a/b | ace2e8a | CCTGCCTCTGTTGTCTCCCATTTA | (SEQ ID NO:50) |
| | ace2e8b | GAAAATTCCATGCTAACGGACCCAG | (SEQ ID NO:51) |
| ace2e8c/d | ace2e8c | TGGGATGGCAGACTGCTTTCTGAA | (SEQ ID NO:52) |
| | ace2e8d | CGGTGCCTGGCTTATTTAATTTAAGA | (SEQ ID NO:53) |
| ace2e9a/b | ace2e9a | CTCATACCTCATACCTTATGTGGCAA | (SEQ ID NO:54) |
| | ace2e9b | GGCATATGCTGCACAACCTTTTC | (SEQ ID NO:55) |
| ace2e9c/d | ace2e9c | CCCAACAGCTTCATGGAATCCTTCA | (SEQ ID NO:56) |
| | ace2e9d | CCCATACAACTCCACTGTAATGGTT | (SEQ ID NO:57) |
| ace2e10a/b | ace2e10a | CGCCAGTCAAATGCTTTTAAATACAC | (SEQ ID NO:58) |
| | ace2e10b | CATCCACTGTCATCTTCATCGTAAT | (SEQ ID NO:59) |
| ace2e11a/b | ace2e11a | GTTATTAGCACAGCTGTCCACAAAC | (SEQ ID NO:60) |
| | ace2e11b | GATGAAACTGCACTAGTTATGCCC | (SEQ ID NO:61) |
| ace2e12a/b | ace2e12a | CTAGGCATGGAAATGAGTAATACTG | (SEQ ID NO:62) |
| | ace2e12b | GGTTACTTGGGCTCCAGATTTAAAT | (SEQ ID NO:63) |
| ace2e13a/b | ace2e13a | CTGTGTCACAAGTCCTCATGAGACT | (SEQ ID NO:64) |
| | ace2e13b | TGTACATCTGGAACCCCTCAAAAG | (SEQ ID NO:65) |
| ace2e14a/b | ace2e14a | GAACCACATGGCCTCTCTTCTTTC | (SEQ ID NO:66) |
| | ace2e14b | CAGTTACCCCTGTCTCATCATTTCT | (SEQ ID NO:67) |
| ace2e15a/b | ace2e15a | CAGAGTATCTCCTCAGACTCAAGA | (SEQ ID NO:68) |
| | ace2e15b | GGTCACTGACTTAATGAATAGCAAG | (SEQ ID NO:69) |
| ace2e16a/b | ace2e16a | GGCACACAGGAAGAACACACAAAAT | (SEQ ID NO:70) |
| | ace2e16b | CTCTGTGCCACAAGTGAAGATGT | (SEQ ID NO:71) |
| ace2e17a/b1 | ace2e17a | GGTCTATACAATCTACCACTTACTG | (SEQ ID NO:72) |
| | ace2e17b1 | AGCCAACACTTGGACCTCCTAAC | (SEQ ID NO:73) |
| ace2e17c/d | ace2e17c | GTGAAGATCAGGATGACAATGCC | (SEQ ID NO:74) |
| | ace2e17d | GCTCTATTATATCCTTTCAGGAACA | (SEQ ID NO:75) |
| ace2e18a/b | ace2e18a | CCCCAGACACTCAGATGATAACTT | (SEQ ID NO:76) |
| | ace2e18b | CAGAGCATGCCTGATAGAAACTCA | (SEQ ID NO:77) |
| ace2e18c/d | ace2e18c | TACCCACTTCAGAGGGTGAACAT | (SEQ ID NO:78) |
| | ace2e18d | GTCAAGGATGACATGCTTTCTTCAC | (SEQ ID NO:79) |
| ace2e18e/f | ace2e18e | CATGATCGATTCCAAACATCACTGT | (SEQ ID NO:80) |
| | ace2e18f | CTGTCTCTGGATTTGACTTCTGTTC | (SEQ ID NO:81) |
| ace2e18g/h | ace2e18g | GCCTGTGAGACCAAATACACACTTT | (SEQ ID NO:82) |
| | ace2e18h | CACTGATGATGTTCAGACCTCCTTT | (SEQ ID NO:83) |
| ace2e18i/j | ace2e18i | CTTGGCCATGTTGTCTTTGGACAA | (SEQ ID NO:84) |
| | ace2e18j | CTCCTTAACACAGATTCCCCTGAA | (SEQ ID NO:85) |

Five polymorphisms were uncovered in the Caucasian population (FIG. 9 and FIG. 13) and three polymorphisms were uncovered in the Asian population (FIG. 13).

The first polymorphism (or variation) in the Caucasian population is a G to T change in intron 3, which can be detected using primers 3a/3b (ace2e3a and ace2e3b). The sequence encompassing the polymorphism is: 5' TTGAAC-CAGGTAgGCTACTAATTTT3' (SEQ ID NO:86; the variant nucleotide is indicated in lower case). The corresponding variant sequence is 5' TTGAACCAGGTAtGCTAC-TAATTTT3' (SEQ ID NO:87).

The second polymorphism in the Caucasian population is a 5 bp insertion (CTTAT) in intron 9, which can be detected with primers 9a/9b (ace2e9a and ace2e9b). The sequence encompassing the polymorphism is: 5'GGTATTTATTATG-TAGGAAATA3' (SEQ ID NO:88). The corresponding variant sequence is 5'GGTATTTATTATcttatGTAGGAAATA3' (SEQ ID NO:89; the variant nucleotides are indicated in lower case).

The third polymorphism in the Caucasian population is a T to G change in intron 14, which can be detected with primers 14a/14b (ace2e14a and ace2e14b). The sequence encompassing the polymorphism is: 5' TGAATTGATTATTtTTGAGT-GCACAG3' (SEQ ID NO:90; the variant nucleotide is indicated in lower case). The corresponding variant sequence is 5'TGAATTGATTATTgTTGAGTGCACAG3' (SEQ ID NO:91).

The fourth polymorphism in the Caucasian population is an A to G change at residue 2239 in exon 17, which can be detected with primers 17c/d (ace2e17c and ace2e17d), and which results in a change of the asparagine at amino acid 720 to an aspartic acid. The sequence encompassing the polymorphism has the sequence: 5'CGTCTGAATGACaACAGC-CTAGA G3' (SEQ ID NO:92; the variant nucleotide is indicated in lower case). The corresponding variant sequence is 5'CGTCTGAATGACgACAGCCTAGAG3' (SEQ ID NO:93).

The fifth polymorphism in the Caucasian population is a G to T change at residue 2834 in the 3' untranslated region in exon 18, which can be detected with primers 18e/f (ace2e18e/ace2e18f). The sequence encompassing the polymorphism has the sequence: 5'AGTTGAAAACAAgGATATATCAT-TGG3' (SEQ ID NO:94; the variant nucleotide is indicated in lower case). The corresponding variant sequence is 5'AGT-TGAAAAC AAtGATATATCATTGG3' (SEQ ID NO:95).

The first polymorphism (or variation) in the Asian population is an A to G change in the 5' untranslated region, which can be detected using primers 1c/1d (ace2e1c and ace2e1d). The sequence encompassing the polymorphism is: 5' CTAGGGAAAGTCaTTCAGTGGATGTG3' (SEQ ID NO:96); the variant nucleotide is indicated in lower case). The corresponding variant sequence is 5' CTAGG-GAAAGTCgTTCAGTGGATGTG 3' (SEQ ID NO:97).

The second polymorphism (or variation) in the Asian population is a A to G change in intron 3, which can be detected using primers 3a/3b (ace2e3a and ace2e3b). The sequence encompassing the polymorphism is: 5' TTGAACCAGG-TAaGCTACTAATTTT 3' (SEQ ID NO:98); the variant nucleotide is indicated in lower case). The corresponding variant sequence is 5' TTGAACCAGGTAgGCTAC-TAATTTT 3' (SEQ ID NO:99).

The third polymorphism (or variation) in the Asian population is a G to A change in the 3' untranslated region in exon 18, which can be detected with primers 18c/d (ace2e18c/ace2e18d). The sequence encompassing the polymorphism has the sequence: 5'GTTCTCTAACTGTgGAGTGAATG-GAAA3' (SEQ ID NO:100); the variant nucleotide is indicated in lower case). The corresponding variant sequence is 5' GTTCTCTAACTGTaGAGTGAATGGAAA 3' (SEQ ID NO:101). MMM

5.11. ACE-2 Transgenic Mice

This Example describes the generation of transgenic mice expressing human ACE-2 cDNA.

The transgenic mice were created by injecting a nucleic acid comprising the full length human ACE-2 cDNA (3396 base pairs) under the control of the 5.5 kb α-myosin heavy chain into pronuclei of FVB mice according to well known methods. Under control of this promoter, the ACE-2 protein is expressed in cardiac myocytes. Ten male founders were bred with wild type females and 70% demonstrated germ line transmission in the F1 generation.

Northern analysis of transgenic hearts demonstrated the presence of the full length transcript as well as the presence of a smaller, more abundant message. Following RT-PCR of this smaller transcript, the first ATG encoded the longest open reading frame (ORF) which was in frame with ACE-2 sequence. Western analysis with an anti-peptide antibody specific for this region demonstrated the presence of only the full length ACE-2 protein and not the alternately spliced form. Western analysis also demonstrated the presence of the human ACE-2 protein in transgenic murine hearts but not in lung, liver, kidney or spleen.

The presence of ACE-2 in the serum of the transgenic and wildtype animals was tested by combining 5 µl of serum of the mice and 45 µl of 55 µM ACE-2 substrate (see above) in ACE-2 buffer and measuring the rate of proteolytic degradation of the substrate by measuring the production of fluorescence (in fluorescence units) per second for 30 minutes at room temperature at a gain setting of 10. The average rate of fluoresence units per second (FU/sec) correlates directly with the amount of ACE-2 in the serum. As a control for the specificity of ACE-2, a standard carboxypeptidase assay was performed (Holmquist and Riordan, Carboxypeptidase A, pp44-60, Peptidase and their Inhibitors in Method of Enzymatic Analysis (1984). The results are shown in Table IV.

TABLE IV

ACE-2 Transgenic versus Wildtype Serum Activity

| Line and mouse a3320 | Type | Av. Rate FU/sec | Line and mouse a3503 | Type | Av. Rate FU/sec |
|---|---|---|---|---|---|
| cardiac bleed | | | | | |
| a3617-2.2f | wt | 0.103 | 99-8082.24 | wt | 0.088 |
| a3617-2.3f | wt | 0.113 | 99-8082.27 | wt | 0.106 |
| a3614-2.1f | tg | 0.234 | 99-8082.25 | tg | 0.622 |
| a3615-2.1f | tg | 0.191 | 99-8082.26 | tg | 0.412 |
| a3617-2.1m | wt | 0.148 | | | |
| a3617-5.2m | wt | 0.130 | | | |
| a3614-2.1m | tg | 0.211 | | | |
| a3617-5.1m | tg | 0.296 | | | |

Enzymatic cleavage of ACE-2 assay substrate was approximately 5 fold higher in line 2 serum and 2 fold higher in line 1 serum relative to littermate controls. This indicates that there is circulating ACE-2 in the blood of these transgenic animals. These animals can be used for analyzing any potential inhibitors of ACE-2.

Mice from line 1 were also analyzed for weight and length. These mice were slightly shorter in length than their littermate counterparts and were significantly lower in body weight. Weight to length ratios were significantly lower in transgenics than littermate controls, suggesting that transgenic mice may be leaner than normal.

Blood chemistries (glucose, blood urea nitrogen, creatinine, total bilirubin, and a number of cardiac markers including alanine amino transferase, asparagine amino transferase, creatine phosphokinase, sodium, potassium, chloride, calcium, IP, and magnesium) from transgenic line 1 animals and from littermate controls were examined. A significant increase in chloride levels were found in transgenics (114.8 mmol/l) versus controls (112.0 mmol/l) (students T-test p=0.0009). The liver enzymes ALT and AST also were higher in transgenics than in controls (p=0.024 and p=0.084, respectively).

Sudden death has been observed in both lines. In line 2 mice, deaths start to occur at 4 weeks of age with only 40% of the transgenic mice surviving at day 45 (100% of wild type mice survive at day 45). Deaths start to occur in line 1 after 3 months of age. The mice from line 1 have been evaluated for functional cardiac changes. In these mice, cardiac contractility was found to be normal, however, their blood pressure was reduced relative to wild type littermates.

Phenotypic analysis of these mice was undertaken in 2 lines of these transgenic mice (designated line 1 and line 2). Histological analysis of hearts from both of these lines shows subtle mycoyte vaculolization, focal ischemic changes and myocyte loss, splaying of the myofibrils, and focal areas of hemorrhage. The spleens of several animals showed signs of congestion. Livers have chronic passive congestion and centrilobular hepatocyte necrosis and hypotensive changes. The brains of several animals showed mild to moderate selective neuronal necrosis, particularly in the CA1, 2, and 3 subsectors onf the hippocampus and in the frontoparietal cortex. These changes are consistent with hypotensive and global ischemic insults. In older transgenic mice, the ischemic changes in the myocardium (myocyte contraction bands; increase in eosin uptake by injured myocytes) appears moire diffuse and prominent.

To eliminate the possibility that the smaller transcript in line 1 and 2 transgenics caused any observable phenotype, transgenic mice were created using the human ACE-2 cDNA, in which the cryptic splice acceptor site was removed by changing bases 2167-2172, from CCTAGA to CCGCGC. These changes were made such that the mRNA would still encode the identical full-length ACE-2 protein, however, the bases in the RNA would not be recognized as a splice acceptor site. This ACE-2 cDNA was then operably linked to the myosin heavy chain promoter, introduced into pronuclei, to obtain transgenic mice. The resulting transgenic mice, designated as line 3, contained only the correct size transcript as determined by Northern blots of mRNA from their heart. Results indicate that mice from this group of animals also die at a very young age, demonstrating that the smaller transcript in lines 1 and 2 was not the cause of early death.

ACE-2 transgenic mice were also subjected to surface electrocardiograms (ECG) and Holter monitoring. For surface EGC recordings, mice were anesthetized with 2.5% Avertin and 27 G needles electrodes (positive, negative, and ground) were subdermally placed onto the left hind limb, tail and right forepaw, respectively. The leads were connected to a differential amplifier and the data was digitized at 4 K/s and analyzed using the Chart analysis software. ACE-2 transgenic mice exhibited complete atrioventricular block as measured by independent P waves and ORS complexes (FIGS. 11A-C). In addition these mice exhibited a higher preponderance of premature ventricular beats (PVB) (FIGS. 11A-C).

In order to determine whether the high incidence of mortality observed in these transgenic mice was due to sudden cardiac death, these mice were telemetered (using a Holter monitor, described in, for example, Gehrmann J. and Beroul C. I. (2000) *J. Cardiovascular Electrophysiology* 11:354-68) and continuous conscious ECG were recorded. In one of the transgenic telemetered mice which exhibited the usual pattern of complete atrioventricular block there was recorded evidence of non sustained ventricular tachycardia which progressed into ventricular fibrillation and ultimately resulted in asystole and death, suggesting the appearance of sudden cardiac death (FIG. 12).

12. ACE-2 Knock-Out Mice

This example describes the generation of mice having one or both ACE-2 genes disrupted by the insertion of a neo/ura cassette in the site encoding the active site of the enzyme.

A BAC clone, BAC145d21, containing a genomic fragment that includes the exon encoding the active site of the ACE-2 enzyme was isolated by screening an RPCI-22 mouse BAC library with a 1.8 Kb EcoRI fragment from the human ACE-2 cDNA. A 5.4 kb murine genomic ACE-2 fragment containing the exon including the active site of ACE-2 was subcloned into the yeast shuttle vector YCplac22.

A random sheared library was prepared from BAC145d21 for sequencing. Base perfect sequence was obtained from the region flanking and including the exon encoding the active site. A PCR primer containing 45 bp of murine ACE-2 sequence corresponding to the region flanking the active site on the 5' end was prepared. The 3' end of this primer contained 21-24 bp of sequence corresponding to the neo/ura cassette in the plasmid pRAY-1 and desigated as the forward primer. The reverse primer was similarly designed with ACE-2 sequences downstream of the active site and the 3' end of the neo/ura cassette. The PCR product obtained from amplification of mouse DNA using these two primers contained the neo/ura cassette flanked by ACE-2 sequence. This PCR product was then co-transformed with the YCplac22-ACE-2 construct into the yeast strain YPH501 to obtain homologously recombinated DNA, i.e., YCplac-ACE-2 having an neo/ura cassette in the site encoding the active site of the ACE-2 enzyme. Replacement of the exon encoding the active site with the neo/ura cassette was confirmed by restriction digestion of transformants. Integrity of the neo/ura cassette in the knock-out construct was confirmed by transfection into CHOK1 cells and selection with G418.

The ACE-2 knockout construct was linearized and electroporated into ES cells. ES cells having undergone homologous recombination were selected by culture of the ES cells in the presence of G418. Clones were screened by Southern blot using 5' and 3' flanking probes to confirm recombination. ES cell clones having undergone homologous recombination were then injected into blastocyts and transferred to pseudopregant female mice for generating chimeric mice. Male chimeras were mated with C57B16 females to obtain germline transmission of knockout. Ten pups of the correct coat color (agouti) indicating germline transmission, were obtained. Since the ACE-2 gene has been mapped to the X chromosome (see below), heterozygous females were generated. These can be mated by standard crossings to obtain hemizygous males, heterozygous females, and homozygous females for the widtype or the knock-out allele.

13. The Human ACE-2 Gene is Located on the X Chromosome at p21-22

This example demonstrates that the human and mouse ACE-2 genes are located on the X chromosome.

Chromosome localization of the human ACE-2 gene was performed by amplifying the 93 DNAs from the Genebridge 4 Radiation Hybrid Panel in duplicate. The primers were chosen based on their ability to hybridize to the DNA of a human cell line, but not to that of a control hamster cell line, and consisted of the following sequences: 5' GGATCACT- TGTAAGGACAGTGCC 3' (forward primer; SEQ ID NO:102) and 5' GATCGATTCCAAACATCACTGTAGGC 3' (reverse primer; SEQ ID NO:103). Amplification results in a 169 bp DNA fragment.

The PCR reactions were performed by mixing 5 µl Template DNA 10 ng/µl; 1.5 µl 10× Perkin Elmer PCR Buffer; 1.2 µl Pharmacia dNTP mix 2.5 mM; 1.15 µl Forward primer 6.6 µM; 1.15 µl Reverse primer 6.6 µM; 5 µl Gibco/BRL Platinum Taq 0.05 U/µl (Hot Start); by heating the reaction at 95° C. for 10'; conducting 35 cycles of [94° C. for 40"; 55° C. for 40"; 72° C. for 40"] and terminating by incubating the reactions at 72° C. for 5'. The PCR products were run on 2% agarose gels, post-stained with SYBR Gold (1:10,000 dilution in 1× TBE), and scanned on a Molecular Dynamics 595 Fluorimager.

The results indicated that ACE2 maps to the p-arm of the human X chromosome, 37.1 cR$_{3000}$ centromeric to the Whitehead Institute framework marker DXS1223, and 42.0 cR$_{3000}$ telomeric of the Whitehead framework marker DXS1061. LOD scores for linkage were 6.6 for DXS1223 and 6.1 for DXS1061. This region corresponds to the cytogenetic location Xp21-22, which is syntenic to the mouse X chromosome.

14. The Mouse ACE-2 Gene is Located on the X Chromosome

Chromosome localization of the mouse ACE-2 gene was performed as follows. PCR primers were designed from conserved regions flanking a CA microsatellite of 28 repeat units (56 bp long) in mouse genomic ACE-2 DNA. The forward primer had the sequence 5' ATTGACCATTGTTGGAACAC-TACCG 3' (SEQ ID NO:104) and the reverse primer had the sequence 5' GTGTGTTAGCCCCTCCTGGC 3' (SEQ ID NO: 105). These primers were used to amplify a 321 bp PCR product from C57BL/6J DNA and a smaller PCR product from wild type derived *Mus spretus* strain SPRET/Ei DNA. PCR reactions were performed by combining 6 µl Template DNA 10 ng/µl; 1.4 µl 10× Perkin Elmer PCR Buffer; 1.12 µl dNTPs 2.5 mM; 1.05 µl Forward primer 6.6 µM; 1.05 µl Reverse primer 6.6 µM; 0.38 µl H$_2$O; 3 µl AmpliTaq 0.05 U/µl (Hot Start), and incubating the reaction mixture for 35 cycles of [94° C. for 40"; 55° C. for 50"; 72° C. for 30"]. The products were run on a nondenaturing 8% polyacrylamide gel at 45 W at room temperature for 3 hrs for size determination (SSLP analysis). Gels were stained, postelectrophoresis, with SYBR Gold and scanned on a Molecular Dynamics 595 Fluorimager.

The genetic segregation of the *M. spretus* allele was followed in 186 progeny of a (C57BL/6J×*M. spretus*)×C57BL/6J mapping panel by SSLP (Simple Sequence Length Polymorphism) analysis. The segregation pattern of the *M. spretus* allele was compared with the segregation pattern of 394 other genetic loci that have been mapped in this backcross panel. By minimizing the number of multiple crossovers between ACE-2 and other markers, it was determined that ACE maps to the murine X chromosome, approximately 29.71±3.45 cM distal to the marker DXMIT8 and 7.39±1.97 cM proximal of the marker DXMIT12.

Equivalents

Those skilled in the art will recognize, or be able to ascertain using no more than routine experimentation, many equivalents of the specific embodiments of the invention described herein. Such equivalents are intended to be encompassed by the following claims.

The invention claimed is:

1. A method for identifying an ACE-2 antagonist, comprising
   (i) combining an ACE-2 polypeptide, an ACE-2 binding partner and a test compound under conditions wherein, but for the test compound, the ACE-2 polypeptide and ACE-2 binding partner form a complex; and
   (ii) detecting the formation of an ACE-2 polypeptide/ACE-2 binding partner complex, wherein a reduction in the formation of an ACE-2 polypeptide/ACE-2 binding partner complex in the presence of a test compound relative to the absence of the test compound indicates that the test compound is an ACE-2 antagonist.

2. The method of claim 1, wherein the ACE-2 binding partner is a target peptide or analog thereof.

3. The method of claim 2, wherein the binding partner is angiotensin I or a portion thereof or an analog thereof sufficient for binding to an ACE-2 polypeptide.

4. The method of claim 2, wherein the binding partner is angiotensin I or a portion thereof or an analog thereof sufficient for binding to, and being hydrolyzed by, an ACE-2 polypeptide.

5. The method of claim 2, wherein the binding partner is kinetensin or a portion thereof or an analog thereof sufficient for binding to an ACE-2 polypeptide.

6. The method of claim 2, wherein the binding partner is kinetensin or a portion thereof or an analog thereof sufficient for binding to, and being hydrolyzed by, an ACE-2 polypeptide.

* * * * *

SEQUENCE LISTING

```
<160> NUMBER OF SEQ ID NOS: 107

<210> SEQ ID NO 1
<211> LENGTH: 3396
<212> TYPE: DNA
<213> ORGANISM: Homo sapiens
<220> FEATURE:
<221> NAME/KEY: CDS
<222> LOCATION: (82)..(2496)

<400> SEQUENCE: 1
gaattcggct tccatcctaa tacgactcac tatagggctc gagcggccgc ccggggcagg        60
tatcttggct cacaggggac g atg tca agc tct tcc tgg ctc ctt ctc agc       111
                        Met Ser Ser Ser Ser Trp Leu Leu Leu Ser
                         1               5                  10 ctt gtt gct gta act gct gct cag tcc acc att gag gaa cag gcc aag       159
Leu Val Ala Val Thr Ala Ala Gln Ser Thr Ile Glu Glu Gln Ala Lys
                 15                  20                  25 aca ttt ttg gac aag ttt aac cac gaa gcc gaa gac ctg ttc tat caa       207
Thr Phe Leu Asp Lys Phe Asn His Glu Ala Glu Asp Leu Phe Tyr Gln
             30                  35                  40 agt tca ctt gct tct tgg aat tat aac acc aat att act gaa gag aat       255
Ser Ser Leu Ala Ser Trp Asn Tyr Asn Thr Asn Ile Thr Glu Glu Asn
         45                  50                  55 gtc caa aac atg aat aat gct ggg gac aaa tgg tct gcc ttt tta aag       303
Val Gln Asn Met Asn Asn Ala Gly Asp Lys Trp Ser Ala Phe Leu Lys
     60                  65                  70 gaa cag tcc aca ctt gcc caa atg tat cca cta caa gaa att cag aat       351
Glu Gln Ser Thr Leu Ala Gln Met Tyr Pro Leu Gln Glu Ile Gln Asn
```

```
              75                  80                  85                  90
ctc aca gtc aag ctt cag ctg cag gct ctt cag caa aat ggg tct tca            399
Leu Thr Val Lys Leu Gln Leu Gln Ala Leu Gln Gln Asn Gly Ser Ser
                     95                 100                 105 gtg ctg tca gaa gac aag agc aaa cgg ttg aac aca att cta aat aca            447
Val Leu Ser Glu Asp Lys Ser Lys Arg Leu Asn Thr Ile Leu Asn Thr
            110                 115                 120 atg agc acc atc tac agt act gga aaa gtt tgt aac cca gat aat cca            495
Met Ser Thr Ile Tyr Ser Thr Gly Lys Val Cys Asn Pro Asp Asn Pro
        125                 130                 135 caa gaa tgc tta tta ctt gaa cca ggt tgt aat gaa ata atg gca aac            543
Gln Glu Cys Leu Leu Leu Glu Pro Gly Leu Asn Glu Ile Met Ala Asn
    140                 145                 150 agt tta gac tac aat gag agg ctc tgg gct tgg gaa agc tgg aga tct            591
Ser Leu Asp Tyr Asn Glu Arg Leu Trp Ala Trp Glu Ser Trp Arg Ser
155                 160                 165                 170 gag gtc ggc aag cag ctg agg cca tta tat gaa gag tat gtg gtc ttg            639
Glu Val Gly Lys Gln Leu Arg Pro Leu Tyr Glu Glu Tyr Val Val Leu
                175                 180                 185 aaa aat gag atg gca aga gca aat cat tat gag gac tat ggg gat tat            687
Lys Asn Glu Met Ala Arg Ala Asn His Tyr Glu Asp Tyr Gly Asp Tyr
            190                 195                 200 tgg aga gga gac tat gaa gta aat ggg gta gat ggc tat gac tac agc            735
Trp Arg Gly Asp Tyr Glu Val Asn Gly Val Asp Gly Tyr Asp Tyr Ser
        205                 210                 215 cgc ggc cag ttg att gaa gat gtg gaa cat acc ttt gaa gag att aaa            783
Arg Gly Gln Leu Ile Glu Asp Val Glu His Thr Phe Glu Glu Ile Lys
    220                 225                 230 cca tta tat gaa cat ctt cat gcc tat gtg agg gca aag ttg atg aat            831
Pro Leu Tyr Glu His Leu His Ala Tyr Val Arg Ala Lys Leu Met Asn
235                 240                 245                 250 gcc tat cct tcc tat atc agt cca att gga tgc ctc cct gct cat ttg            879
Ala Tyr Pro Ser Tyr Ile Ser Pro Ile Gly Cys Leu Pro Ala His Leu
                255                 260                 265 ctt ggt gat atg tgg ggt aga ttt tgg aca aat ctg tac tct ttg aca            927
Leu Gly Asp Met Trp Gly Arg Phe Trp Thr Asn Leu Tyr Ser Leu Thr
            270                 275                 280 gtt ccc ttt gga cag aaa cca aac ata gat gtt act gat gca atg gtg            975
Val Pro Phe Gly Gln Lys Pro Asn Ile Asp Val Thr Asp Ala Met Val
        285                 290                 295 gac cag gcc tgg gat gca cag aga ata ttc aag gag gcc gag aag ttc           1023
Asp Gln Ala Trp Asp Ala Gln Arg Ile Phe Lys Glu Ala Glu Lys Phe
    300                 305                 310 ttt gta tct gtt ggt ctt cct aat atg act caa gga ttc tgg gaa aat           1071
Phe Val Ser Val Gly Leu Pro Asn Met Thr Gln Gly Phe Trp Glu Asn
315                 320                 325                 330 tcc atg cta acg gac cca gga aat gtt cag aaa gca gtc tgc cat ccc           1119
Ser Met Leu Thr Asp Pro Gly Asn Val Gln Lys Ala Val Cys His Pro
                335                 340                 345 aca gct tgg gac ctg ggg aag ggc gac ttc agg atc ctt atg tgc aca           1167
Thr Ala Trp Asp Leu Gly Lys Gly Asp Phe Arg Ile Leu Met Cys Thr
            350                 355                 360 aag gtc aca atg gac gac ttc ctg aca gct cat cat gag atg ggg cat           1215
Lys Val Thr Met Asp Asp Phe Leu Thr Ala His His Glu Met Gly His
        365                 370                 375 atc cag tat gat atg gca tat gct gca caa cct ttt ctg cta aga aat           1263
Ile Gln Tyr Asp Met Ala Tyr Ala Ala Gln Pro Phe Leu Leu Arg Asn
    380                 385                 390 gga gct aat gaa gga ttc cat gaa gct gtt ggg gaa atc atg tca ctt           1311
```

```
Gly Ala Asn Glu Gly Phe His Glu Ala Val Gly Glu Ile Met Ser Leu
395                 400                 405                 410 tct gca gcc aca cct aag cat tta aaa tcc att ggt ctt ctg tca ccc      1359
Ser Ala Ala Thr Pro Lys His Leu Lys Ser Ile Gly Leu Leu Ser Pro
            415                 420                 425 gat ttt caa gaa gac aat gaa aca gaa ata aac ttc ctg ctc aaa caa      1407
Asp Phe Gln Glu Asp Asn Glu Thr Glu Ile Asn Phe Leu Leu Lys Gln
        430                 435                 440 gca ctc acg att gtt ggg act ctg cca ttt act tac atg tta gag aag      1455
Ala Leu Thr Ile Val Gly Thr Leu Pro Phe Thr Tyr Met Leu Glu Lys
    445                 450                 455 tgg agg tgg atg gtc ttt aaa ggg gaa att ccc aaa gac cag tgg atg      1503
Trp Arg Trp Met Val Phe Lys Gly Glu Ile Pro Lys Asp Gln Trp Met
460                 465                 470 aaa aag tgg tgg gag atg aag cga gag ata gtt ggg gtg gtg gaa cct      1551
Lys Lys Trp Trp Glu Met Lys Arg Glu Ile Val Gly Val Val Glu Pro
475                 480                 485                 490 gtg ccc cat gat gaa aca tac tgt gac ccc gca tct ctg ttc cat gtt      1599
Val Pro His Asp Glu Thr Tyr Cys Asp Pro Ala Ser Leu Phe His Val
            495                 500                 505 tct aat gat tac tca ttc att cga tat tac aca agg acc ctt tac caa      1647
Ser Asn Asp Tyr Ser Phe Ile Arg Tyr Tyr Thr Arg Thr Leu Tyr Gln
        510                 515                 520 ttc cag ttt caa gaa gca ctt tgt caa gca gct aaa cat gaa ggc cct      1695
Phe Gln Phe Gln Glu Ala Leu Cys Gln Ala Ala Lys His Glu Gly Pro
    525                 530                 535 ctg cac aaa tgt gac atc tca aac tct aca gaa gct gga cag aaa ctg      1743
Leu His Lys Cys Asp Ile Ser Asn Ser Thr Glu Ala Gly Gln Lys Leu
540                 545                 550 ttc aat atg ctg agg ctt gga aaa tca gaa ccc tgg acc cta gca ttg      1791
Phe Asn Met Leu Arg Leu Gly Lys Ser Glu Pro Trp Thr Leu Ala Leu
555                 560                 565                 570 gaa aat gtt gta gga gca aag aac atg aat gta agg cca ctg ctc aac      1839
Glu Asn Val Val Gly Ala Lys Asn Met Asn Val Arg Pro Leu Leu Asn
            575                 580                 585 tac ttt gag ccc tta ttt acc tgg ctg aaa gac cag aac aag aat tct      1887
Tyr Phe Glu Pro Leu Phe Thr Trp Leu Lys Asp Gln Asn Lys Asn Ser
        590                 595                 600 ttt gtg gga tgg agt acc gac tgg agt cca tat gca gac caa agc atc      1935
Phe Val Gly Trp Ser Thr Asp Trp Ser Pro Tyr Ala Asp Gln Ser Ile
    605                 610                 615 aaa gtg agg ata agc cta aaa tca gct ctt gga gat aaa gca tat gaa      1983
Lys Val Arg Ile Ser Leu Lys Ser Ala Leu Gly Asp Lys Ala Tyr Glu
620                 625                 630 tgg aac gac aat gaa atg tac ctg ttc cga tca tct gtt gca tat gct      2031
Trp Asn Asp Asn Glu Met Tyr Leu Phe Arg Ser Ser Val Ala Tyr Ala
635                 640                 645                 650 atg agg cag tac ttt tta aaa gta aaa aat cag atg att ctt ttt ggg      2079
Met Arg Gln Tyr Phe Leu Lys Val Lys Asn Gln Met Ile Leu Phe Gly
            655                 660                 665 gag gag gat gtg cga gtg gct aat ttg aaa cca aga atc tcc ttt aat      2127
Glu Glu Asp Val Arg Val Ala Asn Leu Lys Pro Arg Ile Ser Phe Asn
        670                 675                 680 ttc ttt gtc act gca cct aaa aat gtg tct gat atc att cct aga act      2175
Phe Phe Val Thr Ala Pro Lys Asn Val Ser Asp Ile Ile Pro Arg Thr
    685                 690                 695 gaa gtt gaa aag gcc atc agg atg tcc cgg agc cgt atc aat gat gct      2223
Glu Val Glu Lys Ala Ile Arg Met Ser Arg Ser Arg Ile Asn Asp Ala
700                 705                 710
```

-continued

```
ttc cgt ctg aat gac aac agc cta gag ttt ctg ggg ata cag cca aca      2271
Phe Arg Leu Asn Asp Asn Ser Leu Glu Phe Leu Gly Ile Gln Pro Thr
715                 720                 725                 730 ctt gga cct cct aac cag ccc cct gtt tcc ata tgg ctg att gtt ttt      2319
Leu Gly Pro Pro Asn Gln Pro Pro Val Ser Ile Trp Leu Ile Val Phe
                735                 740                 745 gga gtt gtg atg gga gtg ata gtg gtt ggc att gtc atc ctg atc ttc      2367
Gly Val Val Met Gly Val Ile Val Val Gly Ile Val Ile Leu Ile Phe
            750                 755                 760 act ggg atc aga gat cgg aag aag aaa aat aaa gca aga agt gga gaa      2415
Thr Gly Ile Arg Asp Arg Lys Lys Lys Asn Lys Ala Arg Ser Gly Glu
        765                 770                 775 aat cct tat gcc tcc atc gat att agc aaa gga gaa aat aat cca gga      2463
Asn Pro Tyr Ala Ser Ile Asp Ile Ser Lys Gly Glu Asn Asn Pro Gly
    780                 785                 790 ttc caa aac act gat gat gtt cag acc tcc ttt tagaaaaatc tatgtttttc    2516
Phe Gln Asn Thr Asp Asp Val Gln Thr Ser Phe
795                 800                 805 ctcttgaggt gattttgttg tatgtaaatg ttaatttcat ggtatagaaa atataagatg    2576
ataaagatat cattaaatgt caaaactatg actctgttca gaaaaaaaat tgtccaaaga    2636
caacatggcc aaggagagag catcttcatt gacattgctt tcagtattta tttctgtctc    2696
tggatttgac ttctgttctg tttcttaata aggattttgt attagagtat attagggaaa    2756
gtgtgtattt ggtctcacag gctgttcagg gataatctaa atgtaaatgt ctgttgaatt    2816
tctgaagttg aaaacaagga tatatcattg gagcaagtgt tggatcttgt atggaatatg    2876
gatggatcac ttgtaaggac agtgcctggg aactggtgta gctgcaagga ttgagaatgg    2936
catgcattag ctcactttca tttaatccat tgtcaaggat gacatgcttt cttcacagta    2996
actcagttca agtactatgg tgatttgcct acagtgatgt ttggaatcga tcatgctttc    3056
ttcaaggtga caggtctaaa gagagaagaa tccagggaac aggtagagga cattgctttt    3116
tcacttccaa ggtgcttgat caacatctcc ctgacaacac aaaactagag ccaggggcct    3176
ccgtgaactc ccagagcatg cctgatagaa actcatttct actgttctct aactgtggag    3236
tgaatggaaa ttccaactgt atgttcaccc tctgaagtgg gtacccagtc tcttaaatct    3296
tttgtatttg ctcacagtgt ttgagcagtg ctgagcacaa agcagacact caataaatgc    3356
tagatttaca cactccaaaaa aaaaaaaaaa gggcggccgc                         3396
```

<210> SEQ ID NO 2
<211> LENGTH: 805
<212> TYPE: PRT
<213> ORGANISM: Homo sapiens

<400> SEQUENCE: 2

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95
```

-continued

```
Leu Gln Ala Leu Gln Gln Asn Gly Ser Ser Val Leu Ser Glu Asp Lys
            100                 105                 110
Ser Lys Arg Leu Asn Thr Ile Leu Asn Thr Met Ser Thr Ile Tyr Ser
        115                 120                 125
Thr Gly Lys Val Cys Asn Pro Asp Asn Pro Gln Glu Cys Leu Leu Leu
    130                 135                 140
Glu Pro Gly Leu Asn Glu Ile Met Ala Asn Ser Leu Asp Tyr Asn Glu
145                 150                 155                 160
Arg Leu Trp Ala Trp Glu Ser Trp Arg Ser Glu Val Gly Lys Gln Leu
                165                 170                 175
Arg Pro Leu Tyr Glu Glu Tyr Val Val Leu Lys Asn Glu Met Ala Arg
            180                 185                 190
Ala Asn His Tyr Glu Asp Tyr Gly Asp Tyr Trp Arg Gly Asp Tyr Glu
        195                 200                 205
Val Asn Gly Val Asp Gly Tyr Asp Tyr Ser Arg Gly Gln Leu Ile Glu
    210                 215                 220
Asp Val Glu His Thr Phe Glu Glu Ile Lys Pro Leu Tyr Glu His Leu
225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
            260                 265                 270
Arg Phe Trp Thr Asn Leu Tyr Ser Leu Thr Val Pro Phe Gly Gln Lys
        275                 280                 285
Pro Asn Ile Asp Val Thr Asp Ala Met Val Asp Gln Ala Trp Asp Ala
    290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
            340                 345                 350
Lys Gly Asp Phe Arg Ile Leu Met Cys Thr Lys Val Thr Met Asp Asp
        355                 360                 365
Phe Leu Thr Ala His His Glu Met Gly His Ile Gln Tyr Asp Met Ala
    370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
            420                 425                 430
Glu Thr Glu Ile Asn Phe Leu Leu Lys Gln Ala Leu Thr Ile Val Gly
        435                 440                 445
Thr Leu Pro Phe Thr Tyr Met Leu Glu Lys Trp Arg Trp Met Val Phe
    450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
            500                 505                 510
```

```
Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
        530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 3
<211> LENGTH: 2415
<212> TYPE: DNA
<213> ORGANISM: Homo sapiens

<400> SEQUENCE: 3
atgtcaagct cttcctggct ccttctcagc cttgttgctg taactgctgc tcagtccacc      60
attgaggaac aggccaagac atttttggac aagtttaacc acgaagccga agacctgttc     120
tatcaaagtt cacttgcttc ttggaattat aacaccaata ttactgaaga gaatgtccaa     180
aacatgaata atgctgggga caaatggtct gcctttttaa aggaacagtc cacacttgcc     240
caaatgtatc cactacaaga aattcagaat ctcacagtca agcttcagct gcaggctctt     300
cagcaaaatg ggtcttcagt gctgtcagaa gacaagagca acggttgaa cacaattcta     360 aatacaatga gcaccatcta cagtactgga aaagtttgta cccagataa tccacaagaa     420
```

```
tgcttattac ttgaaccagg tttgaatgaa ataatggcaa acagtttaga ctacaatgag      480
aggctctggg cttgggaaag ctggagatct gaggtcggca agcagctgag gccattatat      540
gaagagtatg tggtcttgaa aaatgagatg caagagcaa atcattatga ggactatggg       600
gattattgga gaggagacta tgaagtaaat ggggtagatg gctatgacta cagccgcggc      660
cagttgattg aagatgtgga acatacctt gaagagatta accattata tgaacatctt        720 catgcctatg tgagggcaaa gttgatgaat gcctatcctt cctatatcag tccaattgga      780
tgcctccctg ctcatttgct tggtgatatg tggggtagat tttggacaaa tctgtactct      840
ttgacagttc cctttggaca gaaaccaaac atagatgtta ctgatgcaat ggtggaccag      900
gcctgggatg cacagagaat attcaaggag ccgagaagt tctttgtatc tgttggtctt       960
cctaatatga ctcaaggatt ctgggaaaat tccatgctaa cggacccagg aaatgttcag     1020
aaagcagtct gccatcccac agcttgggac ctggggaagg gcgacttcag gatccttatg     1080
tgcacaaagg tgacaatgga cgacttcctg acagctcatc atgagatggg gcatatccag     1140
tatgatatgg catatgctgc acaaccttt ctgctaagaa atggagctaa tgaaggattc      1200
catgaagctg ttggggaaat catgtcactt tctgcagcca cacctaagca tttaaaatcc     1260
attggtcttc tgtcacccga ttttcaagaa gacaatgaaa cagaaataaa cttcctgctc     1320
aaacaagcac tcacgattgt tgggactctg ccatttactt acatgttaga gaagtggagg     1380
tggatggtct ttaaagggga aattcccaaa gaccagtgga tgaaaaagtg gtgggagatg     1440
aagcgagaga tagttggggt ggtggaacct gtgccccatg atgaaacata ctgtgacccc     1500
gcatctctgt ccatgttc taatgattac tcattcattc gatattacac aaggacccct       1560
taccaattcc agtttcaaga agcactttgt caagcagcta acatgaaggg ccctctgcac     1620
aaatgtgaca tctcaaactc tacagaagct ggacagaaac tgttcaatat gctgaggctt     1680
ggaaaatcag aaccctggac cctagcattg aaaatgttg taggagcaaa gaacatgaat      1740
gtaaggccac tgctcaacta cttttgagccc ttatttacct ggctgaaaga ccagaacaag    1800 aattctttg tgggatggag taccgactgg agtccatatg cagaccaaag catcaaagtg     1860
aggataagcc taaaatcagc tcttggagat aaagcatatg aatggaacga caatgaaatg    1920
tacctgttcc gatcatctgt tgcatatgct atgaggcagt actttttaaa agtaaaaaat     1980
cagatgattc ttttttgggga ggaggatgtg cgagtggcta atttgaaacc aagaatctcc    2040
tttaatttct ttgtcactgc acctaaaaat gtgtctgata tcattcctag aactgaagtt     2100
gaaaaggcca tcaggatgtc ccggagccgt atcaatgatg ctttccgtct gaatgacaac    2160
agcctagagt tctctgggat acagccaaca cttggacctc ctaaccagcc ccctgttttcc   2220 atatggctga ttgttttggg agttgtgatg ggagtgatag tggttggcat tgtcatcctg    2280
atcttcactg ggatcagaga tcggaagaag aaaaataaag caagaagtgg agaaaatcct    2340
tatgcctcca tcgatattag caaaggagaa ataatccag gattccaaaa cactgatgat     2400
gttcagacct cctt                                                       2415
```

<210> SEQ ID NO 4
<211> LENGTH: 732
<212> TYPE: PRT
<213> ORGANISM: Homo sapiens

<400> SEQUENCE: 4

```
Met Gly Gln Gly Trp Ala Thr Ala Gly Leu Pro Ser Leu Leu Phe Leu
 1               5                  10                  15
```

-continued

```
Leu Leu Cys Tyr Gly His Pro Leu Leu Val Pro Ser Gln Glu Ala Ser
            20                  25                  30
Gln Gln Val Thr Val Thr His Gly Thr Ser Ser Gln Ala Thr Thr Ser
        35                  40                  45
Ser Gln Thr Thr Thr His Gln Ala Thr Ala His Gln Thr Ser Ala Gln
    50                  55                  60
Ser Pro Asn Leu Val Thr Asp Glu Ala Glu Ala Ser Lys Phe Val Glu
65                  70                  75                  80
Glu Tyr Asp Arg Thr Ser Gln Val Val Trp Asn Glu Tyr Ala Glu Ala
                85                  90                  95
Asn Trp Asn Tyr Asn Thr Asn Ile Thr Thr Glu Thr Ser Lys Ile Leu
            100                 105                 110
Leu Gln Lys Asn Met Gln Ile Ala Asn His Thr Leu Lys Tyr Gly Thr
        115                 120                 125
Gln Ala Arg Lys Phe Asp Val Asn Gln Leu Gln Asn Thr Thr Ile Lys
    130                 135                 140
Arg Ile Ile Lys Lys Val Gln Asp Leu Glu Arg Ala Ala Leu Pro Ala
145                 150                 155                 160
Gln Glu Leu Glu Glu Tyr Asn Lys Ile Leu Leu Asp Met Glu Thr Thr
                165                 170                 175
Tyr Ser Val Ala Thr Val Cys His Pro Asn Gly Ser Cys Leu Gln Leu
            180                 185                 190
Glu Pro Asp Leu Thr Asn Val Met Ala Thr Ser Arg Lys Tyr Glu Asp
        195                 200                 205
Leu Leu Trp Ala Trp Glu Gly Trp Arg Asp Lys Ala Gly Arg Ala Ile
    210                 215                 220
Leu Gln Phe Tyr Pro Lys Tyr Val Glu Leu Ile Asn Gln Ala Ala Arg
225                 230                 235                 240
Leu Asn Gly Tyr Val Asp Ala Gly Asp Ser Trp Arg Ser Met Tyr Glu
                245                 250                 255
Thr Pro Ser Leu Glu Gln Asp Leu Glu Arg Leu Phe Gln Glu Leu Gln
            260                 265                 270
Pro Leu Tyr Leu Asn Leu His Ala Tyr Val Arg Arg Ala Leu His Arg
        275                 280                 285
His Tyr Gly Ala Gln His Ile Asn Leu Glu Gly Pro Ile Pro Ala His
    290                 295                 300
Leu Leu Gly Asn Met Trp Ala Gln Thr Trp Ser Asn Ile Tyr Asp Leu
305                 310                 315                 320
Val Val Pro Phe Pro Ser Ala Pro Ser Met Asp Thr Thr Glu Ala Met
                325                 330                 335
Leu Lys Gln Gly Trp Thr Pro Arg Arg Met Phe Lys Glu Ala Asp Asp
            340                 345                 350
Phe Phe Thr Ser Leu Gly Leu Leu Pro Val Pro Pro Glu Phe Trp Asn
        355                 360                 365
Lys Ser Met Leu Glu Lys Pro Thr Asp Gly Arg Glu Val Val Cys His
    370                 375                 380
Ala Ser Ala Trp Asp Phe Tyr Asn Gly Lys Asp Phe Arg Ile Lys Gln
385                 390                 395                 400
Cys Thr Thr Val Asn Leu Glu Asp Leu Val Val Ala His His Glu Met
                405                 410                 415
Gly His Ile Gln Tyr Phe Met Gln Tyr Lys Asp Leu Pro Val Ala Leu
            420                 425                 430
Arg Glu Gly Ala Asn Pro Gly Phe His Glu Ala Ile Gly Asp Val Leu
```

-continued

```
              435                 440                 445
Ala Leu Ser Val Ser Thr Pro Lys His Leu His Ser Leu Asn Leu Leu
        450                 455                 460

Ser Ser Glu Gly Gly Ser Asp Glu His Asp Ile Asn Phe Leu Met Lys
465                 470                 475                 480

Met Ala Leu Asp Lys Ile Ala Phe Ile Pro Phe Ser Tyr Leu Val Asp
                485                 490                 495

Gln Trp Arg Trp Arg Val Phe Asp Gly Ser Ile Thr Lys Glu Asn Tyr
            500                 505                 510

Asn Gln Glu Trp Trp Ser Leu Arg Leu Lys Tyr Gln Gly Leu Cys Pro
        515                 520                 525

Pro Val Pro Arg Thr Gln Gly Asp Phe Asp Pro Gly Ala Lys Phe His
    530                 535                 540

Ile Pro Ser Ser Val Pro Tyr Ile Arg Tyr Phe Val Ser Phe Ile Ile
545                 550                 555                 560

Gln Phe Gln Phe His Glu Ala Leu Cys Gln Ala Ala Gly His Thr Gly
                565                 570                 575

Pro Leu His Lys Cys Asp Ile Tyr Gln Ser Lys Glu Ala Gly Gln Arg
            580                 585                 590

Leu Ala Thr Ala Met Lys Leu Gly Phe Ser Arg Pro Trp Pro Glu Ala
        595                 600                 605

Met Gln Leu Ile Thr Gly Gln Pro Asn Met Ser Ala Ser Ala Met Leu
    610                 615                 620

Ser Tyr Phe Lys Pro Leu Leu Asp Trp Leu Arg Thr Glu Asn Glu Leu
625                 630                 635                 640

His Gly Glu Lys Leu Gly Trp Pro Gln Tyr Asn Trp Thr Pro Asn Ser
                645                 650                 655

Ala Arg Ser Glu Gly Pro Leu Pro Asp Ser Gly Arg Val Ser Phe Leu
            660                 665                 670

Gly Leu Asp Leu Asp Ala Gln Gln Ala Arg Val Gly Gln Trp Leu Leu
        675                 680                 685

Leu Phe Leu Gly Ile Ala Leu Leu Val Ala Thr Leu Gly Leu Ser Gln
    690                 695                 700

Arg Leu Phe Ser Ile Arg His Arg Ser Leu His Arg His Ser His Gly
705                 710                 715                 720

Pro Gln Phe Gly Ser Glu Val Glu Leu Arg His Ser
                725                 730
```

<210> SEQ ID NO 5
<211> LENGTH: 732
<212> TYPE: PRT
<213> ORGANISM: Murine sp.
<220> FEATURE:
<223> OTHER INFORMATION: Description of Artificial Sequence:motifs

<400> SEQUENCE: 5

```
Met Gly Gln Gly Trp Ala Thr Pro Gly Leu Pro Ser Phe Leu Phe Leu
1               5                   10                  15

Leu Leu Cys Cys Gly His His Leu Leu Val Leu Ser Gln Val Ala Thr
                20                  25                  30

Asp His Val Thr Ala Asn Gln Gly Ile Thr Asn Gln Ala Thr Thr Arg
            35                  40                  45

Ser Gln Thr Thr Thr His Gln Ala Thr Ile Asp Gln Thr Thr Gln Ile
        50                  55                  60

Pro Asn Leu Glu Thr Asp Glu Ala Lys Ala Asp Arg Phe Val Glu Glu
```

-continued

```
             65                  70                  75                  80
Tyr Asp Arg Thr Ala Gln Val Leu Leu Asn Glu Tyr Ala Glu Ala Asn
                     85                  90                  95

Trp Gln Tyr Asn Thr Asn Ile Thr Ile Glu Gly Ser Lys Ile Leu Leu
                    100                 105                 110

Glu Lys Ser Thr Glu Val Ser Asn His Thr Leu Lys Tyr Gly Thr Arg
                    115                 120                 125

Ala Lys Thr Phe Asp Val Ser Asn Phe Gln Asn Ser Ser Ile Lys Arg
            130                 135                 140

Ile Ile Lys Lys Leu Gln Asn Leu Asp Arg Ala Val Leu Pro Pro Lys
145                 150                 155                 160

Glu Leu Glu Glu Tyr Asn Gln Ile Leu Leu Asp Met Glu Thr Thr Tyr
                    165                 170                 175

Ser Leu Ser Asn Ile Cys Tyr Thr Asn Gly Thr Cys Met Pro Leu Glu
                180                 185                 190

Pro Asp Leu Thr Asn Met Met Ala Thr Ser Arg Lys Tyr Glu Glu Leu
            195                 200                 205

Leu Trp Ala Trp Lys Ser Trp Arg Asp Lys Val Gly Arg Ala Ile Leu
        210                 215                 220

Pro Phe Phe Pro Lys Tyr Val Glu Phe Ser Asn Lys Ile Ala Lys Leu
225                 230                 235                 240

Asn Gly Tyr Thr Asp Ala Gly Asp Ser Trp Arg Ser Leu Tyr Glu Ser
                245                 250                 255

Asp Asn Leu Glu Gln Asp Leu Glu Lys Leu Tyr Gln Glu Leu Gln Pro
            260                 265                 270

Leu Tyr Leu Asn Leu His Ala Tyr Val Arg Arg Ser Leu His Arg His
        275                 280                 285

Tyr Gly Ser Glu Tyr Ile Asn Leu Asp Gly Pro Ile Pro Ala His Leu
    290                 295                 300

Leu Gly Asn Met Trp Ala Gln Thr Trp Ser Asn Ile Tyr Asp Leu Val
305                 310                 315                 320

Ala Pro Phe Pro Ser Ala Pro Asn Ile Asp Ala Thr Glu Ala Met Ile
                325                 330                 335

Lys Gln Gly Trp Thr Pro Arg Arg Ile Phe Lys Glu Ala Asp Asn Phe
            340                 345                 350

Phe Thr Ser Leu Gly Leu Leu Pro Val Pro Pro Glu Phe Trp Asn Lys
        355                 360                 365

Ser Met Leu Glu Lys Pro Thr Asp Gly Arg Glu Val Val Cys His Pro
    370                 375                 380

Ser Ala Trp Asp Phe Tyr Asn Gly Lys Asp Phe Arg Ile Lys Gln Cys
385                 390                 395                 400

Thr Ser Val Asn Met Glu Asp Leu Val Ile Ala His His Glu Met Gly
                405                 410                 415

His Ile Gln Tyr Phe Met Gln Tyr Lys Asp Leu Pro Val Thr Phe Arg
            420                 425                 430

Glu Gly Ala Asn Pro Gly Phe His Glu Ala Ile Gly Asp Ile Met Ala
        435                 440                 445

Leu Ser Val Ser Thr Pro Lys His Leu Tyr Ser Leu Asn Leu Leu Ser
    450                 455                 460

Thr Glu Gly Ser Gly Tyr Glu Tyr Asp Ile Asn Phe Leu Met Lys Met
465                 470                 475                 480

Ala Leu Asp Lys Ile Ala Phe Ile Pro Phe Ser Tyr Leu Ile Asp Gln
                485                 490                 495
```

Trp Arg Trp Arg Val Phe Asp Gly Ser Ile Thr Lys Glu Asn Tyr Asn
          500                 505                 510

Gln Glu Trp Trp Ser Leu Arg Leu Lys Tyr Gln Gly Leu Cys Pro Pro
          515                 520                 525

Val Pro Arg Ser Gln Gly Asp Phe Asp Pro Gly Ser Lys Phe His Val
          530                 535                 540

Pro Ala Asn Val Pro Tyr Val Arg Tyr Phe Val Ser Phe Ile Ile Gln
545                 550                 555                 560

Phe Gln Phe His Glu Ala Leu Cys Arg Ala Ala Gly His Thr Gly Pro
                565                 570                 575

Leu His Lys Cys Asp Ile Tyr Gln Ser Lys Glu Ala Gly Lys Leu Leu
                580                 585                 590

Ala Asp Ala Met Lys Leu Gly Tyr Ser Lys Pro Trp Pro Glu Ala Met
                595                 600                 605

Lys Leu Ile Thr Gly Gln Pro Asn Met Ser Ala Ser Ala Met Met Asn
          610                 615                 620

Tyr Phe Lys Pro Leu Thr Glu Trp Leu Val Thr Glu Asn Arg Arg His
625                 630                 635                 640

Gly Glu Thr Leu Gly Trp Pro Glu Tyr Asn Trp Ala Pro Asn Thr Ala
                645                 650                 655

Arg Ala Glu Gly Ser Thr Ala Glu Ser Asn Arg Val Asn Phe Leu Gly
                660                 665                 670

Leu Tyr Leu Glu Pro Gln Gln Ala Arg Val Gly Gln Trp Val Leu Leu
                675                 680                 685

Phe Leu Gly Val Ala Leu Leu Val Ala Thr Val Gly Leu Ala His Arg
          690                 695                 700

Leu Tyr Asn Ile Arg Asn His His Ser Leu Arg Arg Pro His Arg Gly
705                 710                 715                 720

Pro Gln Phe Gly Ser Glu Val Glu Leu Arg His Ser
                725                 730

<210> SEQ ID NO 6
<211> LENGTH: 737
<212> TYPE: PRT
<213> ORGANISM: Oryctolagus cuniculus
<220> FEATURE:
<223> OTHER INFORMATION: Description of Artificial Sequence:motifs

<400> SEQUENCE: 6

Met Gly Gln Gly Trp Ala Ala Pro Gly Leu Pro Ser Leu Leu Leu Leu
  1               5                  10                  15

Leu Leu Cys Cys Gly His Ser Leu Leu Val Pro Ser Arg Val Ala Ala
                20                  25                  30

Arg Arg Val Thr Val Asn Gln Gly Thr Thr Ser Gln Ala Thr Thr Thr
            35                  40                  45

Ser Lys Ala Thr Thr Ser Ile Arg Ala Thr Thr His Gln Thr Thr Ala
    50                  55                  60

His Gln Thr Thr Gln Ser Pro Asn Leu Val Thr Asp Glu Ala Glu Ala
65                  70                  75                  80

Ser Arg Phe Val Glu Glu Tyr Asp Arg Ser Phe Gln Ala Val Trp Asn
                85                  90                  95

Glu Tyr Ala Glu Ala Asn Trp Asn Tyr Asn Thr Asn Ile Thr Thr Glu
                100                 105                 110

Ala Ser Lys Ile Leu Leu Gln Lys Asn Met Gln Ile Ala Asn His Thr
            115                 120                 125

```
Leu Thr Tyr Gly Asn Trp Ala Arg Arg Phe Asp Val Ser Asn Phe Gln
    130                 135                 140

Asn Ala Thr Ser Lys Arg Ile Ile Lys Lys Val Gln Asp Leu Gln Arg
145                 150                 155                 160

Ala Val Leu Pro Val Lys Glu Leu Glu Glu Tyr Asn Gln Ile Leu Leu
                165                 170                 175

Asp Met Glu Thr Ile Tyr Ser Val Ala Asn Val Cys Arg Val Asp Gly
            180                 185                 190

Ser Cys Leu Gln Leu Glu Pro Asp Leu Thr Asn Leu Met Ala Thr Ser
        195                 200                 205

Arg Lys Tyr Asp Glu Leu Leu Trp Val Trp Thr Ser Trp Arg Asp Lys
    210                 215                 220

Val Gly Arg Ala Ile Leu Pro Tyr Phe Pro Lys Tyr Val Glu Phe Thr
225                 230                 235                 240

Asn Lys Ala Ala Arg Leu Asn Gly Tyr Val Asp Ala Gly Asp Ser Trp
                245                 250                 255

Arg Ser Met Tyr Glu Thr Pro Thr Leu Glu Gln Asp Leu Glu Arg Leu
            260                 265                 270

Phe Gln Glu Leu Gln Pro Leu Tyr Leu Asn Leu His Ala Tyr Val Gly
        275                 280                 285

Arg Ala Leu His Arg His Tyr Gly Ala Gln His Ile Asn Leu Glu Gly
    290                 295                 300

Pro Ile Pro Ala His Leu Leu Gly Asn Met Trp Ala Gln Thr Trp Ser
305                 310                 315                 320

Asn Ile Tyr Asp Leu Val Ala Pro Phe Pro Ser Ala Ser Thr Met Asp
                325                 330                 335

Ala Thr Glu Ala Met Ile Lys Gln Gly Trp Thr Pro Arg Arg Met Phe
            340                 345                 350

Glu Glu Ala Asp Lys Phe Phe Ile Ser Leu Gly Leu Leu Pro Val Pro
        355                 360                 365

Pro Glu Phe Trp Asn Lys Ser Met Leu Glu Lys Pro Thr Asp Gly Arg
    370                 375                 380

Glu Val Val Cys His Ala Ser Ala Trp Asp Phe Tyr Asn Gly Lys Asp
385                 390                 395                 400

Phe Arg Ile Lys Gln Cys Thr Thr Val Asn Met Glu Asp Leu Val Val
                405                 410                 415

Val His His Glu Met Gly His Ile Gln Tyr Phe Met Gln Tyr Lys Asp
            420                 425                 430

Leu Pro Val Ala Leu Arg Glu Gly Ala Asn Pro Gly Phe His Glu Ala
        435                 440                 445

Ile Gly Asp Val Leu Ala Leu Ser Val Ser Thr Pro Lys His Leu His
    450                 455                 460

Ser Ile Asn Leu Leu Ser Ser Glu Gly Gly Tyr Glu His Asp Ile
465                 470                 475                 480

Asn Phe Leu Met Lys Met Ala Leu Asp Lys Ile Ala Phe Ile Pro Phe
                485                 490                 495

Ser Tyr Leu Val Asp Glu Trp Arg Trp Arg Val Phe Asp Gly Ser Ile
            500                 505                 510

Thr Lys Glu Asn Tyr Asn Gln Glu Trp Trp Ser Leu Arg Leu Lys Tyr
        515                 520                 525

Gln Gly Leu Cys Pro Pro Ala Pro Arg Ser Gln Gly Asp Phe Asp Pro
    530                 535                 540
```

-continued

Gly Ala Lys Phe His Ile Pro Ser Ser Val Pro Tyr Ile Arg Tyr Phe
545                 550                 555                 560

Val Ser Phe Ile Ile Gln Phe Gln Phe His Glu Ala Leu Cys Lys Ala
                565                 570                 575

Ala Gly His Thr Gly Pro Leu His Thr Cys Asp Ile Tyr Gln Ser Lys
            580                 585                 590

Glu Ala Gly Lys Arg Leu Ala Asp Ala Met Lys Leu Gly Tyr Ser Lys
        595                 600                 605

Pro Trp Pro Glu Ala Met Lys Val Ile Thr Gly Gln Pro Asn Met Ser
    610                 615                 620

Ala Ser Ala Met Met Asn Tyr Phe Lys Pro Leu Met Asp Trp Leu Leu
625                 630                 635                 640

Thr Glu Asn Gly Arg His Gly Glu Lys Leu Gly Trp Pro Gln Tyr Thr
                645                 650                 655

Trp Thr Pro Asn Ser Ala Arg Ser Glu Gly Ser Leu Pro Asp Ser Gly
            660                 665                 670

Arg Val Asn Phe Leu Gly Met Asn Leu Asp Ala Gln Gln Ala Arg Val
        675                 680                 685

Gly Gln Trp Val Leu Leu Phe Leu Gly Val Ala Leu Leu Leu Ala Ser
    690                 695                 700

Leu Gly Leu Thr Gln Arg Leu Phe Ser Ile Arg Tyr Gln Ser Leu Arg
705                 710                 715                 720

Gln Pro His His Gly Pro Gln Phe Gly Ser Glu Val Glu Leu Arg His
                725                 730                 735

Ser

<210> SEQ ID NO 7
<211> LENGTH: 1306
<212> TYPE: PRT
<213> ORGANISM: Homo sapiens
<220> FEATURE:
<223> OTHER INFORMATION: Description of Artificial Sequence:motifs

<400> SEQUENCE: 7

Met Gly Ala Ala Ser Gly Arg Arg Gly Pro Gly Leu Leu Leu Pro Leu
1               5                   10                  15

Pro Leu Leu Leu Leu Leu Pro Pro Gln Pro Ala Leu Ala Leu Asp Pro
                20                  25                  30

Gly Leu Gln Pro Gly Asn Phe Ser Ala Asp Glu Ala Gly Ala Gln Leu
            35                  40                  45

Phe Ala Gln Ser Tyr Asn Ser Ser Ala Glu Gln Val Leu Phe Gln Ser
        50                  55                  60

Val Ala Ala Ser Trp Ala His Asp Thr Asn Ile Thr Ala Glu Asn Ala
65                  70                  75                  80

Arg Arg Gln Glu Glu Ala Ala Leu Leu Ser Gln Glu Phe Ala Glu Ala
                85                  90                  95

Trp Gly Gln Lys Ala Lys Glu Leu Tyr Glu Pro Ile Trp Gln Asn Phe
            100                 105                 110

Thr Asp Pro Gln Leu Arg Arg Ile Ile Gly Ala Val Arg Thr Leu Gly
        115                 120                 125

Ser Ala Asn Leu Pro Leu Ala Lys Arg Gln Gln Tyr Asn Ala Leu Leu
    130                 135                 140

Ser Asn Met Ser Arg Ile Tyr Ser Thr Ala Lys Val Cys Leu Pro Asn
145                 150                 155                 160

Lys Thr Ala Thr Cys Trp Ser Leu Asp Pro Asp Leu Thr Asn Ile Leu

-continued

```
                165                 170                 175
Ala Ser Ser Arg Ser Tyr Ala Met Leu Leu Phe Ala Trp Glu Gly Trp
            180                 185                 190
His Asn Ala Ala Gly Ile Pro Leu Lys Pro Leu Tyr Glu Asp Phe Thr
            195                 200                 205
Ala Leu Ser Asn Glu Ala Tyr Lys Gln Asp Gly Phe Thr Asp Thr Gly
            210                 215                 220
Ala Tyr Trp Arg Ser Trp Tyr Asn Ser Pro Thr Phe Glu Asp Asp Leu
225                 230                 235                 240
Glu His Leu Tyr Gln Gln Leu Glu Pro Leu Tyr Leu Asn Leu His Ala
                245                 250                 255
Phe Val Arg Arg Ala Leu His Arg Arg Tyr Gly Asp Arg Tyr Ile Asn
            260                 265                 270
Leu Arg Gly Pro Ile Pro Ala His Leu Leu Gly Asp Met Trp Ala Gln
            275                 280                 285
Ser Trp Glu Asn Ile Tyr Asp Met Val Val Pro Phe Pro Asp Lys Pro
            290                 295                 300
Asn Leu Asp Val Thr Ser Thr Met Leu Gln Gln Gly Trp Asn Ala Thr
305                 310                 315                 320
His Met Phe Arg Val Ala Glu Glu Phe Phe Thr Ser Leu Glu Leu Ser
                325                 330                 335
Pro Met Pro Pro Glu Phe Trp Glu Gly Ser Met Leu Glu Lys Pro Ala
            340                 345                 350
Asp Gly Arg Glu Val Val Cys His Ala Ser Ala Trp Asp Phe Tyr Asn
            355                 360                 365
Arg Lys Asp Phe Arg Ile Lys Gln Cys Thr Arg Val Thr Met Asp Gln
            370                 375                 380
Leu Ser Thr Val His His Glu Met Gly His Ile Gln Tyr Tyr Leu Gln
385                 390                 395                 400
Tyr Lys Asp Leu Pro Val Ser Leu Arg Arg Gly Ala Asn Pro Gly Phe
                405                 410                 415
His Glu Ala Ile Gly Asp Val Leu Ala Leu Ser Val Ser Thr Pro Glu
            420                 425                 430
His Leu His Lys Ile Gly Leu Leu Asp Arg Val Thr Asn Asp Thr Glu
            435                 440                 445
Ser Asp Ile Asn Tyr Leu Leu Lys Met Ala Leu Glu Lys Ile Ala Phe
            450                 455                 460
Leu Pro Phe Gly Tyr Leu Val Asp Gln Trp Arg Trp Gly Val Phe Ser
465                 470                 475                 480
Gly Arg Thr Pro Pro Ser Arg Tyr Asn Phe Asp Trp Trp Tyr Leu Arg
                485                 490                 495
Thr Lys Tyr Gln Gly Ile Cys Pro Pro Val Thr Arg Asn Glu Thr His
            500                 505                 510
Phe Asp Ala Gly Ala Lys Phe His Val Pro Asn Val Thr Pro Tyr Ile
            515                 520                 525
Arg Tyr Phe Val Ser Phe Val Leu Gln Phe Gln Phe His Glu Ala Leu
            530                 535                 540
Cys Lys Glu Ala Gly Tyr Glu Gly Pro Leu His Gln Cys Asp Ile Tyr
545                 550                 555                 560
Arg Ser Thr Lys Ala Gly Ala Lys Leu Arg Lys Val Leu Gln Ala Gly
                565                 570                 575
Ser Ser Arg Pro Trp Gln Glu Val Leu Lys Asp Met Val Gly Leu Asp
            580                 585                 590
```

-continued

```
Ala Leu Asp Ala Gln Pro Leu Leu Lys Tyr Phe Gln Pro Val Thr Gln
            595                 600                 605

Trp Leu Gln Glu Gln Asn Gln Gln Asn Gly Glu Val Leu Gly Trp Pro
        610                 615                 620

Glu Tyr Gln Trp His Pro Pro Leu Pro Asp Asn Tyr Pro Glu Gly Ile
625                 630                 635                 640

Asp Leu Val Thr Asp Glu Ala Glu Ala Ser Lys Phe Val Glu Glu Tyr
            645                 650                 655

Asp Arg Thr Ser Gln Val Val Trp Asn Glu Tyr Ala Glu Ala Asn Trp
        660                 665                 670

Asn Tyr Asn Thr Asn Ile Thr Thr Glu Thr Ser Lys Ile Leu Leu Gln
    675                 680                 685

Lys Asn Met Gln Ile Ala Asn His Thr Leu Lys Tyr Gly Thr Gln Ala
690                 695                 700

Arg Lys Phe Asp Val Asn Gln Leu Gln Asn Thr Thr Ile Lys Arg Ile
705                 710                 715                 720

Ile Lys Lys Val Gln Asp Leu Glu Arg Ala Ala Leu Pro Ala Gln Glu
            725                 730                 735

Leu Glu Glu Tyr Asn Lys Ile Leu Leu Asp Met Glu Thr Thr Tyr Ser
        740                 745                 750

Val Ala Thr Val Cys His Pro Asn Gly Ser Cys Leu Gln Leu Glu Pro
    755                 760                 765

Asp Leu Thr Asn Val Met Ala Thr Ser Arg Lys Tyr Glu Asp Leu Leu
770                 775                 780

Trp Ala Trp Glu Gly Trp Arg Asp Lys Ala Gly Arg Ala Ile Leu Gln
785                 790                 795                 800

Phe Tyr Pro Lys Tyr Val Glu Leu Ile Asn Gln Ala Ala Arg Leu Asn
            805                 810                 815

Gly Tyr Val Asp Ala Gly Asp Ser Trp Arg Ser Met Tyr Glu Thr Pro
        820                 825                 830

Ser Leu Glu Gln Asp Leu Glu Arg Leu Phe Gln Glu Leu Gln Pro Leu
    835                 840                 845

Tyr Leu Asn Leu His Ala Tyr Val Arg Arg Ala Leu His Arg His Tyr
    850                 855                 860

Gly Ala Gln His Ile Asn Leu Glu Gly Pro Ile Pro Ala His Leu Leu
865                 870                 875                 880

Gly Asn Met Trp Ala Gln Thr Trp Ser Asn Ile Tyr Asp Leu Val Val
            885                 890                 895

Pro Phe Pro Ser Ala Pro Ser Met Asp Thr Thr Glu Ala Met Leu Lys
        900                 905                 910

Gln Gly Trp Thr Pro Arg Arg Met Phe Lys Glu Ala Asp Asp Phe Phe
    915                 920                 925

Thr Ser Leu Gly Leu Leu Pro Val Pro Glu Phe Trp Asn Lys Ser Met
    930                 935                 940

Met Leu Glu Lys Pro Thr Asp Gly Arg Glu Val Val Cys His Ala Ser
945                 950                 955                 960

Ala Trp Asp Phe Tyr Asn Gly Lys Asp Phe Arg Ile Lys Gln Cys Thr
            965                 970                 975

Thr Val Asn Leu Glu Asp Leu Val Val Ala His His Glu Met Gly His
        980                 985                 990

Ile Gln Tyr Phe Met Gln Tyr Lys Asp Leu Pro Val Ala Leu Arg Glu
    995                 1000                1005
```

```
Gly Ala Asn Pro Gly Phe His Glu Ala Ile Gly Asp Val Leu Ala Leu
        1010                1015                1020

Ser Val Ser Thr Pro Lys His Leu His Ser Leu Asn Leu Leu Ser Ser
1025                1030                1035                1040

Glu Gly Gly Ser Asp Glu His Asp Ile Asn Phe Leu Met Lys Met Ala
                1045                1050                1055

Leu Asp Lys Ile Ala Phe Ile Pro Phe Ser Tyr Leu Val Asp Gln Trp
            1060                1065                1070

Arg Trp Arg Val Phe Asp Gly Ser Ile Thr Lys Glu Asn Tyr Asn Gln
        1075                1080                1085

Glu Trp Trp Ser Leu Arg Leu Lys Tyr Gln Gly Leu Cys Pro Pro Val
    1090                1095                1100

Pro Arg Thr Gln Gly Asp Phe Asp Pro Gly Ala Lys Phe His Ile Pro
1105                1110                1115                1120

Ser Ser Val Pro Tyr Ile Arg Tyr Phe Val Ser Phe Ile Ile Gln Phe
                1125                1130                1135

Gln Phe His Glu Ala Leu Cys Gln Ala Ala Gly His Thr Gly Pro Leu
            1140                1145                1150

His Lys Cys Asp Ile Tyr Gln Ser Lys Glu Ala Gly Gln Arg Leu Ala
        1155                1160                1165

Thr Ala Met Lys Leu Gly Phe Ser Arg Pro Trp Pro Glu Ala Met Gln
    1170                1175                1180

Leu Ile Thr Gly Gln Pro Asn Met Ser Ala Ser Ala Met Leu Ser Tyr
1185                1190                1195                1200

Phe Lys Pro Leu Leu Asp Trp Leu Arg Thr Glu Asn Glu Leu His Gly
                1205                1210                1215

Glu Lys Leu Gly Trp Pro Gln Tyr Asn Trp Thr Pro Asn Ser Ala Arg
            1220                1225                1230

Ser Glu Gly Pro Leu Pro Asp Ser Gly Arg Val Ser Phe Leu Gly Leu
        1235                1240                1245

Asp Leu Asp Ala Gln Gln Ala Arg Val Gly Gln Trp Leu Leu Leu Phe
    1250                1255                1260

Leu Gly Ile Ala Leu Leu Val Ala Thr Leu Gly Leu Ser Gln Arg Leu
1265                1270                1275                1280

Phe Ser Ile Arg His Arg Ser Leu His Arg His Ser His Gly Pro Gln
                1285                1290                1295

Phe Gly Ser Glu Val Glu Leu Arg His Ser
            1300                1305

<210> SEQ ID NO 8
<211> LENGTH: 1312
<212> TYPE: PRT
<213> ORGANISM: Murine sp.
<220> FEATURE:
<223> OTHER INFORMATION: Description of Artificial Sequence:motifs

<400> SEQUENCE: 8

Met Gly Ala Ala Ser Gly Gln Arg Gly Arg Trp Pro Leu Ser Pro Pro
1               5                   10                  15

Leu Leu Met Leu Ser Leu Leu Val Leu Leu Gln Pro Ser Pro Ala
                20                  25                  30

Pro Ala Leu Asp Pro Gly Leu Gln Pro Gly Asn Phe Ser Pro Asp Glu
            35                  40                  45

Ala Gly Ala Gln Leu Phe Ala Glu Ser Tyr Asn Ser Ser Ala Glu Val
        50                  55                  60
```

-continued

```
Val Met Phe Gln Ser Thr Val Ala Ser Trp Ala His Asp Thr Asn Ile
 65                  70                  75                  80

Thr Glu Glu Asn Ala Arg Arg Gln Glu Glu Ala Ala Leu Val Ser Gln
                 85                  90                  95

Glu Phe Ala Glu Val Trp Gly Lys Lys Ala Lys Glu Leu Tyr Glu Ser
            100                 105                 110

Ile Trp Gln Asn Phe Thr Asp Ser Lys Leu Arg Arg Ile Ile Gly Ser
        115                 120                 125

Ile Arg Thr Leu Gly Pro Ala Asn Leu Pro Leu Ala Gln Arg Gln Gln
    130                 135                 140

Tyr Asn Ser Leu Leu Ser Asn Met Ser Arg Ile Tyr Ser Thr Gly Lys
145                 150                 155                 160

Val Cys Phe Pro Asn Lys Thr Ala Thr Cys Trp Ser Leu Asp Pro Glu
                165                 170                 175

Leu Thr Asn Ile Leu Ala Ser Ser Arg Ser Tyr Ala Lys Leu Leu Phe
            180                 185                 190

Ala Trp Glu Gly Trp His Asp Ala Val Gly Ile Pro Leu Lys Pro Leu
        195                 200                 205

Tyr Gln Asp Phe Thr Ala Ile Ser Asn Glu Ala Tyr Arg Gln Asp Asp
    210                 215                 220

Phe Ser Asp Thr Gly Ala Phe Trp Arg Ser Trp Tyr Glu Ser Pro Ser
225                 230                 235                 240

Phe Glu Glu Ser Leu Glu His Ile Tyr His Gln Leu Glu Pro Leu Tyr
                245                 250                 255

Leu Asn Leu His Ala Tyr Val Arg Arg Ala Leu His Arg Arg Tyr Gly
            260                 265                 270

Asp Lys Tyr Val Asn Leu Arg Gly Pro Ile Pro Ala His Leu Leu Gly
        275                 280                 285

Asp Met Trp Ala Gln Ser Trp Glu Asn Ile Tyr Asp Met Val Val Pro
    290                 295                 300

Phe Pro Asp Lys Pro Asn Leu Asp Val Thr Ser Thr Met Val Gln Lys
305                 310                 315                 320

Gly Trp Asn Ala Thr His Met Phe Arg Val Ser Glu Glu Phe Phe Thr
                325                 330                 335

Ser Leu Gly Leu Ser Pro Met Pro Pro Glu Phe Trp Ala Glu Ser Met
            340                 345                 350

Leu Glu Lys Pro Thr Asp Gly Arg Glu Val Val Cys His Ala Ser Ala
        355                 360                 365

Trp Asp Phe Tyr Asn Arg Lys Asp Phe Arg Ile Lys Gln Cys Thr Arg
    370                 375                 380

Val Thr Met Glu Gln Leu Ala Thr Val His His Glu Met Gly His Val
385                 390                 395                 400

Gln Tyr Tyr Leu Gln Tyr Lys Asp Leu His Val Ser Leu Arg Arg Gly
                405                 410                 415

Ala Asn Pro Gly Phe His Glu Ala Ile Gly Asp Val Leu Ala Leu Ser
            420                 425                 430

Val Ser Thr Pro Ala His Leu His Lys Ile Gly Leu Leu Asp His Val
        435                 440                 445

Thr Asn Asp Ile Glu Ser Asp Ile Asn Tyr Leu Leu Lys Met Ala Leu
    450                 455                 460

Glu Lys Ile Ala Phe Leu Pro Phe Gly Tyr Leu Val Asp Gln Trp Arg
465                 470                 475                 480

Trp Gly Val Phe Ser Gly Arg Thr Pro Pro Ser Arg Tyr Asn Phe Asp
```

-continued

```
                485                 490                 495
Trp Trp Tyr Leu Arg Thr Lys Tyr Gln Gly Ile Cys Pro Val Ala
            500                 505                 510

Arg Asn Glu Thr His Phe Asp Ala Gly Ala Lys Phe His Ile Pro Asn
            515                 520                 525

Val Thr Pro Tyr Ile Arg Tyr Phe Val Ser Phe Val Leu Gln Phe Gln
            530                 535                 540

Phe His Gln Ala Leu Cys Lys Glu Ala Gly His Gln Gly Pro Leu His
545                 550                 555                 560

Gln Cys Asp Ile Tyr Gln Ser Thr Gln Ala Gly Ala Lys Leu Lys Gln
                565                 570                 575

Val Leu Gln Ala Gly Cys Ser Arg Pro Trp Gln Glu Val Leu Lys Asp
            580                 585                 590

Leu Val Gly Ser Asp Ala Leu Asp Ala Lys Ala Leu Leu Glu Tyr Phe
            595                 600                 605

Gln Pro Val Ser Gln Trp Leu Glu Glu Gln Asn Gln Arg Asn Gly Glu
            610                 615                 620

Val Leu Gly Trp Pro Glu Asn Gln Trp Arg Pro Pro Leu Pro Asp Asn
625                 630                 635                 640

Tyr Pro Glu Gly Ile Asp Leu Glu Thr Asp Glu Ala Lys Ala Asp Arg
                645                 650                 655

Phe Val Glu Glu Tyr Asp Arg Thr Ala Gln Val Leu Leu Asn Glu Tyr
            660                 665                 670

Ala Glu Ala Asn Trp Gln Tyr Asn Thr Asn Ile Thr Ile Glu Gly Ser
            675                 680                 685

Lys Ile Leu Leu Glu Lys Ser Thr Glu Val Ser Asn His Thr Leu Lys
            690                 695                 700

Tyr Gly Thr Arg Ala Lys Thr Phe Asp Val Ser Asn Phe Gln Asn Ser
705                 710                 715                 720

Ser Ile Lys Arg Ile Ile Lys Lys Leu Gln Asn Leu Asp Arg Ala Val
                725                 730                 735

Leu Pro Pro Lys Glu Leu Glu Glu Tyr Asn Gln Ile Leu Leu Asp Met
            740                 745                 750

Glu Thr Thr Tyr Ser Leu Ser Asn Ile Cys Tyr Thr Asn Gly Thr Cys
            755                 760                 765

Met Pro Leu Glu Pro Asp Leu Thr Asn Met Met Ala Thr Ser Arg Lys
            770                 775                 780

Tyr Glu Glu Leu Leu Trp Ala Trp Lys Ser Trp Arg Asp Lys Val Gly
785                 790                 795                 800

Arg Ala Ile Leu Pro Phe Phe Pro Lys Tyr Val Glu Phe Ser Asn Lys
                805                 810                 815

Ile Ala Lys Leu Asn Gly Tyr Thr Asp Ala Gly Asp Ser Trp Arg Ser
            820                 825                 830

Leu Tyr Glu Ser Asp Asn Leu Glu Gln Asp Leu Glu Lys Leu Tyr Gln
            835                 840                 845

Glu Leu Gln Pro Leu Tyr Leu Asn Leu His Ala Tyr Val Arg Arg Ser
850                 855                 860

Leu His Arg His Tyr Gly Ser Glu Tyr Ile Asn Leu Asp Gly Pro Ile
865                 870                 875                 880

Pro Ala His Leu Leu Gly Asn Met Trp Ala Gln Thr Trp Ser Asn Ile
                885                 890                 895

Tyr Asp Leu Val Ala Pro Phe Pro Ser Ala Pro Asn Ile Asp Ala Thr
            900                 905                 910
```

```
Glu Ala Met Ile Lys Gln Gly Trp Thr Pro Arg Arg Ile Phe Lys Glu
            915                 920                 925

Ala Asp Asn Phe Phe Thr Ser Leu Gly Leu Leu Pro Val Pro Pro Glu
    930                 935                 940

Phe Trp Asn Lys Ser Met Leu Glu Lys Pro Thr Asp Gly Arg Glu Val
945                 950                 955                 960

Val Cys His Pro Ser Ala Trp Asp Phe Tyr Asn Gly Lys Asp Phe Arg
                965                 970                 975

Ile Lys Gln Cys Thr Ser Val Asn Met Glu Asp Leu Val Ile Ala His
            980                 985                 990

His Glu Met Gly His Ile Gln Tyr Phe Met Gln Tyr Lys Asp Leu Pro
        995                 1000                1005

Val Thr Phe Arg Glu Gly Ala Asn Pro Gly Phe His Glu Ala Ile Gly
    1010                1015                1020

Asp Ile Met Ala Leu Ser Val Ser Thr Pro Lys His Leu Tyr Ser Leu
1025                1030                1035                1040

Asn Leu Leu Ser Thr Glu Gly Ser Gly Tyr Glu Tyr Asp Ile Asn Phe
                1045                1050                1055

Leu Met Lys Met Ala Leu Asp Lys Ile Ala Phe Ile Pro Phe Ser Tyr
            1060                1065                1070

Leu Ile Asp Gln Trp Arg Trp Arg Val Phe Asp Gly Ser Ile Thr Lys
        1075                1080                1085

Glu Asn Tyr Asn Gln Glu Trp Trp Ser Leu Arg Leu Lys Tyr Gln Gly
    1090                1095                1100

Leu Cys Pro Pro Val Pro Arg Ser Gln Gly Asp Phe Asp Pro Gly Ser
1105                1110                1115                1120

Lys Phe His Val Pro Ala Asn Val Pro Tyr Val Arg Tyr Phe Val Ser
                1125                1130                1135

Phe Ile Ile Gln Phe Gln Phe His Glu Ala Leu Cys Arg Ala Ala Gly
            1140                1145                1150

His Thr Gly Pro Leu His Lys Cys Asp Ile Tyr Gln Ser Lys Glu Ala
        1155                1160                1165

Gly Lys Leu Leu Ala Asp Ala Met Lys Leu Gly Tyr Ser Lys Pro Trp
    1170                1175                1180

Pro Glu Ala Met Lys Leu Ile Thr Gly Gln Pro Asn Met Ser Ala Ser
1185                1190                1195                1200

Ala Met Met Asn Tyr Phe Lys Pro Leu Thr Glu Trp Leu Val Thr Glu
                1205                1210                1215

Asn Arg Arg His Gly Glu Thr Leu Gly Trp Pro Glu Tyr Asn Trp Ala
            1220                1225                1230

Pro Asn Thr Ala Arg Ala Glu Gly Ser Thr Ala Glu Ser Asn Arg Val
        1235                1240                1245

Asn Phe Leu Gly Leu Tyr Leu Glu Pro Gln Gln Ala Arg Val Gly Gln
    1250                1255                1260

Trp Val Leu Leu Phe Leu Gly Val Ala Leu Leu Val Ala Thr Val Gly
1265                1270                1275                1280

Leu Ala His Arg Leu Tyr Asn Ile Arg Asn His His Ser Leu Arg Arg
                1285                1290                1295

Pro His Arg Gly Pro Gln Phe Gly Ser Glu Val Glu Leu Arg His Ser
            1300                1305                1310

<210> SEQ ID NO 9
<211> LENGTH: 1313
```

```
<212> TYPE: PRT
<213> ORGANISM: Rattus rattus
<220> FEATURE:
<223> OTHER INFORMATION: Description of Artificial Sequence:motifs

<400> SEQUENCE: 9
```

| | | | | | | | | | | | | | | | |
|---|---|---|---|---|---|---|---|---|---|---|---|---|---|---|---|
| Met | Gly | Ala | Ala | Ser | Gly | Gln | Arg | Gly | Arg | Trp | Pro | Leu | Ser | Pro | Pro |
| 1 | | | | 5 | | | | | 10 | | | | | 15 | |
| Leu | Leu | Met | Leu | Ser | Leu | Leu | Leu | Leu | Leu | Leu | Pro | Pro | Ser | Pro | |
| | | | 20 | | | | | 25 | | | | | 30 | | |
| Ala | Pro | Ala | Leu | Asp | Pro | Gly | Leu | Gln | Pro | Gly | Asn | Phe | Ser | Ala | Asp |
| | | 35 | | | | | 40 | | | | | 45 | | | |
| Glu | Ala | Gly | Ala | Gln | Leu | Phe | Ala | Asp | Ser | Tyr | Asn | Ser | Ser | Ala | Glu |
| | 50 | | | | | 55 | | | | | 60 | | | | |
| Val | Val | Met | Phe | Gln | Ser | Thr | Ala | Ala | Ser | Trp | Ala | His | Asp | Thr | Asn |
| 65 | | | | | 70 | | | | | 75 | | | | | 80 |
| Ile | Thr | Glu | Glu | Asn | Ala | Arg | Leu | Gln | Glu | Glu | Ala | Ala | Leu | Ile | Asn |
| | | | | 85 | | | | | 90 | | | | | 95 | |
| Gln | Glu | Phe | Ala | Glu | Val | Trp | Gly | Lys | Lys | Ala | Lys | Glu | Leu | Tyr | Glu |
| | | | 100 | | | | | 105 | | | | | 110 | | |
| Ser | Ile | Trp | Gln | Asn | Phe | Thr | Asp | Gln | Lys | Leu | Arg | Arg | Ile | Ile | Gly |
| | | 115 | | | | | 120 | | | | | 125 | | | |
| Ser | Val | Gln | Thr | Leu | Gly | Pro | Ala | Asn | Leu | Pro | Leu | Thr | Gln | Arg | Leu |
| | 130 | | | | | 135 | | | | | 140 | | | | |
| Gln | Tyr | Asn | Ser | Leu | Leu | Ser | Asn | Met | Ser | Arg | Ile | Tyr | Ser | Thr | Gly |
| 145 | | | | | 150 | | | | | 155 | | | | | 160 |
| Lys | Val | Cys | Phe | Pro | Asn | Lys | Thr | Ala | Thr | Cys | Trp | Ser | Leu | Asp | Pro |
| | | | | 165 | | | | | 170 | | | | | 175 | |
| Glu | Leu | Thr | Asn | Ile | Leu | Ala | Ser | Ser | Arg | Asn | Tyr | Ala | Lys | Val | Leu |
| | | | 180 | | | | | 185 | | | | | 190 | | |
| Phe | Ala | Trp | Glu | Gly | Trp | His | Asp | Ala | Val | Gly | Ile | Pro | Leu | Arg | Pro |
| | | 195 | | | | | 200 | | | | | 205 | | | |
| Leu | Tyr | Gln | Asp | Phe | Thr | Ala | Leu | Ser | Asn | Glu | Ala | Tyr | Arg | Gln | Asp |
| | 210 | | | | | 215 | | | | | 220 | | | | |
| Gly | Phe | Ser | Asp | Thr | Gly | Ala | Tyr | Trp | Arg | Ser | Trp | Tyr | Glu | Ser | Pro |
| 225 | | | | | 230 | | | | | 235 | | | | | 240 |
| Ser | Phe | Glu | Glu | Ser | Leu | Glu | His | Leu | Tyr | His | Gln | Val | Glu | Pro | Leu |
| | | | | 245 | | | | | 250 | | | | | 255 | |
| Tyr | Leu | Asn | Leu | His | Ala | Phe | Val | Arg | Arg | Ala | Leu | His | Arg | Arg | Tyr |
| | | | 260 | | | | | 265 | | | | | 270 | | |
| Gly | Asp | Lys | Tyr | Ile | Asn | Leu | Arg | Gly | Pro | Ile | Pro | Ala | His | Leu | Leu |
| | | 275 | | | | | 280 | | | | | 285 | | | |
| Gly | Asp | Met | Trp | Ala | Gln | Ser | Trp | Glu | Asn | Ile | Tyr | Asp | Met | Val | Val |
| | 290 | | | | | 295 | | | | | 300 | | | | |
| Pro | Phe | Pro | Asp | Lys | Pro | Asn | Leu | Asp | Val | Thr | Ser | Thr | Met | Val | Gln |
| 305 | | | | | 310 | | | | | 315 | | | | | 320 |
| Lys | Gly | Trp | Asn | Ala | Thr | His | Met | Phe | Arg | Val | Ala | Glu | Glu | Phe | Phe |
| | | | | 325 | | | | | 330 | | | | | 335 | |
| Thr | Ser | Leu | Gly | Leu | Ser | Pro | Met | Pro | Pro | Glu | Phe | Trp | Ala | Glu | Ser |
| | | | 340 | | | | | 345 | | | | | 350 | | |
| Met | Leu | Glu | Lys | Pro | Ala | Asp | Gly | Arg | Glu | Val | Val | Cys | His | Ala | Ser |
| | | 355 | | | | | 360 | | | | | 365 | | | |
| Ala | Trp | Asp | Phe | Tyr | Asn | Arg | Lys | Asp | Phe | Arg | Ile | Lys | Gln | Cys | Thr |
| | 370 | | | | | 375 | | | | | 380 | | | | |

-continued

```
Arg Val Thr Met Asp Gln Leu Ser Thr Val His His Glu Met Gly His
385                 390                 395                 400

Val Gln Tyr Tyr Leu Gln Tyr Lys Asp Leu His Val Ser Leu Arg Arg
            405                 410                 415

Gly Ala Asn Pro Gly Phe His Glu Ala Ile Gly Asp Val Leu Ala Leu
            420                 425                 430

Ser Val Ser Thr Pro Ala His Leu His Lys Ile Gly Leu Leu Asp Arg
            435                 440                 445

Val Ala Asn Asp Ile Glu Ser Asp Ile Asn Tyr Leu Leu Lys Met Ala
        450                 455                 460

Leu Glu Lys Ile Ala Phe Leu Pro Phe Gly Tyr Leu Val Asp Gln Trp
465                 470                 475                 480

Arg Trp Gly Val Phe Ser Gly Arg Thr Pro Ser Arg Tyr Asn Tyr
            485                 490                 495

Asp Trp Trp Tyr Leu Arg Thr Lys Tyr Gln Gly Ile Cys Pro Pro Val
            500                 505                 510

Ala Arg Asn Glu Thr His Phe Asp Ala Gly Ala Lys Phe His Ile Pro
            515                 520                 525

Ser Val Thr Pro Tyr Ile Arg Tyr Phe Val Ser Phe Val Leu Gln Phe
            530                 535                 540

Gln Phe His Gln Ala Leu Cys Lys Glu Ala Gly His Gln Gly Pro Leu
545                 550                 555                 560

His Gln Cys Asp Ile Tyr Gln Ser Thr Lys Ala Gly Ala Lys Leu Gln
            565                 570                 575

Gln Val Leu Gln Ala Gly Cys Ser Arg Pro Trp Gln Glu Val Leu Lys
            580                 585                 590

Asp Leu Val Gly Ser Asp Ala Leu Asp Ala Ser Ala Leu Met Glu Tyr
            595                 600                 605

Phe Gln Pro Val Ser Gln Trp Leu Gln Glu Gln Asn Gln Arg Asn Gly
        610                 615                 620

Glu Val Leu Gly Trp Pro Glu Tyr Gln Trp Arg Pro Pro Leu Pro Asp
625                 630                 635                 640

Asn Tyr Pro Glu Gly Ile Asp Leu Glu Thr Asp Glu Ala Lys Ala Asn
            645                 650                 655

Arg Phe Val Glu Glu Tyr Asp Arg Thr Ala Lys Val Leu Trp Asn Glu
            660                 665                 670

Tyr Ala Glu Ala Asn Trp His Tyr Asn Thr Asn Ile Thr Ile Glu Gly
        675                 680                 685

Ser Lys Ile Leu Leu Gln Lys Asn Lys Glu Val Ser Asn His Thr Leu
        690                 695                 700

Lys Tyr Gly Thr Trp Ala Lys Thr Phe Asp Val Ser Asn Phe Gln Asn
705                 710                 715                 720

Ser Thr Ile Lys Arg Ile Ile Lys Lys Val Gln Asn Val Asp Arg Ala
            725                 730                 735

Val Leu Pro Pro Asn Glu Leu Glu Glu Tyr Asn Gln Ile Leu Leu Asp
            740                 745                 750

Met Glu Thr Thr Tyr Ser Val Ala Asn Val Cys Tyr Thr Asn Gly Thr
            755                 760                 765

Cys Leu Ser Leu Glu Pro Asp Leu Thr Asn Ile Met Ala Thr Ser Arg
770                 775                 780

Lys Tyr Glu Glu Leu Leu Trp Val Trp Lys Ser Trp Arg Asp Lys Val
785                 790                 795                 800

Gly Arg Ala Ile Leu Pro Phe Phe Pro Lys Tyr Val Asp Phe Ser Asn
```

805                 810                 815
Lys Ile Ala Lys Leu Asn Gly Tyr Ser Asp Ala Gly Asp Ser Trp Arg
            820                 825                 830

Ser Ser Tyr Glu Ser Asp Asp Leu Glu Gln Asp Leu Glu Lys Leu Tyr
            835                 840                 845

Gln Glu Leu Gln Pro Leu Tyr Leu Asn Leu His Ala Tyr Val Arg Arg
        850                 855                 860

Ser Leu His Arg His Tyr Gly Ser Glu Tyr Ile Asn Leu Asp Gly Pro
865                 870                 875                 880

Ile Pro Ala His Leu Leu Gly Asn Met Trp Ala Gln Thr Trp Ser Asn
                885                 890                 895

Ile Tyr Asp Leu Val Ala Pro Phe Pro Ser Ala Pro Ser Ile Asp Ala
            900                 905                 910

Thr Glu Ala Met Ile Lys Gln Gly Trp Thr Pro Arg Arg Ile Phe Lys
        915                 920                 925

Glu Ala Asp Asn Phe Phe Thr Ser Leu Gly Leu Leu Pro Val Pro Pro
    930                 935                 940

Glu Phe Trp Asn Lys Ser Met Leu Glu Lys Pro Thr Asp Gly Arg Glu
945                 950                 955                 960

Val Val Cys His Ala Ser Ala Trp Asp Phe Tyr Asn Gly Lys Asp Phe
                965                 970                 975

Arg Ile Lys Gln Cys Thr Ser Val Asn Met Glu Glu Leu Val Ile Ala
            980                 985                 990

His His Glu Met Gly His Ile Gln Tyr Phe Met Gln Tyr Lys Asp Leu
        995                 1000                1005

Pro Val Thr Phe Arg Glu Gly Ala Asn Pro Gly Phe His Glu Ala Ile
    1010                1015                1020

Gly Asp Val Leu Ala Leu Ser Val Ser Thr Pro Lys His Leu His Ser
1025                1030                1035                1040

Leu Asn Leu Leu Ser Ser Glu Gly Ser Gly Tyr Glu His Asp Ile Asn
                1045                1050                1055

Phe Leu Met Lys Met Ala Leu Asp Lys Ile Ala Phe Ile Pro Phe Ser
            1060                1065                1070

Tyr Leu Ile Asp Gln Trp Arg Trp Arg Val Phe Asp Gly Ser Ile Thr
        1075                1080                1085

Lys Glu Asn Tyr Asn Gln Glu Trp Trp Ser Leu Arg Leu Lys Tyr Gln
    1090                1095                1100

Gly Leu Cys Pro Pro Val Pro Arg Ser Gln Gly Asp Phe Asp Pro Gly
1105                1110                1115                1120

Ser Lys Phe His Val Pro Ala Asn Val Pro Tyr Ile Arg Tyr Phe Ile
                1125                1130                1135

Ser Phe Ile Ile Gln Phe Gln Phe His Glu Ala Leu Cys Arg Ala Ala
            1140                1145                1150

Gly His Thr Gly Pro Leu Tyr Lys Cys Asp Ile Tyr Gln Ser Lys Glu
        1155                1160                1165

Ala Gly Lys Leu Leu Ala Asp Ala Met Lys Leu Gly Tyr Ser Lys Gln
    1170                1175                1180

Trp Pro Glu Ala Met Lys Ile Ile Thr Gly Gln Pro Asn Met Ser Ala
1185                1190                1195                1200

Ser Ala Ile Met Asn Tyr Phe Lys Pro Leu Thr Glu Trp Leu Val Thr
                1205                1210                1215

Glu Asn Arg Arg His Gly Glu Thr Leu Gly Trp Pro Glu Tyr Thr Trp
            1220                1225                1230

```
Thr Pro Asn Thr Ala Arg Ala Glu Gly Ser Leu Pro Glu Ser Ser Arg
        1235                1240                1245

Val Asn Phe Leu Gly Met Tyr Leu Glu Pro Gln Gln Ala Arg Val Gly
        1250                1255                1260

Gln Trp Val Leu Leu Phe Leu Gly Val Ala Leu Leu Val Ala Thr Val
1265                1270                1275                1280

Gly Leu Ala His Arg Leu Tyr Asn Ile His Asn His Ser Leu Arg
                1285                1290                1295

Arg Pro His Arg Gly Pro Gln Phe Gly Ser Glu Val Glu Leu Arg His
                1300                1305                1310

Ser

<210> SEQ ID NO 10
<211> LENGTH: 1310
<212> TYPE: PRT
<213> ORGANISM: Oryctolagus cuniculus
<220> FEATURE:
<223> OTHER INFORMATION: Description of Artificial Sequence:motifs

<400> SEQUENCE: 10

Met Gly Ala Ala Pro Gly Arg Arg Gly Pro Arg Leu Leu Arg Pro Pro
1               5                   10                  15

Pro Pro Leu Leu Leu Leu Leu Leu Leu Arg Pro Pro Ala Ala
            20                  25                  30

Leu Thr Leu Asp Pro Gly Leu Leu Pro Gly Asp Phe Ala Ala Asp Glu
        35                  40                  45

Ala Gly Ala Arg Leu Phe Ala Ser Ser Tyr Asn Ser Ser Ala Glu Gln
    50                  55                  60

Val Leu Phe Arg Ser Thr Ala Ala Ser Trp Ala His Asp Thr Asn Ile
65              70                  75                  80

Thr Ala Glu Asn Ala Arg Arg Gln Glu Glu Ala Leu Leu Ser Gln
                85                  90                  95

Glu Phe Ala Glu Ala Trp Gly Lys Lys Ala Lys Glu Leu Tyr Asp Pro
            100                 105                 110

Val Trp Gln Asn Phe Thr Asp Pro Glu Leu Arg Arg Ile Ile Gly Ala
        115                 120                 125

Val Arg Thr Leu Gly Pro Ala Asn Leu Pro Leu Ala Lys Arg Gln Gln
    130                 135                 140

Tyr Asn Ser Leu Leu Ser Asn Met Ser Gln Ile Tyr Ser Thr Gly Lys
145             150                 155                 160

Val Cys Phe Pro Asn Lys Thr Ala Ser Cys Trp Ser Leu Asp Pro Asp
                165                 170                 175

Leu Asn Asn Ile Leu Ala Ser Ser Arg Ser Tyr Ala Met Leu Leu Phe
            180                 185                 190

Ala Trp Glu Gly Trp His Asn Ala Val Gly Ile Pro Leu Lys Pro Leu
        195                 200                 205

Tyr Gln Glu Phe Thr Ala Leu Ser Asn Glu Ala Tyr Arg Gln Asp Gly
    210                 215                 220

Phe Ser Asp Thr Gly Ala Tyr Trp Arg Ser Trp Tyr Asp Ser Pro Thr
225             230                 235                 240

Phe Glu Glu Asp Leu Glu Arg Ile Tyr His Gln Leu Glu Pro Leu Tyr
                245                 250                 255

Leu Asn Leu His Ala Tyr Val Arg Arg Val Leu His Arg Arg Tyr Gly
            260                 265                 270
```

```
Asp Arg Tyr Ile Asn Leu Arg Gly Pro Ile Pro Ala His Leu Leu Gly
        275                 280                 285

Asn Met Trp Ala Gln Ser Trp Glu Ser Ile Tyr Asp Met Val Val Pro
    290                 295                 300

Phe Pro Asp Lys Pro Asn Leu Asp Val Thr Ser Thr Met Val Gln Lys
305                 310                 315                 320

Gly Trp Asn Ala Thr His Met Phe Arg Val Ala Glu Glu Phe Phe Thr
                    325                 330                 335

Ser Leu Gly Leu Leu Pro Met Pro Pro Glu Phe Trp Ala Glu Ser Met
            340                 345                 350

Leu Glu Lys Pro Glu Asp Gly Arg Glu Val Val Cys His Ala Ser Ala
        355                 360                 365

Trp Asp Phe Tyr Asn Arg Lys Asp Phe Arg Ile Lys Gln Cys Thr Gln
    370                 375                 380

Val Thr Met Asp Gln Leu Ser Thr Val His His Glu Met Gly His Val
385                 390                 395                 400

Gln Tyr Tyr Leu Gln Tyr Lys Asp Gln Pro Val Ser Leu Arg Arg Ala
                    405                 410                 415

Asn Pro Gly Phe His Glu Ala Ile Gly Asp Val Leu Ala Leu Ser Val
            420                 425                 430

Ser Thr Pro Ala His Leu His Lys Ile Gly Leu Leu Asp His Val Thr
        435                 440                 445

Asn Asp Thr Glu Ser Asp Ile Asn Tyr Leu Leu Lys Met Ala Leu Glu
    450                 455                 460

Lys Ile Ala Phe Leu Pro Phe Gly Tyr Leu Val Asp Gln Trp Arg Trp
465                 470                 475                 480

Gly Val Phe Ser Gly Arg Thr Pro Ser Ser Arg Tyr Asn Phe Asp Trp
                    485                 490                 495

Trp Tyr Leu Arg Thr Lys Tyr Gln Gly Ile Cys Pro Pro Val Val Arg
            500                 505                 510

Asn Glu Thr His Phe Asp Ala Gly Ala Lys Phe His Ile Pro Ser Val
        515                 520                 525

Thr Pro Tyr Ile Arg Tyr Phe Val Ser Phe Val Leu Gln Phe Gln Phe
    530                 535                 540

His Gln Ala Leu Cys Met Glu Ala Gly His Gln Gly Pro Leu His Gln
545                 550                 555                 560

Cys Asp Ile Tyr Gln Ser Thr Arg Ala Gly Ala Lys Leu Arg Ala Val
                    565                 570                 575

Leu Gln Ala Gly Cys Ser Arg Pro Trp Gln Glu Val Leu Lys Asp Met
            580                 585                 590

Val Ala Ser Asp Ala Leu Asp Ala Gln Pro Leu Leu Asp Tyr Phe Gln
        595                 600                 605

Pro Val Thr Gln Trp Leu Gln Glu Gln Asn Glu Arg Asn Gly Glu Val
    610                 615                 620

Leu Gly Trp Pro Glu Tyr Gln Trp Arg Pro Leu Pro Asn Asn Tyr
625                 630                 635                 640

Pro Glu Gly Ile Asp Leu Val Thr Asp Glu Ala Glu Ala Ser Arg Phe
                    645                 650                 655

Val Glu Glu Tyr Asp Arg Ser Phe Gln Ala Val Trp Asn Glu Tyr Ala
            660                 665                 670

Glu Ala Asn Trp Asn Tyr Asn Thr Asn Ile Thr Thr Glu Ala Ser Lys
        675                 680                 685

Ile Leu Leu Gln Lys Asn Met Gln Ile Ala Asn His Thr Leu Thr Tyr
```

```
                690              695              700
Gly Asn Trp Ala Arg Arg Phe Asp Val Ser Asn Phe Gln Asn Ala Thr
705              710              715              720

Ser Lys Arg Ile Ile Lys Lys Val Gln Asp Leu Gln Arg Ala Val Leu
            725              730              735

Pro Val Lys Glu Leu Glu Glu Tyr Asn Gln Ile Leu Leu Asp Met Glu
            740              745              750

Thr Ile Tyr Ser Val Ala Asn Val Cys Arg Val Asp Gly Ser Cys Leu
            755              760              765

Gln Leu Glu Pro Asp Leu Thr Asn Leu Met Ala Thr Ser Arg Lys Tyr
770              775              780

Asp Glu Leu Leu Trp Val Trp Thr Ser Trp Arg Asp Lys Val Gly Arg
785              790              795              800

Ala Ile Leu Pro Tyr Phe Pro Lys Tyr Val Glu Phe Thr Asn Lys Ala
            805              810              815

Ala Arg Leu Asn Gly Tyr Val Asp Ala Gly Asp Ser Trp Arg Ser Met
            820              825              830

Tyr Glu Thr Pro Thr Leu Glu Gln Asp Leu Glu Arg Leu Phe Gln Glu
            835              840              845

Leu Gln Pro Leu Tyr Leu Asn Leu His Ala Tyr Val Gly Arg Ala Leu
850              855              860

His Arg His Tyr Gly Ala Gln His Ile Asn Leu Glu Gly Pro Ile Pro
865              870              875              880

Ala His Leu Leu Gly Asn Met Trp Ala Gln Thr Trp Ser Asn Ile Tyr
            885              890              895

Asp Leu Val Ala Pro Phe Pro Ser Ala Ser Thr Met Asp Ala Thr Glu
            900              905              910

Ala Met Ile Lys Gln Gly Trp Thr Pro Arg Arg Met Phe Glu Glu Ala
            915              920              925

Asp Lys Phe Phe Ile Ser Leu Gly Leu Leu Pro Val Pro Pro Glu Phe
            930              935              940

Trp Asn Lys Ser Met Leu Glu Lys Pro Thr Asp Gly Arg Glu Val Val
945              950              955              960

Cys His Ala Ser Ala Trp Asp Phe Tyr Asn Gly Lys Asp Phe Arg Ile
            965              970              975

Lys Gln Cys Thr Thr Val Asn Met Glu Asp Leu Val Val His His
            980              985              990

Glu Met Gly His Ile Gln Tyr Phe Met Gln Tyr Lys Asp Leu Pro Val
            995              1000             1005

Ala Leu Arg Glu Gly Ala Asn Pro Gly Phe His Glu Ala Ile Gly Asp
        1010             1015             1020

Val Leu Ala Leu Ser Val Ser Thr Pro Lys His Leu His Ser Ile Asn
1025             1030             1035             1040

Leu Leu Ser Ser Glu Gly Gly Tyr Glu His Asp Ile Asn Phe Leu
            1045             1050             1055

Met Lys Met Ala Leu Asp Lys Ile Ala Phe Ile Pro Phe Ser Tyr Leu
        1060             1065             1070

Val Asp Glu Trp Arg Trp Arg Val Phe Asp Gly Ser Ile Thr Lys Glu
        1075             1080             1085

Asn Tyr Asn Gln Glu Trp Trp Ser Leu Arg Leu Lys Tyr Gln Gly Leu
        1090             1095             1100

Cys Pro Pro Ala Pro Arg Ser Gln Gly Asp Phe Asp Pro Gly Ala Lys
1105             1110             1115             1120
```

```
Phe His Ile Pro Ser Ser Val Pro Tyr Ile Arg Tyr Phe Val Ser Phe
            1125                1130                1135

Ile Ile Gln Phe Gln Phe His Glu Ala Leu Cys Lys Ala Ala Gly His
        1140                1145                1150

Thr Gly Pro Leu His Thr Cys Asp Ile Tyr Gln Ser Lys Glu Ala Gly
    1155                1160                1165

Lys Arg Leu Ala Asp Ala Met Lys Leu Gly Tyr Ser Lys Pro Trp Pro
1170                1175                1180

Glu Ala Met Lys Val Ile Thr Gly Gln Pro Asn Met Ser Ala Ser Ala
1185                1190                1195                1200

Met Met Asn Tyr Phe Lys Pro Leu Met Asp Trp Leu Leu Thr Glu Asn
                1205                1210                1215

Gly Arg His Gly Glu Lys Leu Gly Trp Pro Gln Tyr Thr Trp Thr Pro
            1220                1225                1230

Asn Ser Ala Arg Ser Glu Gly Ser Leu Pro Asp Ser Gly Arg Val Asn
        1235                1240                1245

Phe Leu Gly Met Asn Leu Asp Ala Gln Gln Ala Arg Val Gly Gln Trp
    1250                1255                1260

Val Leu Leu Phe Leu Gly Val Ala Leu Leu Leu Ala Ser Leu Gly Leu
1265                1270                1275                1280

Thr Gln Arg Leu Phe Ser Ile Arg Tyr Gln Ser Leu Arg Gln Pro His
                1285                1290                1295

His Gly Pro Gln Phe Gly Ser Glu Val Glu Leu Arg His Ser
            1300                1305                1310

<210> SEQ ID NO 11
<211> LENGTH: 615
<212> TYPE: PRT
<213> ORGANISM: Drosophila melanogaster
<220> FEATURE:
<223> OTHER INFORMATION: Description of Artificial Sequence:motifs

<400> SEQUENCE: 11

Met Arg Leu Phe Leu Leu Ala Leu Leu Ala Thr Leu Ala Val Thr Gln
 1               5                  10                  15

Ala Leu Val Lys Glu Glu Ile Gln Ala Lys Glu Tyr Leu Glu Asn Leu
            20                  25                  30

Asn Lys Glu Leu Ala Lys Arg Thr Asn Val Glu Thr Glu Ala Ala Trp
        35                  40                  45

Ala Tyr Gly Ser Asn Ile Thr Asp Glu Asn Glu Lys Lys Lys Asn Glu
    50                  55                  60

Ile Ser Ala Glu Leu Ala Lys Phe Met Lys Glu Val Ala Ser Asp Thr
65                  70                  75                  80

Thr Lys Phe Gln Trp Arg Ser Tyr Gln Ser Glu Asp Leu Lys Arg Gln
                85                  90                  95

Phe Lys Ala Leu Thr Lys Leu Gly Tyr Ala Ala Leu Pro Glu Asp Asp
            100                 105                 110

Tyr Ala Glu Leu Leu Asp Thr Leu Ser Ala Met Glu Ser Asn Phe Ala
        115                 120                 125

Lys Val Lys Val Cys Asp Tyr Lys Asp Ser Thr Lys Cys Asp Leu Ala
    130                 135                 140

Leu Asp Pro Glu Ile Glu Glu Val Ile Ser Lys Ser Arg Asp His Glu
145                 150                 155                 160

Glu Leu Ala Tyr Tyr Trp Arg Glu Phe Tyr Asp Lys Ala Gly Thr Ala
                165                 170                 175
```

```
Val Arg Ser Gln Phe Glu Arg Tyr Val Glu Leu Asn Thr Lys Ala Ala
            180                 185                 190

Lys Leu Asn Asn Phe Thr Ser Gly Ala Glu Ala Trp Leu Asp Glu Tyr
        195                 200                 205

Glu Asp Asp Thr Phe Glu Gln Gln Leu Glu Asp Ile Phe Ala Asp Ile
        210                 215                 220

Arg Pro Leu Tyr Gln Gln Ile His Gly Tyr Val Arg Phe Arg Leu Arg
225                 230                 235                 240

Lys His Tyr Gly Asp Ala Val Val Ser Glu Thr Gly Pro Ile Pro Met
                245                 250                 255

His Leu Leu Gly Asn Met Trp Ala Gln Gln Trp Ser Glu Ile Ala Asp
            260                 265                 270

Ile Val Ser Pro Phe Pro Glu Lys Pro Leu Val Asp Val Ser Ala Glu
        275                 280                 285

Met Glu Lys Gln Ala Tyr Thr Pro Leu Lys Met Phe Gln Met Gly Asp
        290                 295                 300

Asp Phe Phe Thr Ser Met Asn Leu Thr Lys Leu Pro Gln Asp Phe Trp
305                 310                 315                 320

Asp Lys Ser Ile Ile Glu Lys Pro Thr Asp Gly Arg Asp Leu Val Cys
                325                 330                 335

His Ala Ser Ala Trp Asp Phe Tyr Leu Ile Asp Asp Val Arg Ile Lys
            340                 345                 350

Gln Cys Thr Arg Val Thr Gln Asp Gln Leu Phe Thr Val His His Glu
        355                 360                 365

Leu Gly His Ile Gln Tyr Phe Leu Gln Tyr Gln His Gln Pro Phe Val
        370                 375                 380

Tyr Arg Thr Gly Ala Asn Pro Gly Phe His Glu Ala Val Gly Asp Val
385                 390                 395                 400

Leu Ser Leu Ser Val Ser Thr Pro Lys His Leu Glu Lys Ile Gly Leu
                405                 410                 415

Leu Lys Asp Tyr Val Arg Asp Asp Glu Ala Arg Ile Asn Gln Leu Phe
            420                 425                 430

Leu Thr Ala Leu Asp Lys Ile Val Phe Leu Pro Phe Ala Phe Thr Met
        435                 440                 445

Asp Lys Tyr Arg Trp Ser Leu Phe Arg Gly Glu Val Asp Lys Ala Asn
        450                 455                 460

Trp Asn Cys Ala Phe Trp Lys Leu Arg Asp Glu Tyr Ser Gly Ile Glu
465                 470                 475                 480

Pro Pro Val Val Arg Ser Glu Lys Asp Phe Asp Ala Pro Ala Lys Tyr
                485                 490                 495

His Ile Ser Ala Asp Val Glu Tyr Leu Arg Tyr Leu Val Ser Phe Ile
            500                 505                 510

Ile Gln Phe Gln Phe Tyr Lys Ser Ala Cys Ile Lys Ala Gly Gln Tyr
        515                 520                 525

Asp Pro Asp Asn Val Glu Leu Pro Leu Asp Asn Cys Asp Ile Tyr Gly
        530                 535                 540

Ser Ala Arg Ala Gly Ala Phe His Asn Met Leu Ser Met Gly Ala
545                 550                 555                 560

Ser Lys Pro Trp Pro Asp Ala Leu Glu Ala Phe Asn Gly Glu Arg Ile
                565                 570                 575

Met Ser Gly Lys Ala Ile Ala Glu Tyr Phe Glu Pro Leu Arg Val Trp
            580                 585                 590
```

```
Leu Glu Ala Glu Asn Ile Lys Asn Asn Val His Ile Gly Trp Thr Thr
        595                 600                 605

Ser Asn Lys Cys Val Ser Ser
    610                 615

<210> SEQ ID NO 12
<211> LENGTH: 907
<212> TYPE: PRT
<213> ORGANISM: Caenorhabditis elegans
<220> FEATURE:
<223> OTHER INFORMATION: Description of Artificial Sequence:motifs

<400> SEQUENCE: 12

Met Lys Phe His Ile Leu Leu Leu Leu Val Gly Ala Cys Leu Pro
  1               5                  10                  15

Val Phe Thr Gln Glu Ile Lys Pro Lys Pro Glu Leu Leu Pro Ala Asp
             20                  25                  30

Glu Ala Pro Lys Asp Pro Glu Ala Val Phe Ser Glu Gly Glu Pro Phe
         35                  40                  45

Glu Leu Thr Asp Ala Leu Asp Thr Pro Lys Asn Gly Ser Val Pro Val
     50                  55                  60

Pro Glu Pro Glu Pro Lys Pro Glu Pro Glu Pro Glu Pro Glu Pro Lys
 65                  70                  75                  80

Pro Glu Pro Glu Pro Ser Pro Thr Pro Glu Pro Glu Pro Ala Ile Lys
                 85                  90                  95

Phe Asp Asn Ile Glu Ser Glu Asp Tyr Gly Asp Val Ala Glu Thr Ala
            100                 105                 110

Ala Ser Thr Gln Pro Asp Glu Leu Asn Thr Glu Val Ile Glu Gln Leu
        115                 120                 125

Val Asp Thr Phe Leu Asn Thr Gly Ser Ile Ala Ser Asn Lys Thr Asn
    130                 135                 140

Lys Gly Pro Val Phe Ala Asn Pro Val Ala Gln Ala Leu Val Asn Ser
145                 150                 155                 160

Ser Asn Tyr Trp Lys Thr Asp Asn Leu Gln Ala Pro Gly Ser Ile Lys
                165                 170                 175

Asp Glu Glu Lys Leu Arg Ser Trp Leu Ala Gly Tyr Glu Ala Glu Ala
            180                 185                 190

Ile Lys Val Leu Arg Glu Val Ala Leu Ser Gly Trp Arg Tyr Phe Asn
        195                 200                 205

Asp Ala Ser Pro Ser Leu Lys Leu Ala Leu Asp Glu Ala Glu Asn Val
    210                 215                 220

Leu Thr Met Phe Val Arg Ser Thr Ser Met Gln Ala Lys Gln Phe Asp
225                 230                 235                 240

Met Ala Ser Val Thr Asp Glu Lys Val Met Arg Gln Leu Gly Tyr Val
                245                 250                 255

Ser Phe Glu Gly Met Ser Ala Leu Ala Pro Ser Arg Phe Ala Asp Tyr
            260                 265                 270

Ser Gln Ala Gln Ala Ala Leu Asn Arg Asp Ser Lys Asp Ser Thr Ile
        275                 280                 285

Cys Asp Lys Asp Val Pro Pro Cys Ala Leu Gln Lys Ile Asp Met
    290                 295                 300

Asp Ser Ile Phe Arg Asn Glu Lys Asp Ala Ser Arg Leu Gln His Leu
305                 310                 315                 320

Trp Val Ser Tyr Val Thr Ala Ile Ala Lys Ser Lys Pro Ser Tyr Asn
                325                 330                 335
```

```
Asn Ile Ile Thr Ile Ser Asn Glu Gly Ala Lys Leu Asn Gly Phe Ala
                340                 345                 350

Asn Gly Gly Ala Met Trp Arg Ser Ala Phe Asp Met Ser Ser Lys Val
            355                 360                 365

His Lys Ala Glu Phe Asp Leu Asn Lys Gln Ile Asp Lys Ile Tyr Ser
        370                 375                 380

Thr Ile Gln Pro Phe Tyr Gln Leu Leu His Ala Tyr Met Arg Arg Gln
385                 390                 395                 400

Leu Ala Gly Ile Tyr Ser Asn Pro Val Gly Leu Ser Lys Asp Gly Pro
                405                 410                 415

Ile Pro Ala His Leu Phe Gly Ser Leu Asp Gly Asp Trp Ser Ala
                420                 425                 430

His Tyr Glu Gln Thr Lys Pro Phe Glu Glu Ser Glu Thr Pro Glu
        435                 440                 445

Ala Met Leu Ser Ala Phe Asn Thr Gln Asn Tyr Thr Thr Lys Lys Met
    450                 455                 460

Phe Val Thr Ala Tyr Arg Tyr Phe Lys Ser Ala Gly Phe Pro His Leu
465                 470                 475                 480

Pro Lys Ser Tyr Trp Thr Ser Ser Ile Phe Ala Arg Val Trp Ser Lys
                485                 490                 495

Asp Met Ile Cys His Pro Ala Ala Ala Leu Asp Met Arg Ala Pro Asn
            500                 505                 510

Asp Phe Arg Val Lys Ala Cys Ala Gln Leu Gly Glu Pro Asp Phe Glu
        515                 520                 525

Gln Ala His Ser Leu Leu Val Gln Thr Tyr Tyr Gln Tyr Leu Tyr Lys
    530                 535                 540

Asp Gln Ser Leu Leu Phe Arg Glu Gln Ala Ser Pro Val Ile Thr Asp
545                 550                 555                 560

Ala Ile Ala Asn Ala Phe Ala His Leu Ser Thr Asn Pro His Tyr Leu
                565                 570                 575

Tyr Ser Gln Lys Leu Val Pro Ser Glu His Leu Asp Ile Lys Asp Ser
            580                 585                 590

Val Ile Ile Asn Lys Leu Tyr Lys Glu Ser Leu Glu Ser Phe Thr Lys
        595                 600                 605

Leu Pro Phe Thr Ile Ala Ala Asp Asn Trp Arg Tyr Glu Leu Phe Asp
    610                 615                 620

Gly Thr Val Pro Lys Asn Lys Leu Asn Asp Arg Trp Glu Ile Arg
625                 630                 635                 640

Asn Lys Tyr Glu Gly Val Arg Ser Pro Gln Pro Tyr Asn Thr Ser Asn
                645                 650                 655

Leu Asp Ala Leu Ile His Asn Ser Val Ser Gln Val His Ser Pro Ala
            660                 665                 670

Thr Arg Thr Leu Ile Ser Tyr Val Leu Lys Phe Gln Ile Leu Lys Ala
        675                 680                 685

Leu Cys Gln Arg Glu Leu Phe Trp Leu Ser Glu Gly Cys Ile Leu Ser
    690                 695                 700

Glu Asp Thr Thr Glu Lys Leu Arg Glu Thr Met Lys Leu Gly Ser Ser
705                 710                 715                 720

Ile Thr Trp Leu Lys Ala Leu Glu Met Ile Ser Gly Lys Gly Glu Leu
                725                 730                 735

Asp Ala Gln Pro Leu Leu Glu Tyr Tyr Glu Pro Leu Ile Asn Trp Leu
            740                 745                 750

Arg Asn Thr Asn Glu Ile Asp Gln Val Val Val Gly Trp Asp Gly Glu
```

-continued

```
                755                 760                 765
Gly Thr Pro Phe Thr Val Glu Glu Ile Pro Lys Thr Arg Gln Pro Gly
        770                 775                 780

Asp Gly Gly Asn Gly Leu Pro Ser Glu Asp Arg Val Ala Phe Pro Gly
785                 790                 795                 800

Gly Glu Cys Val Asn Gly Gln Glu Cys Leu Leu Asp Ser His Cys Asn
                805                 810                 815

Gly Thr Ile Cys Val Cys Asn Asp Gly Leu Tyr Thr Leu Glu Ile Gly
            820                 825                 830

Asn Thr Phe Asn Cys Val Pro Gly Asn Pro Ala Asp Ser Gly Phe Gly
        835                 840                 845

Asp Gly Lys Gly Gly Leu Val Ile Gly Leu Phe Asn Asn Glu Val Thr
    850                 855                 860

Thr Pro Glu Pro Ser Ala Glu Pro Glu Pro Thr Ala Lys Thr Thr Thr
865                 870                 875                 880

Lys Met Pro Pro Arg Val Arg Ala Ala Thr Ser Pro Phe Ser Leu Tyr
                885                 890                 895

Leu Thr Val Leu Leu Ile Ile Tyr Phe Ala Leu
            900                 905
```

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:motifs

<400> SEQUENCE: 13
cacaggttcc accacccaa ctatctc                                27

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:motifs

<400> SEQUENCE: 14

```
His His Glu Met Gly His
  1               5
```

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:motifs

<400> SEQUENCE: 15

```
Asp Arg Val Tyr Ile His Pro Phe His Leu
  1               5                  10
```

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:motifs

<400> SEQUENCE: 16

```
Asp Arg Val Tyr Ile His Pro Phe His
  1               5
```

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:motifs

<400> SEQUENCE: 17

Asp Arg Val Tyr Ile His Pro Phe
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:motifs

<400> SEQUENCE: 18

Asp Arg Val Tyr Ile His Pro
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:motifs

<400> SEQUENCE: 19

Asp Arg Val Tyr Ile His
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence:motifs

<400> SEQUENCE: 20

Asp Arg Val Tyr Ile
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence:motifs

<400> SEQUENCE: 21

Arg Val Tyr Ile His Pro Phe His Leu
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence:motifs

<400> SEQUENCE: 22

Arg Val Tyr Ile His Pro Phe
 1               5

```
<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence:motifs

<400> SEQUENCE: 23

Lys Ile Asn Glu Thr Glu Asn Ser Ile Asn
 1               5                  10

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:motifs

<400> SEQUENCE: 24

Ile Ala Arg Arg His Pro Tyr Phe
 1               5

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence:motifs

<400> SEQUENCE: 25

Asn Thr Asn Ile Thr Glu Glu Asn Val Gln Asn Met Asn Asn Ala Gly
 1               5                  10                  15

Asp Lys Trp

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence:motifs

<400> SEQUENCE: 26

Asn His Tyr Glu Asp Tyr Gly Asp Tyr Trp Arg Gly Asp Tyr Glu Val
 1               5                  10                  15

Asn Gly Val Asp Gly
                20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence:motifs

<400> SEQUENCE: 27

Glu Pro Val Pro His Asp Glu Thr Tyr Cys Asp Pro Ala Ser Leu Phe
 1               5                  10                  15

His Val Ser Asn
                20

<210> SEQ ID NO 28
<211> LENGTH: 20
<212> TYPE: PRT
<213> ORGANISM: Artificial Sequence
<220> FEATURE:
```

-continued

<223> OTHER INFORMATION: Description of Artificial Sequence:motifs

<400> SEQUENCE: 28

Ile Arg Met Ser Arg Ser Arg Ile Asn Asp Ala Phe Arg Leu Asn Asp
 1               5                   10                  15

Asn Ser Leu Glu
            20

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence:motifs

<400> SEQUENCE: 29

Asp Ile Ser Lys Gly Glu Asn Asn Pro Gly Phe Gln Asn Thr Asp Asp
 1               5                   10                  15

Val Gln

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 30
ttcccttttc agtttcacgg gcag                                              24

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:motifs

<400> SEQUENCE: 31
tcttcctggc tccttctcag c                                                 21

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:motifs

<400> SEQUENCE: 32
tcttggcctg ttcctcaatg gtg                                               23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:motifs

<400> SEQUENCE: 33
agcgcccaac ccaagttcaa ag                                                22

<210> SEQ ID NO 34
<211> LENGTH: 25
<212> TYPE: DNA
<213> ORGANISM: Artificial Sequence
<220> FEATURE:

```
<223> OTHER INFORMATION: Description of Artificial Sequence:motifs

<400> SEQUENCE: 34
atggacacct tacctaggca tagag                                              25

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 35
atctcacagt caagcttcag ctgc                                               24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 36
tgctcttgtc ttctgagagc actg                                               24

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 37
tctgttctat ctcttcaagc aatgcc                                             26

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence:motifs

<400> SEQUENCE: 38
catctatgtg ttgaaacaca catatctgc                                          29

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence:motifs

<400> SEQUENCE: 39
aggatatctt tatattagca ttctcttcag c                                       31

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 40
taatgcagaa gaaatagccc cgtgg                                              25
```

```
<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 41
ttgtgtgctt tgggataaca ggtttg                                           26

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 42
atgtgttaag aatgagccag aatgcc                                           26

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 43
ctctttcttt cccttatgtt cttccc                                           26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 44
gcgatttcta caatgttact aaccac                                           26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 45
gtggaatgga aattagaatt ggttac                                           26

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 46
ctgcttttcc atgaaactat agctac                                           26

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence:motifs
```

```
<400> SEQUENCE: 47
ggtgatatgt ggggtagatt ttgga                                      25

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 48
ggtccaccat tgcatcagta acat                                       24

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 49
ccaacactag gaattactaa cagctt                                     26

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 50
cctgcctctg ttgtctccca ttta                                       24

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 51
gaaaattcca tgctaacgga cccag                                      25

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 52
tgggatggca gactgctttc tgaa                                       24

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 53
cggtgcctgg cttatttaat ttaaga                                     26

<210> SEQ ID NO 54
<211> LENGTH: 26
```

```
<212> TYPE: DNA
<213> ORGANISM: Artificial Sequence
<220> FEATURE:
<223> OTHER INFORMATION: Description of Artificial Sequence:motifs

<400> SEQUENCE: 54
ctcatacctc ataccttatg tggcaa                                          26

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence:motifs

<400> SEQUENCE: 55
ggcatatgct gcacaacctt ttc                                             23

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 56
cccaacagct tcatggaatc cttca                                           25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 57
cccatacaac tccactgtaa tggtt                                           25

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 58
cgccagtcaa atgcttttaa atacac                                          26

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 59
catccactgt catcttcatc gtaat                                           25

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 60
```

```
gttattagca cagctgtcca caaac                                            25

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 61
gatgaaactg cactagttat gccc                                             24

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 62
ctaggcatgg aaatgagtaa tactg                                            25

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 63
ggttacttgg gctccagatt taaat                                            25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 64
ctgtgtcaca agtcctcatg agact                                            25

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 65
tgtacatctg gaacccctca aaag                                             24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 66
gaaccacatg gcctctcttc tttc                                             24

<210> SEQ ID NO 67
<211> LENGTH: 25
<212> TYPE: DNA
<213> ORGANISM: Artificial Sequence
```

```
<220> FEATURE:
<223> OTHER INFORMATION: Description of Artificial Sequence:motifs

<400> SEQUENCE: 67
cagttacccc tgtctcatca tttct                                         25

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 68
cagagtatct cctcagactc aaga                                          24

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 69
ggtcactgac ttaatgaata gcaag                                         25

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 70
ggcacacagg aagaacacac aaaat                                         25

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence:motifs

<400> SEQUENCE: 71
ctctgtgcca caagtgaaga tgt                                           23

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 72
ggtctataca atctaccact tactg                                         25

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence:motifs

<400> SEQUENCE: 73
agccaacact tggacctcct aac                                           23
```

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence:motifs

<400> SEQUENCE: 74
gtgaagatca ggatgacaat gcc						23

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 75
gctctattat atcctttcag gaaca					25

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 76
ccccagacac tcagatgata actt					24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 77
cagagcatgc ctgatagaaa ctca					24

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence:motifs

<400> SEQUENCE: 78
tacccacttc agagggtgaa cat					23

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 79
gtcaaggatg acatgctttc ttcac					25

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence:motifs

```
<400> SEQUENCE: 80
catgatcgat tccaaacatc actgt                                          25

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 81
ctgtctctgg atttgacttc tgttc                                          25

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 82
gcctgtgaga ccaaatacac acttt                                          25

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 83
cactgatgat gttcagacct ccttt                                          25

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 84
cttggccatg ttgtctttgg acaa                                           24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 85
ctccttaaca cagattcccc tgaa                                           24

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 86
ttgaaccagg taggctacta atttt                                          25

<210> SEQ ID NO 87
```

```
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 87
ttgaaccagg tatgctacta atttt                                              25

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence:motifs

<400> SEQUENCE: 88
ggtatttatt atgtaggaaa ta                                                 22

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence:motifs

<400> SEQUENCE: 89
ggtatttatt atcttatgta ggaaata                                            27

<210> SEQ ID NO 90
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 90
tgaattgatt atttttgagt gcacag                                             26

<210> SEQ ID NO 91
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 91
tgaattgatt attgttgagt gcacag                                             26

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence:motifs

<400> SEQUENCE: 92
cgtctgaatg acaacagcct aga                                                23

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence:motifs

<400> SEQUENCE: 93
```

```
cgtctgaatg acgacagcct agag                                              24

<210> SEQ ID NO 94
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 94
agttgaaaac aaggatatat cattgg                                            26

<210> SEQ ID NO 95
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 95
agttgaaaac aatgatatat cattgg                                            26

<210> SEQ ID NO 96
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 96
ctagggaaag tcattcagtg gatgtg                                            26

<210> SEQ ID NO 97
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 97
ctagggaaag tcgttcagtg gatgtg                                            26

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 98
ttgaaccagg taagctacta atttt                                             25

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 99
ttgaaccagg taggctacta atttt                                             25

<210> SEQ ID NO 100
<211> LENGTH: 27
<212> TYPE: DNA
```

<213> ORGANISM: Artificial Sequence
<220> FEATURE:
<223> OTHER INFORMATION: Description of Artificial Sequence:motifs

<400> SEQUENCE: 100
gttctctaac tgtggagtga atggaaa                                27

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence:motifs

<400> SEQUENCE: 101
gttctctaac tgtagagtga atggaaa                                27

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence:motifs

<400> SEQUENCE: 102
ggatcacttg taaggacagt gcc                                    23

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence:motifs

<400> SEQUENCE: 103
gatcgattcc aaacatcact gtaggc                                 26

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence:motifs

<400> SEQUENCE: 104
attgaccatt gttggaacac taccg                                  25

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence:motifs

<400> SEQUENCE: 105
gtgtgttagc ccctcctggc                                        20

<210> SEQ ID NO 106
<211> LENGTH: 805
<212> TYPE: PRT
<213> ORGANISM: Homo sapiens

<400> SEQUENCE: 106

Met Ser Ser Ser Ser Trp Leu Leu Leu Ser Leu Val Ala Val Thr Ala
 1               5                  10                  15

-continued

```
Ala Gln Ser Thr Ile Glu Glu Gln Ala Lys Thr Phe Leu Asp Lys Phe
                20                  25                  30
Asn His Glu Ala Glu Asp Leu Phe Tyr Gln Ser Ser Leu Ala Ser Trp
            35                  40                  45
Asn Tyr Asn Thr Asn Ile Thr Glu Glu Asn Val Gln Asn Met Asn Asn
        50                  55                  60
Ala Gly Asp Lys Trp Ser Ala Phe Leu Lys Glu Gln Ser Thr Leu Ala
65                  70                  75                  80
Gln Met Tyr Pro Leu Gln Glu Ile Gln Asn Leu Thr Val Lys Leu Gln
                85                  90                  95
Leu Gln Ala Leu Gln Gln Asn Gly Ser Ser Val Leu Ser Glu Asp Lys
            100                 105                 110
Ser Lys Arg Leu Asn Thr Ile Leu Asn Thr Met Ser Thr Ile Tyr Ser
        115                 120                 125
Thr Gly Lys Val Cys Asn Pro Asp Asn Pro Gln Glu Cys Leu Leu Leu
130                 135                 140
Glu Pro Gly Leu Asn Glu Ile Met Ala Asn Ser Leu Asp Tyr Asn Glu
145                 150                 155                 160
Arg Leu Trp Ala Trp Glu Ser Trp Arg Ser Glu Val Gly Lys Gln Leu
                165                 170                 175
Arg Pro Leu Tyr Glu Glu Tyr Val Val Leu Lys Asn Glu Met Ala Arg
            180                 185                 190
Ala Asn His Tyr Glu Asp Tyr Gly Asp Tyr Trp Arg Gly Asp Tyr Glu
        195                 200                 205
Val Asn Gly Val Asp Gly Tyr Asp Tyr Ser Arg Gly Gln Leu Ile Glu
210                 215                 220
Asp Val Glu His Thr Phe Glu Glu Ile Lys Pro Leu Tyr Glu His Leu
225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
            260                 265                 270
Arg Phe Trp Thr Asn Leu Tyr Ser Leu Thr Val Pro Phe Gly Gln Lys
        275                 280                 285
Pro Asn Ile Asp Val Thr Asp Ala Met Val Asp Gln Ala Trp Asp Ala
290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
            340                 345                 350
Lys Gly Asp Phe Arg Ile Leu Met Cys Thr Lys Val Thr Met Asp Asp
        355                 360                 365
Phe Leu Thr Ala His His Glu Met Gly His Ile Gln Tyr Asp Met Ala
370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
            420                 425                 430
Glu Thr Glu Ile Asn Phe Leu Leu Lys Gln Ala Leu Thr Ile Val Gly
```

-continued

```
            435                 440                 445
Thr Leu Pro Phe Thr Tyr Met Leu Glu Lys Trp Arg Trp Met Val Phe
450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
                500                 505                 510
Ile Arg Tyr Tyr Thr Arg Thr Leu Tyr Gln Phe Gln Phe Gln Glu Ala
            515                 520                 525
Leu Cys Gln Ala Ala Lys His Glu Gly Pro Leu His Lys Cys Asp Ile
530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Pro Leu Leu Asn Tyr Phe Glu Pro Leu Phe
                580                 585                 590
Thr Trp Leu Lys Asp Gln Asn Lys Asn Ser Phe Val Gly Trp Ser Thr
            595                 600                 605
Asp Trp Ser Pro Tyr Ala Asp Gln Ser Ile Lys Val Arg Ile Ser Leu
            610                 615                 620
Lys Ser Ala Leu Gly Asp Lys Ala Tyr Glu Trp Asn Asp Asn Glu Met
625                 630                 635                 640
Tyr Leu Phe Arg Ser Ser Val Ala Tyr Ala Met Arg Gln Tyr Phe Leu
                645                 650                 655
Lys Val Lys Asn Gln Met Ile Leu Phe Gly Glu Asp Val Arg Val
            660                 665                 670
Ala Asn Leu Lys Pro Arg Ile Ser Phe Asn Phe Val Thr Ala Pro
            675                 680                 685
Lys Asn Val Ser Asp Ile Ile Pro Arg Thr Glu Val Glu Lys Ala Ile
            690                 695                 700
Arg Met Ser Arg Ser Arg Ile Asn Asp Ala Phe Arg Leu Asn Asp Asn
705                 710                 715                 720
Ser Leu Glu Phe Leu Gly Ile Gln Pro Thr Leu Gly Pro Pro Asn Gln
                725                 730                 735
Pro Pro Val Ser Ile Trp Leu Ile Val Phe Gly Val Val Met Gly Val
                740                 745                 750
Ile Val Val Gly Ile Val Ile Leu Ile Phe Thr Gly Ile Arg Asp Arg
            755                 760                 765
Lys Lys Lys Asn Lys Ala Arg Ser Gly Glu Asn Pro Tyr Ala Ser Ile
770                 775                 780
Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence:motifs
```

-continued

```
<400> SEQUENCE: 107

Glu Leu Tyr Glu Asn Lys Pro Arg Arg Pro Tyr Ile Leu
 1               5                  10
```